US006692949B2

(12) United States Patent
Yan et al.

(10) Patent No.: US 6,692,949 B2
(45) Date of Patent: Feb. 17, 2004

(54) ISOLATED HUMAN PHOSPHATASE PROTEINS, NUCLEIC ACID MOLECULES ENCODING HUMAN PHOSPHATASE PROTEINS, AND USES THEREOF

(75) Inventors: Chunhua Yan, Boyds, MD (US); Weiniu Gan, Gaithersburg, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/370,659

(22) Filed: Feb. 24, 2003

(65) Prior Publication Data

US 2003/0157681 A1 Aug. 21, 2003

Related U.S. Application Data

(62) Division of application No. 09/811,469, filed on Mar. 20, 2001, now Pat. No. 6,551,809.

(51) Int. Cl.$^7$ ............................ C12N 9/12; C12N 1/20; C12N 15/00; C07K 21/04; C07K 1/00

(52) U.S. Cl. ................. 435/194; 435/252.3; 435/320.1; 536/23.2; 530/350

(58) Field of Search .............................. 435/194, 252.3, 435/320.1; 536/23.2; 530/350

(56) References Cited

PUBLICATIONS

Plowman et al. [WO 200112819, (result 1 of sequence comparison between Applicants' SEQ ID No : 2 and accession No. AAB73227)].*

* cited by examiner

*Primary Examiner*—Tekchand Saidha
(74) *Attorney, Agent, or Firm*—Celera Genomics; Lin Sun-Hoffman

(57) ABSTRACT

The present invention provides amino acid sequences of peptides that are encoded by genes within the human genome, the phosphatase peptides of the present invention. The present invention specifically provides isolated peptide and nucleic acid molecules, methods of identifying orthologs and paralogs of the phosphatase peptides, and methods of identifying modulators of the phosphatase peptides.

4 Claims, 54 Drawing Sheets

```
   1 GAGAGCTTTA CGCCCGGAGG CGTCGGCGCT GCCACTGGCC CGCGACGGGA
  51 ACGGGGCGAA AAGGCGGCGG CACCATGTTC TCCCTCAAGC CGCCCAAACC
 101 CACCTTCAGG TCCTACCTCC TGCCACCGCC CCAGACTGAC GATAAGATCA
 151 ATTCGGAACC GAAGATTAAA AAACTGGAGC CAGTCCTTTT GCCAGGAGAA
 201 ATTGTCGTAA ATGAAGTCAA TTTTGTGAGA AAATGCATTG CAACAGACAC
 251 AAGCCAGTAC GATTTGTGGG GAAAGCTGAT ATGCAGTAAC TTCAAAATCT
 301 CCTTTATTAC AGATGACCCA ATGCCATTAC AGAAATTCCA TTACAGAAAC
 351 CTTCTTCTTG GTGAACACGA TGTCCCTTTA ACATGTATTG AACAAATTGT
 401 CACAGTAAAC GACCACAAGA GGAAGCAGAA AGTCCTAGGC CCCAACCAGA
 451 AACTGAAATT TAATCCAACA GAGTTAATTA TTTATTGTAA AGATTTCAGA
 501 ATTGTCAGAT TTCGCTTTGA TGAATCAGGT CCCGAAAGTG CTAAAAAGGT
 551 ATGCCTTGCA ATAGCTCATT ATTCCCAGCC AACAGACCTC CAGCTACTCT
 601 TTGCATTTGA ATATGTTGGG AAAAAATACC ACAATTCAGC AAACAAAATT
 651 AATGGAATTC CCTCAGGAGA TGGAGGAGGA GGAGGAGGAG GAGGTAATGG
 701 AGCTGGTGGT GGCAGCAGCC AGAAAACTCC ACTCTTTGAA ACTTACTCGG
 751 ATTGGGACAG AGAAATCAAG AGGACAGGTG CTTCCGGGTG GAGAGTTTGT
 801 TCTATTAACG AGGGTTACAT GATATCCACT TGCCTTCCAG AATACATTGT
 851 AGTGCCAAGT TCTTTAGCAG ACCAAGATCT AAAGATCTTT TCCCATTCTT
 901 TTGTTGGGAG AAGGATGCCA CTCTGGTGCT GGAGCCACTC TAACGGCAGT
 951 GCTCTTGTGC GAATGGCCCT CATCAAAGAC GTGCTGCAGC AGAGGAAGAT
1001 TGACCAGAGG ATTTGTAATG CAATAACTAA AAGTCACCCA CAGAGAAGTG
1051 ATGTTTACAA ATCAGATTTG GATAAGACCT TGCCTAATAT TCAAGAAGTA
1101 CAGGCAGCAT TTGTAAAACT GAAGCAGCTA TGCGTTAATG AGCCTTTTGA
1151 AGAAACTGAA GAGAAATGGT TATCTTCACT GGAAAATACT CGATGGTTAG
1201 AATATGTAAG GGCATTCCTT AAGCATTCAG CAGAACTTGT ATACATGCTA
1251 GAAAGCAAAC ATCTCTCTGT AGTCCTACAA GAGGAGGAAG GAAGAGACTT
1301 GAGCTGTTGT GTAGCTTCTC TTGTTCAAGT GATGCTGGAT CCCTATTTTA
1351 GGACAATTAC TGGATTTCAG AGTCTGATAC AGAAGGAGTG GGTCATGGCA
1401 GGATATCAGT TTCTAGACAG ATGCAACCAT CTAAAGAGAT CAGAGAAAGA
1451 GTCTCCTTTA TTTTTGCTAT TCTTGGATGC CACCTGGCAG CTGTTAGAAC
1501 AATATCCTGC AGCTTTTGAG TTCTCCGAAA CCTACCTGGC AGTGTTGTAT
1551 GACAGCACCC GGATCTCACT GTTTGGCACC TTCCTGTTCA ACTCCCCTCA
1601 CCAGCGAGTG AAGCAAAGCA CGGAATTTGC TATAAGCAAA AACATCCAAT
1651 TGGGTGATGA GAAGGGCTTA AAATTCCCCT CTGTTTGGGA CTGGTCTCTC
1701 CAGTTTACAG CAAAGGATCG CACCCTTTTC CATAACCCCT TCTACATTGG
1751 AAAGAGCACA CCTTGTATAC AGAATGGCTC CGTGAAGTCT TTTAAACGGA
1801 CAAAGAAAAG CTACAGCTCC ACACTAAGAG GAATGCCGTC TGCCTTAAAG
1851 AATGGAATCA TCAGTGACCA AGAATTACTT CCAAGGAGAA ATTCATTGAT
1901 ATTAAAACCA AAGCCAGATC CAGCTCAGCA AACCGACAGC CAGAACAGTG
1951 ATACGGAGCA GTATTTTAGA GAATGGTTTT CCAAACCCGC CAACCTGCAC
2001 GGTGTTATTC TGCCACGTGT CTCTGGAACA CACATAAAAC TGTGGAAACT
2051 GTGCTACTTC CGCTGGGTTC CCGAGGCCCA GATCAGCCTG GGTGGCTCCA
2101 TCACAGCCTT TCACAAGCTC TCCCTCCTGG CTGATGAAGT CGACGTACTG
2151 AGCAGGATGC TGCGGCAACA GCGCAGTGGC CCCCTGGAGG CCTGCTATGG
2201 GGAGCTGGGC CAGAGCAGGA TGTACTTCAA CGCCAGCGGC CCTCACCACA
2251 CCGACACCTC GGGGACACCG GAGTTTCTCT CCTCCTCATT TCCATTTTCT
2301 CCTGTAGGGA ATCTGTGCAG ACGAAGCATT TTAGGAACAC CATTAAGCAA
2351 ATTTTTAAGT GGGGCCAAAA TATGGTTGTC TACTGAGACA TTAGCAAATG
2401 AAGACTAAAA TAGGGTGTTT TCTGAACATT TTGAGGGAAG CTGTCAACTT
2451 TTTTCCTCTG AATTAACATT GCTAACCTAG GCGTTTGAAT CTCTAATAAC
2501 TTTATATGTA AGAATAATAG TTGGAATTTG CACTAATATT TAAAAACATG
2551 TTGAATCATG CTTCTTTCAC ACTTATTTTA AGAGAGATGT AAATTTTGTT
2601 CCTGTCCTCT TTCTGTCATT ACAGGTCTGG CTCTTGTAAC CGTGATCAAA
2651 CTGTTCATGT TGTCTGCTAC ATTTTTGTCT CCATCCATTT TTCCTACCAC
2701 CTCCTGAAGG CTATCTGATA GTCAGTCACA TTAGCAGCCC CAGGCAGCAG
2751 ACAACAGGAA AGTTAGGAAA TTTGTGTTTC GTGTCATTTT TAGGAGCATC
2801 TGATAAAACC TCCAGCAGGT TTTAGGAAGT ATTCATGTAT TTTTCTGGTT
2851 ACTTTCTGTC ATCTCTAATT GAACTCACCT GATGAAGGTT CAGTGTTCTG
2901 GGGCCAGAAT TTATGATTTT AGATCACCTT CTTTGGAACC TTAGATCACT
2951 GTGTTTTGAA ATCATGAGTT TGCTTTTAAC TTCATAGGGT CAACTTTAAA
3001 ATGATATGCA CTGTTAATTT TAAAGCATTT GCTGCAGATA ATTAAACTTA
3051 GAAGTGCCTT TGACTTTAGG ATACAAATAT TACAGAAGAA AATATAATTT
3101 CACTTTTTAA AATTGGGGTG GGAAAATCCC ATTGCATATT TGAAATAGGC
3151 TTTTCATACT AAGCTTCATA GCCAGGAGTC CCCAGAGTCT TGTTCCTCTG
3201 AAAGCCACTG GGGAGTGGCC TCTGGGGTGC TGATTCCACA GAGGTGTATG
3251 CTGTAGACAG GAGAGTGCCA TCTATGCCAA AACTCGCCCT CAAAAACAAA
3301 CAAGGCTTGC TGGGAGGCGT GCTGGGCTTG GCCATCAGTA TTTCCAGTGT
3351 GGTAAACTAT TGCTGGCACT TCCCCCTGGA AATAACTAAT GAGGTTACGA
```

FIGURE 1A

```
3401 GTTGGGCACC TGCACAGATG TCCTTCTCTC ATAGTTCCTA ATGCTTAGGA
3451 ATAGAGGAGA AATAAAAAAA TGGATTCTCT CAAAACACTG CCATTTGAAT
3501 AGCGACAGAA GTGCTCCCCC AGCCCCCAAC TTTGGACAGC AAAGTTGAGG
3551 AGAATGAGCA GACACAGTTG TTTGCTTGAT CTGAATCTCT CTAAAGTAAA
3601 GTATTTCCAA ACTGTGTGAC AAGAGCCTAC CTACCACTGT AGCGGTCAAA
3651 GCTGAAGCTT CTTACAGCAG TGAAACGGGG CACCACCTCC CCCACACTCC
3701 TCATTCCCCG CTTAAAACAT GGATACTTTC AAATTTGACT GTTTCTTAAA
3751 CTGCCATCCT AAGATATGGA AAATTTTTAT AGTAAAGTGT CTAGTTAGCT
3801 TATTTCCTTT TCTAAAACAA GTGTTTTCAA GATAACTGTA TTTTACCTTT
3851 ATATGTACTG AATAGCTGTT TCTTTTTGAA TTATTTGCCT TTTAAAATTT
3901 GATAATGTCT CTGGATATAA CAGGACAGGA GTTCTTAAAA AATATCTTAA
3951 GAAATTCACT TTATGGGTAA ACCCAAGGTT TTTGCCAACT TGTTGCCTAG
4001 AAAATAAGGG CTAGTTTCAG TTTATACAAA TAGAATTATT AAACATTTTA
4051 CAGTCCTTGA TTAGAAACCA GACCCAATCT CCTTATAACA CCACAGCGTA
4101 TCCTGCCATT GACAGTGTAA TCACAATTCT CCCTTTTTCA TTTAGCTGCT
4151 TTTTTATTAT TACTAAATGT TTTGGATTGA GCATTTTTCC CTCTGTAATT
4201 TTCTTCCTTC ACGTTTATTT TATTTTAACT CTTGTAGTAT TTTATTGTTG
4251 TTAATTTACA AGTTTAAAAA TATTAGGTAC TATTAATAAT GGTTAAAAAT
4301 AGAAAAATGC ATATTTTTGT ATGATAATCA AATGTAAAAT ACTTTTATTT
4351 TTGCTGGACA GTTGTTATAT CATGATTATT GTGCTACAGT TTATTGTGCA
4401 TAATATGAAA AACAACTATG ACAGCCTTCA GTCGGGCCAG GGTGAAGCTG
4451 CTTATACC (SEQ ID NO:1)
```

FEATURES:

```
5'UTR:        1-74
Start Codon:  75
Stop Codon:   2406
3'UTR:        2409
```

Homologous proteins:

Top 10 BLAST Hits

| | Score | E |
|---|---|---|
| CRA\|335001098689405 /altid=gi\|11433679 /def=ref\|XP_007769.1\| hy... | 987 | 0.0 |
| CRA\|66000019403732 /altid=gi\|8923297 /def=ref\|NP_060232.1\| hypo... | 899 | 0.0 |
| CRA\|113000085275835 /altid=gi\|12697909 /def=dbj\|BAB21773.1\| (AB... | 441 | e-122 |
| CRA\|66000019403839 /altid=gi\|9506679 /def=ref\|NP_061934.1\| hypo... | 291 | 2e-77 |
| CRA\|89000000195580 /altid=gi\|7293003 /def=gb\|AAF48390.1\| (AE003... | 269 | 1e-70 |
| CRA\|1000682317637 /altid=gi\|7705564 /def=ref\|NP_057240.1\| KIAA1... | 167 | 5e-40 |
| CRA\|108000024650128 /altid=gi\|12735904 /def=ref\|XP_011954.1\| si... | 167 | 5e-40 |
| CRA\|108000024650126 /altid=gi\|12735902 /def=ref\|XP_005992.2\| si... | 167 | 5e-40 |
| CRA\|66000019403815 /altid=gi\|7661582 /def=ref\|NP_056273.1\| DKFZ... | 161 | 3e-38 |
| CRA\|335001098685012 /altid=gi\|11425780 /def=ref\|XP_005213.1\| DK... | 161 | 3e-38 |

BLAST dbEST hits:

| | Score | E |
|---|---|---|
| gi\|12907851 /dataset=dbest /taxon=960... | 1657 | 0.0 |
| gi\|12950044 /dataset=dbest /taxon=960... | 1243 | 0.0 |
| gi\|7143189 /dataset=dbest /taxon=9606... | 918 | 0.0 |
| gi\|7114815 /dataset=dbest /taxon=9606... | 918 | 0.0 |
| gi\|4073139 /dataset=dbest /taxon=9606 ... | 908 | 0.0 |
| gi\|8060283 /dataset=dbest /taxon=960... | 904 | 0.0 |
| gi\|11511187 /dataset=dbest /taxon=96... | 864 | 0.0 |
| gi\|2841819 /dataset=dbest /taxon=9606 ... | 852 | 0.0 |
| gi\|9512988 /dataset=dbest /taxon=9606... | 831 | 0.0 |
| gi\|1445380 /dataset=dbest /taxon=9606 ... | 821 | 0.0 |

EXPRESSION INFORMATION FOR MODULATORY USE:

library source:

From BLAST dbEST hits:

```
gi|12907851 B cell Burkitt's lymphoma
gi|12950044 B cell Burkitt's lymphoma
gi|7143189  Lymph germinal center B cell
gi|7114815  Lymph germinal center B cell
gi|4073139  Fetal lung
gi|8060283  Neural tissue normal
gi|11511187 Breast invasive ductal carcinoma
```

FIGURE 1B gi|2841819 Parathyroid tumor
gi|9512988 Lung- carcinoid
gi|1445380 Fetal liver spleen From PCR-based tissue screening panels:
Whole liver

FIGURE 1C

```
  1 MFSLKPPKPT FRSYLLPPPQ TDDKINSEPK IKKLEPVLLP GEIVVNEVNF
 51 VRKCIATDTS QYDLWGKLIC SNFKISFITD DPMPLQKFHY RNLLLGEHDV
101 PLTCIEQIVT VNDHKRKQKV LGPNQKLKFN PTELIIYCKD FRIVRFRFDE
151 SGPESAKKVC LAIAHYSQPT DLQLLFAFEY VGKKYHNSAN KINGIPSGDG
201 GGGGGGGNGA GGGSSQKTPL FETYSDWDRE IKRTGASGWR VCSINEGYMI
251 STCLPEYIVV PSSLADQDLK IFSHSFVGRR MPLWCWSHSN GSALVRMALI
301 KDVLQQRKID QRICNAITKS HPQRSDVYKS DLDKTLPNIQ EVQAAFVKLK
351 QLCVNEPFEE TEEKWLSSLE NTRWLEYVRA FLKHSAELVY MLESKHLSVV
401 LQEEEGRDLS CCVASLVQVM LDPYFRTITG FQSLIQKEWV MAGYQFLDRC
451 NHLKRSEKES PLFLLFLDAT WQLLEQYPAA FEFSETYLAV LYDSTRISLF
501 GTFLFNSPHQ RVKQSTEFAI SKNIQLGDEK GLKFPSVWDW SLQFTAKDRT
551 LFHNPFYIGK STPCIQNGSV KSFKRTKKSY SSTLRGMPSA LKNGIISDQE
601 LLPRRNSLIL KPKPDPAQQT DSQNSDTEQY FREWFSKPAN LHGVILPRVS
651 GTHIKLWKLC YFRWVPEAQI SLGGSITAFH KLSLLADEVD VLSRMLRQQR
701 SGPLEACYGE LGQSRMYFNA SGPHHTDTSG TPEFLSSSFP FSPVGNLCRR
751 SILGTPLSKF LSGAKIWLST ETLANED  (SEQ ID NO:2)
```

FEATURES:
Functional domains and key regions:
[1] PDOC00001 PS00001 ASN_GLYCOSYLATION
N-glycosylation site Number of matches: 3

| | | |
|---|---|---|
| 1 | 290-293 | NGSA |
| 2 | 567-570 | NGSV |
| 3 | 719-722 | NASG |

[2] PDOC00004 PS00004 CAMP_PHOSPHO_SITE
cAMP- and cGMP-dependent protein kinase phosphorylation site 604-607 RRNS

[3] PDOC00005 PS00005 PKC_PHOSPHO_SITE
Protein kinase C phosphorylation site

Number of matches: 11

| | | |
|---|---|---|
| 1 | 3-5 | SLK |
| 2 | 10-12 | TFR |
| 3 | 155-157 | SAK |
| 4 | 215-217 | SQK |
| 5 | 456-458 | SEK |
| 6 | 494-496 | STR |
| 7 | 545-547 | TAK |
| 8 | 569-571 | SVK |
| 9 | 572-574 | SFK |
| 10 | 576-578 | TKK |
| 11 | 583-585 | TLR |

FIGURE 2A

[4] PDOC00006 PS00006 CK2_PHOSPHO_SITE
Casein kinase II phosphorylation site

Number of matches: 15

| | | |
|---|---|---|
| 1 | 60-63 | SQYD |
| 2 | 103-106 | TCIE |
| 3 | 110-113 | TVND |
| 4 | 151-154 | SGPE |
| 5 | 223-226 | TYSD |
| 6 | 225-228 | SDWD |
| 7 | 243-246 | SINE |
| 8 | 263-266 | SLAD |
| 9 | 330-333 | SDLD |
| 10 | 367-370 | SSLE |
| 11 | 456-459 | SEKE |
| 12 | 536-539 | SVWD |
| 13 | 545-548 | TAKD |
| 14 | 597-600 | SDQE |
| 15 | 625-628 | SDTE |

[5] PDOC00007 PS00007 TYR_PHOSPHO_SITE
Tyrosine kinase phosphorylation site 383-390 KHSAELVY

[6] PDOC00008 PS00008 MYRISTYL
N-myristoylation site

Number of matches: 16

| | | |
|---|---|---|
| 1 | 194-199 | GIPSGD |
| 2 | 200-205 | GGGGGG |
| 3 | 201-206 | GGGGGG |
| 4 | 202-207 | GGGGGG |
| 5 | 200-205 | GGGGGG |
| 6 | 201-206 | GGGGGG |
| 7 | 202-207 | GGGGGG |
| 8 | 200-205 | GGGGGG |
| 9 | 201-206 | GGGGGG |
| 10 | 202-207 | GGGGGG |
| 11 | 203-208 | GGGGGN |
| 12 | 204-209 | GGGGNG |
| 13 | 205-210 | GGGNGA |
| 14 | 206-211 | GGNGAG |
| 15 | 207-212 | GNGAGG |
| 16 | 209-214 | GAGGGS |

[7] PDOC00009 PS00009 AMIDATION
Amidation site

Number of matches: 2

| | | |
|---|---|---|
| 1 | 181-184 | VGKK |
| 2 | 277-280 | VGRR |

Membrane spanning structure and domains:

| Helix | Begin | End | Score | Certainty |
|---|---|---|---|---|
| 1 | 246 | 266 | 0.714 | Putative |
| 2 | 728 | 748 | 0.683 | Putative |

FIGURE 2B

```
BLAST Alignment to Top Hit:
>CRA|335001098689405 /altid=gi|11433679 /def=ref|XP_007769.1|
          hypothetical protein FLJ20313 [Homo sapiens] /org=Homo
          sapiens /taxon=9606 /dataset=nraa /length=497
         Length = 497

 Score =  987 bits (2524), Expect = 0.0
 Identities = 476/476 (100%), Positives = 476/476 (100%)

Query: 41  GEIVVNEVNFVRKCIATDTSQYDLWGKLICSNFKISFITDDPMPLQKFHYRNLLLGEHDV 100
            GEIVVNEVNFVRKCIATDTSQYDLWGKLICSNFKISFITDDPMPLQKFHYRNLLLGEHDV
Sbjct: 5   GEIVVNEVNFVRKCIATDTSQYDLWGKLICSNFKISFITDDPMPLQKFHYRNLLLGEHDV 64

Query: 101 PLTCIEQIVTVNDHKRKQKVLGPNQKLKFNPTELIIYCKDFRIVRFRFDESGPESAKKVC 160
            PLTCIEQIVTVNDHKRKQKVLGPNQKLKFNPTELIIYCKDFRIVRFRFDESGPESAKKVC
Sbjct: 65  PLTCIEQIVTVNDHKRKQKVLGPNQKLKFNPTELIIYCKDFRIVRFRFDESGPESAKKVC 124

Query: 161 LAIAHYSQPTDLQLLFAFEYVGKKYHNSANKINGIPSGDGGGGGGGGNGAGGGSSQKTPL 220
            LAIAHYSQPTDLQLLFAFEYVGKKYHNSANKINGIPSGDGGGGGGGGNGAGGGSSQKTPL
Sbjct: 125 LAIAHYSQPTDLQLLFAFEYVGKKYHNSANKINGIPSGDGGGGGGGGNGAGGGSSQKTPL 184

Query: 221 FETYSDWDREIKRTGASGWRVCSINEGYMISTCLPEYIVVPSSLADQDLKIFSHSFVGRR 280
            FETYSDWDREIKRTGASGWRVCSINEGYMISTCLPEYIVVPSSLADQDLKIFSHSFVGRR
Sbjct: 185 FETYSDWDREIKRTGASGWRVCSINEGYMISTCLPEYIVVPSSLADQDLKIFSHSFVGRR 244

Query: 281 MPLWCWSHSNGSALVRMALIKDVLQQRKIDQRICNAITKSHPQRSDVYKSDLDKTLPNIQ 340
            MPLWCWSHSNGSALVRMALIKDVLQQRKIDQRICNAITKSHPQRSDVYKSDLDKTLPNIQ
Sbjct: 245 MPLWCWSHSNGSALVRMALIKDVLQQRKIDQRICNAITKSHPQRSDVYKSDLDKTLPNIQ 304

Query: 341 EVQAAFVKLKQLCVNEPFEETEEKWLSSLENTRWLEYVRAFLKHSAELVYMLESKHLSVV 400
            EVQAAFVKLKQLCVNEPFEETEEKWLSSLENTRWLEYVRAFLKHSAELVYMLESKHLSVV
Sbjct: 305 EVQAAFVKLKQLCVNEPFEETEEKWLSSLENTRWLEYVRAFLKHSAELVYMLESKHLSVV 364

Query: 401 LQEEEGRDLSCCVASLVQVMLDPYFRTITGFQSLIQKEWVMAGYQFLDRCNHLKRSEKES 460
            LQEEEGRDLSCCVASLVQVMLDPYFRTITGFQSLIQKEWVMAGYQFLDRCNHLKRSEKES
Sbjct: 365 LQEEEGRDLSCCVASLVQVMLDPYFRTITGFQSLIQKEWVMAGYQFLDRCNHLKRSEKES 424

Query: 461 PLFLLFLDATWQLLEQYPAAFEFSETYLAVLYDSTRISLFGTFLFNSPHQRVKQST 516
            PLFLLFLDATWQLLEQYPAAFEFSETYLAVLYDSTRISLFGTFLFNSPHQRVKQST
Sbjct: 425 PLFLLFLDATWQLLEQYPAAFEFSETYLAVLYDSTRISLFGTFLFNSPHQRVKQST 480   (SEQ
ID NO:4)

>CRA|66000019403732 /altid=gi|8923297 /def=ref|NP_060232.1|
          hypothetical protein FLJ20313 [Homo sapiens] /org=Homo
          sapiens /taxon=9606 /dataset=nraa /length=451
         Length = 451

 Score =  899 bits (2299), Expect = 0.0
 Identities = 434/434 (100%), Positives = 434/434 (100%)

Query: 83  MPLQKFHYRNLLLGEHDVPLTCIEQIVTVNDHKRKQKVLGPNQKLKFNPTELIIYCKDFR 142
            MPLQKFHYRNLLLGEHDVPLTCIEQIVTVNDHKRKQKVLGPNQKLKFNPTELIIYCKDFR
Sbjct: 1   MPLQKFHYRNLLLGEHDVPLTCIEQIVTVNDHKRKQKVLGPNQKLKFNPTELIIYCKDFR 60

Query: 143 IVRFRFDESGPESAKKVCLAIAHYSQPTDLQLLFAFEYVGKKYHNSANKINGIPSGDGGG 202
            IVRFRFDESGPESAKKVCLAIAHYSQPTDLQLLFAFEYVGKKYHNSANKINGIPSGDGGG
Sbjct: 61  IVRFRFDESGPESAKKVCLAIAHYSQPTDLQLLFAFEYVGKKYHNSANKINGIPSGDGGG 120

Query: 203 GGGGGNGAGGGSSQKTPLFETYSDWDREIKRTGASGWRVCSINEGYMISTCLPEYIVVPS 262
            GGGGGNGAGGGSSQKTPLFETYSDWDREIKRTGASGWRVCSINEGYMISTCLPEYIVVPS
Sbjct: 121 GGGGGNGAGGGSSQKTPLFETYSDWDREIKRTGASGWRVCSINEGYMISTCLPEYIVVPS 180

Query: 263 SLADQDLKIFSHSFVGRRMPLWCWSHSNGSALVRMALIKDVLQQRKIDQRICNAITKSHP 322
            SLADQDLKIFSHSFVGRRMPLWCWSHSNGSALVRMALIKDVLQQRKIDQRICNAITKSHP
Sbjct: 181 SLADQDLKIFSHSFVGRRMPLWCWSHSNGSALVRMALIKDVLQQRKIDQRICNAITKSHP 240

Query: 323 QRSDVYKSDLDKTLPNIQEVQAAFVKLKQLCVNEPFEETEEKWLSSLENTRWLEYVRAFL 382
```

FIGURE 2C

```
           QRSDVYKSDLDKTLPNIQEVQAAFVKLKQLCVNEPFEETEEKWLSSLENTRWLEYVRAFL
Sbjct: 241 QRSDVYKSDLDKTLPNIQEVQAAFVKLKQLCVNEPFEETEEKWLSSLENTRWLEYVRAFL 300

Query: 383 KHSAELVYMLESKHLSVVLQEEEGRDLSCCVASLVQVMLDPYFRTITGFQSLIQKEWVMA 442
           KHSAELVYMLESKHLSVVLQEEEGRDLSCCVASLVQVMLDPYFRTITGFQSLIQKEWVMA
Sbjct: 301 KHSAELVYMLESKHLSVVLQEEEGRDLSCCVASLVQVMLDPYFRTITGFQSLIQKEWVMA 360

Query: 443 GYQFLDRCNHLKRSEKESPLFLLFLDATWQLLEQYPAAFEFSETYLAVLYDSTRISLFGT 502
           GYQFLDRCNHLKRSEKESPLFLLFLDATWQLLEQYPAAFEFSETYLAVLYDSTRISLFGT
Sbjct: 361 GYQFLDRCNHLKRSEKESPLFLLFLDATWQLLEQYPAAFEFSETYLAVLYDSTRISLFGT 420

Query: 503 FLFNSPHQRVKQST 516
           FLFNSPHQRVKQST
Sbjct: 421 FLFNSPHQRVKQST 434  (SEQ ID NO:5)


>CRA|113000085275835 /altid=gi|12697909 /def=dbj|BAB21773.1|
           (AB051469) KIAA1682 protein [Homo sapiens] /org=Homo
           sapiens /taxon=9606 /dataset=nraa /length=775
          Length = 775

 Score =  441 bits (1123), Expect = e-122
 Identities = 265/718 (36%), Positives = 405/718 (55%), Gaps = 73/718 (10%)

Query: 5   KPPKPTFRSYLLPPP-QTDDKINSEPKIKKLEPVLLPGEIVVNEVNFVRKCIATDTSQYD 63
           K PKP+F SY+ P    T++K  +E   K++   LLPGE ++ E + V K +  D+ Q+
Sbjct: 42  KAPKPSFVSYVRPEEIHTNEKEVTE---KEVTLHLLPGEQLLCEASTVLKYVQEDSCQHG 98

Query: 64  LWGKLICSNFKISFITDDPMPLQ--KFHYRNLLLGEHDVPLTCIEQIVTVNDHKRKQKVL 121
           ++G+L+C++FKI+F+ DD   L   +  ++N ++GE+D+ L C++QI  V D K+K  +
Sbjct: 99  VYGRLVCTDFKIAFLGDDESALDNDETQFKNKVIGENDITLHCVDQIYGVFDEKKKT-LF 157

Query: 122 GPNQKLKFNPTELIIYCKDFRIVRFRFDESGPESAKKVCLAIAHYSQ-PTDLQLLFAFEY 180
           G   +LK  P +LII+CKD R+ +F    +  E  K++   I H++Q P  L+ LF F Y
Sbjct: 158 G---QLKKYPEKLIIHCKDLRVFQFCLRYTKEEEVKRIVSGIIHHTQAPKLLKRLFLFSY 214

Query: 181 VGKKYHNSANKINGIPSGDGGGGGGGGGNAGGGSSQKTPLFETYSDWDREIKRT-GASGW 239
                +N+                             T +F+T  DW  E++RT G   +
Sbjct: 215 ATAAQNNTVTD----------------------PKNHTVMFDTLKDWCWELERTKGNMKY 252

Query: 240 RVCSINEGYMISTCLPEYIVVPSSLADQDLKIFSHSFVGRRMPLWCWSHSNGSALVRM-A 298
           +  S+NEGY +   LP Y VVP+ L +++++ F     G  +P+WCWS  NGSAL++M A
Sbjct: 253 KAVSVNEGYKVCERLPAYFVVPTPLPEENVQRFQ----GHGIPIWCWSCHNGSALLKMSA 308

Query: 299 LIKD----VLQQRKIDQRICNAITKS--HPQRSDVYKSDLDKTLPNIQEVQAAFVKLKQL 352
           L K+    +LQ   I +   + I K+   P    V   DL     ++QE+Q A+ K KQL
Sbjct: 309 LPKEQDDGILQ---IQKSFLDGIYKTIHRPPYEIVKTEDLSSNFLSLQEIQTAYSKFKQL 365

Query: 353 CV---NEPFEETEEKWLSSLENTRWLEYVRAFLKHSAELVYMLESKHLSVVLQEEEGRDL 409
            +   +  F +T+ KW S LE++ WL+ +R  LK + E+   +E+++++V+L EE   DL
Sbjct: 366 FLIDNSTEFWDTDIKWFSLLESSSWLDIIRRCLKKAIEITECMEAQNMNVLLLEENASDL 425

Query: 410 SCCVASLVQVMLDPYFRTITGFQSLIQKEWVMAGYQFLDRCNHLKRSEKES-PLFLLFLD 468
            C ++SLVQ+M+DP+ RT  GFQSLIQKEWVM G+ FLDRCNHL++++KE  P+FLLFLD
Sbjct: 426 CCLISSLVQLMMDPHCRTRIGFQSLIQKEWVMGGHCFLDRCNHLRQNDKEEVPVFLLFLD 485

Query: 469 ATWQLLEQYPAAFEFSETYLAVLYDSTRISLFGTFLFNSPHQRVKQSTEFAISKNIQLGD 528
             WQL+ Q+P AFEF+ETYL VL DS  I +F TF FNSPHQ+     +  + +  Q
Sbjct: 486 CVWQLVHQHPPAFEFTETYLTVLSDSLYIPIFSTFFFNSPHQK-----DTNMGREGQDTQ 540

Query: 529 EKGLKFPSVWDWSLQFTAKDRTLFHNPFYIGKSTPCIQNGSVKSFK-RTKKSYSSTLRGM 587
            K L   +VWDWS+QF  K +TL  NP Y+ K  P +  G  K  + + ++  S  L
Sbjct: 541 SKPLNLLTVWDWSVQFEPKAQTLLKNPLYVEK--PKLDKGQRKGMRFKHQRQLSLPLTQS 598

Query: 588 PSALKNGIISDQ------ELLPRRNSLILKPKPDPAQQTDSQNSDTEQYFREWFSKPANL 641
            S+ K G   ++       LL +R S ++         +D    +  +++  W SK  +
Sbjct: 599 KSSPKRGFFREETDHLIKNLLGKRISKLI-------NSSDELQDNFREFYDSWHSKSTDY 651
```

FIGURE 2D

```
Query: 642 HGVILPRVSGTHIKLWKLCYFRWVPEAQISLGGSITAFHKLSLLADEVDVLSRMLRQQ 699
           HG++LP + G  IK+W   Y RW+PEAQI  GG +     KL  + +EV  L   + ++
Sbjct: 652 HGLLLPHIEGPEIKVWAQRYLRWIPEAQILGGGQVATLSKLLEMMEEVQSLQEKIDER 709  (SEQ
ID NO:6)


>CRA|66000019403839 /altid=gi|9506679 /def=ref|NP_061934.1|
           hypothetical protein [Homo sapiens] /org=Homo sapiens
           /taxon=9606 /dataset=nraa /length=637
          Length = 637

 Score =  291 bits (738), Expect = 2e-77
 Identities = 194/548 (35%), Positives = 299/548 (54%), Gaps = 55/548 (10%)

Query: 5   KPPKPTFRSYLLPPP-QTDDKINSEPKIKKLEPVLLPGEIVVNEVNFVRKCIATDTSQYD 63
           K PKP+F SY+ P    T++K  +E   K++   LLPGE ++ E + V K +  D+ Q+
Sbjct: 14  KAPKPSFVSYVRPEEIHTNEKEVTE---KEVTLHLLPGEQLLCEASTVLKYVQEDSCQHG 70

Query: 64  LWGKLICSNFKISFITDDPMPLQ--KFHYRNLLLGEHDVPLTCIEQIVTVNDHKRKQKVL 121
           ++G+L+C++FKI+F+ DD    L   +  ++N ++GE+D+ L C++QI  V D K+K  +
Sbjct: 71  VYGRLVCTDFKIAFLGDDESALDNDETQFKNKVIGENDITLHCVDQIYGVFDEKKKT-LF 129

Query: 122 GPNQKLKFNPTELIIYCKDFRIVRFRFDESGPESAKKVCLAIAHYSQ-PTDLQLLFAFEY 180
           G   +LK  P +LII+CKD R+ +F     +  E  K++  I H++Q P  L+ LF F Y
Sbjct: 130 G---QLKKYPEKLIIHCKDLRVFQFCLRYTKEEEVKRIVSGIIHHTQAPKLLKRLFLFSY 186

Query: 181 VGKKYHNSANKINGIPSGDGGGGGGGGNGAGGGSSQKTPLFETYSDWDREIKRT-GASGW 239
              +N+     +P                   T +F+T  DW  E++RT G   +
Sbjct: 187 ATAAQNNTVT----VPKNH------------------TVMFDTLKDWCWELERTKGNMKY 224

Query: 240 RVCSINEGYMISTCLPEYIVVPSSLADQDLKIFSHSFVGRRMPLWCWSHSNGSALVRM-A 298
           +  S+NEGY +   LP Y VVP+ L +++++ F     G  +P+WCWS  NGSAL++M A
Sbjct: 225 KAVSVNEGYKVCERLPAYFVVPTPLPEENVQRFQ----GHGIPIWCWSCHNGSALLKMSA 280

Query: 299 LIKD----VLQQRKIDQRICNAITKS--HPQRSDVYKSDLDKTLPNIQEVQAAFVKLKQL 352
           L K+    +LQ   I +  + I K+    P    V   DL     ++QE+Q A+ K KQL
Sbjct: 281 LPKEQDDGILQ---IQKSFLDGIYKTIHRPPYEIVKTEDLSSNFLSLQEIQTAYSKFKQL 337

Query: 353 CV---NEPFEETEEKWLSSLENTRWLEYVRAFLKHSAELVYMLESKHLSVVLQEEEGRDL 409
              +  F +T+ KW S LE++ WL+ +R LK + E+   +E+++++V+L EE   DL
Sbjct: 338 FLIDNSTEFWDTDIKWFSLLESSSWLDIIRRCLKKAIEITECMEAQNMNVLLLEENASDL 397

Query: 410 SCCVASLVQVMLDPYFRTITGFQSLIQKEWVMAGYQFLDRCNHLKRSEKESPLFLLFLDA 469
            C ++SLVQ+M+DP+ RT  GFQSLIQKEWVM G+ FLDRCNHL++++KE     L L
Sbjct: 398 CCLISSLVQLMMDPHCRTRIGFQSLIQKEWVMGGHCFLDRCNHLRQNDKEEHQRQLSLPL 457

Query: 470 TWQLLEQYPAAFEFSETYLAVLYDSTRISLFGTFLFNSPHQRVKQSTEFAISKNIQLGDE 529
           T          F     +L          RIS     L NS  +        EF  S + +  D
Sbjct: 458 TQSKSSPKRGFFREETDHLIKNLLGKRISK----LINSSDELQDNFREFYDSWHSKSTDY 513

Query: 530 KGLKFPSV 537
            GL  P +
Sbjct: 514 HGLLLPHI 521  (SEQ ID NO:7)


 Score = 66.0 bits (158), Expect = 2e-09
 Identities = 27/80 (33%), Positives = 44/80 (54%)

Query: 620 TDSQNSDTEQYFREWFSKPANLHGVILPRVSGTHIKLWKLCYFRWVPEAQISLGGSITAF 679
           +D     +  +++  W SK  + HG++LP + G  IK+W   Y RW+PEAQI  GG +
Sbjct: 492 SDELQDNFREFYDSWHSKSTDYHGLLLPHIEGPEIKVWAQRYLRWIPEAQILGGGQVATL 551

Query: 680 HKLSLLADEVDVLSRMLRQQ 699
            KL  + +EV  L   + ++
Sbjct: 552 SKLLEMMEEVQSLQEKIDER 571  (SEQ ID NO:8)

>CRA|89000000195580 /altid=gi|7293003 /def=gb|AAF48390.1| (AE003497)
```

FIGURE 2E

```
          CG14411 gene product [Drosophila melanogaster]
          /org=Drosophila melanogaster /taxon=7227 /dataset=nraa
          /length=843
         Length = 843

 Score =  269 bits (680), Expect = 1e-70
 Identities = 202/708 (28%), Positives = 321/708 (44%), Gaps = 127/708 (17%)

Query: 65  WGKLICSNFKISFITDDPM-------PLQKFHYRNLLLGEHDVPLTCIEQIVTVNDHKRK 117
            +G L  +NFK++F+            PL   +  N  LG +++ L  I+ I T+ +  R
Sbjct: 114 FGLLSVTNFKLAFVPLHEKRNQAITAPLIDLYQENTYLGRNEITLNNIDHIYTITELGRA 173

Query: 118 QKVL----------GPNQKLKFNPTE----------LIIYCKDFRIVRFRFDES------ 151
             L           G +++ K  P +           L I CK+FR+++F F +
Sbjct: 174 ASALQAARGMASHAGMSRRKKLEPFKQQNISGRIAALHIVCKNFRLLKFAFQQQDSKMFG 233

Query: 152 GPESAKKVCLAIAHYSQPTDLQLLFAFEYVGKKYHNSANKINGIPSGDGGGGGGGGNGAG 211
             +  K +  A+  ++ P    L FA+ +  + Y+++                   GA
Sbjct: 234 ASDQGKLIASALVRFAYPMRHDLSFAYAH-REPYYSTL-------------------GAS 273

Query: 212 GGSSQKTPLFETYSDWDREIKRTGASGWRVCSINEGYMISTCL-------PEYIVVPSSL 264
            G     T ++ T +DW RE+ R GA+ W+V S     ++   L        P + V+P S
Sbjct: 274 G-----TSMYATKNDWARELIRCGATEWQVVSCASVQLLQNPLQAGKYTVPPHFVIPKSC 328

Query: 265 ADQDLKIFSHSFVGRRMPLWCWSHSNGSALVRMALIKDVLQQRKIDQRICNAITKSHPQR 324
            +        S +F    R    W +S+ + +ALVR+A ++    QQ      + +    + +
Sbjct: 329 SVDRFLDLSRAFCDSRAAFWVYSYGSSAALVRLAELQPAAQQDTKSENVMLELVRKCDAG 388

Query: 325 SDVYKSDLDKTLPNIQEVQAAFVKLKQLCVNEPFEE---TEEKWLSSLENTRWLEYVRAF 381
              +     L     LP+IQ+V   A+ KL++LC   E   E+     ++K+L   LE T WL YV
Sbjct: 389 RQLKLLLQLTDRLPSIQDVLRAYQKLRRLCTPETPEKFMLQDDKYLGLLEKTNWLFYVSLC 448

Query: 382 LKHSAELVYMLESKHLSVVLQEEEGRDLSCCVASLVQVMLDPYFRTITGFQSLIQKEWVM 441
            L++++E     L S  ++ VLQE  GRDL C ++SL Q++LDP+FRTI GFQSL+QKEWV
Sbjct: 449 LRYASEASATLRSG-VTCVLQESNGRDLCCVISSLAQLLLDPHFRTIDGFQSLVQKEWVA 507

Query: 442 AGYQFLDRCNHLKRSE-----------KESPLFLLFLDATWQLLEQYPAAFEFSETYLAV 490
              + F  R  H+  ++               ++SP+FLLFLD  WQLL+Q+P   FEF++TYL
Sbjct: 508 LEHPFQRRLGHVYPAQPAGGNAELFDSEQSPVFLLFLDCVWQLLQQFPDEFEFTQTYLTT 567

Query: 491 LYDSTRISLFGTFLFNSPHQRVKQSTEFAISKNIQLGDEKGLKFPSVWDWSLQFTAKDRT 550
            L+DS   + +F TF F++  QR+K  T           + L     VWDW  QF+ KD+
Sbjct: 568 LWDSCFMPIFDTFQFDTQAQRLKAVT------------DSQLVLRPVWDWGEQFSDKDKM 615

Query: 551 LFHNPFYIGKSTPCIQNGSVKSFKRTKKSYSSTLRGMPSALKNGIISDQELLPRRNSLIL 610
             F NP Y  +           +  + +R+     S    G  S +
Sbjct: 616 FFSNPLYQRQRGDLGAQAAAVAHRRSLAVGSKGAHGAASGV------------------- 656

Query: 611 KPKPDPAQQTDSQNSDTEQYFREWFSKPANLHGVILPRVSGTHIKLWKLCYFRWVPEAQI 670
                      T S+N+   Q F    S P + +  + P       +++W  CY+RW+P   I
Sbjct: 657 ---------TPSRNTINPQLFATASSVPQDRY--LQPAHRIFDLQVWDQCYYRWLPILDI 705

Query: 671 SLGG--SITAFHKLSLLADEVDVLSRMLRQQRSGPLEACYGEL-GQSR 715
            GG    +  +H+   LL    +  + R L   Q     L     Y E  G+SR
Sbjct: 706 RGGGQPQVDLYHR--LLLSNIAKVQRCLDYQNFDDLPDAYYEFAGESR 751  (SEQ ID NO:9)

>CRA|1000682317637 /altid=gi|7705564 /def=ref|NP_057240.1| KIAA1073
          protein [Homo sapiens] /org=Homo sapiens /taxon=9606
          /dataset=nraa /length=643
         Length = 643

 Score =  167 bits (418), Expect = 5e-40
 Identities = 144/521 (27%), Positives = 228/521 (43%), Gaps = 103/521 (19%)

Query: 35  EPVLLPGEIV---VNEVNFVRKCIATDTSQYDLWGKLICSNFKISFITDDPMPLQKFHYR 91
            EP LLPGE +     +V ++  C  T   +   G L  +N+++ F +
Sbjct: 75  EPPLLPGENIKDMAKDVTYI--CPFTGAVR----GTLTVTNYRLYFKSM----------- 117
```

FIGURE 2F

```
Query: 92   NLLLGEHDVPLTCIEQIVTVNDHKRKQKVLGPNQKLKFNPTELIIYCKDFRIVRFRFDES 151
                 E D P       +  +N   R +K+ G + + + N   L   CKD R +RF
Sbjct: 118  -----ERDPPFVLDASLGVIN---RVEKIGGASSRGE-NSYGLETVCKDIRNLRFAHKPE 168

Query: 152  GPESAKKVCLAIAHYSQPTDLQL-LFAFEYVGKKYHNSANKINGIPSGDGGGGGGGGNGA 210
            G  + + +    +  Y+ P    L LFAFEY      N
Sbjct: 169  G-RTRRSIFENLMKYAFPVSNNLPLFAFEYKEVFPEN----------------------- 204

Query: 211  GGGSSQKTPLFETYSDWDREIKRTGA--SGWRVCSINEGYMISTCLPEYIVVPSSLADQD 268
              G     PL E        +R G     WR+  INE Y +     P  +VVP+++ D++
Sbjct: 205  --GWKLYDPLLE--------YRRQGIPNESWRITKINERYELCDTYPALLVVPANIPDEE 254

Query: 269  LKIFSHSFVGRRMPLWCWSHSNGSALV---RMALIKDVLQQRKIDQRICNAITKSHPQRS 325
            LK   +        R+P+  W H    A +        ++     ++ K D++     AI  S+ Q
Sbjct: 255  LKRVASFRSRGRIPVLSWIHPESQATITRCSQPMVGVSGKRSKEDEKYLQAIMDSNAQSH 314

Query: 326  DVYKSDLDKT----------------------------LPNIQEVQAAFVKLKQLCVNEP 357
             ++  D    +                            + NI  ++ +  KLK++ V
Sbjct: 315  KIFIFDARPSVNAVANKAKGGGYESEDAYQNAELVFLDIHNIHVMRESLRKLKEI-VYPN 373

Query: 358  FEETEEKWLSSLENTRWLEYVRAFLKHSAELVYMLESKHLSVVLQEEEGRDLSCCVASLV 417
             EET   WLS+LE+T WLE+++  L  +  +    +ES    SVV+    +G D +  + SL
Sbjct: 374  IEETH--WLSNLESTHWLEHIKLILAGALRIADKVESGKTSVVVHCSDGWDRTAQLTSLA 431

Query: 418  QVMLDPYFRTITGFQSLIQKEWVMAGYQFLDRCNHLKRSEKE---SPLFLLFLDATWQLL 474
             +MLD Y+RTI GF+ L++KEW+  G++F   R   H   ++  +     SP+FL  F+D   WQ+
Sbjct: 432  MLMLDGYYRTIRGFEVLVEKEWLSFGHRFQLRVGHGDKNHADADRSPVFLQFIDCVWQMT 491

Query: 475  EQYPAAFEFSETYLAVLYDSTRISLFGTFLFNSPHQRVKQS 515
             Q+P AFEF+E +L  + D       LFGTFL NS  QR K++
Sbjct: 492  RQFPTAFEFNEYFLITILDHLYSCLFGTFLCNSEQQRGKEN 532  (SEQ ID NO:10)
```

```
>CRA|108000024650128 /altid=gi|12735904 /def=ref|XP_011954.1|
          similar to myotubularin related protein 2 (H. sapiens)
          [Homo sapiens] /org=Homo sapiens /taxon=9606
          /dataset=nraa /length=619
         Length = 619

 Score =  167 bits (418), Expect = 5e-40
 Identities = 144/521 (27%), Positives = 228/521 (43%), Gaps = 103/521 (19%)

Query: 35   EPVLLPGEIV---VNEVNFVRKCIATDTSQYDLWGKLICSNFKISFITDDPMPLQKFHYR 91
            EP LLPGE +     +V ++  C  T   +    G L  +N+++ F +
Sbjct: 51   EPPLLPGENIKDMAKDVTYI--CPFTGAVR----GTLTVTNYRLYFKSM----------- 93

Query: 92   NLLLGEHDVPLTCIEQIVTVNDHKRKQKVLGPNQKLKFNPTELIIYCKDFRIVRFRFDES 151
                 E D P       +  +N   R +K+ G + + + N   L   CKD R +RF
Sbjct: 94   -----ERDPPFVLDASLGVIN---RVEKIGGASSRGE-NSYGLETVCKDIRNLRFAHKPE 144

Query: 152  GPESAKKVCLAIAHYSQPTDLQL-LFAFEYVGKKYHNSANKINGIPSGDGGGGGGGGNGA 210
            G  + + +    +  Y+ P    L LFAFEY      N
Sbjct: 145  G-RTRRSIFENLMKYAFPVSNNLPLFAFEYKEVFPEN----------------------- 180

Query: 211  GGGSSQKTPLFETYSDWDREIKRTGA--SGWRVCSINEGYMISTCLPEYIVVPSSLADQD 268
              G     PL E        +R G     WR+  INE Y +     P  +VVP+++ D++
Sbjct: 181  --GWKLYDPLLE--------YRRQGIPNESWRITKINERYELCDTYPALLVVPANIPDEE 230

Query: 269  LKIFSHSFVGRRMPLWCWSHSNGSALV---RMALIKDVLQQRKIDQRICNAITKSHPQRS 325
            LK   +        R+P+  W H    A +        ++     ++ K D++     AI  S+ Q
Sbjct: 231  LKRVASFRSRGRIPVLSWIHPESQATITRCSQPMVGVSGKRSKEDEKYLQAIMDSNAQSH 290

Query: 326  DVYKSDLDKT----------------------------LPNIQEVQAAFVKLKQLCVNEP 357
             ++  D    +                            + NI  ++ +  KLK++ V
Sbjct: 291  KIFIFDARPSVNAVANKAKGGGYESEDAYQNAELVFLDIHNIHVMRESLRKLKEI-VYPN 349

Query: 358  FEETEEKWLSSLENTRWLEYVRAFLKHSAELVYMLESKHLSVVLQEEEGRDLSCCVASLV 417
```

FIGURE 2G

```
             EET   WLS+LE+T WLE+++  L  +  +   +ES   SVV+   +G D +  + SL
Sbjct: 350 IEETH--WLSNLESTHWLEHIKLILAGALRIADKVESGKTSVVVHCSDGWDRTAQLTSLA 407

Query: 418 QVMLDPYFRTITGFQSLIQKEWVMAGYQFLDRCNHLKRSEKE---SPLFLLFLDATWQLL 474
             +MLD Y+RTI GF+ L++KEW+  G++F  R  H  ++  +   SP+FL F+D  WQ+
Sbjct: 408 MLMLDGYYRTIRGFEVLVEKEWLSFGHRFQLRVGHGDKNHADADRSPVFLQFIDCVWQMT 467

Query: 475 EQYPAAFEFSETYLAVLYDSTRISLFGTFLFNSPHQRVKQS 515
             Q+P AFEF+E +L  + D     LFGTFL NS  QR K++
Sbjct: 468 RQFPTAFEFNEYFLITILDHLYSCLFGTFLCNSEQQRGKEN 508  (SEQ ID NO:11)
```

FIGURE 2H

```
   1 AAAAACAGAA AAATGGGTGA AGCAGGACAA AACAGTGACA TTAGAGCCAA
  51 AAGCAGGGGG TAGGCAATAA CACCAAACAT ACAGCGTAGT CAAGGGCATC
 101 AGGGTCTGAG AAGAGGTTAT AAAACTAGTT CTACGGACTG AATTGTGTTC
 151 CTCCAAAATG CTAATGTTGA AACCCTAACC CCTGGTATGG CTACATTTGG
 201 AGATTTTAGG AGGTAATTAA AGTTAAATAA GGTAGTAAGA GTGGGGCTCT
 251 AATCTGATAG GATTAGCGTC CTTACAAGAA GAGACATCAA GAGATCCCAG
 301 AGAGCATGTT ATATACCCTC CCCGCACTGT GTGAGGACAT GGTGAGATGG
 351 CAGCCATCTG CAAATCCGGC AGAGAGCCCT CACCTGTCTG CCTGCCACAA
 401 GTTAGGCAGA TCCCTACCTT GCCAACACCT GGATCTTGGA CTTCCTATAC
 451 TCCAGAATTG TGAGAAATTA ATGTCTGCTC TTTAAGCCAT CAACCTGTGG
 501 TATTTTGTTA TGGCAGCCTG AGCAGACTAA TACAACCAGA TATTTGGGAA
 551 ATGCCATAAA ATTTAGTGTT AAGACAATAA TAAATGCTGG AAATAGAGTT
 601 TTTCCACTTT TCAGTTGTAT GGTCACATAT TAGAATTGCA GATCCTAAGA
 651 AAACCTGTAC AGAAAAACCC AAATCACAGA GTCATTTAAG TGTAAAGAAA
 701 AAGCCAATTA TTGCTTAAAG AGTATTTGTA GAAAATATCC GTTGAATATA
 751 GAGGAATAAC AGCATATTCA TAAAAATTTT TTAAAAAGTG TGCACGACAG
 801 TGATTTTAAC ACTTCTAATC CAATGGAACT AACATTTTAA AGTACAATTA
 851 TGGCCAGGCA CGGTGCCTCA TGCCCATAGT CCCGGCTACT TGAGAGGCTA
 901 AGGCACGTGG ATCACTTGAG CCCAGGAGGT GGAGGCAGCA GTGAGCCCTG
 951 ATCATGCCAC TGCACTTCAG CCCAGGTGAT GGTGTGAGAC CCTGACTCTA
1001 AAAAATACAA TTATGGTTAC GGTTCTTGGG CAGAGTGGAA TTCAAACAGG
1051 TTAACCTGAA AGATCAGTAG GGTTCTAAAT CCAGGATAAA TTATTTTCAG
1101 AAAAAGAATA ACTTTTTGAA TCTTTATTTA AATTGTTAAA TGTTCCTGTG
1151 AGTAACACTC ATCAGCGTGA TTGTGACTGG TATGGCTGCA TGGAAGCTTC
1201 CCTGTGGCAT TAATCATAAA ATGCTGGATT GGGGTTTGAT TCTTCAAGGT
1251 ATAAGAAGGA CCTAGTCTCA AGTAATAGAT TCACCAAAAT GTAACACCAC
1301 TAGCCCCCTC CCACCAAAAT CTGCTCCAGT CAGAATTACC GTAAGAGCTC
1351 AGAAGTGACC TGTGCTTGGC GGCACCGGCC CACTTTCCCA GTGCCGGTTC
1401 CTCGCATCCT GGGCGCAGAC GGGGTGACCG CCTGACCCCT GGACCCGAGT
1451 CACCTTTCCC TGCCCTGAGC TCCTCCTTGA GAGCTTCAAA ACAATGCTCG
1501 CCCAGGCCGG AGGGCGAAGT CGGCCCATGT GTAAGTCAAG GGAACTGTCC
1551 CAGGACTGCA GCCCGGCCAG AAGACGCCCC GCGCCGCCGT CCCAGGCAGC
1601 CACCGCTGCC GCCATGGCCC CCGCAGGCCG CCGTAGGCCC CCGCGGGCCG
1651 CCTGACCCCT GCGGGCCGCC GTAGAAGGAC CCTCCAGAGG CCGCGCTCTT
1701 GAGATGGCCG TCGGGCTCCG CTCCCCGCGG GGCCCCGGCT GAGGGCCCGC
1751 CAGCGGGCAC CTGGCGCCAC CGCTGCGTTC CGGCACTAGC ACGGGACACG
1801 GTCAGGGAGC GGCGGGCCGC GGCCTTGCGC GCGCCGTCTC TCGGGGCGGG
1851 GCACCGGGCC CCTTCCGGGG ATGGGCCCCG GCGCCCGCGT CGGCCTGGCT
1901 GTGCCCGGCC CCTCCCCGCT CGGGCGGGCG CTGCGCCGTA TCCCCGCCCG
1951 TCAGTCCGCC CGGCTCGGCT GGCCGCAGAA AGGGCCTGGG CGGCCGCACT
2001 GAGAGCTTTA CGCCCGGAGG CGTCGGCGCT GCCACTGGCC CGCGACGGGA
2051 ACGGGGCGAA AAGGCGGCGG CACCATGTTC TCCCTCAAGC CGCCCAAACC
2101 CACCTTCAGG TCCTACCTCC TGCCACCGCC CCAGGTAAAC AACCCCTCCC
2151 CGCGAGCGCC CGACTCTCCT CTGCGCTTCC GTGGAGCCTC CAGGCCGACC
2201 CCCGGGAACT GGAGGACCCC AGGAGGCTGC GCGCGTCTCC CTGCCCACAG
2251 CAGCGCGGCT GCCTGATTCC CGGCGCCGCG AAATGCGCCT TCTCGGGAGC
2301 CCCCACTGGC TCGGCGAAAA CTTGTAAAAC TCTTCTGCAG CCATTCTCTG
2351 CCCGAAGTTC TGTCGTCCGT AGTTTTGCGG AGTGTTGAGG CCCAGGGGAG
2401 CCTTGGGAGC TGGGGTTTTC TTTAGTTTCC AACCCATCGA CCCTCCCTCC
2451 TATGACCGCC AGCATGATTG CAGCGCTTGG GGTCACTGGT CGAGGCGGTT
2501 ACCCGTCTGT CATAAATGTG AACACCTGGA AGCGACACTG GCAGTTTAAA
2551 CATTTTTTAT TATTAGGCTT CCAAGTCGAT AATGAGCAGA TCTTAAAAAC
2601 AGCTCAGTTA ATATGCGAAA GAATTTAAAT GGGGGGCTGT GTGTCTTTCG
2651 CATGTGTCAT CACTTAGAAA ACAACATTTG CTGTAGCATT TTACGGAGGG
2701 TGGGGGGATT GAGATTTTGA TTTATTTTGC TAATGTATTT CAGACTGACG
2751 ATAAGATCAA TTCGGAACCG AAGATTAAAA AACTGGAGCC AGTCCTTTTG
2801 CCAGGTAAAC ATTAGTTAGG ATTCTAACAG ATACTTTAGC AACGTATTTT
2851 GGTTTAAGAT TATTCTGCCG ACTAGTATCA TGTGGTTAAC TTCCCTTCTC
2901 TCATTAAACT TTCTCCAGTT AAAAGTCTAG TGACTGAGAG GAGAAAAAGG
2951 AACTGTCAAG AATGTCATTA CCTCATTTCC TTTTTTGTCT CCCGAATTTC
3001 TTTTTGAAAA GATGTATATG TTTAATTGCT TGGGTAGTAA AAGTACTCTT
3051 TGCTGACGTG TTTGCCACTT ATTGCATTAA TGATTAATCA TTTTAATGCA
3101 TTTTGATAGT ATAAAAAGAC GCCTTTATTA TGTGTGTGTC TCTATACCAA
3151 TAACAGAGCT TAGTGAACTT TGAATTACTT GCTTGGCAAT TGTTTTTTGA
3201 AGTTGTCAGC TGTATTTGCA AATTTGCTTG TTTCAGTTTA GAACCAGGCT
3251 TTTCCCAGCA GAGACACTTA ATTGACATTT GGGGCCAGAT AATTCATAGT
3301 TGGACGGGCA GGCTGTCCTG TGTATAGCAA CAAAGATGGC CTCCACCCAC
3351 TAGATGCCAG TAGTAGTACC CTTATCCCCC ACCACCTAGT TGCGACCTAG
```

FIGURE 3A

```
3401 TTGCCACACC AAAATGCCAC CAGTCATTGC CAATTTTTTT TTGTCCCCTA
3451 CCTCTGGGGG ACAAAAATCT CACAGTTGAG AATCACTGCT TTAGAACAAA
3501 ATTTGCTATA GGTGACCTTA GAGATGGAAG TAGGGATTGG TGGTAGAAAG
3551 GGGTTTGTTT TAGAGCATAC AGAATATTGG TATGGTATTT TGAATTGTAT
3601 AACAATTGTA TAATAATTAG GAAAAGTCAG TTGTTTAATG CGATTATTAG
3651 GGGAAGTAGC CAGATACTTA GGAAAGCCTG TTTTAAACCT GAAATCGGCC
3701 GGGCACGGTG GCTCATGCCT GTAATCCCAG CACTTTGGGA GGCCGAGGCG
3751 GGTGGATCAC GTGGTCAAGA GACCGAGACC ATCCTGGCTA ACACGGTGAA
3801 ACCCCGTCTC TACTAAAAAT ACAAAAAAAA TTAGCCAGGC ATGGTGGCGG
3851 GCGCCTGTAG TCCCAGCTAC TCGGGAGGCT GAGGCAGGAG AATGGCATGA
3901 ACTCGGGAGG CGGAGCTTGC AGTGAGCCGA GATCCTGCCA CTGCAGTCCA
3951 GCCTGGGCGG CAGAGTGAGA CACCGTCTCA AAAAAAAAAA AAAACCTGAA
4001 ATCAAATACT AGTTTGTGTG GCTACTATCA GCATTGTAAA ATCTGACTCA
4051 TTACTTAAAG CCAAATCGGT AAAATAATTA GAATTTTGTA GGTAAAAATT
4101 GAACAAATGT GGAAACTTTA AAATTTTAAA TATTATATAG GGACAAAATA
4151 TTAAAAACAC CAAACTTTGG TTCCATATGA AAGTTTAAAA AGTGTTTTTT
4201 AAACTTTACT ATGGGAGTCA TAAATATTTT CCCTTGATTT TGTTAGTGCT
4251 TTTCACTCAA CAGTGTGTAC TAATTAATCA TTTGTACTTT TCCTCAGAGT
4301 GAACAGTAGA ATTACTAAGT AACCCTTGCT CCCTGTGTGC TCTGTTTTAG
4351 TCTTAGTCAC TCTGAGCATT TAAAATGCAG GGACGAGGAA ACAGTACTCA
4401 TCTTGAATGA GTGCCTATGA GCTATTGAAC TTTGACTTCG TTTACTCTGA
4451 ACAGGCCTGG TTCTTAGGCT TTGATTCCTC CACTCTGCAT ACTATGATTT
4501 CACACTCAGA AACAACATGG TCTTAGCTGT AAATGTCAGT GCTTGCTTTT
4551 TAATTTTTTA AAATTTTTTT TAAATTTTTT TTTTTTTTTT TTTGAGACAG
4601 AGTCTCACTC TTACTTGGGC TGGAGTGCAG TGGCGTGATC TCGGCTCACT
4651 GCAACCTCTG CCTCCCAGGT TCAAGCGATT CTCCTGCCTC TGTCTCCCAA
4701 GTAGCTGGGA TTACAGGAGC CCACCACCAC ACCTGGCTAA TTTTTCGTAT
4751 TTTTAGTAGA AATGGGGTTT CTCCATGTTG GCCAGGCTGG TCTTGAACTC
4801 CTGCCCTCAG GTGATCCGCC CGCCTTGGCC TCCCAAAGTG CTGGGATTAC
4851 AGGCGTGAGC CACTGGCGCC TGGCCACTTT TTTAAAATTA GCTTTTAAAT
4901 TTAAGATATG TGCTAAGAAA AGGTGTTACT AAGTATGCAT AAACTTGAAG
4951 AACTTTCTCA CTGAGGGTTA TCAATTCTAT AAAATGGCTA AAAGTCAGAG
5001 TTTTCTGGGG AAGTTGTAAA CCAAGTTTCT GACTGTGCTT TTCTTGTCCC
5051 AGAAATGGCA GCTAAATTCC GTATTATTTT TAGAGAAATT CTAAAAGAGC
5101 TGTAACACTA AGTCTGAACC TTTTAGTTGC CCATTAAGGA ATTCTCTGAC
5151 CTGTGTTAAT TTTTATTGCA TTGGCGGCCA AATCATAGCT GAAATCTGTA
5201 CATGCATACA TGACGGCTCT ATCACCCAGC ATTCTGTTTG TACCTGACTT
5251 ATCCTTACCC AACATTTAGC CGGTCCTGAA TTAGGATGTC TTTTGCCCCC
5301 TTCCTCTCCC CTTCTGTTCT TACCCTCTCA TTCTGGCCTT CCTGCACCCA
5351 TCCTGGCTGT GTTCTGTCTG GCTGCCCTGT TGTGGTCTCT GTTTCCTGCT
5401 TTACCTCGCC TGTCACATCT CTCACTGCTA CCATTTGCTC TTTGTTGGCC
5451 TGTAGCCTAC TGCTCTACCC ATGAAATCTG GAAGACAAGT GGAAAGTTAC
5501 CGAACTATTG GTGATCTAAA GACCTAGACT AGGCTAGAGC TTTTACTAAG
5551 AGGGAGTGAA TAATATAGTT CTTGCCTTTG TGACTATCAG AATCAATAGA
5601 AAACCTGGCC ACATCACNNN NNNNNNNNNN NNNNNNNNNN NNNNNNNNNN
5651 NNNNNNNNNN NNNNNNNNNN NNNNNNNNNN NNNNNNNNNN NNNNNNNNNN
5701 NNNNNNNNNN NNNNNNNNNN NNNNNNNNNN NNNNNNNNNN NNNNNNNNNN
5751 NNNNNNNNNN NNNNNNNNNN NNNNNNNNNN NNNNNNNNNN NNNNNNNNNN
5801 NNNNNNNNNN NNNNNNNNNN NNNNNNNNNN NNNNNNNNNN NNNNNNNNNN
5851 NNNTGTTGGG GGTGGGGGAT GAGGGAAGGG AGAGCATTAG GACAAATACC
5901 TAATGCGTGC GGGGCTTGAA ATTCCCGGCG TCATCCCTAA AGACGGGGTT
5951 GATGGGTGCA GCAAACCAGC ATGGCACGTA TATACCTATG TAACAAACCT
6001 GCACATTCTG CACATGTATC CCAGAACTTA AAAAAAAAAA TAAAAAAAGA
6051 ATTAATTGTT AGAGATATGG TATTGCATGC TTTGCTTTGG CATAATGCCT
6101 TGGGTCCAAG GGTATCCTAC TTCAGTTGCC CAAAGTTTGA ACTTCTAATT
6151 CAATAAGCAG ATGAAAATTA GAACACAAAA TGAGTTGTTT ATTTGTGTGC
6201 TGTCACCATG TGCACTGTTG GAACTTAAGC CTAATTTCAA AATGATCCTC
6251 ATCTTTTATT AAGTAAAGAA AACAGAAGAA AATGACTAGT AATTTAATTT
6301 AGATTGTGGT TTATGTTAGT AATTTTCAGC TTTCCTGATA CATGAAACTC
6351 TGAGATGGGT ATTGTGCCTA CTTCAACTTT GTGGTCTTGA TGTCTCACAA
6401 AGTGCCAGGA ATGTGGTAGA CACTGAGATG TTTACTGAGG GACTGAACGA
6451 AAGGACCTCT CAGACCACCT GGCTTAAACT GTTACCTTAC CCAGGCACAC
6501 ACACAGACTA ACTTTCAGAT TTAGGAGTAA AGGGAAGACT GTGTTATTTT
6551 ATGCCAGACA TTTCAAGAGA TTTATGTCGG AGCCTGGAAT TGAAATAGAG
6601 TACTCTGTCA AAGTAGTCAG CTTTTGTGTA GGCTTTCTCT TTATCTTCCT
6651 CTCATTATGT GAATTTCATT CTTTCAGTGA TTATATTGTA TATGTGTAAA
6701 ATCACTCCAA TACTTGAAAA CTGAGTTTGA CTTTTAAAGT GTGTGTGTGT
6751 ATATATGTTT GTGTTCCAGT ATATATTTGT TAAGAGCATG TAATGCCAGA
```

FIGURE 3B

```
6801 CTCTGTCCTG TTTAGCTGCT GGACTGGTGG ATCGGTTCGG TGAGGATGTG
6851 AGTATCTCCT GGGTGCCAGG TCTGTCCTGG ATAGCGAGAA TGCTGGAGGT
6901 GTCATGTGCC TGTATCGCAG AAAGGCGTGG GGTGAGCCCT AAGCTGCCTG
6951 TTGACAAGGT AGAAGACTGT GACCTGGATC ACTGGTACCC AGATTCCAGC
7001 CAGGGCCTGG TATCAGATTT GGATGAAGTT TTTACCAGCC CTTGGTCAAA
7051 GTGAGAAAAT TAAGAAAAGT GCAGTTTTCT TTAATAAAGA TAAATTTATT
7101 TGATTTAAAA GATTGTCTTT TATTCTGAGA TTATGTTCTT CTAACTTACT
7151 TGGAATAGAT ACTTTTTTTG TTAAATGTTG GTGATAATAG CTGTAGCTTT
7201 AAAAAAGTTT TTAAGTTAAC AAAATTAAAA AGTTAAAAAC TCTTTATTGG
7251 TCCTTTAAAT TAGTTTTGCA CTATACCTGG TTTGGAATCT AAACTAGAAC
7301 CTACTAGATG AGATTATTAT AATACTATAG ATACAATTTT GTGAGCACTC
7351 ACACAGAGAA CATTAATTAT TTTGTCTGCC TAGGAGTACT GCCATTTTTT
7401 TGTTTGTGTT TTGAGACAGG GTCTCGCTCT GTCACCCAGT TTGGACTGTA
7451 GTGGTGTGAT CACGGCTTAC TGCAGCTTCA ACCTCCTGGG CTCGAGTGAT
7501 CCTCACAGCT CAGCCTCCCA AGTAGCTAGG ACTACAGACG TGCGCCACCA
7551 CACCTGGCTA ATTTTTGTAT TTTTTGTGGA GATGGGGTCC AACTATATTG
7601 CCCAGGCTGG TTTCGAACTC CTGGGCTCAA GCAATTGGCT CACCTTGGCC
7651 TCCCAAAGTG TTGGGATTAT AGCCGTGAGC CACCACACCC AGCCCCCTTC
7701 CACCATCCTC TGAAAAATGC ATCCTCCCTC TTTTGACAAA TTATCCTTTC
7751 CTGACTAACT CCACCCAACC TTGGGTTCCA GTGTGGCCAG CAAGGTTAAT
7801 AACCCACCCT GGACTGCAAG CATGAACACA GGTCTGCCTC TGGATGTTGT
7851 TAGGTTGGTA CTAAGGGAAG AGGTCCTCTT TGGTAATGCT GCAAGTGGCC
7901 ACAGTTCCAG AAGAATCTGT TGAAAAGAGT GAAGAACCCC AAGGAAGTGC
7951 ACTAATGTGT GTTGAAGTCC CTGGGTTTCA TTGTCCTTGC AGGCCAGGTG
8001 ACACAAAAGC CTTGTATTCT TCTTTTTGCT AAGCTATTAC CAGGCATGTT
8051 TCTGAACATA CTTTGAACGA GGATCCTTAA CTAATATAGC TTGCAGATTA
8101 ATCATCATAA CAGTCTTGTC AGCTAGGATA CCAGTTTATC TCCATTTGAC
8151 AGATGTGAAA ACTATAGTTT GCTGAGGTTA AGTAACTTGC CCAGTGTCAC
8201 ACAGCTAGCA AGGCAGAGCC AGAGTTCTCT GTCCAGCTCC CAGGCTGTGC
8251 CACTAACTGC TAAGTAGCAC GGCCCACCTG GCTGCACTGG TGACACTAGG
8301 GTACAGATTT ATGCTTTGGA ACTGTTGGGG AGTAGATTGG ATGTCAGCCT
8351 AGAGGGAGTT CTCTAGTGAA GTAAAAAGAG CTCTGTCCTT GTCTTTGCCC
8401 TTTTCACAAC AGTGACAGAT TTTGACCCAG CGTGCAGAAG AACTTTCAGA
8451 GAATTTCAGC TGCCAGAAAA TGGAATGTCT TAGGGAGGTA GTGGACTTCC
8501 TGTTGCTGGC TGTGCCGAAG CACAGTCTGG TGAAATGCCA GCAGCTTTGT
8551 ATTGAGGATG TAAGATTTGC AGTGAGTGGG GCTTGATGGC CTTTGCTCTC
8601 TTCTCACCCC AGGGCATGCT CTTTTTTAAG GGAGAAGAGT TGAAATGCCA
8651 AGACTAACGA TAATGAATTT GTTCTGCAGG TATTGAGTGT GTGCTTGATG
8701 CAGTTTGGCA GAAGGGTAAA ATGCTGAGGA GATGGGATCC TGTTCTTAGA
8751 CAGTTTCAGT TCACTGGAGA GATGCTTCAG TAGAGGAGAG AAAAAGTAGT
8801 AAGAGCTCAG AGGAAGGTCA CCTAAGCCAG ATTTGGAGTA GGGCAGGGGT
8851 GTCAAGAAAG ATCTCTGGAA ACAAATGCTT GTGCTCTGAA TCTTGAGTGC
8901 CCGTTGAGCC TGGGCCCCTG TGCTGAGGCT GTGCGTCAGC TCAGTTCTTT
8951 CCCCTGTTCG CATCTACAGT GCTCACAGCA CTTTCATTCT TGAGATTAAC
9001 TATTAGATAA TGAATGCAGT GATTGTCAGA GTCTTTTGTA ATCGGATCAG
9051 AAAAGCATAC AACCATGGGC CATCTGGGAA ATGAAAATAG CCATTGTTGT
9101 ATAGATGTCT TGTTTATTTT TTACAAGCTC ACTGGCCCGT ACTGTTCTTG
9151 TTTTCTGTCT CACCATACGT CTTATTTCCT CAGTTGGGTT GTTAATTCCT
9201 TAAAGGCAAA GACTTTATCT TTCAAGTGTT TTATGTAATT CCTTTTTGTA
9251 GGTAGGCTTC ATAAATGATT GTAGACTGAT TTTTGTAGTA TTTTAATTTG
9301 TGAATGCATT GTTTTTGAAA GACCAAAGGA CTTGTAACAC ACCCTCAGAA
9351 CAGTGAACAG TGTAACTGTA CTATCTTAGC ATTAGCTTTA TACCTTACCC
9401 GTAGAGCCTT AGGAATGTTT GGAGCTGTCC ATTCCTTAGG CTTTTGCTGC
9451 AGTACCTTAG GCCAGCATTT TCTTACCCCT CCAAACTACT CACTATCGTT
9501 GTCAACACCG TTCATGAACC TCCATAAATA AAATCCTACT TAAGCAGGAT
9551 AAAATCCAAA TTCTTTAACC TTGTAATTTG CTAACACTGT ACCTCACTGA
9601 CTTCATTTCT CAGTATTTCC CAATATTGAT ATTTGCTTCA ATCATGCCGC
9651 TTCCTTGGTC TCTTCCAGAT GCCTTATTCC TTATTTAGGA CCTTGTTACT
9701 GTTATTATCA CACATTCTCT ACTATCTCAA TGCTCTTCTT CCTTCAAGAT
9751 TTCATTCTAC AATTTTTCCT GAGATCGGCA CTATACCCTT CCTCCTGCCC
9801 CATCCTATCC TGAGTGCTAC TCACTGGACT TGGTACTTGC TTTTTTACAT
9851 TGTGTGTTAG TACCAGCATT AAAGATTTGT GTTTATCTTC CACATAGTTT
9901 CAATTTCCTG TGATAACTTT TGAGCCACTT TAATTCCTGA ATTTACCTAA
9951 AGCTAGGGTG ACCAGCTTGT CCCAGTTTGC TTGAGACTGT CCTGGTTTTA
10001 GTGCTAAAAA TACCACATCC CAGGGAAACC CCTCTGTCCC AGACAAACTG
10051 GGGCAGTCAC CCTACTGTTA AAAGCCCAAG TTAAGTTATG CTTTTGGCCT
10101 CTACACATCC CACAGGTTAA TTAGCCACGT GTGCCGTGAG ACTTTGCCTT
10151 AAACTGTGTT CCAACCTAAA ATGTATGGGA AACATTATTT CTGTCCATCA
```

FIGURE 3C

10201 AACGTGATGA ATTTCTAAAT GTATAAGGTG TTAGGAAAGA TAATACAACA
10251 TGGTTTTGAG GTCCTCAGGG AGTTAAAAAC TTTCCTAGCC ATATCATTTG
10301 GAGGTTTATT AACTGTAATT GCATTTCCCT TCTTATTTAT ATTTACAGAT
10351 GAAAGGGTCT TGAGAAAATA AACTTGGATT TCTTGATTTC TTCCCAGGTG
10401 TTAGTAGAAA CCTTTGGCTC ATCATCCTCT AATTTAGAAG GTTTTTGCTT
10451 ACCGCACACT GAAGCTAATT TCCTGCTTTT TCTGGCTTCA TGAGGCTTCC
10501 TTGTGGCATC CTGGGAAGTG CTTGGTGCTG TAAATGGTCC CACCGTGGCT
10551 GATGGCATAG CACAGAGCTG GGAGAGAGGA GTCTGGTGGG TTCTCACAAG
10601 CAGGCCAGCC AGCCGTCTCT AGCACACCAC CCTTTTACTG CATAAAAAGC
10651 ACAGGCGTAT AGTCTCCCTG AAAACTTCAG ATCCTCTAGA GCTTTGAAGC
10701 TTTTATTCGG AGTTTTCTCT TCAAGGTCAC TTAATTTAAC ATGTGAACAA
10751 GAGCAGTCTC AGTACCTTCT TTTTATATAT CCTATCTGGG AAGAGGCCAC
10801 TTTGTGTCTT CTTTTTCTTC CCTGTGTATA AGCTAGTTTT CTGGCCCACA
10851 GTGTTTCAGT GCATGGCAGG AGCTTATGAC AGCTCCTCTT CAGCATTCCT
10901 TTTTTTTAAA ATTATGAACA AATGACTTAC GTGAGCAGAC AGCTGTGCTA
10951 CATGATCCAA ATATTTTAAA GACTGGTTCT GCATGAACAA AATTTAGCAT
11001 TATCAAATAA AACTCATGTC ACTAACTCGA CACTTAATTA TTGTAATAGG
11051 AAGACCCAAT TGTAGCATAT CCTCAGAAGT GCCCTTCTTT TCTTTCTTCT
11101 TCCCCTGTAT CCCTCTGTAC TTCTGTTCTT TGCTCTCTTC CAAGGGCTCA
11151 TTTCCATTCT GTAAGAAAAG GCTGTGTGGC GCTTAAAAGA CCCTGGCCCA
11201 GAGAGTCCTT CTTTCACTTT TTTTTTCTTT TTTCTTTTTT TTGGCTGTTG
11251 TTAATGTTGT GTCTCTTGTT TATTTTCTTC TTTAGTAGTT TTATTTTGGA
11301 ATGAATTTGA ATTTGTAAGA GTTGTACAAA AGAGGATAGA GTTAATGTGA
11351 ACTCTTCAGC CAGCTTCCGC TAATGTTAAT AGCTTATGTA ACCTTGGTGA
11401 ATTTAGCTCA ACTGAGAAAC CAACAATACT ATTAGCTAAA CTGCAGGTTT
11451 TATTCGTATT TCCCTAGTTT TTCCACAAAT GTTCTTTACC TGTTTCAGGT
11501 TCACATCCAG GATACTACAT AGCATTTAGT TGTCGTGTCT CCTTATTCTC
11551 AATGTCTCAG TCTGTGACAG CTTTTTCATC TCATCTTTCA AGACCTTGAC
11601 GTGTTTTTTT CTATTGAATT TGATTTTCTT TTTTTTCTTT TTCTTTTCTT
11651 TTTTTTTTTG AGATGGAGTC TTGTTCTGTC ACCCAGGCTG GAGTGCAGTG
11701 GCGTGATCTC CGCTCACCGC AACCTCCAGC TCCCGAGTTT GAGCGATTCT
11751 CCTGCCTCAG CCTGTTGAGT AGCTGGGAGT ACAGGTGCGC ACCACCAGGC
11801 CCAGCTAATT TTTTGTGTTT TTAGTAGAGA CGGGGTTTTA CCATGTTGGC
11851 CAGGCTGGTT TCGAACTCCT GACCTCAAGT GATCTGCCTG CCTCAGCCTC
11901 CCAAAGTGCT AAGATTACAG GCATGAGAAT GAGATTTTTA TTTTGCCTCA
11951 AATAATACAT ATTAAAGCTC TTTAAACATA GAAATATACT ACTACAAAAG
12001 GAAAAATTTT ATAATTACTA GATTTCTGTT CTAACAAACC ACCCCCTAGA
12051 AACGTCATCA AATTGACTTA AAAATGTAGA CGTAATTTCA GACTTAGAGA
12101 AAAGTTGCAA ATAACAGAAG AATCTGTGGA TACCCTTTCC TTAGATTCCC
12151 CAATAAAACC TTGACGCTTT GGAAGATTAT TATTCAGGTA GTGTCTTGTA
12201 GTATGCCTCT TGGTTTGGAT TTGTCCGATG TTTTCTTTTG ATTAAGCAGA
12251 GGTTATGGAT TTTGGGAAAG ACCCACAGAG GTGGTATCCT TTGCCCTTGT
12301 GTCATGTGAG CAGGCACAAG ACATCAACAT GATTGGTTAT TGGTGAGGTT
12351 AACCTCGATC ACTTCAGGTT AAAGTGATAT CTGTCAGGTT TCTCCTCTAG
12401 AAAGTGACTG TTTTTCCTTT TCTGTACTGT TTGTTAGAAA CAAATCACTA
12451 AGTGCAGCCC ACATTCAAGG GATTGGGAAT TAAGCTCCAC TTCCTGGAGA
12501 GAGGAGAATC ACGAATTTAT GGGCATACCT TAAAACTACC ACAGTAATTA
12551 GTCAATACTT TTGGGAAGAT AGCTTTGTGC TTATACAAAT AACCTGTTTC
12601 TCCTTAAAGT TTGGCTCTCT GAATTTAGCA TTCATCAATG CATGTTGCAC
12651 ACAGCAGTCA TTCAGTCTAT GACATTGAGT CCATGATAGT TTCTTGATCT
12701 TTACTGTAAT GTTCTAATCA TGATTTTGTT TCCTTATTCC TCCTACATTT
12751 ATTAATTGGA ATTCTTCTGT GAGGAAGATT TGTCTCTTCT CCGCCATTTA
12801 TTTATTTATT ATTCAGTCAT CTGTTGACAA CAGTATGGAT TCACAGATAC
12851 TTTTTAATTT ACTTTCTAAT CCGGCATTTT TGTTATTTCT TTTGTTGCTC
12901 AGATTGTTCC AGCTTTGGCC ATTGAGAGTT ATTTCATCTT GGCTCTTGTA
12951 TCCTTTGGAA ATGCCGTCCC CCCGCTTTTC TTCACCCCCA CTTCCATATT
13001 TTCTGGTATT CTGGCATTAC CAGAGGCTAC AGACTCATCT TCTGTTTCCC
13051 CTGCCCCAGC CTTGGAATCA GCCATTTCTC TAAAGAGCCC TAGTTCTTTT
13101 TATTGGAAAA TGGTATTTTA AAAGCAAGAG CTGGGTACTG AGTGTGTATG
13151 TTGTTGCTGG AGCGTCACTG CTTTTAGCAC TTTCAGAGGG CAGAGCTAGA
13201 AAACATACAC ACATGTACCA ACCCAGGTGT ACACACATCT GTTACTGCAT
13251 GTCTATTTGT ATATTTATTA AGGCAAGCAT AAGTTCATTC TGCTATCTCA
13301 AACTCTTAAT CTAGCCCCTC GGGGTTCATT TCCAAATTCT TGCTTTTGCT
13351 TTTTGTTGAT GGAGTATGGG CAGTACAGCA GTTAAACCTG GTTTCCATAT
13401 TTACTTTCTG CTGAGTGCTG TAGCTCATTG GTGAGAAAGG GATCTTTTGA
13451 CTTGACTTGC ATGGACACAT TCTAGTAGGA AGGTTGTCTG TCCTCATCAC
13501 TCCTGTGAGT GGTCCTCTAG AGCTCTTTGA AATGGCTACA ACATTGCAGA
13551 TCAAAAACAC CTGCTTTTCA GGTGCTTCAC TTCTCACCTT TCAGATGGGA

FIGURE 3D

```
13601 CATGCCCAGT TGTGTCTTCT AAACCTTGTT TCAGATAATT TTAAGAGTTG
13651 TCGCTTCAGT AACTATCTCT AACACAGGGA TCAGCAAACC TTTTCTGTGA
13701 AGTGCAGTAA ATATTTTAGG CTTTGCGGAC CATAAGGTAT TTGTTTCAAG
13751 TACTCAGCTC TGTCTTTGTC CTGTGAAAGC AGCCATAGAT GGCACATGAA
13801 CAAATGAGTA TGGCTATGTC TTACTAAAAT TTCATTTACA AAAACAAGGT
13851 TTTGTATTTG GCCCGTGGGC CATGGTTTAC CATCCGTTGG ACCCATTAAG
13901 TATATTCTCC TCCTCTTCTT TGTCTCATTC TCACTGCGTT CATAGGCTTG
13951 ATACGTTAAC ATTCGTGCAT CAGTAAAAGA ATCTGGCTTC TAGAGAAGAA
14001 GGGCTGTCCA TGGGCGTTTG ACTCCTAAAT ACAGTTTGTT TATGGTACTA
14051 GTGTGGCCAC AAGGCTCTGC CACACAAGCT CTGTCTCTTC CTTCCTGTTA
14101 TTACTTCTGC TTCCCTTCTC AGGAACCTGA AATCATATGG TAGTTTGTTT
14151 GTTTAAGTGA TTTTTTTTTT TGAGATGGAG TCTAGCTCTG TTGCCCAGTC
14201 TGGAGTGCAC TGCAACCTCC ACCTCCTGGG TTCAAGCAGT TCTCCTGCCT
14251 CAGCCTCCCA AGTAGCTGGG GCTACAGGTG CGCACCACCA CGCCTGGCGC
14301 ACCACCACGC CTGGCTAAAT TTTTTTTTTT TTTAATAGAG ATGGGTTTCA
14351 CCATGTTGGC TCAGGTGGTC TCAAACTGAC TTCAGGTGAT CCACCCGCCT
14401 CAGCCAAAGT GTTGGGATTA TAGATGTGAG CCACCACGCC CAGCCTTTAA
14451 GTGAATTTTT ATTTGAGTAT AACATGCATA ACAAGTTTGT GTGGATCATA
14501 AGTCTTAGAA GTGGATGAAT TTTTGTAGCA AGGTTTGAAG AGTCTGTTTT
14551 TAGATGAGTT TGCTAAGGTG GCACAGTATG TGATGATTCC GTGTAAAGAA
14601 GTCATTGTTA CAGGGCTGTG TCCTCTATCT GAACTGGCAT GGTTAGTTTA
14651 GTTGTTTAAA TTGAGGGCCT GCTTACAATT CATATCTAAG ATTTACTGGA
14701 GAGGAGAAAG GGTTGAGTAT TCAGTGGCCC AGAATCTGAT ATGGGAATTG
14751 GTAAGGTTTA TGTTCAAGGA GCCAAAGAAG ATTTAAATTT TATGTATTTG
14801 AATTACTCAG TGCGTCTATA TATATATATA TTTGGTCATC TTAAATTTTT
14851 TTTCTCGTTA GAATTCAGTT AAGGCCAATA TTTGAACTTT AATAAGTTTT
14901 GGTACTTGCT ACACTGCAGT ACATTTAATT GTATGTAATT ATAGGGAAAG
14951 ACTATGGGAA TTGAAGTCAG AACACTTGGT TATAAGTGCG AAGTCCACTA
15001 CTTCTTTTTA AGATCTTAGG AAAGTGATTT AACCTCTTTG GGTGCAAATC
15051 CTTTATCTGT GTATTAAGGA AACCATCTGC CTTCCTCACC TTACAGGTTG
15101 TTGAAAGAAT CAGACAGGAC AGATGTCCTA TTTATAGCTC TTTAATGCAT
15151 ATGTAGGCAA GCAGTGGCAG TTCTGTGACT CTTCTCTAAC TTACATATCA
15201 TTTACCCAAA CAGCCCTTAT CTTCCAGCCA GCTTGGCTGC TTAGCCATAT
15251 TGAATTACTA GTTTCTCTTA TCTAGAACAA CTTCTGCCCA ACTCATGGTG
15301 GACAGAACCA AGTGTCATGA AGTGATTTTA TTCATTCTTG CATTCAGCAC
15351 TCTTTTCACA GGCACCTACC CTGTGCCAGA CACTGTTCTA GGCACTAACA
15401 TTTCAGCAGT GAATAAAGTC AGTCCATCTT CTACCCTCAT GGAGCATATA
15451 ATCCTGAGGG TAATGCAGGC ATTAATTTAA AAATATATAA ATATAATTGT
15501 AGCTATCATG AGTGCTGGAA ATACAATGCT TCGATATGTG AATGTAAACT
15551 AGATAGGAAG ATTTTTTTAA AGAGGCATTC CCTAGACAGT GGTTGGACTA
15601 AGGTAGAAGA AAAGAATATT CCATGAAATG GGAAGAAGCA TGGTCCCATG
15651 AGGGATTAAT AGGCCACCAC TGTGGGCAGA GCAGTGAGGG TGAGGAAGGC
15701 TGGTAGCTGG CTGGGTATGC AGGGCTCCCA GCCATGAGAG GGAGGCTTGT
15751 CTTCAAAGTG GAAGTTAACT CAAGCTGTTG GCACTGTGAA TTTGACATGA
15801 GCAGATTTTA GGTAAATGTT AAGGGGCAGT TACTAAAACT AGCCTTGTAC
15851 ATTTTTAAGA ACTTCGAATA AAAGTTATTG CAGCTCAAAT TTGTTATAAC
15901 CTATTTGTTA AAGAGAGGAT TGTTTTGAGA CTATAGTTCC ATTCTTCATG
15951 AATTGGTAGG AGTTTGGAGT TTGTCAGCAA ACATTCTATC GGGCTAAAGG
16001 TTTTTATAAT GAAAGAAATA GGCAAAGTGG ATCAGTACAC TCACTTTTCT
16051 ACCATTGACC CTGGAGACAG ATGGCTTAAA ATGTTCTGCG TCTAGTTGAC
16101 TTTTAGATCT TGAAATTAAG GTTTAATGAT GACCAAGCTT TAAATAAATT
16151 GTAGAAAAGT ATTCTTTCAA AAGTACATTA TAACTTTTAT ATTGGTTTCT
16201 TATATTTATT TCTTTTAATC TTTTCTTTTA ACTCAAACTA CGTTTTAAGG
16251 TTTTGTTGCC TACTAAGTTA TAATCTGAGT GCAGAAGGAA ACTTGATTTG
16301 GCTTTATGGA ATACATTTTA CATTCAGTGA AGCTGAGCTC TGTTTCTCAT
16351 TCCTTACAAA AGGAATCAAA GGCATTGGTT TGAGAGATCA AGTCATGTGT
16401 TAATAAAACA CAAATATTCC ATCAAGTAAT ACTCTGAAGG AGCAGGTGTA
16451 GTTTATTTCT TCTCCAGAAA GTCTTCCAGC AGATAAATAA TGAGAGGTAG
16501 TATGGCATAG GAAAAAAGTA CACTGAAGTC AGCCTTTCTG GTTCAACCAG
16551 CTCAGACCCC TGAGCTATTT TTGCCTCAGT TTTACGCCTT GGAGAACAAT
16601 GCCTTGTCAT TACTATTCAC TTTATGACCA TACAGTGCCT GGCACCTGGT
16651 GGGCAATTGG TGAATGTTTT CACTATCCTC ATCCTTGCCC TCATGAAACA
16701 CTCCTTCTAG GTCCCACAAA GACCGTTGGT ATTTTATGAC AAAGTACCTT
16751 ACAAATATTT TTCTTTTTTT AAAGGAGAAA TTGTCGTAAA TGAAGTCAAT
16801 TTTGTGAGAA AATGCATTGC AACAGACACA AGCCAGTACG ATTTGTGGGG
16851 AAAGCTGATA TGCAGTAACT TCAAAATCTC CTTTATTACA GATGACCCAA
16901 TGCCATTACA GGTGTGTTTT ATTAGTACAC TGTTTCATTC TATCAGGCTT
16951 TCAACTCTAA GTGGTACATA TTATTATATA AAACATAGGT ATGGAAAAGT
```

FIGURE 3E

17001 TATAGTAGAA GTATTAGGTA ATGCAATGTT TGGGATAAAT TATATTAAGA
17051 TTTAAAGTAA AGTTTAAGAA GAATGTTGGA ACTTGCTAGA GGAGTATTAG
17101 TGAGAGGATT GTAAGTCACC TTGCTTTATT TATCCTCTGT GATCGTTCAT
17151 TATATGTCCT TTTCATTAAG GAAGTTATTC CCTCTGTTGC AGATCTTTTA
17201 ACCTGCTTAT AAAAATGACA TAAAGAGAAA AGGTTGTTTG CTAAATGATT
17251 TTATAAATGC CACACATTTT AGTGATTTCA TAGGTTTTTT TGTTGTTGGG
17301 TTTTTGATTT TTTTGTTTTG AGCCTGGATC TCGCTCTGTC TTGTCTCCCA
17351 GGCTGGAGTG CAGTGGCATG ATGTCGGCTC ACTGCAACCT CTGTCTGCTT
17401 CCTGGGCTCA AGCTATCCTG CCACCTCAGC CTCCTGAGTA GCTGGGACTA
17451 CAGGTGCATG CCACCACTCC CGGCTAACTG TTGTATTTTT TTGTAGAGAT
17501 GGGGTTTTGT TATGATGCCC GGATTGGTCT TGAACTTCTG AGCCCAAGCA
17551 ATCTGCCTGC CTCCCCCTCC CAAAGTGCCA GAGTACAGGC CACTGCACCC
17601 AGCTACCTTT TTTTTTTTTT TTTAAACTAA TTAGAGTTAT TTTCCTAAAA
17651 AGTTAAATTC TAATTTCTAG GAAGAGTGAA GAATAGTATC GATTTAAAAA
17701 TTTTCAGTAG CCCTCTTGCT ATTTTATGTT CTTACTGGAA AGTAATAGTT
17751 CCATGTAATT TTGGTTTTTA GAAGTTCAGG CATTCATTTG ATTAACTTAA
17801 AAACCCTGGA CTTTTCTGTC AGCCATTTTG TATTTTGTTT TATAAAGTAT
17851 TATACACACT TACCCCTAGA TCTTTCTTTA TAGTAATTGT TCTTTAATGA
17901 AATATTGGTA TATGAACTGT AAACTTTTAA ATTTAAGGAT CTAATAGTTT
17951 AGTGTAAGTA TATTTCATGT AGTCACTCAC TAATTTACCA TAATTATTAT
18001 ACTGTACAAA TATTTATTGT ACTGTATATT TGTGTGTTCA TTACAGTCTT
18051 ATGTAGGTAT ATTTAGACTA AATTTAAGGC ACTTAAAGAT ACCCACTGTG
18101 TAGGGACAGT AGCTTATTTG GATATAGGCT TGTGTGTTTC TCTTTGTTTT
18151 TAGCTTCATA ATGATCATTG GCCCCAGACT TCACTGTAAA TGAGAAGCAG
18201 ATACCTGGAA CAGCTTAAAT CCAGTACCAC TATTAGGAAA AAGTAAACCA
18251 GTGCCCTACT GACAGCAGAT TGATAGTGTT AACTACGTCC TTAGTTTGAA
18301 CATGCAAAAC CTTTTCTAAT GGTTTTTATT TCTAGTAGAC TTTGTGCTTT
18351 AAAAAGATAG TTATTTTGCA CTTTAAAATC TTCAGTGTGA AAATCAAACA
18401 TGATTTTACC CACTTAAAAT CTGATGACCT AAGAGCCCTT TTTTCTTTAA
18451 TATGTTGTGG CCAGCTTATC CAGATCTAGA CATGCAAATG CTTGCTGGTA
18501 AGGTGATTGA TGATATTCCC TATCTTAGGT ATTATAATAA GATTGTTGTG
18551 TACATTTTAA CCTAATTTCT ATCTGTCAAC ATTGGAATGG CCCTAGCTAC
18601 CTAGACAAAA GCTTTTTGTG CTTTTTAGAG ATAACTGTCA CAGTTTATCA
18651 TCACAGTTTA AGGCTTATAC TACCATTGTG AGATTATTGG GAAAAGAATT
18701 AATATGAACA TAATTTTTTA TTCCAGAAAT TCCATTACAG AAACCTTCTT
18751 CTTGGTGAAC ACGATGTCCC TTTAACATGT ATTGAACAAA TTGTCACAGG
18801 TACGTAGTAT TCCGTACATA CTCTAAAAGT CAATTCCACT CTGGAAGTAT
18851 TATTTGAAAA GTCATACCTC TCAAAATACT TGGATTGGCG TTTTATTTCT
18901 GTAAGTTTAC TTTTGCCGTT TTTTTGAGTC CCGGGAACAT AAAGAGGGAT
18951 ATGTTAATAA ATTATTTTAA AAGGAAGATA TAAAATGTAT AACTTTTCAT
19001 AGTTTCTAGG TTTTTTGTCC TCTTTTTAAT TAAAATTAAT CATTAAATGT
19051 ATCTAGATGG TGGTTTTATG CAAATAATCA TTTAAAATAT CTTCCAAAGC
19101 AAAGTTAAAA CCAACCCCCA AGTTCTAGGA ATTACAAGTA TGAAACATTC
19151 TAGACAAGCA GAGCTCAAAT GTTGGGTGAC CTTCCAATTA TTTTCACTAA
19201 GAATTTGTAT TAAAGGGTGA GTAACAAATA ACTGTTACGC ATTTTATTTT
19251 CTCTATTTTT TTTTCTTTTT TAGTAAACGA CCACAAGAGG AAGCAGAAAG
19301 TCCTAGGCCC CAACCAGAAA CTGAAATTTA ATCCAACAGA GTTAATTATT
19351 TATTGTAAAG ATTTCAGAAT TGTCAGATTT CGCTTTGATG AATCAGGTCC
19401 CGAAAGTGCT AAAAAGGTAA TACTGTTAAG GTTTATCAAG TTCTGGGTTC
19451 TGTACTGTGT TTACTGATTT CAATTCCGTA TGGCAGTTTT CATTTCTCAA
19501 TTGCTCAGAT GTTTTTTAGG GGAAGTTATC AGACATCTTC TTAAGTAAAG
19551 TCAAAGCCAA GAATATTAAT AGAACTATTT TCTTGGATTG GTTTATGGCT
19601 GTTTTAAAGT GTTCTATATA ACTTTTTATC AGCTTCTCAA ATATTAAAGA
19651 CTCTTACGTG GAAATTAGCA TTTTTTTACA TAAAGATCAT TACTTGTCAG
19701 TTTCTTGGTT AAAAGGTTGA AAAGTTGGTG ATATACTGTA ATTAAGGTTT
19751 GGTTAGGCTT TTAATTCAGT ACTGCAGAAC TTTACCAACA AACTGTAAGC
19801 TAGACTTATG TTACATAAGA TTTAGGTAAA TATATAATTA CGGGAAAGGC
19851 CTAGTAATTA TTAGTGGTTT AAAGAAATAT TATGAATTGA GTGACACTCA
19901 ACAGGGGCAA CACAAAGCTA GTAACTTTTT AACTGCCTTA TTTTTCCACG
19951 GCCTTCCAGA TAATGACTTA TTACCCTACT TGTAAGAGTC AAGGGCATGT
20001 TTTCCATGTT TTGCTTTGCC AGAGGAGTGA AGCTGGTAGA CCTAATATGG
20051 CCCCCGTTCC AGTCTGTGCT GCAGCAAATG CAGAGTCACA GACTTTCCAG
20101 TAGGAAGCTT GCGCGTGTGT ATGGGAATAG GGCAACAGTA TCTTAGTATA
20151 ATAGGACGTG GCTTTCTCTC AGAATGGAGG CAGTCTTTGC ACCACCAAGC
20201 AATGAGTGCC TTTGTTTTCC ATGGTTAGTC AACTGACTGC AGTAAATCTT
20251 CTGTTGATAC CAAAACAAGG CTGGCAAAAA TACTGTAAGG CAGCTGTCTT
20301 CATATACTTT GGTGAAGAGG TGGTAGATTT GTTTTTAGAT TGAGAACCAA
20351 CAGTTTCTTC ACAGGAAGGC AAGCAGGAGA TGAATATATG AAAATACATC

FIGURE 3F

20401 TGAAAATATG TGACTGTCTA GCAGAGTAGA GTGGTTGTAG GCTCCTCTAT
20451 GGGTAAAAGT TTTCAAATGG TCTGTATAAC CATCTCTCAG CAAGCTGCAT
20501 TATTGAAAAT TCAACTAGAT AACTCTTAAA GCCTCTTTCA CCTGTTCGAT
20551 TGTGCTGTTT GTGATTTTGG CATTTTACTA ATTTAAAGTG CCTATTATAT
20601 AGAAGGACTT TAGAATTCAT GATGTATTAG ACTGTACATA AAATATTTCA
20651 GACAGGTTAA TTCCTCAAGC TTATTTATAT TTGTAATTTA ATTGATCAAA
20701 GCATCAAAGA CCTGCTTATG AAAACCTTAA GATGTGTAGC ATCTCAAGAT
20751 TAGGGACATC ACAGAACTTG CTAGATTGAG TTAGGACAGC ATATTCCTAA
20801 GGAAGAAATT GATGCAATTG ACCGGATCTC TTTCGGAAAG TTCAATTCTC
20851 CCTCTTTTAC TGTATTTTTC AGTTTACACT ATTTTAATGA GTGGAAATAA
20901 TAATTATTTG GCCTAGTTCT TGAACCATCT GTAGTACTTG TTGGTCATTT
20951 TTCATGTTGA GGCAGTGTGC TAAATTTTGC AAGTAGAAAG AAGGGTAAGA
21001 TGCAGTTTCT TGCCCTAGAG AACTTAAATC TAGTGAAGAA GATAAAGCAT
21051 GAACAAATGA AAAGTAATGG TACAAAGTGG CAGCATAAAA TCAACTACAC
21101 AAATAGTTGA TTTCCAGATG AACAGAGCAT AATAAGTGCT GTGGAAATTC
21151 AGAATATCCC CTATGTGTTG TGCTGCTGGT TCATGAAGAG GGCCTTACTA
21201 AACCGTCTGC ACAAAACAAG CCAGTCCCTC ATATGCCCTT TCCTAAGACC
21251 AAGTTTCAGA CAAAAATCTT TTCCCCAGTA TCCTAAAATA TAAAAAGCAT
21301 GTGAGTCTCT GTCTTTTGTA TAGCCACGGG GGTTGCAGGG CAGGGGAGGG
21351 TGCAGGAAAA AAAAATAGAT GCAATGAGAA TATAAATAGT TTTTTTGGGA
21401 TTTACGCATT TCAAACAGGG TTAAGTTGTA TATGGCTACC AAAGCTTGAC
21451 GGCTTTGTGA GTTAAAAACA AAAATTATGG CATATTCTTT TATTTCAAGT
21501 GAAAAGTTTT CATCTAAAAT TCGGTAGCAG TTAGGAAATT ATGGCTCATT
21551 TTTACCTCCT GGAAGCTTGG AATACTGTTT TCTCTGGAAA ATGCTTTGCT
21601 ATTTTATCAG TTGCTTTAAA ATGATGAAAT GCATGTTTGG AGTTCTCTGG
21651 TGGGTAAACC GTTGATTCAT TTTGAAATAC CTAAGCCATT TATGTTTTTG
21701 TTTTGAAAAA TGAAATTCAA GAATACTAAA TTGGTTCACA TTTTGTTAAA
21751 TGTTCTGAAC CCTTCTGGTT GTCTTGTTGG TGTTGTTTCA ATTGTATTAT
21801 GACAAAATTA GATTGCTTTG GGCACTTGTA CTCATTAATA TTCATCCTCA
21851 TTATCCTCGA GCTGTCACAG GAAAATAGTG ATATTTGGGA AAGGTCTGTA
21901 TAAAGAAAGA AGGAATTTGA TGGTGCAGAA TTGGACATCT AACCTCATAG
21951 CAACTTAGAA CCACCATTTT CTTTTGCAGA ACCTTTGCTC AAAACTGAAG
22001 GGCAAAATAA TAAAGGTTGT TTTTAATGAT TTATCTATAT ATCTGTCTGT
22051 GTAGATAAAG ATAAATATAT AGATACACAT GAGTGACAAG TGAAATACAT
22101 GCCTTTTGTC TCCACTTTGT TCTCTGATTA GTGGGTTGTG AATCACTTCT
22151 TCAGGAATAC TTTATAGAAG TGAATTCCAT TCATCTGATT AAGGAACAAG
22201 TTGGCCTTTT CATGAACTGT CATTTTTGAC TTGAATCTGG TACTGTTTTT
22251 TGGTGGCTTT CAGGCCACAG AAATAAACCA CTTTTGTTTG CAAATGAGAT
22301 AGAACTTAAT GAGGTTTGAG TGTTTCCTGG ATTTGAGTTT CTTCAGTACT
22351 GCACCCCAGG TGATCTTAGG AAAGAAACCA TCCACTGTGG GTACTTCTGG
22401 CTTCTGTCCA GAGAAGATTA TCAGCTTTGG TCCAAAAATT GATTTAAAAG
22451 TAGTTTACTT CTTTTTCTCC AATAAAATAT TTGCCATAAT TTAATGTCTT
22501 TAATACCAAC ATTTTCTTCA TTTCCTGTGG TAGCCAGGAC AAATGAAGTA
22551 TTTCAGATCT TTCAAAAACT CTTAGGATGA AAGGTAGGAA TTTGGACTTA
22601 GGTTTTTAAA ATAGTGTGTA TGTAAAAGTG CAAAGAATGG GGCCCTGGCT
22651 TTCTCTTCTC GGAGTGTTCC ACAGTAACAA CATGAAGACA ATCCAGGTAC
22701 ACAAGTTTGT ATGTGCCTTA GTCTGTGTGT CCAAAGAGGC CTCTTACTTA
22751 GGTCATATGA ACATAAGTTA TACACTTGAA ATTCACTACT GAAAAACAAT
22801 GTATTTAGTT CGAGTTCTGC CACCCCAAAA AAATCAACGA GTAATTCAAC
22851 TGACTTGCAG TTTTACAATA TTTTTATAGA CTTCTTTCAG CGTAGATGCT
22901 TTTGGACATA CTCATTTGTT TCCTAACCTG ATGTGATATT GTGCTATTTT
22951 TAAGGGGCTT TTAAAAAATA CGCTGTGTTG GGTTTTGCCT TGAAAATAGG
23001 CTTTATTTCT TTTTTGCCTC ATGGCCACAA AAAAAGGATG TCCATGATCA
23051 ATGATCTGTG AATTTCTTTT CTGTAAACAG AAAGAGCATG TAACTGCTTT
23101 CTAATTGTTT TGGAGAATGT GATAGACATT AGTATTATTA TTATTGGCTT
23151 GGAGCATTTT CCTTAATATG TTGGTAACTA CTTTTGTCAG TGAATATTAG
23201 TGTAGCCACT GTTGGACACA GAGCACCGTC AGAAAGCTAC TGAAGTGGTG
23251 CTGCAAAGTG CAGACATCTT CAGATCTTTA CTCAAGTCTG TGCAGAGAGG
23301 TCTTTCTTGG TCTCCTTCTC TACTTTTTAG CCTGTCTCCC TCTTCTCACT
23351 GTAACACTTC ATATTCCCCT TCCCTGCTCT ATTATTTTTC TCTTTTAGCA
23401 TTCATAGTTA TCTAACTTTC TGTATTTTTT CTCTTTATCT TGTTTAGTGT
23451 CTGTCTTCCC ACTAGAATGT AAGCTTCATG AGGACAGGGA TTAGTGTCTG
23501 TTTTGTTCAC TGCATCTCTA GGGCTTACAA CATTGTAGGT ACTCAGTAAA
23551 TATTTGTTAA ATCAATGTGA AATGTGTCAT TTATCCTTAA GGAATTGACC
23601 TTCATGGTAG AAGTGTAACA GAACCACCTA TATCCTACTT TTCATCCACA
23651 TCATAACTAT TATGTGAATA CCTTGGAAGT AAAGCAAAAT AAGCACTTAA
23701 CTAAAGAGAC GCTTTATATT GAAACTGTTG TTCTGGGTTT CTGGAATTAG
23751 TACTCTGAAA TTGGCTCCCT CTAGGAAGGC TTGTGAAGAG AGTAGTGTTG

FIGURE 3G

23801 AACAGACATG ACAGTTTCCA AGAAAGCATA GTTGGCTAAG AGGAGTAGGA
23851 TTTTCCAAGC AAAGAGTGTG ACAGTGGAGA TGGCTGGGGC TAAGTCAGGC
23901 AGAATGTGTT CAAACCTGTT TTTCTCTGAC CTGAGATTGC GGAGGGAATA
23951 TTGGGAAGGT ATAGTTACCT GGTGAGGAGA GCCAGTTTTG TGAAGAATCA
24001 AGAATGAGGA GATTTAATTT GTTATGCAGA TGTCTGGGAA CCACAGCAGA
24051 TTATCAGGAG AGCAAAATTG TTAGTCAGAA TTACATCGTT AGAAGGTAAT
24101 CCTTAAGTTT TGTAGATTTC TAGAATGTAA GGAAGCTCTC AGAGGTGCCA
24151 TAAGGTGAGT ATGGCCTAAG GATGTGGCTA TGGCAGTGTA GCAAAATGGA
24201 CAACTATGAA AAATGTCTAG AGAAAAGTGC AACATAGCTT ATCAACGGTG
24251 CCCAAACAAA TAGGAAGGAT GAGAACTTTT TCAAGCTACA GATTTCAGTA
24301 GTTTTGCTGC TAGAAATGCT TTAAGGAAAA CTGTTAAAAA GATTAGGAAT
24351 GGGAATATAG ATAACCGGCT CCTAAATTTT GCAAGTGGGA CCGTCATAGA
24401 AAGCTCTCCT ATAGGTATTG AGAAATCGAG ATACCACGTA AGTTTCAAGA
24451 AGCAGTTTTT TTTTTCTTTT TGGTCAAAAC TAATGACAAA TTCTGTCCCC
24501 TTGTTTGTAT ATTTTAACTT AGTGAGACAG GAAACATTTA TTCTATAGAA
24551 GACTTTTAAA ATGTAGTTTA AACAAGTTGA CACATGCTTA CTGGTTAATG
24601 AAATGTGCAT CAACCCACTC CAAACACCAC TAATTTGACA TGAACTAACA
24651 ATTAACTTTT CTTACTCACT GTCAAAAGTA TATCATTCTG CCTTAACTTA
24701 ACGCTTTACC TTCTAAATAA AATTTAATCT TTTAAATAAG TTTTTCTGCT
24751 ATGTTTTCCT TGCATATGTC TTAAATTTCT TCTTTCGTCT TTGCTCACTG
24801 AAGAGCATTT TCTCCCACAT TCTAGTGACT ACCAGGGTTT GTAAGCCTAG
24851 AGCACCATCC TTCATTCTAT CTAGCAGCAG TTGAGAATAA TAACAGCCAT
24901 ATTTCTATAT ATGGAGCTCC TCCAAAGGCC TAGCCTGCAT TAAGCTTGTT
24951 AATTCTTACC ACAGCCTAGG TATTACTTTT GTTTTACAAG TGAGCAAACT
25001 GAGGCTAGAA AAGAGGAAAT GACTTCACAC ATGTTATGTA GCAAGTACTT
25051 GACAGAGCTA GGATTCAAGC CCCCTGATCT GTTTGATTCT AAAGCCCGCA
25101 CGTTTTCCAC CACAGGGCAC ACAGTCCCAA ACCATTTTAC TTAAACACAG
25151 TTTGTGTGTG TGTGTGTGTG TGTGTGTGTG TGTGTGTGTG TGTGTGTTGT
25201 TTTTTTGATG TACCTCTTTG AGCCACCCAT GCATTTTTGG AGTTTCTTGC
25251 TAATTTTAAT TTTTTGTAAT TATGTTTCTC TATTTAGATG TTTAAATCCA
25301 TGAGGCGTAA ACTTTAAAGT TTCATGCCTT ATATTAATCC TTTATAGTCC
25351 ACCAAAAATG AAACTTTTTT CTTCCTTTTT TGGAGTGGAC ATGTAGTCAC
25401 TGCCTTTTTG GAGAATGCTT CTTTAGTTTG AAGCTTTCTT TATTGGACTA
25451 AAATTACTTT CCAATTAAAA TTTAACTCAG CAAATACTTA CTGAATACTT
25501 GCCATGTGCT AGCTAAAGAT AAACAATGTC TTGAGGGCAT GAAAGTGAAT
25551 GAGATACCTG GCCTTAAGGA GCTCTTTTAT ATTCTAGGTC AACAGAAAAA
25601 CATGTAAATA GTATCTATAA TCACTGCCCC AAGATGATGC TCCCAGTGCC
25651 CAAGGCCTTA TTGTACATTT CATTTAACTA AGTGTGTTAA AATCAAATTC
25701 TAAATGTAGA ATTTTTCCTA GGTATGCCTT GCAATAGCTC ATTATTCCCA
25751 GCCAACAGAC CTCCAGCTAC TCTTTGCATT TGAATATGTT GGGAAAAAAT
25801 ACCACAATTC AGGTAAATAT GAAAATATTA AATATTGTGA CTAATTTTAC
25851 ATGTGTAAAT TTTACTCTTA TGTTTACCGG AAGCCTCCAA GTACATGAGC
25901 TTTAATGATT GTAGAATTAC TAGCTTCATA CCTTAGAGAA GTAAGCACTA
25951 CATGCTAAAA GAGCCAATAG TTTGTCAGAT TATTTCTTGA CAAGTTACCA
26001 GGAAGAACCT TTAATGCTAT GAATATGGGC TTATAAGTTA TGTCAGATAT
26051 TTAATCTCCA GTCACTGGCT TGTATTTTAT GATGAAGAAT ATATAACCCA
26101 CCCTTTTTAA TTGATAGCTT GAGTTAAAGT AATCTTATCT TTTAAGAAAA
26151 CTGGCAGAAA ACTAAAAGAT ATATTAAAAG CATAATCTTT TCTGGCAAGG
26201 TGTGATTTCA TGCAAAAGCT AAAGTGATTA AAAACTTTTT GTGGACTTCA
26251 TTAAGATTCT CAGAATACTG AGTTTCTATT TCTGAGTAAT ACTGATGAAA
26301 GGAAGATGAG CATTTTTCCA AGGACAAGTA TATTACTAGA CAGCTTTTGT
26351 GAAAGTAAAT AGTTTTGTCT ATATATCTGA CAGTCATGAC ATGACCAGGG
26401 AAGATTCCAG ATGATCATGC AANNNNNNNN NNNNNNNNNN NNNNNNNNNN
26451 NNNNNNNNNN NNNNNNNNNN NNNNNNNNNN NNNNNNNNNN NNNNNNNNNN
26501 NNNNNNNNNN NNNNNNNNNN NNNNNNNNNN NNNNNNNNNN NNNNNNNNNN
26551 NNNNNNNNNN NNNNNNNNNN NNNNNNNNNN NNNNNNNNNN NNNNNNNNNN
26601 NNNNNNNNNN NNNNNNNNNN NNNNNNNNNN NNNNNNNNNN NNNNNNNNNN
26651 NNNNNNNNNN NNNNNNNNNN NNNNNNNNNN NNNNNNNNNN NNNNNNNNNN
26701 NNNNNNNNNN NNNNNNNNNN NNNNNNNNNN NNNNNNNNNN NNNNNNNNNN
26751 NNNNNNNNNN NNNNNNNNNN NNNNNNNNNN NNNNNNNNNN NNNNNNNNNN
26801 NNNNNNNNNN NNNNNNNNNN NNNNNNNNNN NNNNNNNNNN NNNNNNNNNN
26851 NNNNNNNNNN NNNNNNNNNN NNNNNNNNNN NNNNNNNNNN NNNNNNNNNN
26901 NNNNNNNNNN NNNNNNNNNN NNNNNNNNNN NNNNNNNNNN NNNNNNNNNN
26951 NNNNNNNNNN NNNNNNNNNN NNNNNNNNNN NNNNNNNNNN NNNNNNNNNN
27001 NNNNNNNNNN NNNNNNNNNN NNNNNNNNNN NNNNNNNNNN NNNNNNNNNN
27051 NNNNNNNNNN NNNNNNNNNN NNNNNNNNNN NNNNNNNNNN NNNNNNNNNN
27101 NNNNNNNNNN NNNNNNNNNN NNNNNNNNNN NNNNNNNNNN NNNNNNNNNN
27151 NNNNNNNNNN NNNNNNNNNN NNNNNNNNNN NNNNNNNNNN NNNNNNNNNN

FIGURE 3H

27201 NNNNNNNNNN NNNNNNNNNN NNNNNNNNNN NNNNNNNNNN NNNNNNNNNN
27251 NNNNNNNNNN NNNNNNNNNN NNNNNNNNNN NNNNNNNNNN NNNNNNNNNN
27301 NNNNNNNNNN NNNNNNNNNN NNNNNNNNNN NNNNNNNNNN NNNNNNNNNN
27351 NNNNNNNNNN NNNNNNNNNN NNNNNNNNNN NNNNNNNNNN NNNNNNNNNN
27401 NNNNNNNNNN NNNNNNNNNN NNNNNNNNNN NNNNNNNNNN NNNNNNNNNN
27451 NNNNNNNNNN NNNNNNNNNN NNNNNNNNNN NNNNNNNNNN NNNNNNNNNN
27501 NNNNNNNNNN NNNNNNNNNN NNNNNNNNNN NNNNNNNNNN NNNNNNNNNN
27551 NNNNNNNNNN NNNNNNNNNN NNNNNNNNNN NNNNNNNNNN NNNNNNNNNN
27601 NNNNNNNNNN NNNNNNNNNN NNNNNNNNNN NNNNNNNNNN NNNNNNNNNN
27651 NNNNNNNNNN NNNNNNNNNN NNNNNNNNNN NNNNNNNNNN NNNNNNNNNN
27701 NNNNNNNNNN NNNNNNNNNN NNNNNNNNNN NNNNNNNNNN NNNNNNNNNN
27751 NNNNNNNNNN NNNNNNNNNN NNNNNNNNNN NNNNNNNNNN NNNNNNNNNN
27801 NNNNNNNNNN NNNNNNNNNN NNNNNNNNNN NNNNNNNNNN NNNNNNNNNN
27851 NNNNNNNNNN NNNNNNNNNN NNNNNNNNNN NNNNNNNNNN NNNNNNNNNN
27901 NNNNNNNNNN NNNNNNNNNN NNNNNNNNNN NNNNNNNNNN NNNNNNNNNN
27951 NNNNNNNNNN NNNNNNNNNN NNNNNNNNNN NNNNNNNNNN NNNNNNNNNN
28001 NNNNNNNNNN NNNNNNNNNN NNNNNNNNNN NNNNNNNNNN NNNNNNNNNN
28051 NNNNNNNNNN NNNNNNNNNN NNNNNNNNNN NNNNNNNNNN NNNNNNNNNN
28101 NNNNNNNNNN NNNNNNNNNN NNNNNNNNNN NNNNNNNNNN NNNNNNNNNN
28151 NNNNNNNNNN NNNNNNNNNN NNNNNNNNNN NNNNNNNNNN NNNNNNNNNN
28201 NNNNNNNNNN NNNNNNNNNN NNNNNNNNNN NNNNNNNNNN NNNNNNNNNN
28251 NNNNNNNNNN NNNNNNNNNN NNNNNNNNNN NNNNNNNNNN NNNNNNNNNN
28301 NNNNNNNNNN NNNNNNNNNN NNNNNNNNNN NNNNNNNNNN NNNNNNNNNN
28351 NNNNNNNNNN NNNNNNNNNN NNNNNNNNNN NNNNNNNNNN NNNNNNNNNN
28401 NNNNNNNNNN NNNNNNNNNN NNNNNNNNNN NNNNNNNNNN NNNNNNNNNN
28451 NNNNNNNNNN NNNNNNNNNN NNNNNNNNNN NNNNNNNNNN NNNNNNNNNN
28501 NNNNNNNNNN NNNNNNNNNN NNNNNNNNNN NNNNNNNNNN NNNNNNNNNN
28551 NNNNNNNNNN NNNNNNNNNN NNNNNNNNNN NNNNNNNNNN NNNNNNNNNN
28601 NNNNNNNNNN NNNNNNNNNN NNNNNNNNNN NNNNNNNNNN NNNNNNNNNN
28651 NNNNNNNNNN NNNNNNNNNN NNNNNNNNNN NNNNNNNNNN NNNNNNNNNN
28701 NNNNNNNNNN NNNNNNNNNN NNNNNNNNNN NNNNNNNNNN NNNNNNNNNN
28751 NNNNNNNNNN NNNNNNNNNN NNNNNNNNNN NNNNNNNNNN NNNNNNNNNN
28801 NNNNNNNNNN NNNNNNNNNN NNNNNNNNNN NNNNNNNNNN NNNNNNNNNN
28851 NNNNNNNNNN NNNNNNNNNN NNNNNNNNNN NNNNNNNNNN NNNNNNNNNN
28901 NNNNNNNNNN NNNNNNNNNN NNNNNNNNNN NNNNNNNNNN NNNNNNNNNN
28951 NNNNNNNNNN NNNNNNNNNN NNNNNNNNNN NNNNNNNNNN NNNNNNNNNN
29001 NNNNNNNNNN NNNNNNNNNN NNNNNNNNNN NNNNNNNNNN NNNNNNNNNN
29051 NNNNNNNNNN NNNNNNNNNN NNNNNNNNNN NNNNNNNNNN NNNNNNNNNN
29101 NNNNNNNNNN NNNNNNNNNN NNNNNNNNNN NNNNNNNNNN NNNNNNNNNN
29151 NNNNNNNNNN NNNNNNNNNN NNNNNNNNNN NNNNNNNNNN NNNNNNNNNN
29201 NNNNNNNNNN NNNNNNNNNN NNNNNNNNNN NNNNNNNNNN NNNNNNNNNN
29251 NNNNNNNNNN NNNNNNNNNN NNNNNNNNNN NNNNNNNNNN NNNNNNNNNN
29301 NNNNNNNNNN NNNNNNNNNN NNNNNNNNNN NNNNNNNNNN NNNNNNNNNN
29351 NNNNNNNNNN NNNNNNNNNN NNNNNNNNNN NNNNNNNNNN NNNNNNNNNN
29401 NNNNNNNNNN NNNNNNNNNN NNNNNNNNNN NNNNNNNNNN NNNNNNNNNN
29451 NNNNNNNNNN NNNNNNNNNN NNNNNNNNNN NNNNNNNNNN NNNNNNNNNN
29501 NNNNNNNNNN NNNNNNNNNN NNNNNNNNNN NNNNNNNNNN NNNNNNNNNN
29551 NNNNNNNNNN NNNNNNNNNN NNNNNNNNNN NNNNNNNNNN NNNNNNNNNN
29601 NNNNNNNNNN NNNNNNNNNN NNNNNNNNNN NNNNNNNNNN NNNNNNNNNN
29651 NNNNNNNNNN NNNNNNNNNN NNNNNNNNNN NNNNNNNNNN NNNNNNNNNN
29701 NNNNNNNNNN NNNNNNNNNN NNNNNNNNNN NNNNNNNNNN NNNNNNNNNN
29751 NNNNNNNNNN NNNNNNNNNN NNNNNNNNNN NNNNNNNNNN NNNNNNNNNN
29801 NNNNNNNNNN NNNNNNNNNN NNNNNNNNNN NNNNNNNNNN NNNNNNNNNN
29851 NNNNNNNNNN NNNNNNNNNN NNNNNNNNNN NNNNNNNNNN NNNNNNNNNN
29901 NNNNNNNNNN NNNNNNNNNN NNNNNNNNNN NNNNNNNNNN NNNNNNNNNN
29951 NNNNNNNNNN NNNNNNNNNN NNNNNNNNNN NNNNNNNNNN NNNNNNNNNN
30001 NNNNNNNNNN NNNNNNNNNN NNNNNNNNNN NNNNNNNNNN NNNNNNNNNN
30051 NNNNNNNNNN NNNNNNNNNN NNNNNNNNNN NNNNNNNNNN NNNNNNNNNN
30101 NNNNNNNNNN NNNNNNNNNN NNNNNNNNNN NNNNNNNNNN NNNNNNNNNN
30151 NNNNNNNNNN NNNNNNNNNN NNNNNNNNNN NNNNNNNNNN NNNNNNNNNN
30201 NNNNNNNNNN NNNNNNNNNN NNNNNNNNNN NNNNNNNNNN NNNNNNNNNN
30251 NNNNNNNNNN NNNNNNNNNN NNNNNNNNNN NNNNNNNNNN NNNNNNNNNN
30301 NNNNNNNNNN NNNNNNNNNN NNNNNNNNNN NNNNNNNNNN NNNNNNNNNN
30351 NNNNNNNNNN NNNNNNNNNN NNNNNNNNNN NNNNNNNNNN NNNNNNNNNN
30401 NNNNNNNNNN NNNNNNNNNN NNNNNNNNNN NNNNNNNNNN NNNNNNNNNN
30451 NNNNNNNNNN NNNNNNNNNN NNNNNNNNNN NNNNNNNNNN NNNNNNNNNN
30501 NNNNNNNNNN NNNNNNNNNN NNNNNNNNNN NNNNNNNNNN NNNNNNNNNN
30551 NNNNNNNNNN NNNNNNNNNN NNNNNNNNNN NNNNNCAGTG ATGGAAAGTA

FIGURE 3I

30601 GGGCAGCCCA CTAGAAGCCA CTAGCCACAT GTGGCTGTTA AGTACTTGAA
30651 ATGTGGCTAG TGCAAACTGA TGGACTGAAT TTTTAATTTT ATTTAATTTT
30701 CATTTCAGTT TAAATTTAAA TGGGCTTGTG TGGCTAGAAG TTACGTTTTT
30751 GGGAAACATA CTAGAGTCTA GGCCCTATTT GATTTCCCGC CTCTCTTCCA
30801 CCACCTGTTG AATCCCTATG CTCTAGCTGT ATTTAGTTAC TTGATATTAT
30851 ACAGTTATAC CATCTTTTTA AAGTTCTTCT CTGTCTAGCA TGCCTACCTC
30901 CTCCTCACCA GCTACCTGGC AACTTTTGAC TTGTTCCTTA GAACTCTCTT
30951 TAGTTGTGGT CAAGTCATGA AGCTTTTCCT GCCCCGGCCT CTCTCTGCAG
31001 CGAGAGTTAG GGGACTTCTC TTTTGCATCT TCATTGCACT CAGACATCTG
31051 GTACTCTGTG ATTATCACAC TTATTAATGC TCTCAAGATA GAGATAAAAT
31101 CTTATTCATC TTTTTGCTCT CAGGCATTAG CACATGGGGA GTTCTCAGAA
31151 AATACCTGTC TTATACCAGG AATTAATGAA TAATCAGTAG GAATGAGCAT
31201 GACATGTTCA TGGGACGTTG GAGGGTAGTG CATGGCTGCA GAGGAGAATG
31251 GGAAATGAAG GTCAGATAAG TTACGTGAGG GATCTCTAAG GCCAAGAGAA
31301 GCCATTTAGG TTTGATTTGG TTGGAAAATG AGCTTATTGA AAGTTTAAGG
31351 CAAGGGACTA GCATCATGAA CACATCTTTT TAGGGAAGTG TGTCTTGTGG
31401 TAAGCTGCTG GCTGGTTTAA ATGCAGCAGA ATATTCCATT GGGGATGCCA
31451 GCTGGGAGAC TTGCCACAGT TGCAGCCTGC AGCAGAAAGA CCCTGGGCCA
31501 GAATGGGTTG TGCCATCTGT CACCAGATAT TGCCAAGGTA GATCTGGCTG
31551 ACTTTGTGGG ACAGCTTGTT TCTCAATAAT CACTTTGCAG GCACTCTTGA
31601 GGCTGTGAGC ATGCTCCCAG AAGATAGCAT TACTTCTCTC TCAGAGCAGG
31651 CTCCTTTCTA AGGAAATGCA AGTCTAGGCC TGCCCTGCTG TAATCTTCAT
31701 GTGGAAACAG CACTCTAGCA AAGAACAAGG AACCTGATGA GCTTTTCAAA
31751 GGAAAATCGA GTAGATACAG GAAACCAAGA ATTTTCTAAT GAGCAGATAG
31801 AAAAGAGCAG GTAGGTGAGA AGTTGGTATT AGAAAAATTA AAGATTTGAA
31851 GGGCTTGAGG ACAGAGATGA TTGTTGGATG TTTCATTTTT CCAGGCAAAA
31901 TATGTGGAGC AAATAATCAA ATGACATGGA CTTACCCCAC AATTAGGGAC
31951 GGAGATGAGG AAGGGTTAGG AATAGTTTCT GTTAGAATGG TAGGGATGGA
32001 AGACAATTGA AAATTAAAGA GAAAATAAAT GGAGAGGAAA TCTAGGCAGC
32051 AGCCATTCTT CATTCTGGGG GAAGGTGGTC AGGAAAAGGA AGGAAGAAAA
32101 ATGTATAGCA TAGTAGCTAG AGTGGTCCGG CGTGATCAAA GTGTTTTCAA
32151 TATCATGTTG ACTGACCTGT TTACGTTTGA AGGCAGAGAA GATAGAGCCA
32201 GTAGAAGGAG AGAAAAATCA AAGCTGTTTT ACGGAGTTGT GAAAGAGCTG
32251 GATAAGGACA AGACTAAATG AGTTATTTTT AGGCCAGGCA TGGTGGCTCA
32301 TGCCTGTAAT CCCAGCACTT TGGGAGGCCA AGGCAGGTGG GGCACCTGAG
32351 GTCAGGAGTT CAAGAGCAGC CTGGCCAACA TGGTGAAACC CTGTCTCTAT
32401 TAAAAATACA AAAATTAGCT GGACATGGTG CATGGTGGCA GGTGCCTGTA
32451 ATCCCAGCTA CTCAAGAGGC TGAGGCAGGA GAATAGCTTG AACCCGGGGG
32501 GCGGAGGTTG CAGTCAGCCG AGATCATGCC AGTGCATTCC AGCCTGGGCG
32551 ACAGAACGAG ACTCCGTCAA AAAAAAAAAA AGGAGTTATT TTTAAATGGA
32601 AAGGGCAAGA CAGTTACTCG GAGAGACTTG GAAGGTGAAG CAGGTTAGAG
32651 ACAGCACATC AGAGTATGCA TGTGACAGGA GGCTCAGAGA AGAGGGAATG
32701 CTGGGGAAAA TGTGACTGTT AAAATTCATA ATGTTGCTTT TTCCTACAGC
32751 AAACAAAATT AATGGAATTC CCTCAGGAGA TGGAGGAGGA GGAGGAGGAG
32801 GAGGTAATGG AGCTGGTGGT GGCAGCAGCC AGAAAACTCC ACTCTTTGAA
32851 ACTTACTCGG ATTGGGACAG AGAAATCAAG AGGACAGGTG CTTCCGGGTG
32901 GAGAGTTTGT TCTATTAACG AGGGTTACAT GATATCCACT TGGTAAGTAC
32951 AATTTTAGCA ATGTTATATA TGGCTGGAAG TCACTTCCCT ATGAATAATC
33001 ATCAAACTCT GTTGTCATTG ATGACTTTCA AGTTGTGGTT AATGGAATAT
33051 TTGTTTTTAA TAATGTTTTA ATAAATATTT TATTTTAAAG ATCAAGGCTT
33101 ATTAATATAA ATTACGGTAT CCCTTAAAAG AAGTTGATAG TAATTCCTTA
33151 CTGTCATCAG TAGTCAGTGT TTATTGCATT ATATCTTGTA ACTGGTGTTT
33201 TACAGTTGGT TTGTTCATAT CAGGATCTAA AGTCTTCACA TTGAATTTGC
33251 TTAATATGTC TCTTAGGCCT TTTAATCTAC AACAGTCTCC TCCCACCTCT
33301 TTTTTACCTA CTATTTGTTG ACAAACCAGG TCATTTGTTC CCTAGAATTT
33351 TCCACATTGT AGATATTGCT TGTTTTATCC CCAGGGTGTC CCGTAATGTG
33401 TTCCTCTGTC TCTAATATTT CCTTTAAAAT GTTAGCAACA GAGGCTTAAT
33451 CGGATTCAGG TTCAGTACTT TTGGCAAGAA TGTTTCATTA GGTGGTTCTG
33501 TGTTCTCCTG TGGAGTCACA TCCCATCTCA GGCTGGCTGG CTGTGTCTCT
33551 CTCATTGTAA TCCTGACGAC CAGTGGGCTT AGAGGGTGTC AACCTGATCC
33601 ACCCAGTAAA AGTTCCCCTC TTATATCATG GTTTGAGCTC CCAAAAATAG
33651 TTTTGCACTG GGAGGGAGGA TCATTGCTCA GATCGTTATT TCACTAAGGA
33701 TTGCTATTGT TCACCTTCTA ATTCTATCAT CTTTCTGCTT TTATCGAACT
33751 TTTCTCTCAC CAGCTCTTTA GTGCCCTGTA ACACAGTTCG TACAAGAAAA
33801 GCAATATAAA TATCTACATT TTCTCCTTTA CTTAACATTT TTCCAAATAG
33851 TGAGCTGGTT CCCTAGGGGA TCTTTCTAGA AGTGACTAGG AATTTGTTTT
33901 TTTAATTTGT TTAATGTCAT TTAGTTATTA TGAATTTTTT GGAATGCCTT
33951 ATTTTAAGGT CATTGAAGTC CTCATTAGTT CACGCACATA AGCAGCTTTT

FIGURE 3J

34001 TAGAAAAAGG AAGAAAAGCA CTACTGTGTT ATTACTGGTT AATCCAGTAC
34051 CAGGAACTTC TAGTACAGTT CTAGAAAGGT GCTTTGCAGC ATGTAGCTTG
34101 TATGCTTTTG CTTCCCCTGG AATTTAAGCT TCAAGGCCAG CACACTCTGG
34151 TATATGTGCT GAGAAACATG TGATGGGGCT GCCNNNNNNN NNNNNNNNNN
34201 NNNNNNNNNN NNNNNNNNNN NNNNNNNNNN NNNNNNNNNN NNNNNNNNNN
34251 NNNNNNNNNN NNNNNNNNNN NNNNNNNNNN NNNNNNNNNN NNNNNNNNNN
34301 NNNNNNNNNN NNNNNNNNNN NNNNNNNNNN NNNNNNNNNN NNNNNNNNNN
34351 NNNNNNNNNN NNNNNNNNNN NNNNNNNNNN NNNNNNNNNN NNNNNNNNNN
34401 NNNNNNNNNN NNNNNNNNNN NNNNNNNNNN NNNNNNNNNN NNNNNNNNNN
34451 NNNNNNNNNN NNNNNNNNNN NNNNNNNNNN NNNNNNNNNN NNNNNNNNNN
34501 NNNNNNNNNN NNNNNNNNNN NNNNNNNNNN NNNNNNNNNN NNNNNNNNNN
34551 NNNNNNNNNN NNNNNNNNNN NNNNNNNNNN NNNNNNNNNN NNNNNNNNNN
34601 NNNNNNNNNN NNNNNNNNNN NNNNNNNNNN NNNNNNNNNN NNNNNNNNNN
34651 NNNNNNNNNN NNNNNNNNNN NNNNNNNNNN NNNNNNNNNN NNNNNNNNNN
34701 NNNNNNNNNN NNNNNNNNNN NNNNNNNNNN NNNNNNNNNN NNNNNNNNNN
34751 NNNNNNNNNN NNNNNNNNNN NNNNNNNNNN NNNNNNNNNN NNNNNNNNNN
34801 NNNNNNNNNN NNNNNNNNNN NNNNNNNNNN NNNNNNNNNN NNNNNNNNNN
34851 NNNNNNNNNN NNNNNNNNNN NNNNNNNNNN NNNNNNNNNN NNNNNNNNNN
34901 NNNNNNNNNN NNNNNNNNNN NNNNNNNNNN NNNNNNNNNN NNNNNNNNNN
34951 NNNNNNNNNN NNNNNNNNNN NNNNNNNNNN NNNNNNNNNN NNNNNNNNNN
35001 NNNNNNNNNN NNNNNNNNNN NNNNNNNNNN NNNNNNNNNN TGGTAAAACC
35051 CCGCCTCTAC TAAAAATACA AAAATTTAGC CAGGTGTGGT GGCGGGTGCC
35101 TGTAATCCCA ACTACTCGGG AGGGTGAGGC AGGAGAATCG CTTGAACCCG
35151 GGAGGGGGAG GTTGCAGTGA GCCGAGATGG TGCCACTGCA CTCCAGCCTG
35201 GGCGACAGTA TGAGACTCCG TCTCAAAAAG AAAAAGAAGG AAATGATCTA
35251 ATTTGTTCTG TGCACTGCAC GTGGGGGTGG CAGTGAGGTG AATGGCAGCA
35301 TTCTGCAGTA GTCAAAGCCA GATGGGTGGG AGAAGTTGGG TGCTAAGAGG
35351 GAAACAAAGT TTACCTGTCT TCTCCTTGAT TTCACTCTCA GTTTTATGAG
35401 AATACAGAAA AATCATGCAG AGAAACCTGA TGGAATAGTC TCTAAAACTA
35451 AAAAATAAGA TAAGCAATGG TTCTGTCTTA AAAAAAAAAA AGTAAACTCC
35501 ATGAAGGCAG AGACCTTACC TGTCTCATTC CTCTCTCTAT CCCCTGGTCT
35551 ATAGTAAGGG TTAAATAAAT ATATGCTGAA ATGAATGAGT AATGACTAAA
35601 GTATTTTTGT CTTTATTAGG ATTTGTAATG CAATAACTAA AAGTCACCCA
35651 CAGAGAAGTG ATGTTTACAA ATCAGATTTG GATAAGCCCT TGCCTAATAT
35701 TCANNNNNNN NNNNNNNNNN NNNNNNNNNN NNNNNNNNNN NNNNNNNNNN
35751 NNNNNNNNNN NNNNNNNNNN NNNNNNNNNN NNNNNNNNNN NNNNNNNNNN
35801 NNCAGCTCAA ATTTGTTATA ACCTATTTGT TAAAGAGAGG ATTGTTTTGA
35851 GACTATAGTT CCATTCTTCA TGAATTGGTA GGAGTTTGGA GTTTGTCAGC
35901 AAACATTCTA TCGGGCTAAA GGTTTTTATA ATGAAAGAAA TAGGCAAAGT
35951 GGATCAGTAC ACTCACTTTT CTACCATTGA CCCTGGAGAC AGATGGCTTA
36001 AAATGTTCTG CGTCTAGTTG ACTTTTAGAT CTTGAAATTA AGGTTTAATG
36051 ATGACCAAGC TTTAAATAAA TTGTAGAAAA GTATTCTTTC AAAAGTACAT
36101 TATAACTTTT ATATTGGTTT CTTATATTTA TTTCTTTTAA TCTTTTCTTT
36151 TAACACAAAC TACGTTTTAA GGTTTTGTTG CCTACTAAGT TATAATCTGA
36201 GTGCAGAAGG AAACTTGATT TGGCTTTATG GAATACATTT TACATTCAGT
36251 GAAGCTGAGC TCTGTTTCTC ATTCCTTACA AAAGGAATCA AAGGCATTGG
36301 TTTGAGAGAT CAAGTCATGT GTTAATAAAA CACAAATATT CCATCAAGTA
36351 ATACTCTGAA GGAGCAGGTG TAGTTTATTT CTTCTCCAGA AAGTCTTCCA
36401 GCAGATAAAT AATGAGAGGT AGTATGGCAT AGGAAAAAAG TACACTGAAG
36451 TCAGCCTTTC TGGTTCAACC AGCTCAGACC CCTGAGCTAT TTTTGCCTCA
36501 GTTTTACGCC TTGGAGAACA ATGCCTTGTC ATTACTATTC ACTTTATGAC
36551 CATACAGTGC CTGGCACCTG GTGGGCAATT GGTGAATGTT TTCACTATCC
36601 TCATCCTTGC CCTCATGAAA CACTCCTTCT AGGTCCCACA AAGACCGTTG
36651 GTATTTTATG ACAAAGTACC TTACAAATAT TTTTCTTTTT TTAAAGGAGA
36701 AATTGTCGTA AATGAAGTCA ATTTTGTGAG AAAATGCATT GCAACAGACA
36751 CAAGCCAGTA CGATTTGTGG GGAAAGCTGA TATGCAGTAA CTTCAAAATC
36801 TCCTTTATTA CAGATGACCC AATGCCATTA CAGGTGTGTT TTATTAGTAC
36851 ACTGTTTCAT TCTATCAGGC TTTCAACTCT AAGTGGTACA TATTATTATA
36901 TAAAACATAG GTATGGAAAA GTTATAGTAG AAGTATTAGG TAATGCAATG
36951 TTTGGGATAA ATTATATTAA GATTTAAAGT AAAGTTTAAG AAGAATGTTG
37001 GAACTTGCTA GAGGAGTATT AGTGAGAGGA TTGTAAGTCA CCTTGCTTTA
37051 TTTATCCTCT GTGATCGTTC ATTATATGTC CTTTTCATTA AGGAAGTTAT
37101 TCCCTCTGTT GCAGATCTTT TAACCTGCTT ATAAAAATGA CATAAAGAGA
37151 AAAGGTTGTT TGCTAAATGA TTTTATAAAT GCCACACATT TTAGTGATTT
37201 CATAGGTTTT TTTGTTGTTG GGTTTTTGAT TTTTTTGTTT TGAGCCTGGA
37251 TCTCGCTCTG TCTTGTCTCC CAGGCTGGAG TGCAGTGGCA TGATGTCGGC
37301 TCACTGCAAC CTCTGTCTGC TTCCTGGGCT CAAGCTATCC TGCCACCTCA
37351 GCCTCCTGAG TAGCTGGGAC TACAGGTGCA TGCCACCACT CCCGGCTAAC

FIGURE 3K

37401 TGTTGTATTT TTTTGTAGAG ATGGGGTTTT GTTATGATGC CCGGATTGGT
37451 CTTGAACTTC TGAGCCCAAG CAATCTGCCT GCCTCCCCCT CCCAAAGTGC
37501 CAGAGTACAG GCCACTGCAC CCAGCTACCT TTTTTTTTTT TTTTTAAACT
37551 AATTAGTGTT ATTTTCCTAA AAAGTTAAAT TCTAATTTCT AGGAAGAGTG
37601 AAGAATAGTA TCGATTTAAA AATTTTCAGT AGCCCTCTTG CTATTTTATG
37651 TTCTTACTGG AAAGTAATAG TTCCATGTAA TTTTGGTTTT TAGAAGTTCA
37701 GGCATTCATT TGATTAACTT AAAAACCCTG GACTTTTCTG TCAGCCATTT
37751 TGTATTTTGT TTTATAAAGT ATTATACACA CTTACCCCTA GATCTTTCTT
37801 TATAGTAATT GTTCTTTAAT GAAATATTGG TATATGAACT GTAAACTTTT
37851 AAATTTAAGG ATCTAATAGT TTAGTGTAAG TATATTTCAT GTAGTCACTC
37901 ACTAATTTAC CATAATTATT ATACTGTACA AATATTTATT GTACTGTATA
37951 TTTGTGTGTT CATTACAGTC TTATGTAGGT ATATTTAGAC TAAATTTAAG
38001 GCACTTAAAG ATACCCACTG TGTAGGGACA GTAGCTTATT TGGATATAGG
38051 CTTGTGTGTT TCTCTTTGTT TTTAGCTTCA TAATGATCAT TGGCCCCAGA
38101 CTTCACTGTA AATGAGAAGC AGATACCTGG AACAGCTTAA ATCCAGTACC
38151 ACTATTAGGA AAAAGTAAAC CAGTGCCCTA CTGACAGCAG ATTGATAGTG
38201 TTAACTACGT CCTTAGTTTG AACATGCAAA ACCTTTTCTA ATGGTTTTTA
38251 TTTCTAGTAG ACTTTGTGCT TTAAAAAGAT AGTTATTTTG CACTTTAAAA
38301 TCTTCAGTGT GAAAATCAAA CATGATTTTA CCCACTTAAA ATCTGATGAC
38351 CTAAGAGCCC TTTTTTCTTT AATATGTTGT GGCCAGCTTA TCCAGATCTA
38401 GACATGCAAA TGCTTGCTGG TAAGGTGATT GATGATATTC CCTATCTTAG
38451 GTATTATAAT AAGATTGTTG TGTACATTTT AACCTAATTT CTATCTGTCA
38501 ACATTGGAAT GGCCCTAGCT ACCTAGACAA AAGCTTTTTG TGCTTTTTAG
38551 AGATAACTGT CACAGTTTAT CATCACAGTT TAAGGCTTAT ACTACCATTG
38601 TGAGATTATT GGGAAAAGAA TTAATATGAA CATAATTTTT TATTCCAGAA
38651 ATTCCATTAC AGAAACCTTC TTCTTGGTGA ACACGATGTC CCTTTAACAT
38701 GTATTGAGCA AATTGTCACA GGTACGTAGT ATTCCGTACA TACTCTAAAA
38751 GTCAATTCCA CTCTGGAAGT ATTATTTGAA AAGTCATACC TCTCAAAATA
38801 CTTGGATTGG CGTTTTATTT CTGTAAGTTT ACTTTTGCCG TTTTTTTGAG
38851 TCCCGGGAAC ATAAAGAGGG ATATGTTAAT AAATTATTTT AAAAGGAAGA
38901 TATAAAATGT ATAACTTTTC ATAGTTTCTA GGTTTTTTGT CCTCTTTTTA
38951 ATTAAAATTA ATCATTAAAT GTGTCTAGAT GGTGGTTTTA TGCAAATAAT
39001 CATTTAAAAT ATCTTCCAAA GCAAAGTTAA AACCAACCCC CAAGTTCTAG
39051 GAATTACAAG TATGAAACAT TCTAGACAAG CAGAGCTCAA ATGTTGGGTG
39101 ACCTTCCAAT TATTTTCACT AAGAATTTGT ATTAAAGGGT GAGTAACAAA
39151 TAACTGTTAC GCATTTTATT TTCTCTATTT TTTTTTCTTT TTTAGTAAAC
39201 GACCACAAGA GGAAGCAGAA AGTCCTAGGC CCCAACCAGA AACTGAAATT
39251 TAATCCAACA GAGTTAATTA TTTATTGTAA AGATTTCAGA ATTGTCAGAT
39301 TTCGCTTTGA TGAATCAGGT CCCGAAAGTG CTAAAAAGGT AATACTGTTA
39351 AGGTTTATCA AGTTCTGGGT TCTGTACTGT GTTTACTGAT TTCAATTCCG
39401 TATGGCAGTT TTCATTTCTC AATTGCTCAG ATGTTTTTTA GGGGAAGTTA
39451 TCAGACATCT TCTTAAGTAA AGTCAAAGCC AAGAATATTA ATAGAACTAT
39501 TTTCTTGGAT TGGTTTATGG CTGTTTTAAA GTGTTCTATA TAACTTTTTA
39551 TCAGCTTCTC AAATATTAAA GACTCTTACG TGGAAATTAG CATTTTTTTA
39601 CATAAAGATC ATTACTTGTC AGTTTCTTGG TTAAAAGGTT GAAAAGTTGG
39651 TGATATACTG TAATTAAGGT TTGGTTAGGC TTTTAATTCA GTACTGCAGA
39701 ACTTTACCAA CAAACTGTAA GCTAGACTTA TGTTACATAA GATTTAGGTA
39751 AATATATAAT TACGGGAAAG GCCTAGTAAT TATTAGTGGT TTAAAGAAAT
39801 ATTATGAATT GAGTGACACT CAACAGGGGC AACACAAAGC TAGTAACTTT
39851 TTAACTGCCT TATTTTTCCA CGGCCTTCCA GATAATGACT TATTACCCTA
39901 CTTGTAAGAG TCAAGGGCAT GTTTTCCATG TTTTGCTTTG CCAGAGGAGT
39951 GAAGCTGGTA GACCTAATAT GGCCCCCGTT CCAGTCTGTG CTGCAGCAAA
40001 TGCAGAGTCA CAGACTTTCC AGTAGGAAGC TTGCGCGTGT GTATGGGAAT
40051 AGGGCAACAG TATCTTAGTA TAATAGGACG TGGCTTTCTC TCAGAATGGA
40101 GGCAGTCTTT GCACCACCAA GCAATGAGTG CCTTTGTTTT CCATGGTTAG
40151 TCAACTGACT GCAGTAAATC TTCTGTTGAT ACCAAAACAA GGCTGGCAAA
40201 AATACTGTAA GGCAGCTGTC TTCATATACT TTGGTGAAGA GGTGGTAGAT
40251 TTGTTTTTAG ATTGAGAACC AACAGTTTCT TCACAGGAAG GCAAGCAGGA
40301 GATGAATATA TGAAAATACA TCTGAAAATA TGTGACTGTC TAGCAGAGTA
40351 GAGTGGTTGT AGGCTCCTCT ATGGGTAAAA GTTTTCAAAT GGTCTGTATA
40401 ACCATCTCTC AGCAAGCTGC ATTATTGAAA ATTCAACTAG ATAACTCTTA
40451 AAGCCTCTTT CACCTGTTCG ATTGTGCTGT TTGTGATTTT GGCATTTTAC
40501 TAATTTAAAG TGCCTATTAT ATAGAAGGAC TTTAGAATTC ATGATGTATT
40551 AGACTGTACA TAAAATATTT CAGACAGGTT AATTCCTCAA GCTTATTTAT
40601 ATTTGTAATT TAATTGATCA AAGCATCAAA GACCTGCTTA TGAAAACCTT
40651 AAGATGTGTA GCATCTCAAG ATTAGGGACA TCACAGAACT TGCTAGATTG
40701 AGTTAGGACA GCATATTCCT AAGGAAGAAA TTGATGCAAT TGACCGGATC
40751 TCTTTCGGAA AGTTCAATTC TCCCTCTTTT ACTGTATTTT TCAGTTTACA

FIGURE 3L

```
40801 CTATTTTAAT GAGTGGAAAT AATAATTATT TGGCCTAGTT CTTGAACCAT
40851 CTGTAGTACT TGTTGGTCAT TTTTCATGTT GAGGCAGTGT GCTAAATTTT
40901 GCAAGTAGAA AGAAGGGTAA GATGCAGTTT CTTGCCCTAG AGAACTTAAA
40951 TCTAGTGAAG AAGATAAAGC ATGAACAAAT GAAAAGTAAT GGTACAAAGT
41001 GGCAGCATAA AATCAACTAC ACAAATAGTT GATTTCCAGA TGAACAGAGC
41051 ATAATAAGTG CTGTGGAAAT TCAGAATATC CCCTATGTGT TGTGCTGCTG
41101 GTTCATGAAG AGGGCCTTAC TAAACCGTCT GCACAAAACA AGCCAGTCCC
41151 TCATATGCCC TTTCCTAAGA CCAAGTTTCA GACAAAAATC TTTTCCCCAG
41201 TATCCTAAAA TATAAAAAGC ATGTGAGTCT CTGTCTTTTG TATAGCCACG
41251 GGGGTTGCAG GGCAGGGGAG GGTGCAGGAA AAAAAAATAG ATGCAATGAG
41301 AATATAAATA GTTTTTTTGG GATTTACGCA TTTCAAACAG GGTTAAGTTG
41351 TATATGGCTA CCAAAGCTTG ACGGCTTTGT GAGTTAAAAA CAAAAATTAT
41401 GGCATATTCT TTTATTTCAA GTGAAAAGTT TTCATCTAAA ATTCGGTAGC
41451 AGTTAGGAAA TTATGGCTCA TTTTTACCTC CTGGAAGCTT GGAATACTGT
41501 TTTCTCTGGA AAATGCTTTG CTATTTTATC AGTTGCTTTA AAATGATGAA
41551 ATGCATGTTT GGAGTTCTCT GGTGGGTAAA CCGTTGATTC ATTTTGAAAT
41601 ACCTAAGCCA TTTATGTTTT TGTTTTGAAA AATGAAATTC AAGAATACTA
41651 AATTGGTTCA CATTTTGTTA AATGTTCTGA ACCCTTCTGG TTGTCTTGTT
41701 GGTGTTGTTT CAATTGTATT ATGACAAAAT TAGATTGCTT TGGGCACTTG
41751 TACTCATTAA TATTCATCCT CATTATCCTC GAGCTGTCAC AGGAAAATAG
41801 TGATATTTGG GAAAGGTCTG TATAAAGAAA GAAGGAATTT GATGGTGCAG
41851 AATTGGACAT CTAACCTCAT AGCAACTTAG AACCACCATT TTCTTTTGCA
41901 GAACCTTTGC TCAAAACTGA AGGGCAAAAT AATAAAGGTT GTTTTTAATG
41951 ATTTATCTAT ATATCTGTCT GTGTAGATAA AGATAAATAT ATAGATACAC
42001 ATGAGTGACA AGTGAAATAC ATGCCTTTTG TCTCCACTTT GTTCTCTGAT
42051 TAGTGGGTTG TGAATCACTT CTTCAGGAAT ACTTTATAGA AGTGAATTCC
42101 ATTCATCTGA TTAAGGAACA AGTTGGCCTT TTCATGAACT GTCATTTTTG
42151 ACTTGAATCT GGTACTGTTT TTTGGTGGCT TTCAGGCCAC AGAAATAAAC
42201 CACTTTTGTT TGCAAATGAG ATAGAACTTA ATGAGGTTTG AGTGTTTCCT
42251 GGATTTGAGT TTCTTCAGTA CTGCACCCCA GGTGATCTTA GGAAAGAAAC
42301 CATCCACTGT GGGTACTTCT GGCTTCTGTC CAGAGAAGAT TATCAGCTTT
42351 GGTCCAAAAA TTGATTTAAA AGTAGTTTAC TTCTTTTTCT CCAATAAAAT
42401 ATTTGCCATA ATTTAATGTC TTTAATACCA ACATTTTCTT CATTTCCTGT
42451 GGTAGCCAGG ACAAATGAAG TATTTCAGAT CTTTCAAAAA CTCTTAGGAT
42501 GAAAGGTAGG AATTTGGACT TAGGTTTTTA AAATAGTGTG TATGTAAAAG
42551 TGCAAAGAAT GGGGCCCTGG CTTTCTCTTC TCGGAGTGTT CCACAGTAAC
42601 AACATGAAGA CAATCCAGGT ACACAAGTTT GTATGTGCCT TAGTCTGTGT
42651 GTCCAAAGAG GCCTCTTACT TAGGTCATAT GAACATAAGT TATACACTTG
42701 AAATTCACTA CTGAAAAACA ATGTATTTAG TTCGAGTTCT GCCACCCCAA
42751 AAAAATCAAC GAGTAATTCA ACTGACTTGC AGTTTTACAA TATTTTTATA
42801 GACTTCTTTC AGCGTAGATG CTTTTGGACA TACTCATTTG TTTCCTAACC
42851 TGATGTGATA TTGTGCTATT TTTAAGGGGC TTTTAAAAAA TACGCTGTGT
42901 TGGGTTTTGC CTTGAAAATA GGCTTTATTT CTTTTTTGCC TCATGGCCAC
42951 AAAAAAAGGA TGTCCATGAT CAATGATCTG TGAATTTCTT TTCTGTAAAC
43001 AGAAAGAGCA TGTAACTGCT TTCTAATTGT TTTGGAGAAT GTGATAGACA
43051 TTAGTATTAT TATTATTGGC TTGGAGCATT TTCCTTAATA TGTTGGTAAC
43101 TACTTTTGTC AGTGAATATT AGTGTAGCCA CTGTTGGACA CAGAGCACCG
43151 TCAGAAAGCT ACTGAAGTGG TGCTGCAAAG TGCAGACATC TTCAGATCTT
43201 TACTCAAGTC TGTGCAGAGA GGTCTTTCTT GGTCTCCTTC TCTACTTTTT
43251 AGCCTGTCTC CCTCTTCTCA CTGTAACACT TCATATTCCC CTTCCCTGCT
43301 CTATTATTTT TCTCTTTTAG CATTCATAGT TATCTAACTT TCTGTATTTT
43351 TTCTCTTTAT CTTGTTTAGT GTCTGTCTTC CCACTAGAAT GTAAGCTTCA
43401 TGAGGACAGG GATTAGTGTC TGTTTTGTTC ACTGCATCTC TAGGGCTTAC
43451 AACATTGTAG GTACTCAGTA AATATTTGTT AAATCAATGT GAAATGTGTC
43501 ATTTATCCTT AAGGAATTGA CCTTCATGGT AGAAGTGTAA CAGAACCACC
43551 TATATCCTAC TTTTCATCCA CATCATAACT ATTATGTGAA TACCTTGGAA
43601 GTAAAGCAAA ATAAGCACTT AACTAAAGAG ACGCTTTATA TTGAAACTGT
43651 TGTTCTGGGT TTCTGGAATT AGTACTCTGA AATTGGCTCC CTCTAGGAAG
43701 GCTTGTGAAG AGAGTAGTGT TGAACAGACA TGACAGTTTC CAAGAAAGCA
43751 TAGTTGGCTA AGAGGAGTAG GATTTTCCAA GCAAAGAGTG TGACAGTGGA
43801 GATGGCTGGG GCTAAGTCAG GCAGAATGTG TTCAAACCTG TTTTTCTCTG
43851 ACCTGAGATT GCGGAGGGAA TATTGGGAAG GTATAGTTAC CTGGTGAGGA
43901 GAGCCAGTTT TGTGAAGAAT CAAGAATGAG GAGATTTAAT TTGTTATGCA
43951 GATGTCTGGG AACCACAGCA GATTATCAGG AGAGCAAAAT TGTTAGTCAG
44001 AATTACATCG TTAGAAGGTA ATCCTTAAGT TTTGTAGATT TCTAGAATGT
44051 AAGGAAGCTC TCAGAGGTGC CATAAGGTGA GTATGGCCTA AGGATGTGGC
44101 TATGGCAGTG TAGCAAAATG GACAACTATG AAAAATGTCT AGAGAAAAGT
44151 GCAACATAGC TTATCAACGG TGCCCAAACA AATAGGAAGG ATGAGAACTT
```

FIGURE 3M

44201 TTTCAAGCTA CAGATTTCAG TAGTTTTGCT GCTAGAAATG CTTTAAGGAA
44251 AACTGTTAAA AAGATTAGGA ATGGGAATAT AGATAACCGG CTCCTAAATT
44301 TTGCAAGTGG GACCGTCATA GAAAGCTCTC CTATAGGTAT TGAGAAATCG
44351 AGATACCACG TAAGTTTCAA GAAGCAGTTT TTTTTTTCTT TTTGGTCAAA
44401 ACTAATGACA AATTCTGTCC CCTTGTTTGT ATATTTTAAC TTAGTGAGAC
44451 AGGAAACATT TATTCTATAG AAGACTTTTA AAATGTAGTT TAAACAAGTT
44501 GACACATGCT TACTGGTTAA TGAAATGTGC ATCAACCCAC TCCAAACACC
44551 ACTAATTTGA CATGAACTAA CAATTAACTT TTCTTACTCA CTGTCAAAAG
44601 TATATCATTC TGCCTTAACT TAACGCTTTA CCTTCTAAAT AAAATTTAAT
44651 CTTTTAAATA AGTTTTTCTG CTATGTTTTC CTTGCATATG TCTTAAATTT
44701 CTTCTTTCGT CTTTGCTCAC TGAAGAGCAT TTTCTCCCAC ATTCTAGTGA
44751 CTACCAGGGT TTGTAAGCCT AGAGCACCAT CCTTCATTCT ATCTAGCAGC
44801 AGTTGAGAAT AATAACAGCC ATATTTCTAT ATATGGAGCT CCTCCAAAGG
44851 CCTAGCCTGC ATTAAGCTTG TTAATTCTTA CCACAGCCTA GGTATTACTT
44901 TTGTTTTACA AGTGAGCAAA CTGAGGCTAG AAAAGAGGAA ATGACTTCAC
44951 ACATGTTATG TAGCAAGTAC TTGACAGAGC TAGGATTCAA GCCCCCTGAT
45001 CTGTTTGATT CTAAAGCCCG CACGTTTTCC ACCACAGGGC ACACAGTCCC
45051 AAACCATTTT ACTTAAACAC AGTTTGTGTG TGTGTGTGTG TGTGTGTGTG
45101 TGTGTGTGTG TGTGTGTTGT TTTTTTGATG TACCTCTTTG AGCCACCCAT
45151 GCATTTTTGG AGTTTCTTGC TAATTTTAAT TTTTTGTAAT TATGTTTCTC
45201 TATTTAGATG TTTAAATCCA TGAGGCGTAA ACTTTAAAGT TTCATGCCTT
45251 ATATTAATCC TTTATAGTCC ACCAAAAATG AAACTTTTTT CTTCCTTTTT
45301 TGGAGTGGAC ATGTAGTCAC TGCCTTTTTG GAGAATGCTT CTTTAGTTTG
45351 AAGCTTTCTT TATTGGACTA AAATTACTTT CCAATTAAAA TTTAACTCAG
45401 CAAATATTTA CTGAATACTT GCCATGTGCT AGCTAAAGAT AAACAATGTC
45451 TTGAGGGCAT GAAAGTGAAT GAGATACCTG GCCTTAAGGA GCTCTTTTAT
45501 ATTCTAGGTC AACAGAAAAA CATGTAAATA GTATCTATAA TCACTGCCCC
45551 AAGATGATGC TCCCAGTGCC CAAGGCCTTA TTGTACATTT CATTTAACTA
45601 AGTGTGTTAA AATCAAATTC TAAATGTAGA ATTTTTCCTA GGTATGCCTT
45651 GCAATAGCTC ATTATTCCCA GCCAACAGAC CTCCAGCTAC TCTTTGCATT
45701 TGAATATGTT GGGAAAAAAT ACCACAATTC AGGTAAATAT GAAAATATTA
45751 AATATTGTGA CTAATTTTAC ATGTGTAAAT TTTACTCTTA TGTTTACCGG
45801 AAGCCTCCAA GTACATGAGC TTTAATGATT GTAGAATTAC TAGCTTCATA
45851 CCTTAGAGAA GTAAGCACTA CATGCTAAAA GAGCCAATAG TTTGTCAGAT
45901 TATTTCTTGA CAAGTTACCA GGAAGAACCT TTAATGCTAT GAATATGGGC
45951 TTATAAGTTA TGTCAGATAT TTAATCTCCA GTCACTGGCT TGTATTTTAT
46001 GATGAAGAAT ATATAACCCA CCCTTTTTAA TTGATAGCTT GAGTTAAAGT
46051 AATCTTATCT TTTAAGAAAA CTGGCAGAAA ACTAAAAGAT ATATTAAAAG
46101 CATAATCTTT TCTGGCAAGG TGTGATTTCA TGCAAAAGCT AAAGTGATTA
46151 AAAACTTTTT GTGGACTTCA TTAAGATTCT CAGAATACTG AGTTTCTATT
46201 TCTGAGTAAT ACTGATGAAA GGAAGATGAG CATTTTTCCA AGGACAAGTA
46251 TATTCTAGAC AGCTTTTGTG AAAGTAAATA GTTTTGTCTA TATATCTGAC
46301 AGTCATGACA TGACCAGGGA AGATTCCAGA TGATCATGCA ATTCTGTACA
46351 TTCTGTTTCG TACAAATGTA ATTTTAATAA ACAATTTTTA AAAATATCTT
46401 GATAGAGAAA AACAAAGAGC CGTGTCTCCT GTTAGCCCCA TTGTCAGTTA
46451 GTGACTGCAA GTCAGTTAAC TGAGCGAAGC CTGTGTTCTT TTATTTAAGC
46501 AAGAAAAATA AATCAGCTGT GTATTTATAA TGAAAAATCC ATTCACCCAG
46551 CATGCTCTGG GCCATACAAA TTATTAATTG TACTGAAATT TTATATTTTG
46601 TTACCACGAA ACATGGTAGT AATTTAAATA ACTGGCATAA TAAAAGTATA
46651 TTCCAGCAAC ACTATATTGT AAATACATTA AAATGTATCA GTGTACGGTA
46701 TCTGAAGATG CATGTGTATA AGTAAATTTT CCTTAGTTTA AAAGATAACT
46751 ACCTTTCTGT TAAGCACTGA GAGGACCAAA AAAAAAAAAA AAAGAAAATA
46801 CAGTAGAGAT AATATATGAA AATAATGCTT TGCAGAGCAG CTTTTATCAT
46851 ACAGTATTAT ATTTATAGAA ATTGTATAAC AAAAGTATTT GTAACTTAAT
46901 TTTTCTTATC GATATATACA TAATTGTAAC TGAGGCTTAA GCAATACAGT
46951 TATTTTTTGA AGTTTATTAA TATTAAGTAA ATTCACTTAC TGTCTAAAAA
47001 TAAAGTATAC AGATCCTGCA CTATTAGGTA AACACTCCTT GGGATCATCG
47051 TCAAGCTACA GAACAGTGAT CAAGGTTATC TTCAATAAGA TCCTCACCCA
47101 GAGTTGCAAG GGTTGTAGGA GTGAGTCTTT GATTCCTGCT CAACTGTTTA
47151 TGATACAGAC CAGTTCTTCA TGCTGCTGTT TTTCCAATAG AAATGATTCA
47201 TTTCAGTTTA CAGATCCATA ACTTCTACAG TAATGTAGTG ACTTGGGCTC
47251 AGCAAAGACA GTAAACTTCA TTATACAGTT GGTAACCTGA TGCCTGCTTC
47301 AGTTACTTTC CACATTTTTC TTCATTCATA CCTTGTGGGC ATCTCTGGTT
47351 TACAGTACTT TAGTTTATCC ACCCATAGGT CTTCTACTAC TGGAATTTTA
47401 AAATCTACAT CATTCAGTTC CACTATTTCT TCTTATATAG CTTATTGATA
47451 AAATTTGATG ATTAATACTG AAAATATTCA GGGATGCTTT TTTATATTAC
47501 ATCCTTCAGA CTCCTCCTTT GACAAGTACC TCATAAACAT AACACTGGCC
47551 ATAGTTTTGT TAAGATTCCT CGTAGGGTAA CATCCTTTAA TATCCTTCCA

FIGURE 3N

47601 TGCTGTTACA GAAGCATAAA TACTGCATCT TTAAGATCAA AAGGAGCCTG
47651 AAATTTCCAC ACACTGCAGT CAGAATTCAT TAATTTGTGA GTGAAAGATG
47701 CCCACTCATC CACTCTTGAA CTTCTGGATG ACACCTTGAT TCATTGGCTG
47751 GATTAAAGAA GTCCTTTTTG CAGGCAGGTA GGTGACAAAG CTGTTTCCAC
47801 AAATAAGATC CAAAGTTGGA GGAGCTCCCC TGCAGTTATC TGAGAAAATG
47851 ATATTTTAGC TGGCCTTAGT CACTCAGGTT TTCATTCATA TTCAGTATCA
47901 CATGAGGAAA AGCCATCTCT GAAAGGTCCT GCAGTCATCC CAACACTTCT
47951 GTGAATATCC TGGAGTAAAG TAAGATGTGT AGCACCCAGG CTTTGGAACA
48001 TCGCTTTGCA CAAACACCCC AGGAGATATT ACTAGCACAA ACAAGAACAA
48051 TGATTCTGTT TTTTCTCTTT TAACTTTAAA GAAACCATGA GGACTCTGTT
48101 TTCATCAGTC AGATTATTAT TGGGCAAATA ACGTCAAAAA AGTACAGATT
48151 CATCTTTCTT ATAGAATTGA TAAGATGTCA GATTATGCTT CTGGACCAAA
48201 AATATTGAAA GTTTCATGAA GTTATCTGCA GCCTAGTGTC AGCAACTGCT
48251 TCATGACAGA CATCCTGCTT ACAGATGCTG TGATGTAATC TGAAGTTGTA
48301 ATGAAATTTC ACATCAGAAG TTGTACATTT TCAGTGACAT TTAATTTTAT
48351 CCTTTTTATT AACATAGATC TTGTTATTAG ATTTTCCTTA AAATGCCTAT
48401 TTGAAAAACA CAAGGTACAC AATCCATTTG AAACAGTATA GGAATTTTTA
48451 AACTTTGTTG CTTAAGATTC TCAGAATAGC TATAAATGAT TGTTGAATAT
48501 TGGTGGTTCC AGCCAGCTGT ATACATCAGG ATTACTGGAG GAACCTTTAG
48551 AAATGCAGCC ATGTTGGCTC CAGCACAGGT CAGAATCTCC CAGTTAAGAA
48601 CCACTTTGTT GACTCATGCT TTTGAACTGA TTAATACTCA CAGTCCTCTT
48651 TTTACCTTAT TCCTTTGTGA CTTCTAATTT CTGCAGTATC ATCAGAGTGG
48701 TGGGCTTTCT TTTCATATAT TGATGACTTG TATTTTCTGT TGCTTGAAGC
48751 CATTCTAGAT ATCAATTGGC CAATTCAGTG GAAATTATCT AAAATAACCC
48801 CAACAGTATA GGATTAGACT TTTGTACTGT CACAGAAGAT AGCCAAGGTC
48851 AGGAGCATAT AATATCTATT TCACGCTTAG TCTGCTGTGG AGGCATGTCA
48901 TAAAACCTCA GTCAGGTAGC GGTCAGCGGA GCCAGGTCTC CCTGAGATGA
48951 CCCACCTTTC ACTGTGTTGG TCCAGCCCCT CATAGCGATC CACTCATAGA
49001 GCAGGCCACT GGTATCAGGT CTTTTGAACT TTGGAAAGCA TTCAAATTTC
49051 TGGACTATAA AACCAGATTG AGTATACATT ACACATTCTG TAATGAGCTC
49101 TAACTGAAGA TGATATAGAA CATATAAAAG ACCTAGTCCC AGTTGTTTAG
49151 AAAAGTACAG GATTTGAACG AGAGAAATGG CAAAAATAAC AAACGATAGA
49201 GGATCTCACT TTATGCTTAG AAAATATAGA TGTTCTCATT TTACGTTTAG
49251 AAAAATTTGT GTAAGTTAGA TCTTGAAACA AAATTTGGCC AGAGAAACAA
49301 TCTCATAAAC AATAGCACAT TCTTAGCCTA GCTTATTAAA GTCTGCAACC
49351 CAAAACACTA AAAAGTATTC AGTGCTGCTG GACTCAGTCA CCAAACTGTT
49401 TTACATAACT GTTAAAATTT TGAGTGTGTT TTTTATAATT CTTTTTTGGT
49451 GGTGGTGGTT TTATTGTTTG GCTAGGACTG CTGGTTCAGT GTTGAATAGC
49501 AGTAATATTA GCAGGCATAA TTTCACTTCC CGCTTTTAAT GAAGATGCTC
49551 TTAGCTATGT CTTTTTGATA AACACCCTCT ATCCAGTTAA GGAAATTCCC
49601 TTTTATTCCA AACTTGCTAA CGTTGTTGGG TTTTTTTTTT TAAGTCATAA
49651 ACAGGTATCT ATCATATGTT TTTCTGCACT TACAGAGCTA GTCATTCATA
49701 TAGCCTTTTT CGTGTTTAAT GTAGTCATAT GATGAATTAC TTAGATTTTC
49751 TAATATTGAA TAGCTTTCTT TGTTTTGGTG CACTGGAACA CTGTATAGAT
49801 TGGGCTTTGC CAAAAATTCC ATATGCAGGT TTTGTGTTCT GGAGAGATCA
49851 TAACTCCTAA GTCTTCCTTC TCACAGACAC GCTTTTTAGT TGTGTTACTC
49901 CAGAGAAGGC CCTGAGATGG AGTGGGACTC TAGGATGTGG GCTTAGAATG
49951 AGCATTTTAC TATCTATCTA TCTATCTATC TGTCTGTCTA TCTATCTATC
50001 TGTCTATTTA TTTTTGAGAC AGAGTCTCGC TGTGTCGCTC AGGCTGGAGT
50051 GCACTGGTAC GATCTCGGCT CACTGCAAGC TCTGCCTGCC AGGTTCACAC
50101 CATCTCCTGC CTCACCCTCC CAAGTAGCTG GGACTACAGG CACGTGCCGC
50151 CACACCCGGC TTATTTTTTT TTTTTTAGTA TTTTTAATAG AGACAGGGTT
50201 TCACCGTGTT AGCCAAGATG GTCTCGATCT CCTGACCTTG TGATCCGCCC
50251 ACCTCGGCCT CCCAAAGTGT TGGGATTACA GGCATGAGCC ACCGCGCCCA
50301 GCAACATTTT ACTTTTTAAT GAGCTTTGTT AAAATCAGAA TCACTGGATA
50351 ATTCTGATAC CACTTAAGAG GAGTCCAAAT TCCTAACATA GCCCCTCCGT
50401 AATCTAGAGC AGCACCGTCC AGTGATGGAA GTAGGGCAGC CACTAGAGCC
50451 ACTAGCCACA TGTGGCTGTT AAGTACTTGA AATGTGGCTA GTGCAACTGA
50501 TGGACTGAAT TTTTAATTTT ATTTAATTTT CATTTCAGTT TAAATTTAAA
50551 TGGGCTTGTG TGGCTAGAAG TTACGTTTTT GGGAAACATA CTAGAGTCTA
50601 GGCCCTATTT GATTTCCCGC CTCTCTTCCA CCACCTGTTG AATCCCTATG
50651 CTCTAGCTGT ATTTAGTTAC TTGATATTAT ACAGTTATAC CATCTTTTTA
50701 AAGTTCTTCT CTGTCTAGCA TGCCTACCTC CTCCTCACCA GCTACCTGGC
50751 AACTTTTGAC TTGTTCCTTA GAACTCTCTT TAGTTGTGGT CAAGTCATGA
50801 AGCTTTTCCT GCCCCGGCCT CTCTCTGCAG CGAGAGTTAG GGGACTTCTC
50851 TTTTGCATCT TCATTGCACT CAGACATCTG GTACTCTGTG ATTATCACAC
50901 TTATTAATGC TCTCAAGATA GAGATAAAAT CTTATTCATC TTTTTGCTCT
50951 CAGGCATTAG CACATGGGGA GTTCTCAGAA AATACCTGTC TTATACCAGG

FIGURE 3O

51001 AATTAATGAA TAATCAGTAG GAATGAGCAT GACATGTTCA TGGGACGTTG
51051 GAGGGTAGTG CATGGCTGCA GAGGAGAATG GGAAATGAAG GTCAGATAAG
51101 TTACGTGAGG GATCTCTAAG GCCAAGAGAA GCCATTTAGG TTTGATTTGG
51151 TTGGAAAATG AGCTTATTGA AAGTTTAAGG CAAGGGACTA GCATCATGAA
51201 CACATCTTTT TAGGGAAGTG TGTCTTGTGG TAAGCTGCTG GCTGGTTTAA
51251 ATGCAGCAGA ATATTCCATT GGGGATGCCA GCTGGGAGAC TTGCCACAGT
51301 TGCAGCCTGC AGCAGAAAGA CCCTGGGCCA GAATGGGTTG TGCCATCTGT
51351 CACCAGATAT TGCCAAGGTA GATCTGGCTG ACTTTGTGGG ACAGCTTGTT
51401 TCTCAATAAT CACTTTGCAG GCACTCTTGA GGCTGTGAGC ATGCTCCCAG
51451 AAGATAGCAT TACTTCTCTC TCAGAGCAGG CTCCTTTCTA AGGAAATGCA
51501 AGTCTAGGCC TGCCCTGCTG TAATCTTCAT GTGGAAACAG CACTCTAGCA
51551 AAGAACAAGG AACCTGATGA GCTTTTCAAA GGAAAATCGA GTAGATACAG
51601 GAAACCAAGA ATTTTCTAAT GAGCAGATAG AAAAGAGCAG GTAGGTGAGA
51651 AGTTGGTATT AGAAAAATTA AAGATTTGAA GGGCTTGAGG ACAGAGATGA
51701 TTGTTGGATG TTTCATTTTT CCAGGCAAAA TATGTGGAGC AAATAATCAA
51751 ATGACATGGA CTTACCCCAC AATTAGGGAC GGAGATGAGG AAGGGTTAGG
51801 AATAGTTTCT GTTAGAATGG TAGGGATGGA AGACAATTGA AAATTAAAGA
51851 GAAAATAAAT GGAGAGGAAA TCTAGGCAGC AGCCATTCTT CATTCTGGGG
51901 GAAGGTGGTC AGGAAAAGGA AGGAAGAAAA ATGTATAGCA TAGTAGCTAG
51951 AGTGGTCCGG CGTGATCAAA GTGTTTTCAA TATCATGTTG ACTGACCTGT
52001 TTACGTTTGA AGGCAGAGAA GATAGAGCCA GTAGAAGGAG AGAAAAATCA
52051 AAGCTGTTTT ACGGAGTTGT GAAAGAGCTG GATAAGGACA AGACTAAATG
52101 AGTTATTTTT AGGCCAGGCG TGGTGGCTCA TGCCTGTAAT CCCAGCACTT
52151 TGGGAGGCCA AGGCAGGTGG GGCACCTGAG GTCAGGAGTT CAAGAGCAGC
52201 CTAGCCAACA TGGTGAAACC CTGTCTCTAT TAAAAATACA AAAATTAGCT
52251 GGACATGGTG CATGGTGGCA GGTGCCTGTA ATCCCAGCTA CTCAAGAGGC
52301 TGAGGCAGGA GAATAGCTTG AACCCGGGGG GCGGAGGTTG CAGTCAGCCG
52351 AGATCATGCC AGTGCATTCC AGCCTGGGCG ACAGAACGAG ACTCCGTCAA
52401 AAAAAAAAAA AGGAGTTATT TTTAAATGGA AAGGGCAAGA CAGTTCTCGG
52451 AGAGACTTGG AAGGTGAAGC AGGTTAGAGA CAGCACATCA GAGTATGCAT
52501 GTGACAGGAG GCTCAGAGAA GAGGGAATGC TGGGGAAAAT GTGACTGTTA
52551 AAATTCATAA TGTTGCTTTT TCCTACAGCA AACAAAATTA ATGGAATTCC
52601 CTCAGGAGAT GGAGGAGGAG GAGGAGGAGG AGGTAATGGA GCTGGTGGTG
52651 GCAGCAGCCA GAAAACTCCA CTCTTTGAAA CTTACTCGGA TTGGGACAGA
52701 GAAATCAAGA GGACAGGTGC TTCCGGGTGG AGAGTTTGTT CTATTAACGA
52751 GGGTTACATG ATATCCACTT GGTAAGTACA ATTTTAGCAA TGTTATATAT
52801 GGCTGGAAGT CACTTCCCTA TGAATAATCA TCAAACTCTG TTGTCATTGA
52851 TGACTTTCAA GTTGTGGTTA ATGGAATATT TGTTTTTAAT AATGTTTTAA
52901 TAAATATTTT ATTTTAAAGA TCAAGGCTTA TTAATATAAA TTACGGTATC
52951 CCTTAAAAGA AGTTGATAGT AATTCCTTAC TGTCATCAGT AGTCAGTGTT
53001 TATTGCATTA TATCTTGTAA CTGGTGTTTT ACAGTTGGTT TGTTCATATC
53051 AGGATCTAAA GTCTTCACAT TGAATTTGCT TAATATGTCT CTTAGGCCTT
53101 TTAATCTACA ACAGTCTCCT CCCACCTCTT TTTTACCTAC TATTTGTTGA
53151 CAAACCAGGT CATTTGTTCC CTAGAATTTT CCACATTGTA GATATTGCTT
53201 GTTTTATCCC CAGGGTGTCC CGTAATGTGT TCCTCTGTCT CTAATATTTC
53251 CTTTAAAATG TTAGCAACAG AGGCTTAATC GGATTCAGGT TCAGTACTTT
53301 TGGCAAGAAT GTTTCATTAG GTGGTTCTGT GTTCTCCTGT GGAGTCACAT
53351 CCCATCTCAG GCTGGCTGGC TGTGTCTCTC TCATTGTAAT CCTGACGACC
53401 AGTGGGCTTA GAGGGTGTCA ACCTGATCCA CCCAGTAAAA GTTCCCCTCT
53451 TATATCATGG TTTGAGCTCC CAAAAATAGT TTTGCACTGG GAGGGAGGAT
53501 CATTGCTCAG ATCGTTATTT CACTAAGGAT TGCTATTGTT CACCTTCTAA
53551 TTCTATCATC TTTCTGCTTT TATCGAACTT TTCTCTCACC AGCTCTTTAG
53601 TGCCCTGTAA CACAGTTCGT ACAAGAAAAG CAATATAAAT ATCTACATTT
53651 TCTCCTTTAC TTAACATTTT TCCAAATAGT GAGCTGGTTC CCTAGGGGAT
53701 CTTCTAGAAG TGACTAGGAA TTTGTTTTTT TAATTTGTTT AATGTCATTT
53751 AGTTATTATG AATTTTTTGG AATGCCTTAT TTTAAGGTCA TTGAAGTCCT
53801 CATTAGTTCA CGCACATAAG CAGCTTTTTA GAAAAAGGAA GAAAAGCACT
53851 ACTGTGTTAT TACTGGTTAA TCCAGTACCA GGAACTTCTA GTACAGTTCT
53901 AGAAAGGTGC TTTGCAGCAT GTAGCTTGTA TCTTTTGCTT CCCCTGGAAT
53951 TTAAGCTTCA AGGCCAGCAC ACTCTGGTAT ATGTGCTGAG AAACATGTGA
54001 TGGGGCTGCC CAGCCACGTC GGGGAAAGAA GGAAGATGTC TTGAGGTGCA
54051 GTGAGCTTGC CCACTAGTAA TTATTGTCTG ATCAGTGTCC TAGAGTCTGA
54101 CTGTGCCTTT TAGGCATGGG GAAAGGTAGA AGAGGGACTT AAGAAGAGAG
54151 CTAAAGCTCC TGGTAGATTT GTGGGGTTTT CTTTTGTTTG CCTGGTGTCC
54201 TTAACCATAG CCTGTCAAGA GAACAAAGGT GGATATATTT TTCAGTGAAC
54251 ACATACATGT TTAATAGTCA TTCTGGAAAA TATTTCTAAT ACCTTCTTTG
54301 GAATTTTCTC ATGCTATAAA TTTAGATTTT TAAGAATTGG TCATATCGCA
54351 CCAATTTTAG ACTAAGAGGT GTAGGATCGT CACTGCCCCC CCATGGTGCC

FIGURE 3P

54401 CACCATGTGG CTACTAAGTG GGGTGCACAT TAAATGCGGA CAACTTGCTT
54451 AATTATTTAT AGGGTCTGCA GGAGCACACT ATTCCTGCTT TTAGCACAGC
54501 ACTCATATAA TTTTTTTTTT CCCCTCCAGC CTTCCAGAAT ACATTGTAGT
54551 GCCAAGTTCT TTAGCAGACC AAGATCTAAA GATCTTTTCC CATTCTTTTG
54601 TTGGGAGAAG GATGCCAGTA AGTGATTTCT GTTGGATTTT ATGAATGCTG
54651 ACGTCCATTG TTTCTACACA GTGAAGTAAG GATTCTACCT CTCCCCTAGC
54701 TCTGGTGCTG GAGCCACTCT AACGGCAGTG CTCTTGTGCG AATGGCCCTC
54751 ATCAAAGACG TGCTGCAGCA GAGGAAGATT GACCAGAGGT AATTGAGAAA
54801 TGGTCATTGT CACTTTAGAT AGTTTTACTT GTTGTGTAAC TACAGTGAGT
54851 TCCCTACTAA TTGAAAATAA CAAAATGCAT AGTCTTACTA ATTAGTTAGC
54901 ACCATGTTTT ATATAAGAAT TGCCATTTTG AAAAGAATGT GATAATATTA
54951 AAATTAACTG ACATTGGAGT TACACTAAAT ATAATTTAAT TATTTGGTTT
55001 GTAAGACACT TGTGGATCTT ACATTGCTGA CATCTTGCTA TAGCATTTCC
55051 TATAACATAC TTTCAAAGTG CAGTGATATC CAGTTGAGAC ACTTCAGGAT
55101 AAATCAAACT TTTCTTGTAG ATCTGATGTG TCTTATTTAG GTCTACACAT
55151 TTGCAAATAG CCTAGACAGT GCTTTTAATT AGCCACCACA GACGAGTCTG
55201 GCATCATCTG CTGTGGGTCA TAGTAACTCC CCGTCATTAA AGTAGGAGGC
55251 CTTTCTCAGT TGTGCTCATA GCAGTGAGCA ATACTATTGA TCACTCTCTC
55301 CTTAAACCCG CCTGGGCCCT CAGCCTCTGC TCCTCTCCAC TCTCCTGAAG
55351 CTCCTCTTCC TCACTGGCAC TCCGTGCCTT CTGCAGACCC ATCCTCTTCT
55401 CTCCAGACAT TACACAGATT CTAAGGCCGC TTCCTCATGT TCTGTATTCT
55451 TTTCCTAAAG AAGTTTCCCC AAGAATGTGG CTTTAGTGAC CAACACATTT
55501 ATATCTTCAG TCTACCTTGA CTTCTACATG GAGGTCTCAA AGACCCCTTA
55551 AACTCATTAT GTCCAAAACC AAACTCAAGG ATATGGCCTC CATGCCCTCC
55601 CCCAGCCTGC TCTCAGAAAC CGGGGGGTCA TCCTGGATGC CTTCCTCTTT
55651 CTTTCCCTTC CCCATCACCA ATCCCTCCTC AGGTTTTCTC ACTTCACTTT
55701 TCAGACACCT TGCAAACCCA TGTGCTTCCA CAAACCCAGC TCCACCTCTG
55751 CCTGTGTGTT ATAAGTGCTA TCATTTCCTC CTTCCATGTC TCCTCCACCC
55801 CTGGGCTCCA GCCCCCTGGA CTTTCCCTGG TGTTTTCAAC CTCCTGACAT
55851 TGTCCAGCGC TCTTCCCTTC TGGACTGCCT TCTTTGCACT CATCTGGGAA
55901 CACTCTCCAC GCTTACCCAC TTGGCACTCC TTGTTTCTTT TTTTTTGAGA
55951 CAGAGTCTCA CTCTGTCACC CATGCTGGAG TGCAGTGGTA CGATCTCGGC
56001 TCCCGGGTTC AAGTGATTAT CATGCCTCAG CCTCCTGAGT AGCTGGGATT
56051 ACAGGCACCC ACCACCACAT CCAGCTGATT TTTGTATTTT TAATAGAGAC
56101 AAGATTTCAC CATGTCGGCC AGGCTGGTCT CGAACTCCTG ACCTCAGGTG
56151 ATCCACCCGC CTCGGCCTAC CGAAGTGCTG GGATTACAGG CGTGAGCCAC
56201 TGCACCCGGC TCACTCATTC TTTATATCTC AATTCAAACA TCATTTCCTC
56251 AAGATAAGCC TTCTCTCCCC TCTAAAGTTT GATCAGACCT CAAAAGTCTA
56301 TGTTCTTAGA GCTCCTGAGT TTTTAACATT TATTTCAGTT TTTAATTATA
56351 TATGTGTGTG TTACAGTTTG ATTACCGCCT GTCGTTTTTA CTCCATGAGA
56401 TGAGGGACTA TGTCTGTTTT GCACACCGTT ATATATTTAG CACCCAGGAA
56451 GCATATATGA TATTTATTCA ATACTTGTTG AATAAATGAG GAGTAAATGA
56501 ACAGATCTTA TAAAACAGGC TTATGGAGCC TCAGAAATTG TGTATCACAG
56551 TCCTTTTTGG TACAGCCAGA GTGTAGGGTT TTTCCACTGT ACCGTAACTG
56601 ACAGAGCCAT ATTCACTGAA GCAAATAACC ATCAAGTGAC CCTCAAATGA
56651 CCTTCAGTTT TCTGGAAAGG AAGGTGACTA TAGTTCACAC GAGTCCGTAT
56701 TCTCTGTGGA TTTTGATTTA CCTGAACTCC ATTTGGAATT AACTGTCTGC
56751 TGTGTCATAC TCCAAGCCTT GTTTTCATTA GCATACATGC TGATGAAGTG
56801 CACAGTTAGG AATTTTGCTG TTAAAGGGAC AATTGTAGCA TTGTTGGGTG
56851 AGAGTTAGTT ATAAAACCTT ATAATCAGTG GCAGTTTCAG TGATTTATTA
56901 AGCTGAAAAT TACTTTAATG CCTTTTGTGT TTTCAGCTAT CCTATTCTTC
56951 ATAAGTAGAA CAGATCCTCT TTTTTGTCCA ACCTCGTCTC CTAACCTTTT
57001 TCCCTCAGGT GTGTCATCTA GCCCCACTGG CCTTCTTTAG GTTTCTCAGC
57051 AGCCATGCTT GTTACCTGCC ACAGGGCCCT TGCACTAGCT GCCCTCTGCC
57101 TAGAACATTT TCACCCCAGA TCTTTACATT GCTTCTCTAT TCATTTAGGT
57151 TTCGGCTTCA GTACCATCTT CACAGAGCAG CTGTTTTTCA CCATGTGACC
57201 TAAAGTAGCC TGTAATCTCA TGATTACATC ATCCATGGCA TTCACCACAG
57251 CCCATTTATC TTATCATCTA CCCCACCCCA CGAAGAATGT CAACCCCCCA
57301 CTTGCTTGGG CAACACCAGT AGTAAAATTG GAATGATACA GGGAAGGTTA
57351 GCATAGCCCT TGCACAAAGA TGACATGCAG GTTCATGACA CATTACATAT
57401 TTTAATGAAA TGGGAGCATA TTCTTGTTAT TTAATTTTTA AAAATCAGTT
57451 TATCAAGCAA ATGTACAGCG CCATTTTATT TTTCATGCCT ACATTAAATT
57501 CCATACACAT AAAGGTGCAT AGAGGAAACC TAGAAAGATT GCACCAAAAT
57551 TTTAGAATTC TGAGTGATTT TGTTTTTCTT ATCTTTTCTA GGTGTTTTTA
57601 AACATTCCAC ACTAATTTAT ATTACTTTTT CTATTCAGGA AAAAAAAAAA
57651 CAACAGCAGG GTTTTGTTTT GTTTTTTTAA AGTGGTGTGG AAGTTACCCA
57701 TTGAATATAG ATGGGAATCC CAGTCCTGGC TGTTTCCTTT GAAAAGATCT
57751 AGAGACCCCA TGGCACATAT TTATAGTAGC CCATTCTCTC CTAAGAATAG

FIGURE 3Q

57801 AGGAAGGGTG GGAGGAATTT TGGTGAATGT CTGTACTTGC AGTTTATCCT
57851 ACAGCAAATC GTTAAGACTG TGGGAATAGG TGCTTTGCAT TCTCTAGAGC
57901 TGGAGAATGT GCATCTGGTT TGCCATCCTT CTGTCTACAT CATGTGGAAA
57951 GATGTGGGAG TGTAGGGTCT CCTTAATCTA AATGCAGTGC TGCCCCGCCC
58001 CCCCCTTGGC AGTGTTTCTG TTTCCCAGGC AAGTGTTCCA ATGGATGTGC
58051 TTTATTTTCT CCCATCAGAA ATAAGGGAAT GAGCCCGGGC GCGGTGGCTC
58101 ACGCCTGTAA TCCCAGCACT TTGGGAGGCC AAGGGGGGTG AATCACAAGG
58151 TCAGGAGTTT GAGACCAGCC TGGCCAACAT GGTGAAACCC CGCCTCTACT
58201 AAAAATACAG AAATTTAGCC AGGTGTGGTG GCGGGTGCCT GTAATCCCAA
58251 CTACTCGGGA GGGTGAGGCA GGAGAATCGC TTGAACCCGG GAGGGGGAGG
58301 TTGCAGTGAG CCGAGATGGT GCCACTGCAC TCCAGCCTGG GCGACAGTAT
58351 GAGACTCCGT CTCAAAAAGA AAAAGAAGGA AATGATCTAA TTTGTTCTGT
58401 GCACTGCACG TGGGGGTGGC AGTGAGGTGA ATGGCAGCAT TCTGCAGTAG
58451 TCAAAGCCAG ATGGGTGGGA GAAGTTGGGT GCTAAGAGGG AAACAAAGTT
58501 TACCTGTCTT CTCCTTGATT TCACTCTCAG TTTTATGAGA ATACAGAAAA
58551 ATCATGCAGA GAAACCTGAT GGAATAGTCT CTAAAACTAA AAAATAAGAT
58601 AAGCAATGGT TCTGTCTTAA AAAAAAAAAA GTAAACTCCA TGAAGGCAGA
58651 GACCTTACCT GTCTCATTCC TCTCTCTATC CCCTGGTCTA TAGTAAGGGT
58701 TAAATAAATA TATGCTGAAA TGAATGAGTA ATGACTAAAG TATTTTTGTC
58751 TTTATTAGGA TTTGTAATGC AATAACTAAA AGTCACCCAC AGAGAAGTGA
58801 TGTTTACAAA TCAGATTTGG ATAAGACCTT GCCTAATATT CAAGAAGTAC
58851 AGGCAGCATT TGTAAAACTG AAGCAGCTAT GCGTTAATGG TAATTTCATT
58901 CTTATTTCAT ATATATAATG AACACAGGAT ACAGAGTTGC ATGAGATGTC
58951 AGGAAAAGTG ATGTTCTTAA AAATGTAGAA ATAGATATAT TTAAGGAGTC
59001 TATGGAACTA TTTGTACAAA TTATATATTA TTGTATGAGA ACTTCAGAAC
59051 CTCCTAAGGA ATTAAGTTTA AACTACTTTT TGTTTTAGAG GGGGAAAAAT
59101 GAGTGTATTA AATTTCCTTC AGATGATGAA AGGTATAGGA GAATACTTTT
59151 ATAAAAGCAT TTGCTGAGTA GAACACTGTA TTACCTTACA GACAAACTTA
59201 TTAAGATTGT AATACATACA GTTATACTTT GAGATAGGTG ACTTGACATG
59251 GGTATCAAAC AGCTGTGTTA TATCTGTAGC ATCAGAATTC TGATATATCT
59301 GAGCAAACGT ACCAGGTGGC TTTCATGTGT CCTGCGGGAT GAGTCACATG
59351 AAAGCATCTT TGGTGTAATG TGGGTCCTCC TCAAGAGATC CTCTAAGTCA
59401 CCAGGGAGTC AGCAAAGGCA GCCTTGCAGC AGATCTTGAG CAATGAGTAA
59451 GCACTTCCCT GGGGGAGGGC CTTGCAGGGG CGGGGCAGGG GCAAGTTGTT
59501 GAAAAAACTA GTGTCCTGAA TGATTATGTG CACTCTGGGC AGGGCAGTGA
59551 GGATGCCTGT CCTCATGCAG TGGCTAGCCC TCGGCCACGT GAGCCATGCA
59601 CAGAGGCACC ACTGGCAGCA GGGGTGGGGC AGGGAAGCAG GAGGGCAAGG
59651 CTTGCAGTGA GAAAGCCAAG GGCTAGGGCC TGGGCAGCTG ACCTCACAGG
59701 TCAGGAGGGC CAGGATCAAG GCATAGGCTG AGCAGGGACG GCTGGAATTC
59751 TTAGCTGTTG GGAGTCAGAG TTGGTTGGAC TCCAAGATTT CCCTGAAAGA
59801 GCGAGAGAGA AGATGATGGA GCCCCAGGGG AATGCTTTGT TTTGCTTTGT
59851 TACAGAATTG TAATGTCTTC TTAAATGCTT ATTCCATGTT ATTAAAGTGA
59901 AAATGCATGA TATTTACTTA AAGCTAACTT TTAAATATTA GAAACTGATG
59951 TATCTCTTTA CTCTGATAGG GATCGTATAA AATAAAAAGT AAAAATGTGT
60001 ATGTATATAA TTTATTACAG AGCCTTTTGA AGAAACTGAA GAGAAATGGT
60051 TATCTTCACT GGAAAATACT CGATGGTTAG AATATGTAAG GTTTGTACTT
60101 CTTTACTTTC TTTTCCTTTA ACTTTTTATT TTGAGATAAC TACAGACTCA
60151 CTGGAGGTAC AAAAATAGCA CAGAGGGCCA TGTACTTACT CTTCATCCAA
60201 CTTCCCCCAA TAGTAACATC TCGTAACTAG AGTACAGCAT CCAAACCAGG
60251 AAGCTGACAC TGGGACACTG GATAGCTCTT ACTCACCAGT TCATACATGC
60301 TGTCGTCTGT GTGCATGCCC TTAACACAGC TGTGCGATTT TATCACGTGT
60351 GTAGGTTCAC GTAACCACCA CCACAGGGAG ATACAGACCT GTTCCATGAC
60401 AAGGCTCCCC TGTGCTAGCC TTCTTATAGG TGCACCCTCA TCGCCATCTG
60451 TGTCTGTTGA CTACCACTAA TCTCTTCTCA ATCTCTATAG TTTTGTCATA
60501 AGTCAACCCC TTCCTTTTCA TAAAGGGTTT ATGAATTTCC CTGATGAAAA
60551 AGTACAAAAT GAGGCCAGGC GTGGTGGCTC ATGCCTGTAA TCCCAGCACT
60601 TTGGGAGGCC AAGGCGGGTG GCTCACCTGA GGTCAGGAGT TCAAGACCAG
60651 CCTGGCCAAC ATGGTGAAAC CTTGTCTCTG CTAAAAATAC AAAAATTAGC
60701 CAAGCATGGT GGCACGCACC TGTAGTCCCA GCTACTCAGG AGGCTGAGGC
60751 AGGAGAATCA CTTGAACCTG GGAGGCAGAG GTTGCATTGA GTCAAGATCA
60801 CGCCACTGCA CTGCAGCCTG GGTGATAGAG CAAGTCTCCA TCTCAAAAAA
60851 AAAAATTTAC AAAGTGGGGC CGGTTGTGGT AGCTCATGCC AGTAATTCCA
60901 AAGCTCTGGG GAGGAAGATC ACTTGAGGCC AGTAGTTCAC AACCAGCCTG
60951 AGCAACACAG TGAGACCCCA TCTCCACAAA AAAGTTGGAA ACTAGCCAGG
61001 CATGGTGGCA TGTGCCTGCT GTCCTAGGGA GCCTGAGGCA GGAGGATCAC
61051 TTGAGGCCAG GAGTTCACAA CCAGCCGAGG AACATAGTGA GATGCCCATC
61101 TCCACAAAAA AATTTTAAAA CTAGGCAGGC ATGGTGGCTC GTGCCTGTGG
61151 TCCTAGCTGC TCAGGAGGTG GAGGCAGGAG GATCACTTGA GGCCAGGAGT

FIGURE 3R

```
61201 TCAGGGTTAC AATGAGCTGT GATATGCCAC TGCACTCTAG TGTGGGTGAC
61251 AAAATGAGAG CCTGTCTCTT AAAAAGAAAA CAAAAATTAC AAAATATACT
61301 CCTTTGAGAA ATCGTATAAG TAACTAAAGA AACTTTACGG TAATGCGAAA
61351 GCTATGTGCA TTCAGTAGAA AGCAGTCAAT CCTCTCTTGT GATGCTGAGT
61401 AGCAGCAGGG AGCCACAGCT GCCAGTCAGC CACACAGTCT CAGTTTAGGG
61451 TATTTTCAGC TTACAGTGGG TTATCATGGG TCATGAGTTA TGGGAATATC
61501 ATGATCAGAG AGCATCTGTA AAGTGAGAAA TTAGATTTGC TTGATTTCAA
61551 GTACTTTATG TATTTGTAGT GGAAATTTGA TTTTTAACAC TGCTTTTCCT
61601 TTTCTCTCTT CAGGGCATTC CTTAAGCATT CAGCAGAACT TGTATACATG
61651 CTAGAAAGCA AACATCTCTC TGTAGTCCTA CAAGGTAACT AAAGTAACTC
61701 CTGAAAGCAC CATGACCACC ATACCAGCCA GCCTTGGTTT ACTGCTTGTC
61751 CCCATTCAAG TAAATCACAT CAGTTTTAGC TATTTCTTAT TTACTACAGT
61801 ACCATCAAAT ACATTACAGA TTTTGCACAT CATTTGAGTA AAACAGTGGC
61851 ACAGGCTGGG CGCAGTGGCT GAAGCCTGTA ATCCCAGACT TTGGGAGGTC
61901 GAGGCGGGCG GATCACTTGA GGTCAGAAGT TTGAGATCAG CCTGGCCAAC
61951 GTGGTGAAAC CTTGTCTCTA CTAAAAATAC AAAAATTAGT CAGGAGTGGT
62001 GGTGTGCGCC TGTAGTCTCA GCTACTCGGG AGGCCGAGGC AGGAGTATCA
62051 CTTGAACCTA GGAGGCGGAG GTTGCAGTGA GCAGAGATCG CACCACTGCA
62101 CTCCAGCCTG GGCAACACAG CAAGACTCAA AAAAAAAATA AATAAAAACC
62151 AGTGGCACAA GGACTGCAAA TAGAAGAATA GAAAGTAGTC CAGTTTTTAC
62201 CCTTTATTAA ATTATCCTTC CTATTTTATG GGAAGGGTGG GTCCCATCCC
62251 CTAATGGATT AATACTTAGT GTTAATTTTG ACAGGGCATT CTCTCTCTGT
62301 AATTTTGCTG TCTAATTTGT ACAAATTTGT TTTAGTTTAA ATACCTTCTG
62351 GCTCATGCTA GATTATGACT CTAAGGAAGC AGTTTGAGAT GAAGAAATTT
62401 AGACTGAACT GCTGAATAGC TAGTAATGTA ATATTTGGTA GGAATAAACG
62451 GTGATGTAAA AATCTTTCAG TTAAGCAAAG GATAATTACA TATTAAATAA
62501 CTTACAGCTA ATAGAATTTG TAAGTTTGCA GATAAAGTTC AATAGACTAA
62551 AAACTACCTT CGTATAATAC AGTAGTAGGT CCTTTGTACC CATGGCTTCC
62601 CCATCTGTGG TCAACCAACC CAGGACTGAA AATATTGGCG GGGGAAAGCT
62651 TTGGCCGTAA TGAACATGAA CAGACTTTTT TTTTGTTGTC ATTATTCTCT
62701 AAACAGTATA GTATAACAAC TGTTTACATA GCATTTACAT TGTATTAGGT
62751 GTTATAAGTA ATCTAGAGGT AACTTAAAGT GTACAGGAGG ATGTGCATAG
62801 GTTATATGCA AATATTAACA TCATTTTATA TCCAGGACTT AAGCATTTGT
62851 GGATCTTGGT ATCCAAAGGA GGCCCTGGAA TGAGTTCCCC ATGGATACTG
62901 AGGGAAGACT ATATACTCAT GTTGCATAGT ATATGAATAC AAAATGTTGC
62951 TTAAGCTTGC AGAAGTACTT TTTTTTTTTT TGAGATGGAG TTTCGCTCCT
63001 GTCACCTAGG CTGGAGTGCA GTGGAACGAT CTCAGCTCAC TGCAACCTCC
63051 ACCTCCTGGG TTCAAGCGAT TCTCCTGCTT CAGCCTCCCA AGTAGCTGGG
63101 ATTACAAGCA TGCACCACCA CGCCCGGCTA ATTTTTGTAT TTTTACTAGA
63151 GATGGGGTTT CACCTTGTTG GCCAGGCTGC TCTCGAACTC CTGCCCTCAG
63201 GTGGTCTGCC CACCTCAGCC TCCCAAAGTG CTAGGATTAT AGGCGTGAGC
63251 CACCGTGCCT GGCCAGGCTT GCAGAAGTAC ATTTAACAAC TGCCAAACTT
63301 GATTGACTTT AACAAGGCAA AAATCTTTAA GACTCTTAGA AAAAAATCAA
63351 ATAGTAATGT GTCATATAAA GTAATCCTGA ACTGATACAG TCAGAGTGTG
63401 TGTTTAACTC ACAAATGCAT GCAGAGCCTA ATAATCACAA TTTCTCTCAT
63451 CCAGTGGGTG TTCTCATCGT ATTGGAGAAC CCTACTCATC CTCCATTTCT
63501 CCATGCATTT GTAATAGAAA AGGCCTCAGA AGTAGCACTG AACCTTCATT
63551 TTACTAGCAT TTTTATATAC GTTTATTTTT AAACAGTTTG TTAAAAATTT
63601 ACATACTATG GAATTCACCC ATTTTTAATT TGTAATTCAG TAAATTTTAG
63651 TAAATATACA GAGTCTAGTT TTGGAAATTT TTCATCACCC CAAAAGTCCC
63701 AGCTCCAGGC AGCCACTAAT CTTTCTGTCT CTAGATTTTC CCTTTCTGGG
63751 CATTTCATAT AAATGGAATC ATACAATATG TGGCCTTTTG CCGCTGGCTT
63801 CTTTCATTCA ACATACATGT TTTTGAGGTT CATTCATGTA GTGTGTATCA
63851 GCAATCTTTT CCTTTTTATT TCTGAATTGT ATTCCACTGT TTGTAAATGC
63901 ATTTTGCTTA CCCATTTACC TGTTGATGGA CATTTGGGTT GTTTCCACTT
63951 TGTGGCTGTT ATGAATTATG CTGCTTCATT TATTTAGATC TTTCATTTTA
64001 TCAGCAGTGT TTTATTATGT AAGTCTTATA TTTATTTTGT TAAATCTCTT
64051 AAGTATTTTA TTTTTATGTC ACTGTGAATA TAATTGTTAA TTTCATTTTC
64101 AGGTTTACTA TGTACTCAGA TTGTTGTGTA CAGAATTTCT GTAACCTTAC
64151 TGACCTCATT TATTAATTCT AGTAGTTATT TTGTGGATTC CGTAGGAGTT
64201 TTTACATACA GGATCATATT GTCTTCAAAG ACAGTTTTTA CCTTTTTCTT
64251 TCTGATCTGA ATGCCTTTTA TTTTCTTTTT CTTGCCTAAT TGCTCTGGCT
64301 AGATTCTCCA GTTCAATGAG ATGGAGAAGT GTAGAGAACA GACATCCTTA
64351 TCATCTTCCT GATCTTAGGG AGAGAGTATC CAGTCTTTCA CCAGTGAAAT
64401 GGGAATAACA TTAATTGTAG GTTTTTGTGG ATGTCTCTGA TCAGTTTAAA
64451 TATGTTTACT TTTATTCCTA ATCAGGAATG AAGGTAGAAT TGTATCAGAT
64501 GCTTTTTCCG CATCTAATGA GATAATCGTG TTGGTTTTGT CCTTTATTAC
64551 TGTGGTACGT TACTACAATT GACAGATGTT AAACCAACTT TGCATTCCTG
```

FIGURE 3S

64601 GATAATTTGG TTTACTCATA TTTTTATTGA TTTTTACATC TGTAATCATA
64651 AGGGATATTG GTCAATAGTT GTCTTCTGAT TTCCCTGGCT GACTTTGATA
64701 GCGTGGCAAT TCTGGCCTTA TTGGAAAGGA CAACAACTAT AAAAGACAGG
64751 AGGGAATCGT TTGCCACAGC TTCAGTTGGT AGTGAACAGT CCCACTCTCC
64801 CCATTCACTT CTCAGTATTG CCATGTGGCC TGTCAGTAGA AAGATTACCT
64851 TATACTTAAT ACCTTGACAA AAGAGCAGTA GAATGGAGTC TAGACGGATT
64901 TTCTACCACA AACCATTCGA ATGTAAAAAG TATGAGTGAT GAGCTTCTAT
64951 TATCTGGCAA ATATCCATGT ATAAAAGACC ATCTCCTATT AAATGCTAAT
65001 TTAGTTTATC TACAAGTCTG TAATATTTTA GAGTTGCTGG AATCCAGTAA
65051 AATTTCCTTA TACAGATTTG GAAGGCAGCC TAGGTGTGCA GAATACTAAA
65101 TTATCTAGTT TACCTTTCCT TCCCTTTCTC TCTCAGCATT TTTCTATGTT
65151 GTAATCATTT TCTTTCCATT TTATTAACAG AGGAGGAAGG AAGAGACTTG
65201 AGCTGTTGTG TAGCTTCTCT TGTTCAAGTG ATGCTGGATC CCTATTTTAG
65251 GACAATTACT GGATTTCAGA GTCTGATACA GAAGGAGTGG GTCATGGCAG
65301 GATATCAGTT TCTAGACAGA TGCAACCATC TAAAGAGATC AGAGAAAGAG
65351 GTAACAAAAT CTTGATGCCT TTTTATCAGT CTTTAAGGAT ACACAAAATA
65401 AAATTTGTGT CATTAAAAGA TGAAGGGGCT TTTAAAAAAT ACTGTATTTA
65451 GTACAACTTA ATTTCCTTAG TCCAAAGCTA ACTAATGGAT TAGAGTTCAA
65501 ATTGATGTAC TTATTATAAA GATTATCGTA ACTATGAAGG TGAAATTTTT
65551 AAAAGTTGTC TATTGAATTT GTCTAAGTGG AAAACTACTG AAAAAATTCT
65601 GAATAAAATA CTGAAAAACA GATAACAAGC ACATTGGCTA TTTTGAAAAA
65651 TCACTTTTGG AATATCATAT TTTCTTAAAA TGGGATACAT AGGTTAAGAT
65701 GAAAAGTTTG AGAGGGCCAC CTTTGCAACA GCTGTGGAGT TAGTGGCTGC
65751 CTCGGATCTC TAGTTAGGCT GCGGAAGGCC TTACAAATAT CTTACCGGCC
65801 AGGCAGGTCA GTCAGATCAG TTTTTAGAAG GTTGTTTCAG AGAGCGCCAT
65851 TTGACTTGTG GTGTCTCATA AAAAATAGTG GTCACCCGCT ACTGCACTTG
65901 GGGACACACC ACGTGACCTA GGCTCATCCC AAAGTGTTTT CTGAAATATG
65951 GGGATGTTTT CTGGATGCTG AGCCTACAGG ATCAACCAAA CATTAGAGAA
66001 GTTTGGTTGA TGGTTTTGTT TTGTTATATA ATCTAAAGAA TTGTTTCTAA
66051 GACATGCTTA AACACATATT TTGCTCTTCC CCCTTCATAT AGTGGCAACC
66101 CGCTCAACTG TGTGCTTTGC TGTTTCAACT TGTTACATGT ACTGGGCAAA
66151 TAAGGGTTGT GATGTTTATC ACGGTTGAAT GTTACTTCTT GGGTTTGATA
66201 GATGTGTATA GCTCAGCTTA GAAGGCAAGT GTTTTAGGCT TCGATGTTTT
66251 CTCATTCATC TCTTCTTTAA CATCAGCAGT ACATTTTGAA GTAAATGTGA
66301 ACGGCTGAAG GATAACATTA AATGATCCCA TTGTCTCTTT GTATTTGCCA
66351 GTCTCCTTTA TTTTTGCTAT TCTTGGATGC CACCTGGCAG CTGTTAGAAC
66401 AATATCCTGC AGCTTTTGAG TTCTCCGAAA CCTACCTGGC AGTGTTGTAT
66451 GACAGCACCC GGATCTCACT GTTTGGCACC TTCCTGTTCA ACTCCCCTCA
66501 CCAGCGAGTG AAGCAAAGCA CGGTAAGCAA CCCTGTGGCT GTGGCTACGT
66551 TTTCCCTGTT TTTACAACTT TATCGAGGCA TAATTGAAGT ATAATTCACT
66601 GCCTATTTAA AATCTTATGA TTTAAAATTC TTACTGCCAT TTTCAGCTGA
66651 AATTTCTGAA TGGATTATTT TGAAGACACA AAAATCTAGG AAATTATTTT
66701 TATGAATGAA CATTTTTTGT TTTACTCTAA TGTAAATGTT TTGTAGTAAA
66751 CCCCTTTAAA GATGTAAATT ACTTTAACCA CCTTAAATGT CATGCTTTTG
66801 TATTTATATT TCACATTTGG GCTATTGGGT AGTAAAAAAC AAAAGCCCTG
66851 TTACACGACA TTTATTTCCT AGGTCAGTAG GATAAAAAGT TGTACAAAAC
66901 AAGATTATTT TCCTTCACGA GTTTGAAGTT TCTGGTCACA ATTCATTGAT
66951 GTAGAGGATT TATGACTAAG CAGGGTCTCA AGCCAAACTT GAAACCATTC
67001 TGAACCAAAG TGCCATTTCA CCCACCTCGA ACCAACAACA GAAGCTGACA
67051 AATGCCGTGG AGACCATTGA GAGAAACAGA AAGGGGCAGC TCTTGTGGAC
67101 CTTCAGGAAG CCTTTCTAGG AAGAGGATTG CCCTCATAGT GAGCTCCGGG
67151 GTCTTCAGCC TCAGCCGTAA GGCCCTGGGC TAGGCAGTGT GACCTAGGGA
67201 GCGGGAAACC TGAGTTCTGG CCCTGGTCTG GGAAAAGTGC TAGGCCCATG
67251 TTCCACTCAG GCTTCAGCCT GAGAGTCCAG GTTGCTAACC TGTAAAATGG
67301 ATCTGTCAAA CTAACACTTA TGCCTTTAGT CTCATTGTAT GAGGTGAAAC
67351 ATTTTGTAAA CTGTGAATCA TTATGCAAAT TTTCCTAAAG ACATATGAAT
67401 TATTCTGGAT TTGTTGGTAT AAAAGACAAA ACACACTGGT CAGTTAAGGA
67451 GCTGATTTTA TTTAGGCTAT TGCAGGAGGG AGAACTTAAT TAATGGGCAT
67501 CCCAAAGAAA AGGACAAGGC CTGGGATTTT ATAGTCAGAA GACAGGGGAA
67551 TCAGGAGGGA GGGCAGTCTC AGTCCACAGG AGCCAGTTCT CAGGACACAA
67601 AAGGCAGGAG AGATTGTCCA GCATTGCCAC TTTTGGGGAA CCCAGGGCTC
67651 AAAGAAACTC AACACCGTCA GCCTGTCTCT ACAAAAAATA CAAAAATTAG
67701 CCAGACATGG TGGTGCGCAC CTGTGGTCCC AGCTACTGGG GAGGCTGAGG
67751 TGGGAGGATG GCTTAAGCCC AGGAGGCAGA GATTGCAGTG AGCTGAGACT
67801 GTGCCACTGC ACTCCAGCCT GGGTGATAGA GCCAGAGTCT GTCCCCTGCC
67851 CACCCCACCA GGAAAGTTTG ACCTTTCCAG ATACTGTGCT GAGAACCAGT
67901 GATACAGGCT TAGAGGCTCC TGAGGCATGG AACGCTCATT TGTTCCTAAA
67951 ATACATGCTC TCCCAGTTGC TTGTTTTTAT TTTTCGTCAC CATAATCATT

FIGURE 3T

68001 CTTGGGGCCC CTCTCTGCCT CGAGCTAGGC TTTCCCCCTG GCCTTGTTTG
68051 CCTCCTTCAG CTCTTCCCCA TTGTCTCCCG TCACTACCCC GTGCGCACAC
68101 AGTGTGAGCC TGCAAAAGGT GCGTGAGGCG AGGACAAAGA CTTTGGGGTC
68151 TGGGGACTGG GCAGTGCATG GGTGGGTATC TGCGTGGAGG ACTCCCAGCC
68201 CCCAGACACC ACTGCCTCTG CTGCTTGGCT GATGCTGTGT GTGCGGACAG
68251 ACTTCTCACC AGGAATGAAC ATTACTGAAT TGTATTGAGG GAGCTGTAAA
68301 AAATACTTTC TACAAGTATT TCCTCTGCTT TCCCTGTTCA TGTTCTAGTG
68351 CTCTTTTTAA TTTGGCTCTT TCAAAAGCCT TTTCTGACAA ATACTAACAT
68401 GAATCCCCCT CTCCCTTCCT CCCTAGCAGG AACTGGTCAT TGTCTAAGGG
68451 TCGTGATTCT TAACCGTTCT CAGCCCCTTC CACACAGGCA AAAGCCCAAA
68501 GCATTTCTTC CTTTTTTTTC CATTCTGAGG CCACCTTAGG TGCTAGTGGC
68551 CAGGTAGTGT TTATAGAAAA TCTGGTCTCT CTTGGGATAA ATATTTTTAA
68601 TTTTTACCTT TTAAAAAAGA GAACATCTTT TTTTTTTTTT TTAAGACAGT
68651 TTGGCTCTGT CACCCAGGCT GGAGTACAGT GGTACAATAT CAGCTCACTG
68701 CAACCTCTGC CTCCTGGGTC CAAGCACTGC TCTCGCCTCA ACCACCTGAG
68751 TAGCTAGGAC TGCAGGCGCA TGCCACCACG CCTAGCTAAT TTTTGTATTT
68801 TTTTGTAGAG TCAGGGTTTC GCCATGTTGC CCAGTCTGGT CTTGAACTCC
68851 TGGACTCAAG CAATCCGCCC ACCTCAGCTT CCCAAAGTAC TGGGATTACA
68901 GGCGTGAGCC ACCGTGCTTG GCCAAGAGGA CATTTTCTAT ATACTTACTG
68951 AAGGGCCATT AAAACACGTT TGGGTTCATG TTTTACTAGA TTTCAGCTCT
69001 TAACAGTGTT TGAAGCAAAT GGATTGTTTT TAATCCATGT ACATGATGAA
69051 ATGTCAAGTA ACTAAAATTT TTTTTTTTTT TTTTTTGAGA CAGAGTCTTG
69101 CTCTATCACC CAGGCTGGAG CACAGTGGCA TGATCTCGGC TCACTGCAAC
69151 CTCTGCCTTC CAGGTTCAGG TGATTCTCCT GCCACAGCCT CCCGAGTAGC
69201 TGGGACTACA GGTGCACACC ACCATGCCTG GCTAATTTTT GTATTTTTAG
69251 TAGAGACGGG GTTTCACCAT ATTGGCCAGG CTGGTCTTGA ACTCCTGACC
69301 TCGTGATCCG CCTGCCTTCG GCCTCCCAAA GTGCTGGGAT TACAGGCATG
69351 AGTCACCACT GCGCCTGGCC AAAACTGTTA AGAGTATGTG TATTTGGTGC
69401 TTAATGAATT TTTACTTATT TGAAATAGAA AATTTTGTAA AACTTTACAA
69451 AATGCCCTGT GCTGTTACAC AGCTTAGCCA TTTCTTGATG ATTCAAGCCG
69501 CCACTGTGCC AGGGAATGCC ACCTGGCTGT GATGTAGTCA TGGCCTCCTG
69551 ACTGCTATAT TCTTGTCCTA ATAACATTCA TTGTTTGCCT TTTTAATAAT
69601 TTCCAAATAA ATTCTTGGGG GTTTTTTTTT GGTAGAAAAT TTGGAGAGTA
69651 CTGAAAGGTA CAGAACAAAG AATCAGACAT TTCCCATCAT CCAGCGACTT
69701 TGTGTCTGGA GTTATTTCCT CCAGCGAACT GTTGTGTATA CACTGCTGTG
69751 GTAGCCTGCT GCCATCAATC AGCTGAGATG AGAGTCCTTT CTCCACATTG
69801 CTAAATGTGA CTGTGCTTCA TAGAAATGGT CTGGGCTGCC TTCCAGAGGA
69851 GCTCCATGTC TTCCTCACAA TGCGGTGGTT GGCTGTCACC CTGTAGCCTT
69901 GTGTTGCCTC AGTTTACTGT GGTGGGAAGC CAGATAACTA GGCTGCACCC
69951 GCCCAGAGTC CGGGCTAGAG GTGGACTCCT GTGAAGGAGG GGTCTCCTGT
70001 GTACATGGTC TCCATGGTTT TAGCCACATG CTAGGACCAC AGGGAGTTGA
70051 TCCCTTCCTT CCTACCCTGA GTCTGTGGTC TGTGATTTGA GATCACTGGC
70101 TCAGTGAAGT GTAGCTCCCC ACTTACGAAG TAAGTTATAA AATTGGTGGC
70151 AGTGATTTCC ATCCAAAGAT TTTGTTAATC CACTTACCAA CAGGTAACTA
70201 CTTAAATGTA CTGACCGTGT GCTCATAAAA GTAAAATACT GTAATTATAG
70251 AAATAAATTC AACATGTTTA AGACTTTCTA GTATCATGTT AGTGAAACTT
70301 CTCTTAATAA CATTCTTATT GCCCAAAGGG CACGGCTTCC TTGGGGTCCT
70351 AAGGCAGAGG GCACCTGAAA AGCACACTCC TTGTTCATGG GGACTGTGGG
70401 GCCCTCTGAG CTCAAAGGCC AGGAGCGTCT CCTCTCTTGA AGTGAAAGTG
70451 CCACTCTGGT GGGTTTTGAG GGCTGCAGTA CAGAACATTT AACCTGTGTA
70501 ATGATGAGTG GCTCATCTGA AAAAAGGCAT TCATGAGAGA ATCTTTAGTT
70551 TTGCAAATAT TTATTTATTT ATTTTGCAGG AATTTGCTAT AAGCAAAAAC
70601 ATCCAATTGG GTGATGAGAA GGGCTTAAAA TTCCCCTCTG TTTGGGACTG
70651 GTCTCTCCAG TTTACAGCAA AGGATCGCAC CCTTTTCCAT AACCCCTTCT
70701 ACATTGGAAA GAGCACACCT TGTATACAGA ATGGCTCCGT GAAGTCTTTT
70751 AAACGGACAA AGGTAAATCA CAGCTAACAA AACGTGATGT TGGCTCACAC
70801 GTAACCAAAC ACCTCTTTTT CAGAACAGAG AGCGTTAAAA GTAAAGGCAC
70851 TTCCAAGAGT AACACTGCTA ATGCGGGTTT CTGAGGGGTC ATTCCCTTTT
70901 TAACTCAAAT GACTGTATCC CAGCTTTCTT CCTGGTGTCT GAGGCCCACA
70951 AAGTCTCAGT ACCTGAGAGT GGGCAGATTG CAGCTTTGAG CCTGCAAGCC
71001 TGATTTACTA AAGCCCCATT TATCCATTTC TTGATGATTC AAGCCGCCAC
71051 TGTGGCAGGG AATGCCGCCT GGCTGTGATG TAGTCATGGC CTCCTGACTG
71101 CTATATTCTT GTCCTAATAA CATTCATTGT TTGCCTTTTT AATAATTCCC
71151 AAATAAATTC TTGGGATTTT TTTTGGTAGA AAATTTGCAG ACTACTGAAA
71201 GGTACAGAAC AAAGAATCAG ACATTTGGCC TCCTGACTGC CTCTGTTCAG
71251 TTTGCCATTG TTCTTGATAG AATCGGCCAG GTCTAGTGTT TTTTCTAGCC
71301 CGTCTTAGAA CTTATCCTTA AGCAAATTAG TGGATAGGAG GTACTCTCAT
71351 CCCGCCCCCA TTCAGGCTGA TAGTAACAGC CTAGGTAGAG TCAACACATA

FIGURE 3U

```
71401 AAAAAGTGTA ATTCCAGGGG AGGAGGATTA GAATAAGGAC ACAAAGGAAG
71451 GGAGGAAAAT GTTCTTTGAG GCTGAAATTC CATTAATTTT TCATAGTATT
71501 GAGTTTATAT TTGCCATTGC ATCCTTCAAT CTTTCTAAAA AGGGAATCCC
71551 CGGAACATAA TAAAATCTCT TCTGTATAGA AAAGCTACAG CTCCACACTA
71601 AGAGGAATGC CGTCTGCCTT AAAGAATGGA ATCATCAGTG ACCAAGAATT
71651 ACTTCCAAGG AGAAATTCAT TGATATTAAA ACCAAAGCCA GATCCAGCTC
71701 AGCAAACCGA CAGCCAGAAC AGTGATACGG AGCAGTATTT TAGAGAATGG
71751 TTTTCCAAAC CCGCCAACCT GCACGGTGTT ATTCTGCCAC GTGTCTCTGG
71801 AACACACATA AAACTGTGGA AACTGTGCTA CTTCCGCTGG GTTCCCGAGG
71851 CCCAGATCAG CCTGGGTGCT CCATCACAGC CTTTCACAAG CTCTCCCTCC
71901 TGGCTGATGA AGTCGACGTA CTGAGCAGGA TGCTGCGGCA ACAGCGCAGT
71951 GGCCCCCTGG AGGCCTGCTA TGGGGAGCTG GGCCAGAGCA GGATGTACTT
72001 CAACGCCAGC GGCCCTCACC ACACCGACAC CTCGGGGACA CCGGAGTTTC
72051 TCTCCTCCTC ATTTCCATTT TCTCCTGTAG GGAATCTGTG CAGACGAAGC
72101 ATTTTAGGAA CACCATTAAG CAAATTTTTA AGTGGGGCCA AAATATGGTT
72151 GTCTACTGAG ACATTAGCAA ATGAAGACTA AAATAGGGTG TTTTCTGAAC
72201 ATTTTGAGGG AAGCTGTCAA CTTTTTTCCT CTGAATTAAC ATTGCTAACC
72251 TAGGCGTTTG AATCTCTAAT AACTTTATAT GTAAGAATAA TAGTTGGAAT
72301 TTGCACTAAT ATTTAAAAAC ATGTTGAATC ATGCTTCTTT CACACTTATT
72351 TTAAGAGAGA TGTAAATTTT GTTCCTGTCC TCTTTCTGTC ATTACAGGTC
72401 TGGCTCTTGT AACCGTGATC AAACTGTTCA TGTTGTCTGC TACATTTTTG
72451 TCTCCATCCA TTTTTCCTAC CACCTCCTGA AGGCTATCTG ATAGTCAGTC
72501 ACATTAGCAC CCCAGGCAGC AGACAACAGG AAAGTTAGGA AATTTGTGTT
72551 TCGTGTCATT TTTAGGAGCA TCTGATAAAA CCTCCAGCAG GTTTTAGGAA
72601 GTATTCATGT ATTTTTCTGG TTACTTTCTG TCGTCTCTAA TTGAACTCAC
72651 CTGATGAAGG TTCAGTGTTC TGGGGCCAGA ATTTATGATT TTAGATCACC
72701 TTCTTTGGAA CCTTAGATCA CTGTGTTTTG AAATCATGAG TTTGCTTTTA
72751 ACTTCATAGG GTCAACTTTA AAATGATATG CACTGTTAAT TTTAAAGCAT
72801 TTGCTGCAGA TAATTAAACT TAGAAGTGCC TTTGACTTTA GGATACAAAT
72851 ATTACAGAAG AAAATATAAT TTCACTTTTT AAAATTGGGG TGGGAAAATC
72901 CCATTGCATA TTTGAAATAG GCTTTTCATA CTAAGCTTCA TAGCCAGGAG
72951 TCCCCAGAGT CTTGTTCCTC TGAAAGCCAC TGGGGAGTGG CCTCTGGGGT
73001 GCTGATTCCA CAGAGGTGTA TGCTGTAGAC AGGAGAGTGC CATCTATGCC
73051 AAAACTCGCC CTCAAAAACA AACAAGGCTT GCTGGGAGGC GTGCTGGGCT
73101 TGGCCATCAG TATTTCCAGT GTGGTAAACT ATTGCTGGCA CTTCCCCCTG
73151 GAAATAACTA ATGAGGTTAC GAGTTGGGCA CCTGCACAGA TGTCCTTCTC
73201 TCATAGTTCC TAATGCTTAG GAATAGAGGA GAAATAAAAA AATGGATTCT
73251 CTCAAAACAC TGCCATTTGA ATAGCGACAG AAGTGCTCCC CCAGCCCCCA
73301 ACTTTGGACA GCAAAGTTGA GGAGAATGAG CAGACACAGT TGTTTGCTTG
73351 ATCTGAATCT CTCTAAAGTA AAGTATTTCC AAACTGTGTG ACAAGAGCCT
73401 ACCTACCACT GTAGCGGTCA AAGCTGAAGC TTCTTACAGC AGTGAAACGG
73451 GGCACCACCT CCCCCACACT CCTCATTCCC CGCTTAAAAC ATGGATACTT
73501 TCAAATTTGA CTGTTTCTTA AACTGCCATC CTAAGATATG GAAAATTTTT
73551 ATAGTAAAGT GTCTAGTTAG CTTATTTCCT TTTCTAAAAC AAGTGTTTTC
73601 AAGATAACTG TATTTTACCT TTATATGTAC TGAATAGCTG TTTCTTTTTG
73651 AATTATTTGC CTTTTAAAAT TTGATAATGT CTCTGGATAT AACAGGACAG
73701 GAGTTCTTAA AAAATATCTT AAGAAATTCA CTTTATGGGT AAACCCAAGG
73751 TTTTTGCCAA CTTGTTGCCT AGAAAATAAG GGCTAGTTTC AGTTTATACA
73801 AATAGAATTA TTAAACATTT TACAGTCCTT GATTAGAAAC CAGACCCAAT
73851 CTCCTTATAA CACCACAGCG TATCCTGCCA TTGACAGTGT AATCACAATT
73901 CTCCCTTTTT CATTTAGCTG CTTTTTTATT ATTACTAAAT GTTTTGGATT
73951 GAGCATTTTT CCCTCTGTAA TTTTCTTCCT TCACGTTTAT TTTAACTCTT
74001 GTAGTATTTT ATTGTTGTTA ATTTACAAGT TTAAAAATAT TAGGTACTAT
74051 TAATAATGGT TAAAAATAGA AAAATGCATA TTTTTGTATG ATAATCAAAT
74101 GTAAAATACT TTTATTTTTG CTGGACAGTT GTTATATCAT GATTATTGTG
74151 CTACAGTTTA TTGTGCATAA TATGAAAAAC AACTATGACA GCCTTCAGTC
74201 GGGCCAGGGT GAAGCTGCTT ATACCACCTC TGCCGTCAGA GGGACATGTG
74251 GTGACAGCAG TGGTGTGGCT GCACAGGGCG CACTAGAGAG AGCTCAGCAC
74301 CCCTGCTGCC CGCCAGCAGA GCCCGTGCTG AGGGAATGCC GCACAGATGC
74351 TGATGCACTG GGTGAAATTT CTAGTATTGA ACGTAAAGGT GTACAGTGTC
74401 TTGCTGTTAT TTTATGATGG AAACTGATTT TGAAACCAAA AATAGCTAAC
74451 TAACTTTATT TAAGGAAAGG ATATTAATTT GTACTAACAG AGGGTGAAAG
74501 CTGTTCACAT TTGTCAACAA AATCTGCTTG CTGCAGTAGT AACCTCAAGT
74551 GGTTAAAACT TGATTTCCCG AGAAAACTAA AACCTTTGTG CCTAAAATTG
74601 ATGACTTGAG TTCAAGTGGG ATGAGCAAGA AGATGTGTTA TCTTGTTGTT
74651 CAACAGTATT GAATGTGAAG GAAATTTTGA TGGCTTAATA AAATTCCACA
74701 GCGACTGTTT GTTGTTGTCA GTATGAAATC ATCTACTGGA ACACAGTGAT
74751 TGATAGAAGA GGTGAAGGCA TCTTCTCCTA CCCATACTTC TGTGTCATCC
```

FIGURE 3V

```
74801 ATGGGATGTT TCTGCTTGCC CTCTAAAGCC AGGTAGTGAT CAGTAACTTT
74851 TTTTAACAGC AATTCGGAAG TGGCTAAAGT TAAAGCCATG TGGATATTGA
74901 TAGATCATGC CCTAACTGGT CCTTCCATTC AATAAATAAA TATAAAAACT
74951 GGGGAGTAAT ATTCCCCCAA GAAGGCTTCA AAGAAGTCAA GAGACAGACT
75001 GGGGTTCCAG TCCCTGACTC CCGGGCCTGG CGCATGGATA AATCACCTTT
75051 CTACCACACC CCCTTGCCCA GCCTGAGACC CTCCCACAAT GGTGATGAGC
75101 AGCCGATTTG ACTGTACTGT CAACAGAGAA AATACCCCTA TCTAGTTATT
75151 AGGGATGGTC CCAGGGAGAT GGACAATGAA GGACAACTGC CTCTGATAAA
75201 GACTTCATTC CTTTCATGAT CCGGGCCCAA TCAGTAGAAC AAGCATTTAC
75251 ATGTTATAAA TCAACACAAC TTCATGAGAA TGTTTTGATT CCTAAAGAAA
75301 TTGGAATTTC AACTGTTTCA GCCCTTCTTA GATAATCATA AAAGTTTAAC
75351 AGCTAAATGT GTATAGGGCA GTAAAGAAAA ACTTAATTCA AGAATCTCGG
75401 TTTCCCATAT AATTAATTAC TTGAAGGAAA CACTGGTTAT GCTAGTTTTT
75451 AAATTTTTTT TTTTTTGAGA CAGAGTCTCG CTCTGTCTCC CAGGCTGGAG
75501 TGCAGTGGTG CAATCTCGGC TCACTGCAAG CTCCACCTCC CGGGTTCACG
75551 CCATCCTCCT GCCTCAGCCT CCTGAGTAGC TGGGACCACA GGCGTGTGCC
75601 ACCAAGCCCA CCCAATTTTT TGTATTTTTA GTAGAGATGG GTTTCACCAT
75651 GTTGGCCAGG ATGGTCTCGA TCTCTTGACC TCATGATGCG CCTGCCTCGC
75701 TCAGCCTCCC AAAGTGCTGG GATTACAGGC ATGAGCCACT GTGCCCAGCC
75751 ACTACTTTTT TATAAAAAAA ACCTAAAGAT GAATCATCAC TTGTTTTTGA
75801 GTTTTCCAGC TTTTTGCACA TCTAATCATA TAGATGCATC CAGCTCCAAT
75851 AATGGTCAAC AAAATTTTTC TCTTTTAAAA AAGTTCATTA TGAGCTGGGT
75901 ACAGTGGCTC AATGCCTGTA ATCCCCAGCA CTTTGGGAGG CCAAGGTGAG
75951 TAGGTCAGTT GAGGTCAGAA GTTCCAGACC AACCTGGCCA ACCAACATGG
76001 TGAAACCCCG TCTCTACTAA AAATACAAAA TTTAGCCAGG CGTGGTGGCG
76051 CACACCTGTA GTCCCAGCTA CTGGGGACCC TGAGGCAGGA GAATCACTTG
76101 AACCTAGCAG GCGGAGGTTG CAGTGAGCCG AGATCACACC ACTGCACTCC
76151 AGCCTGGGTG ACAGAGCGAG ACTCTGTCTC AAAAAAAAAA AAAAAAAAAA
76201 AAGTTTATTA CCCACTGTGT GGAATCAATG AGTGTATTCA AGCAAACACT
76251 GTTTTGTGAT ATGCAGACAC TGTAAAATGA CAAGTCAAAC TATCAGGTTT
76301 ATAATGCACG ATAACAAAAT TAAATAAAAC ATGTTTTATA CTCTTGAAAA
76351 TCTTACATTA ATGTATGACC AAATATCCCC AATTCCATAC CTTTTAGCTA
76401 AGGCTTTGGC TCTTAGCTCC AACTGCAACC ACATGGCAGA CTTCTACTTC
76451 AGCCCCCAGC TTCTGCAGTT CAGCCAGCCA GATCATCTGC TTATGTGAAA
76501 GACGATCATT GGGGCCTTTA ACTTCCACCA GCTGGAAAAG AAATTTTTAA
76551 AAGTTGTTAT TAGTATCTTA CTGAATGAAA AGCCATTCAA GTAAGTTGTA
76601 GTTGTCACTG ACAACTATTT AAATGGCTCT TCTGCTCTCT CACTGTATTT
76651 GTAAGTGTAA CACAAATATA CGGATGGTCC TTCACTTACA ATGGTTCACC
76701 TTAGGATTTT TTGACTTAAA AATGGTGCAA AAGTGATATA CATTCAACAG
76751 AAACCATACT CTGAGTGTTG ATCTTTTCCC AGTATGATAC TCCATGCTGG
76801 GCAGCAGCAG TGAGCCACAG CTCCCAGTCA GCCACATGAT CATGAGGATA
76851 ACCAGTACTC TACGGTTTGC AGTGAACTAC ATGATCTGCC CAACTGTAGG
76901 CTAATGCACA CATTCTGAGC ACATTTAAGG TAGGCTAAGC TAAGCTATGA
76951 GGTTTGGTGG GATAAATATG TTAAATGCAT TTTCAACTTA ACAATATTTT
77001 CAGTTGATGT GTAGGATTTA TCAGGACATA AGGCCATCAT AAGTTGAGAA
77051 GCGTCTGTAT GTAGCTAAGA AATTTATTCA GAAATTCTTC TATTCTGTAG
77101 AAACTAGACA GTTCTTCACA GAGGATGAGT AAACTGATTC TTAGTATAGC
77151 AAATGAAAAA TTGTTTTAAA GCATGCACTG GATTTTACTT CCTTGCTTAA
77201 AACCCTCCGA TTACTCTGTT ACATTTTCAA TTAAATCTAA CCTTCTTGCC
77251 ATGACCAGTC TCTTCCCTAC CCCAAGGCCC TCACTTCCAC TTGCTACTTG
77301 CTGTTCCCGC TGCCTGGGAC ATTTCTCCCT GTTCTTGACA TGCCTGACTT
77351 CTTACCTTTC AATGCTCAGC TTAAACTGAT CTGGAGAGGT CACAGCTCTA
77401 AGTATATCCT CCCTATGCAC TTCTTTCATG GCATTCATAA GATAAAAATA
77451 TATACTACAT GTCATCTTCA TGAAGGCAAG AATTGTGTGT TTTGTTCACT
77501 ACACATCACT AGACTTGAAG ACACAGCAAT AAAAACTATA GGTAAAATAT
77551 AGAAAAAAAT TGTTTAAATA CAGCATTTAG CAGCCTAAGG GACATTTAAT
77601 TAGAGTCCCC AAAGGAACGA GAAAAAAAAA TACTTAAAGA AAAAATGGCC
77651 AAAAATTTTC CAAATTTGAT GAAAACAGTA AACCCAAAGA TTGAAGAAAA
77701 TCAATGAATC CCAGGCACAC AAATGTAACG GCACCCTAGG AAATATCACA
77751 ACTGTATAAT CAGGGGATAT AGTCAAAGCA GCCAGAATTT TTAAAGCCAG
77801 AGGAAAAAAA AAGATTCTCT GATTGGAAAC CATGCTAGTT AGAAGACAGT
77851 AGACTAATAT TTTTAAAGTA TTGAAAAATA ACTGTCAACA TAAAATTCAT
77901 TGCACGGAGA AAATATCTTT CAAAAACAAA GGTGAAATAA AGGCTAAGAC
77951 ATACAAAACC TAAATACAGC CATCCCTCAG TATCCATGGG GGACTGATTC
78001 AAGGACCCCC TCTGTTACCA AAATCCATGG ATGCTCAAGT CCCTGATATA
78051 AAATGGCATC GCATCTGCAT ATTCTAGCAC ATCTTCTCAT ATACTTTAAA
78101 TCATCTCTAC TTATAATACC TAATATAAAT GCTATGAAAA TAGTTGTTAT
78151 GCTGTATTTT TATTTGATTT GTTTATTGTT GTAGTTACTT TTTATTGTTT
```

FIGURE 3W

78201 TTCTTTTTTC CAAATACTTT CAGTCCATGG TTGCATCTAC AGAAGCAGAA
78251 ACCATGGATA CAGAGGGCTA ACTACTGTAA TTCATTACTA GCAGAACTTC
78301 TAGACATGGA AATTTTTTCT TTTTCTTTTT TTCTTTTTTT TTGAGACAAG
78351 GTCTCACTCT GTTGCCCAGG CTGGTATACA GTGGTATGAT CTCAGCACAC
78401 TGCAGCCTTG ACCTCCCAGC CTCAAGCAGT TCTCTCACCT CAGCCTCCCA
78451 AGCAGCTGGG ACTACAAGTG CACACCACCA CACCCAGCTA ATTTGTTTAT
78501 CGTTTTGTAG AGATGAGGTC TCACTGTGTT TGCCCAAGCT GGTCTCCAAC
78551 TCCTGAGCCC AAGCAATCCG CCCACCTCAG CCTCCCAAAG TGCTGGAATT
78601 ACAGGCGTGA AAGGAAATTC TTCAAGCAGG AGAATGAGAC TACACAGAAA
78651 CCTGGATCTA CACAAAAGAA TAGCAAGCAC TGGAAATGCT ATGTACATGA
78701 GTAAATACAG ACTCATTAAT CAACTGTAGA AAGCAAAAAT AATATGTTAT
78751 AGAACATATA ACACGTAGAA GTAAAATATA TGAAAACACC ACAAAGGCTG
78801 GAAGGGAAGA TATATATTAT TGAAAGGTTC TTTTTACTCT AAAGTGTGTA
78851 TCACCTGAAG GTGGATAAGT TTAAGATATA TAATATACTA ACGCAACCAC
78901 TTCAACACAA TGAACAGTTA CAGCTAACAA GCCAGCAAAG CTATCAAATG
78951 CAATCTTTAA AAATAAGACA GGGCCAGGCA CTGTGGCTCA TGCCTGCAAT
79001 CCCAACACTA AGAGACCACG GCAGGTGAAC TGCTTGAGCC TGGGGATTTG
79051 AGATCAGCCT GGGCAACATG GTGGAACCCC ATCTCTAAAA AATACAAAAA
79101 CCACAAAAAT TAGCCAGGCA TGGTGGCGTG CACCTGTGGT TCCAGCTACT
79151 CAGGAAAAAG ACAAGGGACA AAAGAGTTCT GAGACAAAGA GAAAATAAGT
79201 ATCAGGATTT AAAGCTAAGG ATATCAATAA TCAAATTAAA TGTAAATGTT
79251 CCAAACACCC CATTAAAAGA CAGAGGTTAA GTTGGATTCA AAAGTAAGAC
79301 CCAACTATAT GATGCCTACA GGAAATCCAC ATTAAAAATA AGATAAAACA
79351 GGTCAAAAGT AAAAGAATGG AAAAATGTAT CATGTTAACA TTAAAAAAAA
79401 GAAGGCTGAA GTGGCTACAT GTTGACAATA TCGGACAAAG TTGATTTCAG
79451 AGCAAAGATT ACCAGGTGTA AAGGGGGGGT CACTGCATAA TGATAAAAGG
79501 GTAGACTCAT GAAGAGGACA TGACAGTCCT AAAAGTCTAT GCGTCTTATA
79551 ACAGACCTTC AAAATACATG AAGCAAATAG TGATAGAAAC GCAAGAAGAA
79601 ATACACAAAT TGGCTGGGCA CGGTATACTC TCAGCATTTT GGGAGGCCAA
79651 CGTGGAGCCC AGGAGTTTGA GACCAGCCTG GGCAACATGG TGGAACCCCA
79701 TCTCTACAAA AAATAAAAAA AATCAGCTGG GCATGATGGT GCATGCCTAT
79751 AGTTCGGGCT ACTCAACAGG CTGAGGCAGA AGAATTGCTT GAGCCTGGGA
79801 GATCAAGGCT GCAGCGATCC AGGATCGCAC TGCCACTACA CTCCAGCCTA
79851 GGTGATAGTG AGAGTCTGTC TCAAAAAACA AAAACAAAAA AAAAAAGAAA
79901 AGAAATACCA CAATTATAAT CAGAGATATC AATATTCTCT CAATAATTTA
79951 TAGAACAAGT AAATAAGAAA TCAGTAAGGA CACAGACAAC TTAAACAACA
80001 CTATCAACCA ACTTGACCTA ATTGACATTT AAAAATACTG CCCACAACAA
80051 ATGCTAAACA CACATTCTTT TCAAGTACAA ACAGAATATT CACCAGGGAA
80101 TACCATATTC TGGACCATAA AACAAGTCTC AACAAATTTA GTGGGATTCA
80151 AATCATACAA AATATGTCCT CTGAATACAA TGGAGTTAAA TTACAAATCA
80201 ATAGCAGAAA GATACCTGAA AATCTCTCAA GTGTTTGGAA ATGTAAATGA
80251 CTCACTTCTA AATAAGCCAA GGATCAAAGA AGAGTCAAAA GGGAAATCAG
80301 AAAGTATTGT GAACTGAATG AAAATGAAAA CAACTACTAA ATTTGTGAGG
80351 TTCAGATAAA GCAGCACTGA GAAGGAAATT TGGAGCACTA CCTAACTCTA
80401 TTAGAAAAGA AGTTCTCAAA GCAATCACCA TAGCTTCCAC CTTGAGAAAC
80451 TAGGAAATAA AAAAACAAAT GAAACCAAAA GCTGATTCTT CGAGAAAATC
80501 AGTAAATTGA TAAACCTCCT GCCAGACTCA TTAGGGAAAA AAGAGAAAAG
80551 ACACAAATTA CCAATATCAA GAATAAGAGC ATGACAGAGA TAAAGATTCT
80601 ACAGATATTA AAATACAGTA AGAAATACAT GGCCGTGTGC GGTGGCTCAC
80651 ACCCTGTAAT CCCAGCACTT TGGGAGGCCA AGGTGGGCAG ATCTGAAGCC
80701 AGGAGTTCAA GACCAGCCTG GCCAACATGG CAAAACCTCA TCTCTACTAA
80751 AAATACAAAA AAAAAAAAAA ATTATCCAGG CATGGTGGTG CACAGCTGTA
80801 ATCCCAGCTA CTAGGGAGGC TGAGGCACGA GAATCACTTG AACCCAGGAG
80851 GCGGAAGTTG CAGTGAGCTA ACTCACGCTA CTACACTCCA GTCTGGGCGA
80901 CAGAGCGAGA CTCCATCTCA AAAAAAAAAA AAAAGAAAAG AAACAAATAT
80951 AAACAACTTT AAGACAATAC TTAAATGAAA TGGACAAATT CCTTGAAAGA
81001 CACAAACTAG CAAAGCGCAA TCAAGAAGAA ACAGATAATA TGAACAGCCT
81051 TATGTTGTTT AAAAATAAAT TTAATTTATA GCTTTAAATT TTCCTCCCCC
81101 CAAAATCTCC AGGCCCATAC TGCTTCACTG GGGAATTCTA TCAAATGTTT
81151 AGGGAATAAT ACTAATTCTA CACCAACTAT TCCATCCCAC TCTGATGCTG
81201 GTATGACTCT GAAACCAAAA CCCAACAAAG AGATAATAAG AAAAGAAAAG
81251 TACAGCTCAA TATCCTTCAT GAACATATAT GCAAAAATTC TTAATATTTT
81301 ACAAAATCAA CTCCCATTTT TGCTGATCAA AATAATGCTG TTAAGATACC
81351 AATTCCTCTC AGATTGGTCT ACAGATTCAA AGGAATTCCA ATTAAAATCT
81401 CAGCTGGCTT TTTTTTTTTT TTTTTTTTTG AGATGGAGTC TTGCTCTGTC
81451 GCCCAGGCTG GAGGGCAGTG GTGCCATCTC GGCTCTTGAC AACCTCCACC
81501 TCCTGGGTTC AAGCGATTCT CCTGCCTCAG CCTCCCAAGT AGCTGGGACT
81551 ACAGGCGCCC GCCACCACAC CCGGCTAATT TTTTGTATTT TTAGTAGAGA

FIGURE 3X

81601 CGGGGTTTCA CCATGTTAGC CAGGATGGTC TCAATCTCCT GACCTCGTGA
81651 TCCGCCCACC TCTGTCTCCC AAAGTGCTGG GATTACAGGT GTGAGCCACC
81701 GTACCCGGCC TCAGCTGGCT TTTTTTTTTC TTGGAAACTT AAAATTTGAT
81751 GTTATAATTC AAATAAAAAT GCAAAAGAGC CAGAACAACT TTGAAAAACA
81801 AGTCATTATA GGACTTACAC TACCTGACTC CAAGATGTAT CTAAAGCTAC
81851 AATAATCAAG AAATACAGAC AAACAGATCA ATGGAACCGA AGAGTATATA
81901 GAAACAGACC CACATATATA TGGGTTACTG ATTTTTGACA AAGATACAGA
81951 GGGAATTCAG TGGAGGAAGC ATGGTCTTCT TGACACATGG AGCTGGAACA
82001 AGTGGATATC CACACACCAC AAATGAATTC CAGTGCATGC CCCACACTGT
82051 ATACAAATGG CGTCTCAAAT GATCATAAAA CTGAATGTAA AACCTAAAAC
82101 TATAACACTT CTAGAAGAAA ACAAAGGAGA AACTCTTTGT GACCTTGGAT
82151 TAGGCAAGTA TTTCTGACAT GTGACACCAA AAGCATGATC CACTAGAGAA
82201 CAAATAAGTT GGATTTTGTC AAACTTTGAA ACCTCTGCTC TTCAAAAGAC
82251 ACTATTAAGA AAATGAAAAG ACAAGCCATA GACTGGGATG AAATGTCACT
82301 GATAAAGGAC TTGTATCCAG GATATATAAT TTTTTAATCT CAAAACTCAA
82351 TAATGAGAAA ACAAATCACC AGTGATGGGC AGCAGGGCTG GGCTAGTGGA
82401 CAGCGTTCAA GGAAGTGTTC ACTCTCTGAG CTTTTTAAAA AATTTTTTGT
82451 GGGTACATAG TAGATGTATA TATTTATGGG GTACATGAGA TGTTTTGATA
82501 CAGGCATGCA ATGTGAACTA AGCACATCAA GGGGAATGGG GTATCTGTCC
82551 CCTCAAGCAT TTATCCTTTG AGTTACAAAC CATTATACTC TTTAAGTCAT
82601 TTTAAAATGT ACAATTATCG GTAAGCTTCT AAAATAGCTC CTGGTGTCCA
82651 CACCCGTTGT GACCCCCTCC CTTTGAGTGT CAGCTGGACT AGAGACTCGT
82701 TCCTAACCAC AGAATACAGC AGGAGTGATG GAACATCATG TCCACATCAA
82751 GTCATAAGAG ATGGAGCTCT GTCTTGCTCA CACTCTGGGG CTCCTCTCAC
82801 CCGCCTGCTC TGATGAAGCC AGTCGCAGGG GACAGGCCCA CAGGAACCCA
82851 GGCCCTCGGC CCAAAAGCTC TCAAGGAATT CAATCTTGCC AACAGCCACT
82901 CAAGAAATGC CTACTTGTGG CCTCTGATTC AGTTGCTAAT AAGGTTACCA
82951 ACAGGACTTT CCATTCTGCC TCAACTGACC TTAAAGTGAC GGCTCTGGGA
83001 GTTCCACACC ACCAGGTCGG GGAGGCCCCC TCGACAGTGT CGAAAGTCAG
83051 CAGCCAGGTG CCTGCACACA CCACTGAGCA CAGGGCCCCC CAGGCAGGAG
83101 ACAAGATCCT GAACACAAAA CACAGGACAG TTAGCCACTT CCCTCGTGAC
83151 AGAGAATGGA AATAGGCTCC AGGGATCACG AGACGGAGAA AAGCTCAGTG
83201 TATATGTAAT TCAGTGCACA TGGACCCCAG GCCCACCATG CGCTGTTCTG
83251 CTGCTTGTAC CAGAGCTGCA GAGCCATGGC TGGAATCCCA CTGGCAAGTG
83301 GTGGGAGACT GGTCCTCCTG TGGTCAGTTT CCAGGCTTCT GCAGCGTGGC
83351 CATGCTGGGG AGCGCTGAGG AAGAGGGATG TGGAGGATGC ACTCAGGAAC
83401 GCGACAGCAT GGCCTCATAG AGGGCAGCAG TTGAAGGAAC ACAGAAGGTA (SEQ ID NO:3)

CHROMOSOME MAP POSITION:
Chromosome 15

ALLELIC VARIANTS (SNPs):
DNA

| Position | Major | Minor |
|---|---|---|
| 85 | T | C |
| 1614 | A | G |
| 2648 | T | G |
| 6773 | A | G |
| 8144 | A | G |
| 9488 | A | C |
| 9730 | A | G |
| 10317 | A | C |
| 10391 | T | C |
| 10682 | T | A |
| 11633 | - | T |
| 12054 | G | A |
| 12938 | C | G |
| 13719 | G | A |
| 14333 | T | - |
| 14753 | A | G |
| 14831 | - | A T |
| 15157 | G | A |
| 16242 | G | A |
| 16698 | A | G |
| 17152 | A | G |
| 17624 | T | - A |
| 18268 | - | G |

FIGURE 3Y

| | | | |
|---|---|---|---|
| 18786 | A | G | |
| 18813 | - | A | C |
| 22061 | A | G | |
| 22205 | C | T | |
| 22527 | A | G | |
| 22876 | A | G | |
| 23351 | G | A | |
| 23821 | G | A | |
| 25487 | C | T | |
| 30858 | C | T | |
| 31014 | A | C | |
| 31437 | C | T | |
| 35341 | G | A | T |
| 35346 | A | G | |
| 36164 | G | A | |
| 36620 | A | G | |
| 37074 | A | G | |
| 37546 | T | - | A |
| 38190 | - | G | |
| 38708 | A | G | |
| 38735 | - | A | C |
| 41983 | A | G | |
| 42127 | C | T | |
| 42449 | A | G | |
| 42798 | A | G | |
| 43273 | G | A | |
| 43743 | G | A | |
| 45407 | C | T | |
| 45985 | T | C | |
| 46198 | A | G | |
| 46793 | - | A | |
| 46923 | - | A | |
| 47851 | A | G | |
| 48875 | G | T | |
| 50844 | A | C | |
| 51267 | C | T | |
| 54073 | A | G | |
| 54206 | C | G | |
| 54488 | C | T | |
| 54511 | T | - | |
| 56070 | T | A | |
| 57119 | G | C | |
| 58184 | G | A | |
| 58210 | A | G | |
| 59015 | T | C | |
| 59201 | T | C | |
| 60695 | G | A | |
| 61592 | A | G | |
| 62577 | G | A | |
| 62580 | C | T | |
| 62596 | C | G | |
| 62682 | G | T | |
| 64509 | C | T | |
| 64898 | A | G | |
| 67072 | A | G | |
| 67283 | T | C | |
| 67432 | C | T | |
| 68079 | C | T | |
| 69067 | T | A | |
| 69122 | G | A | |
| 69951 | A | G | |
| 70498 | G | A | |
| 70850 | C | G | |
| 70874 | C | T | |
| 70923 | A | G | |
| 71276 | G | A | |
| 74663 | G | A | |
| 74598 | T | C | |

FIGURE 3Z

| | | |
|---|---|---|
| 81794 | A | G |
| 81752 | - | T |
| 81652 | G | T C |
| 81899 | T | C |
| 82828 | G | C |

Context:

DNA
Position

85
AAAAACAGAAAAATGGGTGAAGCAGGACAAAACAGTGACATTAGAGCCAAAAGCAGGGGG
TAGGCAATAACACCAAACATACAG
[T,C]
GTAGTCAAGGGCATCAGGGTCTGAGAAGAGGTTATAAAACTAGTTCTACGGACTGAATTG
TGTTCCTCCAAAATGCTAATGTTGAAACCCTAACCCCTGGTATGGCTACATTTGGAGATT
TTAGGAGGTAATTAAAGTTAAATAAGGTAGTAAGAGTGGGGCTCTAATCTGATAGGATTA
GCGTCCTTACAAGAAGAGACATCAAGAGATCCCAGAGAGCATGTTATATACCCTCCCCGC
ACTGTGTGAGGACATGGTGAGATGGCAGCCATCTGCAAATCCGGCAGAGAGCCCTCACCT

1614
CCAAAATCTGCTCCAGTCAGAATTACCGTAAGAGCTCAGAAGTGACCTGTGCTTGGCGGC
ACCGGCCCACTTTCCCAGTGCCGGTTCCTCGCATCCTGGGCGCAGACGGGGTGACCGCCT
GACCCCTGGACCCGAGTCACCTTTCCCTGCCCTGAGCTCCTCCTTGAGAGCTTCAAAACA
ATGCTCGCCCAGGCCGGAGGGCGAAGTCGGCCCATGTGTAAGTCAAGGGAACTGTCCCAG
GACTGCAGCCCGGCCAGAAGACGCCCCGCGCCGCCGTCCCAGGCAGCCACCGCTGCCGCC
[A,G]
TGGCCCCCGCAGGCCGCCGTAGGCCCCCGCGGGCCGCCTGACCCCTGCGGGCCGCCGTAG
AAGGACCCTCCAGAGGCCGCGCTCTTGAGATGGCCGTCGGGCTCCGCTCCCCGCGGGGCC
CCGGCTGAGGGCCCGCCAGCGGGCACCTGGCGCCACCGCTGCGTTCCGGCACTAGCACGG
GACACGGTCAGGGAGCGGCGGGCCGCGGCCTTGCGCGCGCCGTCTCTCGGGGCGGGGCAC
CGGGCCCCTTCCGGGGATGGGCCCCGGCGCCCGCGTCGGCCTGGCTGTGCCCGGCCCCTC

2648
CTGCCCGAAGTTCTGTCGTCCGTAGTTTTGCGGAGTGTTGAGGCCCAGGGGAGCCTTGGG
AGCTGGGGTTTTCTTTAGTTTCCAACCCATCGACCCTCCCTCCTATGACCGCCAGCATGA
TTGCAGCGCTTGGGGTCACTGGTCGAGGCGGTTACCCGTCTGTCATAAATGTGAACACCT
GGAAGCGACACTGGCAGTTTAAACATTTTTTATTATTAGGCTTCCAAGTCGATAATGAGC
AGATCTTAAAAACAGCTCAGTTAATATGCGAAAGAATTTAAATGGGGGGCTGTGTGTCTT
[T,G]
CGCATGTGTCATCACTTAGAAAACAACATTTGCTGTAGCATTTTACGGAGGGTGGGGGA
TTGAGATTTTGATTTATTTTGCTAATGTATTTCAGACTGACGATAAGATCAATTCGGAAC
CGAAGATTAAAAAACTGGAGCCAGTCCTTTTGCCAGGTAAACATTAGTTAGGATTCTAAC
AGATACTTTAGCAACGTATTTTGGTTTAAGATTATTCTGCCGACTAGTATCATGTGGTTA
ACTTCCCTTCTCTCATTAAACTTTCTCCAGTTAAAAGTCTAGTGACTGAGAGGAGAAAAA

6773
CTTAAACTGTTACCTTACCCAGGCACACACACAGACTAACTTTCAGATTTAGGAGTAAAG
GGAAGACTGTGTTATTTTATGCCAGACATTTCAAGAGATTTATGTCGGAGCCTGGAATTG
AAATAGAGTACTCTGTCAAAGTAGTCAGCTTTTGTGTAGGCTTTCTCTTTATCTTCCTCT
CATTATGTGAATTTCATTCTTTCAGTGATTATATTGTATATGTGTAAAATCACTCCAATA
CTTGAAAACTGAGTTTGACTTTTAAAGTGTGTGTGTGTATATATGTTTGTGTTCCAGTAT
[A,G]
TATTTGTTAAGAGCATGTAATGCCAGACTCTGTCCTGTTTAGCTGCTGGACTGGTGGATC
GGTTCGGTGAGGATGTGAGTATCTCCTGGGTGCCAGGTCTGTCCTGGATAGCGAGAATGC
TGGAGGTGTCATGTGCCTGTATCGCAGAAAGGCGTGGGGTGAGCCCTAAGCTGCCTGTTG
ACAAGGTAGAAGACTGTGACCTGGATCACTGGTACCCAGATTCCAGCCAGGGCCTGGTAT
CAGATTTGGATGAAGTTTTTACCAGCCCTTGGTCAAAGTGAGAAAATTAAGAAAAGTGCA

8144
ATGTTGTTAGGTTGGTACTAAGGGAAGAGGTCCTCTTTGGTAATGCTGCAAGTGGCCACA
GTTCCAGAAGAATCTGTTGAAAAGAGTGAAGAACCCCAAGGAAGTGCACTAATGTGTGTT
GAAGTCCCTGGGTTTCATTGTCCTTGCAGGCCAGGTGACACAAAAGCCTTGTATTCTTCT
TTTTGCTAAGCTATTACCAGGCATGTTTCTGAACATACTTTGAACGAGGATCCTTAACTA
ATATAGCTTGCAGATTAATCATCATAACAGTCTTGTCAGCTAGGATACCAGTTTATCTCC
[A,G]
TTTGACAGATGTGAAAACTATAGTTTGCTGAGGTTAAGTAACTTGCCCAGTGTCACACAG
CTAGCAAGGCAGAGCCAGAGTTCTCTGTCCAGCTCCCAGGCTGTGCCACTAACTGCTAAG
TAGCACGGCCCACCTGGCTGCACTGGTGACACTAGGGTACAGATTTATGCTTTGGAACTG
TTGGGGAGTAGATTGGATGTCAGCCTAGAGGGAGTTCTCTAGTGAAGTAAAAAGAGCTCT
GTCCTTGTCTTTGCCCTTTTCACAACAGTGACAGATTTTGACCCAGCGTGCAGAAGAACT

9488
GTTGTTAATTCCTTAAAGGCAAAGACTTTATCTTTCAAGTGTTTTATGTAATTCCTTTTT

FIGURE 3AA

GTAGGTAGGCTTCATAAATGATTGTAGACTGATTTTTGTAGTATTTTAATTTGTGAATGC
ATTGTTTTTGAAAGACCAAAGGACTTGTAACACACCCTCAGAACAGTGAACAGTGTAACT
GTACTATCTTAGCATTAGCTTTATACCTTACCCGTAGAGCCTTAGGAATGTTTGGAGCTG
TCCATTCCTTAGGCTTTTGCTGCAGTACCTTAGGCCAGCATTTTCTTACCCCTCCAAACT
[A,C]
CTCACTATCGTTGTCAACACCGTTCATGAACCTCCATAAATAAAATCCTACTTAAGCAGG
ATAAAATCCAAATTCTTTAACCTTGTAATTTGCTAACACTGTACCTCACTGACTTCATTT
CTCAGTATTTCCCAATATTGATATTTGCTTCAATCATGCCGCTTCCTTGGTCTCTTCCAG
ATGCCTTATTCCTTATTTAGGACCTTGTTACTGTTATTATCACACATTCTCTACTATCTC
AATGCTCTTCTTCCTTCAAGATTTCATTCTACAATTTTTCCTGAGATCGGCACTATACCC

9730 CATTCCTTAGGCTTTTGCTGCAGTACCTTAGGCCAGCATTTTCTTACCCCTCCAAACTAC
TCACTATCGTTGTCAACACCGTTCATGAACCTCCATAAATAAAATCCTACTTAAGCAGGA
TAAAATCCAAATTCTTTAACCTTGTAATTTGCTAACACTGTACCTCACTGACTTCATTTC
TCAGTATTTCCCAATATTGATATTTGCTTCAATCATGCCGCTTCCTTGGTCTCTTCCAGA
TGCCTTATTCCTTATTTAGGACCTTGTTACTGTTATTATCACACATTCTCTACTATCTCA
[A,G]
TGCTCTTCTTCCTTCAAGATTTCATTCTACAATTTTTCCTGAGATCGGCACTATACCCTT
CCTCCTGCCCCATCCTATCCTGAGTGCTACTCACTGGACTTGGTACTTGCTTTTTTACAT
TGTGTGTTAGTACCAGCATTAAAGATTTGTGTTTATCTTCCACATAGTTTCAATTTCCTG
TGATAACTTTTGAGCCACTTTAATTCCTGAATTTACCTAAAGCTAGGGTGACCAGCTTGT
CCCAGTTTGCTTGAGACTGTCCTGGTTTTAGTGCTAAAAATACCACATCCCAGGGAAACC

10317 ATCCCAGGGAAACCCCTCTGTCCCAGACAAACTGGGGCAGTCACCCTACTGTTAAAAGCC
CAAGTTAAGTTATGCTTTTGGCCTCTACACATCCCACAGGTTAATTAGCCACGTGTGCCG
TGAGACTTTGCCTTAAACTGTGTTCCAACCTAAAATGTATGGGAAACATTATTTCTGTCC
ATCAAACGTGATGAATTTCTAAATGTATAAGGTGTTAGGAAAGATAATACAACATGGTTT
TGAGGTCCTCAGGGAGTTAAAAACTTTCCTAGCCATATCATTTGGAGGTTTATTAACTGT
[A,C]
ATTGCATTTCCCTTCTTATTTATATTTACAGATGAAAGGGTCTTGAGAAAATAAACTTGG
ATTTCTTGATTTCTTCCCAGGTGTTAGTAGAAACCTTTGGCTCATCATCCTCTAATTTAG
AAGGTTTTTGCTTACCGCACACTGAAGCTAATTTCCTGCTTTTTCTGGCTTCATGAGGCT
TCCTTGTGGCATCCTGGGAAGTGCTTGGTGCTGTAAATGGTCCCACCGTGGCTGATGGCA
TAGCACAGAGCTGGGAGAGAGGAGTCTGGTGGGTTCTCACAAGCAGGCCAGCCAGCCGTC

10391 CTTTTGGCCTCTACACATCCCACAGGTTAATTAGCCACGTGTGCCGTGAGACTTTGCCTT
AAACTGTGTTCCAACCTAAAATGTATGGGAAACATTATTTCTGTCCATCAAACGTGATGA
ATTTCTAAATGTATAAGGTGTTAGGAAAGATAATACAACATGGTTTTGAGGTCCTCAGGG
AGTTAAAAACTTTCCTAGCCATATCATTTGGAGGTTTATTAACTGTAATTGCATTTCCCT
TCTTATTTATATTTACAGATGAAAGGGTCTTGAGAAAATAAACTTGGATTTCTTGATTTC
[T,C]
TCCCAGGTGTTAGTAGAAACCTTTGGCTCATCATCCTCTAATTTAGAAGGTTTTTGCTTA
CCGCACACTGAAGCTAATTTCCTGCTTTTTCTGGCTTCATGAGGCTTCCTTGTGGCATCC
TGGGAAGTGCTTGGTGCTGTAAATGGTCCCACCGTGGCTGATGGCATAGCACAGAGCTGG
GAGAGAGGAGTCTGGTGGGTTCTCACAAGCAGGCCAGCCAGCCGTCTCTAGCACACCACC
CTTTTACTGCATAAAAAGCACAGGCGTATAGTCTCCCTGAAAACTTCAGATCCTCTAGAG

10682 CTTGATTTCTTCCCAGGTGTTAGTAGAAACCTTTGGCTCATCATCCTCTAATTTAGAAGG
TTTTTGCTTACCGCACACTGAAGCTAATTTCCTGCTTTTTCTGGCTTCATGAGGCTTCCT
TGTGGCATCCTGGGAAGTGCTTGGTGCTGTAAATGGTCCCACCGTGGCTGATGGCATAGC
ACAGAGCTGGGAGAGAGGAGTCTGGTGGGTTCTCACAAGCAGGCCAGCCAGCCGTCTCTA
GCACACCACCCTTTTACTGCATAAAAAGCACAGGCGTATAGTCTCCCTGAAAACTTCAGA
[T,A]
CCTCTAGAGCTTTGAAGCTTTTATTCGGAGTTTTCTCTTCAAGGTCACTTAATTTAACAT
GTGAACAAGAGCAGTCTCAGTACCTTCTTTTTATATATCCTATCTGGGAAGAGGCCACTT
TGTGTCTTCTTTTTCTTCCCTGTGTATAAGCTAGTTTTCTGGCCCACAGTGTTTCAGTGC
ATGGCAGGAGCTTATGACAGCTCCTCTTCAGCATTCCTTTTTTTTAAAATTATGAACAAA
TGACTTACGTGAGCAGACAGCTGTGCTACATGATCCAAATATTTTAAAGACTGGTTCTGC

11633 AGGATAGAGTTAATGTGAACTCTTCAGCCAGCTTCCGCTAATGTTAATAGCTTATGTAAC
CTTGGTGAATTTAGCTCAACTGAGAAACCAACAATACTATTAGCTAAACTGCAGGTTTTA
TTCGTATTTCCCTAGTTTTTCCACAAATGTTCTTTACCTGTTTCAGGTTCACATCCAGGA
TACTACATAGCATTTAGTTGTCGTGTCTCCTTATTCTCAATGTCTCAGTCTGTGACAGCT
TTTTCATCTCATCTTTCAAGACCTTGACGTGTTTTTTTCTATTGAATTTGATTTTCTTTT
[-,T]
TTTCTTTTTCTTTTCTTTTTTTTTTTTGAGATGGAGTCTTGTTCTGTCACCCAGGCTGGAG
TGCAGTGGCGTGATCTCCGCTCACCGCAACCTCCAGCTCCCGAGTTTGAGCGATTCTCCT
GCCTCAGCCTGTTGAGTAGCTGGGAGTACAGGTGCGCACCACCAGGCCCAGCTAATTTTT

FIGURE 3BB

TGTGTTTTTAGTAGAGACGGGGTTTTACCATGTTGGCCAGGCTGGTTTCGAACTCCTGAC
CTCAAGTGATCTGCCTGCCTCAGCCTCCCAAAGTGCTAAGATTACAGGCATGAGAATGAG

12054 GCCTCAGCCTGTTGAGTAGCTGGGAGTACAGGTGCGCACCACCAGGCCCAGCTAATTTTT
TGTGTTTTTAGTAGAGACGGGGTTTTACCATGTTGGCCAGGCTGGTTTCGAACTCCTGAC
CTCAAGTGATCTGCCTGCCTCAGCCTCCCAAAGTGCTAAGATTACAGGCATGAGAATGAG
ATTTTTATTTTGCCTCAAATAATACATATTAAAGCTCTTTAAACATAGAAATATACTACT
ACAAAAGGAAAAATTTTATAATTACTAGATTTCTGTTCTAACAAACCACCCCCTAGAAAC
[G,A]
TCATCAAATTGACTTAAAAATGTAGACGTAATTTCAGACTTAGAGAAAAGTTGCAAATAA
CAGAAGAATCTGTGGATACCCTTTCCTTAGATTCCCCAATAAAACCTTGACGCTTTGGAA
GATTATTATTCAGGTAGTGTCTTGTAGTATGCCTCTTGGTTTGGATTTGTCCGATGTTTT
CTTTTGATTAAGCAGAGGTTATGGATTTTGGGAAAGACCCACAGAGGTGGTATCCTTTGC
CCTTGTGTCATGTGAGCAGGCACAAGACATCAACATGATTGGTTATTGGTGAGGTTAACC

12938 ATGCATGTTGCACACAGCAGTCATTCAGTCTATGACATTGAGTCCATGATAGTTTCTTGA
TCTTTACTGTAATGTTCTAATCATGATTTTGTTTCCTTATTCCTCCTACATTTATTAATT
GGAATTCTTCTGTGAGGAAGATTTGTCTCTTCTCCGCCATTTATTTATTTATTATTCAGT
CATCTGTTGACAACAGTATGGATTCACAGATACTTTTTAATTTACTTTCTAATCCGGCAT
TTTTGTTATTTCTTTTGTTGCTCAGATTGTTCCAGCTTTGGCCATTGAGAGTTATTTCAT
[C,G]
TTGGCTCTTGTATCCTTTGGAAATGCCGTCCCCCCGCTTTTCTTCACCCCCACTTCCATA
TTTTCTGGTATTCTGGCATTACCAGAGGCTACAGACTCATCTTCTGTTTCCCCTGCCCCA
GCCTTGGAATCAGCCATTTCTCTAAAGAGCCCTAGTTCTTTTTATTGGAAAATGGTATTT
TAAAAGCAAGAGCTGGGTACTGAGTGTGTATGTTGTTGCTGGAGCGTCACTGCTTTTAGC
ACTTTCAGAGGGCAGAGCTAGAAAACATACACACATGTACCAACCCAGGTGTACACACAT

13719 TGTAGCTCATTGGTGAGAAAGGGATCTTTTGACTTGACTTGCATGGACACATTCTAGTAG
GAAGGTTGTCTGTCCTCATCACTCCTGTGAGTGGTCCTCTAGAGCTCTTTGAAATGGCTA
CAACATTGCAGATCAAAAACACCTGCTTTTCAGGTGCTTCACTTCTCACCTTTCAGATGG
GACATGCCCAGTTGTGTCTTCTAAACCTTGTTTCAGATAATTTTAAGAGTTGTCGCTTCA
GTAACTATCTCTAACACAGGGATCAGCAAACCTTTTCTGTGAAGTGCAGTAAATATTTTA
[G,A]
GCTTTGCGGACCATAAGGTATTTGTTTCAAGTACTCAGCTCTGTCTTTGTCCTGTGAAAG
CAGCCATAGATGGCACATGAACAAATGAGTATGGCTATGTCTTACTAAAATTTCATTTAC
AAAAACAAGGTTTTGTATTTGGCCCGTGGGCCATGGTTTACCATCCGTTGGACCCATTAA
GTATATTCTCCTCCTCTTCTTTGTCTCATTCTCACTGCGTTCATAGGCTTGATACGTTAA
CATTCGTGCATCAGTAAAAGAATCTGGCTTCTAGAGAAGAAGGGCTGTCCATGGGCGTTT

14333 AGTTTGTTTATGGTACTAGTGTGGCCACAAGGCTCTGCCACACAAGCTCTGTCTCTTCCT
TCCTGTTATTACTTCTGCTTCCCTTCTCAGGAACCTGAAATCATATGGTAGTTTGTTTGT
TTAAGTGATTTTTTTTTTTTGAGATGGAGTCTAGCTCTGTTGCCCAGTCTGGAGTGCACTG
CAACCTCCACCTCCTGGGTTCAAGCAGTTCTCCTGCCTCAGCCTCCCAAGTAGCTGGGGC
TACAGGTGCGCACCACCACGCCTGGCGCACCACCACGCCTGGCTAAATTTTTTTTTTTTT
[T,-]
AATAGAGATGGGTTTCACCATGTTGGCTCAGGTGGTCTCAAACTGACTTCAGGTGATCCA
CCCGCCTCAGCCAAAGTGTTGGGATTATAGATGTGAGCCACCACGCCCAGCCTTTAAGTG
AATTTTTATTTGAGTATAACATGCATAACAAGTTTGTGTGGATCATAAGTCTTAGAAGTG
GATGAATTTTTGTAGCAAGGTTTGAAGAGTCTGTTTTTAGATGAGTTTGCTAAGGTGGCA
CAGTATGTGATGATTCCGTGTAAAGAAGTCATTGTTACAGGGCTGTGTCCTCTATCTGAA

14753 GAATTTTTATTTGAGTATAACATGCATAACAAGTTTGTGTGGATCATAAGTCTTAGAAGT
GGATGAATTTTTGTAGCAAGGTTTGAAGAGTCTGTTTTTAGATGAGTTTGCTAAGGTGGC
ACAGTATGTGATGATTCCGTGTAAAGAAGTCATTGTTACAGGGCTGTGTCCTCTATCTGA
ACTGGCATGGTTAGTTTAGTTGTTTAAATTGAGGGCCTGCTTACAATTCATATCTAAGAT
TTACTGGAGAGGAGAAAGGGTTGAGTATTCAGTGGCCCAGAATCTGATATGGGAATTGGT
[A,G]
AGGTTTATGTTCAAGGAGCCAAAGAAGATTTAAATTTTATGTATTTGAATTACTCAGTGC
GTCTATATATATATATATATTTGGTCATCTTAAATTTTTTTTCTCGTTAGAATTCAGTTAAG
GCCAATATTTGAACTTTAATAAGTTTTGGTACTTGCTACACTGCAGTACATTTAATTGTA
TGTAATTATAGGGAAAGACTATGGGAATTGAAGTCAGAACACTTGGTTATAAGTGCGAAG
TCCACTACTTCTTTTTAAGATCTTAGGAAAGTGATTTAACCTCTTTGGGTGCAAATCCTT

14831 AGGTTTGAAGAGTCTGTTTTTAGATGAGTTTGCTAAGGTGGCACAGTATGTGATGATTCC
GTGTAAAGAAGTCATTGTTACAGGGCTGTGTCCTCTATCTGAACTGGCATGGTTAGTTTA
GTTGTTTAAATTGAGGGCCTGCTTACAATTCATATCTAAGATTTACTGGAGAGGAGAAAG
GGTTGAGTATTCAGTGGCCCAGAATCTGATATGGGAATTGGTAAGGTTTATGTTCAAGGA
GCCAAAGAAGATTTAAATTTTATGTATTTGAATTACTCAGTGCGTCTATATATATATATA

FIGURE 3CC

```
            [-,A,T]
            TTGGTCATCTTAAATTTTTTTTCTCGTTAGAATTCAGTTAAGGCCAATATTTGAACTTTA
            ATAAGTTTTGGTACTTGCTACACTGCAGTACATTTAATTGTATGTAATTATAGGGAAAGA
            CTATGGGAATTGAAGTCAGAACACTTGGTTATAAGTGCGAAGTCCACTACTTCTTTTTAA
            GATCTTAGGAAAGTGATTTAACCTCTTTGGGTGCAAATCCTTTATCTGTGTATTAAGGAA
            ACCATCTGCCTTCCTCACCTTACAGGTTGTTGAAAGAATCAGACAGGACAGATGTCCTAT

    15157   GTTAGAATTCAGTTAAGGCCAATATTTGAACTTTAATAAGTTTTGGTACTTGCTACACTG
            CAGTACATTTAATTGTATGTAATTATAGGGAAAGACTATGGGAATTGAAGTCAGAACACT
            TGGTTATAAGTGCGAAGTCCACTACTTCTTTTTAAGATCTTAGGAAAGTGATTTAACCTC
            TTTGGGTGCAAATCCTTTATCTGTGTATTAAGGAAACCATCTGCCTTCCTCACCTTACAG
            GTTGTTGAAAGAATCAGACAGGACAGATGTCCTATTTATAGCTCTTTAATGCATATGTAG
            [G,A]
            CAAGCAGTGGCAGTTCTGTGACTCTTCTCTAACTTACATATCATTTACCCAAACAGCCCT
            TATCTTCCAGCCAGCTTGGCTGCTTAGCCATATTGAATTACTAGTTTCTCTTATCTAGAA
            CAACTTCTGCCCAACTCATGGTGGACAGAACCAAGTGTCATGAAGTGATTTTATTCATTC
            TTGCATTCAGCACTCTTTTCACAGGCACCTACCCTGTGCCAGACACTGTTCTAGGCACTA
            ACATTTCAGCAGTGAATAAAGTCAGTCCATCTTCTACCCTCATGGAGCATATAATCCTGA

    16242   TTCTTCATGAATTGGTAGGAGTTTGGAGTTTGTCAGCAAACATTCTATCGGGCTAAAGGT
            TTTTATAATGAAAGAAATAGGCAAAGTGGATCAGTACACTCACTTTTCTACCATTGACCC
            TGGAGACAGATGGCTTAAAATGTTCTGCGTCTAGTTGACTTTTAGATCTTGAAATTAAGG
            TTTAATGATGACCAAGCTTTAAATAAATTGTAGAAAAGTATTCTTTCAAAAGTACATTAT
            AACTTTTATATTGGTTTCTTATATTTATTTCTTTTAATCTTTTCTTTTAACTCAAACTAC
            [G,A]
            TTTTAAGGTTTTGTTGCCTACTAAGTTATAATCTGAGTGCAGAAGGAAACTTGATTTGGC
            TTTATGGAATACATTTTACATTCAGTGAAGCTGAGCTCTGTTTCTCATTCCTTACAAAAG
            GAATCAAAGGCATTGGTTTGAGAGATCAAGTCATGTGTTAATAAAACACAAATATTCCAT
            CAAGTAATACTCTGAAGGAGCAGGTGTAGTTTATTTCTTCTCCAGAAAGTCTTCCAGCAG
            ATAAATAATGAGAGGTAGTATGGCATAGGAAAAAAGTACACTGAAGTCAGCCTTTCTGGT

    16698   TGTTAATAAAACACAAATATTCCATCAAGTAATACTCTGAAGGAGCAGGTGTAGTTTATT
            TCTTCTCCAGAAAGTCTTCCAGCAGATAAATAATGAGAGGTAGTATGGCATAGGAAAAAA
            GTACACTGAAGTCAGCCTTTCTGGTTCAACCAGCTCAGACCCCTGAGCTATTTTTGCCTC
            AGTTTTACGCCTTGGAGAACAATGCCTTGTCATTACTATTCACTTTATGACCATACAGTG
            CCTGGCACCTGGTGGGCAATTGGTGAATGTTTTCACTATCCTCATCCTTGCCCTCATGAA
            [A,G]
            CACTCCTTCTAGGTCCCACAAAGACCGTTGGTATTTTATGACAAAGTACCTTACAAATAT
            TTTTCTTTTTTTAAAGGAGAAATTGTCGTAAATGAAGTCAATTTTGTGAGAAAATGCATT
            GCAACAGACACAAGCCAGTACGATTTGTGGGGAAAGCTGATATGCAGTAACTTCAAAATC
            TCCTTTATTACAGATGACCCAATGCCATTACAGGTGTGTTTTATTAGTACACTGTTTCAT
            TCTATCAGGCTTTCAACTCTAAGTGGTACATATTATTATATAAAACATAGGTATGGAAAA

    17152   AAGCTGATATGCAGTAACTTCAAAATCTCCTTTATTACAGATGACCCAATGCCATTACAG
            GTGTGTTTTATTAGTACACTGTTTCATTCTATCAGGCTTTCAACTCTAAGTGGTACATAT
            TATTATATAAAACATAGGTATGGAAAAGTTATAGTAGAAGTATTAGGTAATGCAATGTTT
            GGGATAAATTATATTAAGATTTAAAGTAAAGTTTAAGAAGAATGTTGGAACTTGCTAGAG
            GAGTATTAGTGAGAGGATTGTAAGTCACCTTGCTTTATTTATCCTCTGTGATCGTTCATT
            [A,G]
            TATGTCCTTTTCATTAAGGAAGTTATTCCCTCTGTTGCAGATCTTTTAACCTGCTTATAA
            AAATGACATAAAGAGAAAAGGTTGTTTGCTAAATGATTTTATAAATGCCACACATTTTAG
            TGATTTCATAGGTTTTTTTTGTTGTTGGGTTTTTGATTTTTTTGTTTTGAGCCTGGATCTC
            GCTCTGTCTTGTCTCCCAGGCTGGAGTGCAGTGGCATGATGTCGGCTCACTGCAACCTCT
            GTCTGCTTCCTGGGCTCAAGCTATCCTGCCACCTCAGCCTCCTGAGTAGCTGGGACTACA

    17624   CTGGATCTCGCTCTGTCTTGTCTCCCAGGCTGGAGTGCAGTGGCATGATGTCGGCTCACT
            GCAACCTCTGTCTGCTTCCTGGGCTCAAGCTATCCTGCCACCTCAGCCTCCTGAGTAGCT
            GGGACTACAGGTGCATGCCACCACCTCCCGGCTAACTGTTGTATTTTTTGTAGAGATGGG
            GTTTTGTTATGATGCCCGGATTGGTCTTGAACTTCTGAGCCCAAGCAATCTGCCTGCCTC
            CCCCTCCCAAAGTGCCAGAGTACAGGCCACTGCACCCAGCTACCTTTTTTTTTTTTTTTT
            [T,-,A]
            AACTAATTAGAGTTATTTTCCTAAAAAGTTAAATTCTAATTTCTAGGAAGAGTGAAGAAT
            AGTATCGATTTAAAAATTTTCAGTAGCCCTCTTGTCTATTTTATGTTCTTACTGGAAAGTA
            ATAGTTCCATGTAATTTTGGTTTTTAGAAGTTCAGGCATTCATTTGATTAACTTAAAAAC
            CCTGGACTTTTCTGTCAGCCATTTTGTATTTTGTTTTATAAAGTATTATACACACTTACC
            CCTAGATCTTTCTTTATAGTAATTGTTCTTTAATGAAATATTGGTATATGAACTGTAAAC

    18268   TGTAGTCACTCACTAATTTACCATAATTATTATACTGTACAAATATTTATTGTACTGTAT
```

FIGURE 3DD

ATTTGTGTGTTCATTACAGTCTTATGTAGGTATATTTAGACTAAATTTAAGGCACTTAAA
GATACCCACTGTGTAGGGACAGTAGCTTATTTGGATATAGGCTTGTGTGTTTCTCTTTGT
TTTTAGCTTCATAATGATCATTGGCCCCAGACTTCACTGTAAATGAGAAGCAGATACCTG
GAACAGCTTAAATCCAGTACCACTATTAGGAAAAAGTAAACCAGTGCCCTACTGACAGCA
[-,G]
ATTGATAGTGTTAACTACGTCCTTAGTTTGAACATGCAAAACCTTTTCTAATGGTTTTTA
TTTCTAGTAGACTTTGTGCTTTAAAAAGATAGTTATTTTGCACTTTAAAATCTTCAGTGT
GAAAATCAAACATGATTTTACCCACTTAAAATCTGATGACCTAAGAGCCCTTTTTTCTTT
AATATGTTGTGGCCAGCTTATCCAGATCTAGACATGCAAATGCTTGCTGGTAAGGTGATT
GATGATATTCCCTATCTTAGGTATTATAATAAGATTGTTGTGTACATTTTAACCTAATTT

18786 AAATGCTTGCTGGTAAGGTGATTGATGATATTCCCTATCTTAGGTATTATAATAAGATTG
TTGTGTACATTTTAACCTAATTTCTATCTGTCAACATTGGAATGGCCCTAGCTACCTAGA
CAAAAGCTTTTTGTGCTTTTTAGAGATAACTGTCACAGTTTATCATCACAGTTTAAGGCT
TATACTACCATTGTGAGATTATTGGGAAAAGAATTAATATGAACATAATTTTTTATTCCA
GAAATTCCATTACAGAAACCTTCTTCTTGGTGAACACGATGTCCCTTTAACATGTATTGA
[A,G]
CAAATTGTCACAGGTACGTAGTATTCCGTACATACTCTAAAAGTCAATTCCACTCTGGAA
GTATTATTTGAAAAGTCATACCTCTCAAAATACTTGGATTGGCGTTTTATTTCTGTAAGT
TTACTTTTGCCGTTTTTTTGAGTCCCGGGAACATAAAGAGGGATATGTTAATAAATTATT
TTAAAAGGAAGATATAAAATGTATAACTTTTCATAGTTTCTAGGTTTTTTGTCCTCTTTT
TAATTAAAATTAATCATTAAATGTATCTAGATGGTGGTTTTATGCAAATAATCATTTAAA

18813 ATATTCCCTATCTTAGGTATTATAATAAGATTGTTGTGTACATTTTAACCTAATTTCTAT
CTGTCAACATTGGAATGGCCCTAGCTACCTAGACAAAAGCTTTTTGTGCTTTTTAGAGAT
AACTGTCACAGTTTATCATCACAGTTTAAGGCTTATACTACCATTGTGAGATTATTGGGA
AAAGAATTAATATGAACATAATTTTTTATTCCAGAAATTCCATTACAGAAACCTTCTTCT
TGGTGAACACGATGTCCCTTTAACATGTATTGAACAAATTGTCACAGGTACGTAGTATTC
[-,A,C]
GTACATACTCTAAAAGTCAATTCCACTCTGGAAGTATTATTTGAAAAGTCATACCTCTCA
AAATACTTGGATTGGCGTTTTATTTCTGTAAGTTTACTTTTGCCGTTTTTTTGAGTCCCG
GGAACATAAAGAGGGATATGTTAATAAATTATTTTAAAAGGAAGATATAAAATGTATAAC
TTTTCATAGTTTCTAGGTTTTTTGTCCTCTTTTTAATTAAAATTAATCATTAAATGTATC
TAGATGGTGGTTTTATGCAAATAATCATTTAAAATATCTTCCAAAGCAAAGTTAAAACCA

22061 CCTTCTGGTTGTCTTGTTGGTGTTGTTTCAATTGTATTATGACAAAATTAGATTGCTTTG
GGCACTTGTACTCATTAATATTCATCCTCATTATCCTCGAGCTGTCACAGGAAAATAGTG
ATATTTGGGAAAGGTCTGTATAAAGAAAGAAGGAATTTGATGGTGCAGAATTGGACATCT
AACCTCATAGCAACTTAGAACCACCATTTTCTTTTGCAGAACCTTTGCTCAAAACTGAAG
GGCAAAATAATAAAGGTTGTTTTTAATGATTTATCTATATATCTGTCTGTGTAGATAAAG
[A,G]
TAAATATATAGATACACATGAGTGACAAGTGAAATACATGCCTTTTGTCTCCACTTTGTT
CTCTGATTAGTGGGTTGTGAATCACTTCTTCAGGAATACTTTATAGAAGTGAATTCCATT
CATCTGATTAAGGAACAAGTTGGCCTTTTCATGAACTGTCATTTTTGACTTGAATCTGGT
ACTGTTTTTTGGTGGCTTTCAGGCCACAGAAATAAACCACTTTTGTTTGCAAATGAGATA
GAACTTAATGAGGTTTGAGTGTTTCCTGGATTTGAGTTTCTTCAGTACTGCACCCCAGGT

22205 GAAAGAAGGAATTTGATGGTGCAGAATTGGACATCTAACCTCATAGCAACTTAGAACCAC
CATTTTCTTTTGCAGAACCTTTGCTCAAAACTGAAGGGCAAAATAATAAAGGTTGTTTTT
AATGATTTATCTATATATCTGTCTGTGTAGATAAAGATAAATATATAGATACACATGAGT
GACAAGTGAAATACATGCCTTTTGTCTCCACTTTGTTCTCTGATTAGTGGGTTGTGAATC
ACTTCTTCAGGAATACTTTATAGAAGTGAATTCCATTCATCTGATTAAGGAACAAGTTGG
[C,T]
CTTTTCATGAACTGTCATTTTTGACTTGAATCTGGTACTGTTTTTTGGTGGCTTTCAGGC
CACAGAAATAAACCACTTTTGTTTGCAAATGAGATAGAACTTAATGAGGTTTGAGTGTTT
CCTGGATTTGAGTTTCTTCAGTACTGCACCCCAGGTGATCTTAGGAAAGAAACCATCCAC
TGTGGGTACTTCTGGCTTCTGTCCAGAGAAGATTATCAGCTTTGGTCCAAAAATTGATTT
AAAAGTAGTTTACTTCTTTTTCTCCAATAAAATATTTGCCATAATTTAATGTCTTTAATA

22527 TGACTTGAATCTGGTACTGTTTTTTGGTGGCTTTCAGGCCACAGAAATAAACCACTTTTG
TTTGCAAATGAGATAGAACTTAATGAGGTTTGAGTGTTTCCTGGATTTGAGTTTCTTCAG
TACTGCACCCCAGGTGATCTTAGGAAAGAAACCATCCACTGTGGGTACTTCTGGCTTCTG
TCCAGAGAAGATTATCAGCTTTGGTCCAAAAATTGATTTAAAAGTAGTTTACTTCTTTTT
CTCCAATAAAATATTTGCCATAATTTAATGTCTTTAATACCAACATTTTCTTCATTTCCT
[A,G]
TGGTAGCCAGGACAAATGAAGTATTTCAGATCTTTCAAAAACTCTTAGGATGAAAGGTAG
GAATTTGGACTTAGGTTTTTAAAATAGTGTGTATGTAAAAGTGCAAAGAATGGGGCCCTG
GCTTTCTCTTCTCGGAGTGTTCCACAGTAACAACATGAAGACAATCCAGGTACACAAGTT

FIGURE 3EE

TGTATGTGCCTTAGTCTGTGTGTCCAAAGAGGCCTCTTACTTAGGTCATATGAACATAAG
TTATACACTTGAAATTCACTACTGAAAAACAATGTATTTAGTTCGAGTTCTGCCACCCCA

22876 GATGAAAGGTAGGAATTTGGACTTAGGTTTTTAAAATAGTGTGTATGTAAAAGTGCAAAG
AATGGGGCCCTGGCTTTCTCTTCTCGGAGTGTTCCACAGTAACAACATGAAGACAATCCA
GGTACACAAGTTTGTATGTGCCTTAGTCTGTGTGTCCAAAGAGGCCTCTTACTTAGGTCA
TATGAACATAAGTTATACACTTGAAATTCACTACTGAAAAACAATGTATTTAGTTCGAGT
TCTGCCACCCCAAAAAAATCAACGAGTAATTCAACTGACTTGCAGTTTTACAATATTTTT
[A,G]
TAGACTTCTTTCAGCGTAGATGCTTTTGGACATACTCATTTGTTTCCTAACCTGATGTGA
TATTGTGCTATTTTTAAGGGGCTTTTAAAAAATACGCTGTGTTGGGTTTTGCCTTGAAAA
TAGGCTTTATTTCTTTTTTGCCTCATGGCCACAAAAAAAGGATGTCCATGATCAATGATC
TGTGAATTTCTTTTCTGTAAACAGAAAGAGCATGTAACTGCTTTCTAATTGTTTTGGAGA
ATGTGATAGACATTAGTATTATTATTATTGGCTTGGAGCATTTTCCTTAATATGTTGGTA

23351 ATGATCTGTGAATTTCTTTTCTGTAAACAGAAAGAGCATGTAACTGCTTTCTAATTGTTT
TGGAGAATGTGATAGACATTAGTATTATTATTATTGGCTTGGAGCATTTTCCTTAATATG
TTGGTAACTACTTTTGTCAGTGAATATTAGTGTAGCCACTGTTGGACACAGAGCACCGTC
AGAAAGCTACTGAAGTGGTGCTGCAAAGTGCAGACATCTTCAGATCTTTACTCAAGTCTG
TGCAGAGAGGTCTTTCTTGGTCTCCTTCTCTACTTTTTAGCCTGTCTCCCTCTTCTCACT
[G,A]
TAACACTTCATATTCCCCTTCCCTGCTCTATTATTTTTCTCTTTTAGCATTCATAGTTAT
CTAACTTTCTGTATTTTTTCTCTTTATCTTGTTTAGTGTCTGTCTTCCCACTAGAATGTA
AGCTTCATGAGGACAGGGATTAGTGTCTGTTTTGTTCACTGCATCTCTAGGGCTTACAAC
ATTGTAGGTACTCAGTAAATATTTGTTAAATCAATGTGAAATGTGTCATTTATCCTTAAG
GAATTGACCTTCATGGTAGAAGTGTAACAGAACCACCTATATCCTACTTTTCATCCACAT

23821 GGGCTTACAACATTGTAGGTACTCAGTAAATATTTGTTAAATCAATGTGAAATGTGTCAT
TTATCCTTAAGGAATTGACCTTCATGGTAGAAGTGTAACAGAACCACCTATATCCTACTT
TTCATCCACATCATAACTATTATGTGAATACCTTGGAAGTAAAGCAAAATAAGCACTTAA
CTAAAGAGACGCTTTATATTGAAACTGTTGTTCTGGGTTTCTGGAATTAGTACTCTGAAA
TTGGCTCCCTCTAGGAAGGCTTGTGAAGAGAGTAGTGTTGAACAGACATGACAGTTTCCA
[G,A]
GAAAGCATAGTTGGCTAAGAGGAGTAGGATTTTCCAAGCAAAGAGTGTGACAGTGGAGAT
GGCTGGGGCTAAGTCAGGCAGAATGTGTTCAAACCTGTTTTTCTCTGACCTGAGATTGCG
GAGGGAATATTGGGAAGGTATAGTTACCTGGTGAGGAGAGCCAGTTTTGTGAAGAATCAA
GAATGAGGAGATTTAATTTGTTATGCAGATGTCTGGGAACCACAGCAGATTATCAGGAGA
GCAAAATTGTTAGTCAGAATTACATCGTTAGAAGGTAATCCTTAAGTTTTGTAGATTTCT

25487 TGTGTGTGTGTTGTTTTTTTGATGTACCTCTTTGAGCCACCCATGCATTTTTGGAGTTTC
TTGCTAATTTTAATTTTTTGTAATTATGTTTCTCTATTTAGATGTTTAAATCCATGAGGC
GTAAACTTTAAAGTTTCATGCCTTATATTAATCCTTTATAGTCCACCAAAAATGAAACTT
TTTTCTTCCTTTTTTGGAGTGGACATGTAGTCACTGCCTTTTTGGAGAATGCTTCTTTAG
TTTGAAGCTTTCTTTATTGGACTAAAATTACTTTCCAATTAAAATTTAACTCAGCAAATA
[C,T]
TTACTGAATACTTGCCATGTGCTAGCTAAAGATAAACAATGTCTTGAGGGCATGAAAGTG
AATGAGATACCTGGCCTTAAGGAGCTCTTTTATATTCTAGGTCAACAGAAAAACATGTAA
ATAGTATCTATAATCACTGCCCCAAGATGATGCTCCCAGTGCCCAAGGCCTTATTGTACA
TTTCATTTAACTAAGTGTGTTAAAATCAAATTCTAAATGTAGAATTTTTCCTAGGTATGC
CTTGCAATAGCTCATTATTCCCAGCCAACAGACCTCCAGCTACTCTTTGCATTTGAATAT

30858 CAGTGATGGAAAGTAGGGCAGCCCACTAGAAGCCACTAGCCACATGTGGCTGTTAAGTAC
TTGAAATGTGGCTAGTGCAAACTGATGGACTGAATTTTTAATTTTATTTAATTTTCATTT
CAGTTTAAATTTAAATGGGCTTGTGTGGCTAGAAGTTACGTTTTTGGGAAACATACTAGA
GTCTAGGCCCTATTTGATTTCCCGCCTCTCTTCCACCACCTGTTGAATCCCTATGCTCTA
GCTGTATTTAGTTACTTGATATTATACAGTTA
[C,T]
ACCATCTTTTTAAAGTTCTTCTCTGTCTAGCATGCCTACCTCCTCCTCACCAGCTACCTG
GCAACTTTTGACTTGTTCCTTAGAACTCTCTTTAGTTGTGGTCAAGTCATGAAGCTTTTC
CTGCCCCGGCCTCTCTCTGCAGCGAGAGTTAGGGGACTTCTCTTTTGCATCTTCATTGCA
CTCAGACATCTGGTACTCTGTGATTATCACACTTATTAATGCTCTCAAGATAGAGATAAA
ATCTTATTCATCTTTTTGCTCTCAGGCATTAG

31014 ATTTAAATGGGCTTGTGTGGCTAGAAGTTACGTTTTTGGGAAACATACTAGAGTCTAGGC
CCTATTTGATTTCCCGCCTCTCTTCCACCACCTGTTGAATCCCTATGCTCTAGCTGTATT
TAGTTACTTGATATTATACAGTTATACCATCTTTTTAAAGTTCTTCTCTGTCTAGCATGC
CTACCTCCTCCTCACCAGCTACCTGGCAACTTTTGACTTGTTCCTTAGAACTCTCTTTAG
TTGTGGTCAAGTCATGAAGCTTTTCCTGCCCCGGCCTCTCTCTGCAGCGAGAGTTAGGGG

FIGURE 3FF

[A,C]
CTTCTCTTTTGCATCTTCATTGCACTCAGACATCTGGTACTCTGTGATTATCACACTTAT
TAATGCTCTCAAGATAGAGATAAAATCTTATTCATCTTTTTGCTCTCAGGCATTAGCACA
TGGGGAGTTCTCAGAAAATACCTGTCTTATACCAGGAATTAATGAATAATCAGTAGGAAT
GAGCATGACATGTTCATGGGACGTTGGAGGGTAGTGCATGGCTGCAGAGGAGAATGGGAA
ATGAAGGTCAGATAAGTTACGTGAGGGATCTCTAAGGCCAAGAGAAGCCATTTAGGTTTG

31437 GGGAGTTCTCAGAAAATACCTGTCTTATACCAGGAATTAATGAATAATCAGTAGGAATGA
GCATGACATGTTCATGGGACGTTGGAGGGTAGTGCATGGCTGCAGAGGAGAATGGGAAAT
GAAGGTCAGATAAGTTACGTGAGGGATCTCTAAGGCCAAGAGAAGCCATTTAGGTTTGAT
TTGGTTGGAAAATGAGCTTATTGAAAGTTTAAGGCAAGGGACTAGCATCATGAACACATC
TTTTTAGGGAAGTGTGTCTTGTGGTAAGCTGCTGGCTGGTTTAAATGCAGCAGAATATTC
[C,T]
ATTGGGGATGCCAGCTGGGAGACTTGCCACAGTTGCAGCCTGCAGCAGAAAGACCCTGGG
CCAGAATGGGTTGTGCCATCTGTCACCAGATATTGCCAAGGTAGATCTGGCTGACTTTGT
GGGACAGCTTGTTTCTCAATAATCACTTTGCAGGCACTCTTGAGGCTGTGAGCATGCTCC
CAGAAGATAGCATTACTTCTCTCTCAGAGCAGGCTCCTTTCTAAGGAAATGCAAGTCTAG
GCCTGCCCTGCTGTAATCTTCATGTGGAAACAGCACTCTAGCAAAGAACAAGGAACCTGA

35341 TGGTAAAACCCCGCCTCTACTAAAAATACAAAAATTTAGCCAGGTGTGGTGGCGGGTGCC
TGTAATCCCAACTACTCGGGAGGGTGAGGCAGGAGAATCGCTTGAACCCGGGAGGGGGAG
GTTGCAGTGAGCCGAGATGGTGCCACTGCACTCCAGCCTGGGCGACAGTATGAGACTCCG
TCTCAAAAAGAAAAAGAAGGAAATGATCTAATTTGTTCTGTGCACTGCACGTGGGGGTGG
CAGTGAGGTGAATGGCAGCATTCTGCAGTAGTCAAAGCCAGATGGGTGGGAGAAGTTGGG
[G,A,T]
GCTAAGAGGGAAACAAAGTTTACCTGTCTTCTCCTTGATTTCACTCTCAGTTTTATGAGA
ATACAGAAAAATCATGCAGAGAAACCTGATGGAATAGTCTCTAAAACTAAAAAATAAGAT
AAGCAATGGTTCTGTCTTAAAAAAAAAAAAGTAAACTCCATGAAGGCAGAGACCTTACCT
GTCTCATTCCTCTCTCTATCCCCTGGTCTATAGTAAGGGTTAAATAAATATATGCTGAAA
TGAATGAGTAATGACTAAAGTATTTTTGTCTTTATTAGGATTTGTAATGCAATAACTAAA

35346 AAACCCCGCCTCTACTAAAAATACAAAAATTTAGCCAGGTGTGGTGGCGGGTGCCTGTAA
TCCCAACTACTCGGGAGGGTGAGGCAGGAGAATCGCTTGAACCCGGGAGGGGGAGGTTGC
AGTGAGCCGAGATGGTGCCACTGCACTCCAGCCTGGGCGACAGTATGAGACTCCGTCTCA
AAAAGAAAAAGAAGGAAATGATCTAATTTGTTCTGTGCACTGCACGTGGGGGTGGCAGTG
AGGTGAATGGCAGCATTCTGCAGTAGTCAAAGCCAGATGGGTGGGAGAAGTTGGGTGCTA
[A,G]
GAGGGAAACAAAGTTTACCTGTCTTCTCCTTGATTTCACTCTCAGTTTTATGAGAATACA
GAAAAATCATGCAGAGAAACCTGATGGAATAGTCTCTAAAACTAAAAAATAAGATAAGCA
ATGGTTCTGTCTTAAAAAAAAAAAAGTAAACTCCATGAAGGCAGAGACCTTACCTGTCTC
ATTCCTCTCTCTATCCCCTGGTCTATAGTAAGGGTTAAATAAATATATGCTGAAATGAAT
GAGTAATGACTAAAGTATTTTTGTCTTTATTAGGATTTGTAATGCAATAACTAAAAGTCA

36164 TTCTTCATGAATTGGTAGGAGTTTGGAGTTTGTCAGCAAACATTCTATCGGGCTAAAGGT
TTTTATAATGAAAGAAATAGGCAAAGTGGATCAGTACACTCACTTTTCTACCATTGACCC
TGGAGACAGATGGCTTAAAATGTTCTGCGTCTAGTTGACTTTTAGATCTTGAAATTAAGG
TTTAATGATGACCAAGCTTTAAATAAATTGTAGAAAAGTATTCTTTCAAAAGTACATTAT
AACTTTTATATTGGTTTCTTATATTTATTTCTTTTAATCTTTTCTTTTAACACAAACTAC
[G,A]
TTTTAAGGTTTTGTTGCCTACTAAGTTATAATCTGAGTGCAGAAGGAAACTTGATTTGGC
TTTATGGAATACATTTTACATTCAGTGAAGCTGAGCTCTGTTTCTCATTCCTTACAAAAG
GAATCAAAGGCATTGGTTTGAGAGATCAAGTCATGTGTTAATAAAACACAAATATTCCAT
CAAGTAATACTCTGAAGGAGCAGGTGTAGTTTATTTCTTCTCCAGAAAGTCTTCCAGCAG
ATAAATAATGAGAGGTAGTATGGCATAGGAAAAAAGTACACTGAAGTCAGCCTTTCTGGT

36620 TGTTAATAAAACACAAATATTCCATCAAGTAATACTCTGAAGGAGCAGGTGTAGTTTATT
TCTTCTCCAGAAAGTCTTCCAGCAGATAAATAATGAGAGGTAGTATGGCATAGGAAAAAA
GTACACTGAAGTCAGCCTTTCTGGTTCAACCAGCTCAGACCCCTGAGCTATTTTTGCCTC
AGTTTTACGCCTTGGAGAACAATGCCTTGTCATTACTATTCACTTTATGACCATACAGTG
CCTGGCACCTGGTGGGCAATTGGTGAATGTTTTCACTATCCTCATCCTTGCCCTCATGAA
[A,G]
CACTCCTTCTAGGTCCCACAAAGACCGTTGGTATTTTATGACAAAGTACCTTACAAATAT
TTTTCTTTTTTTAAAGGAGAAATTGTCGTAAATGAAGTCAATTTTGTGAGAAAATGCATT
GCAACAGACACAAGCCAGTACGATTTGTGGGGAAAGCTGATATGCAGTAACTTCAAAATC
TCCTTTATTACAGATGACCCAATGCCATTACAGGTGTGTTTTATTAGTACACTGTTTCAT
TCTATCAGGCTTTCAACTCTAAGTGGTACATATTATTATATATAAAACATAGGTATGGAAAA

37074 AAGCTGATATGCAGTAACTTCAAAATCTCCTTTATTACAGATGACCCAATGCCATTACAG

FIGURE 3GG

GTGTGTTTTATTAGTACACTGTTTCATTCTATCAGGCTTTCAACTCTAAGTGGTACATAT
TATTATATAAAACATAGGTATGGAAAAGTTATAGTAGAAGTATTAGGTAATGCAATGTTT
GGGATAAATTATATTAAGATTTAAAGTAAAGTTTAAGAAGAATGTTGGAACTTGCTAGAG
GAGTATTAGTGAGAGGATTGTAAGTCACCTTGCTTTATTTATCCTCTGTGATCGTTCATT
[A,G]
TATGTCCTTTTCATTAAGGAAGTTATTCCCTCTGTTGCAGATCTTTTAACCTGCTTATAA
AAATGACATAAAGAGAAAAGGTTGTTTGCTAAATGATTTTATAAATGCCACACATTTTAG
TGATTTCATAGGTTTTTTTGTTGTTGGGTTTTTGATTTTTTTGTTTTGAGCCTGGATCTC
GCTCTGTCTTGTCTCCCAGGCTGGAGTGCAGTGGCATGATGTCGGCTCACTGCAACCTCT
GTCTGCTTCCTGGGCTCAAGCTATCCTGCCACCTCAGCCTCCTGAGTAGCTGGGACTACA

37546 CTGGATCTCGCTCTGTCTTGTCTCCCAGGCTGGAGTGCAGTGGCATGATGTCGGCTCACT
GCAACCTCTGTCTGCTTCCTGGGCTCAAGCTATCCTGCCACCTCAGCCTCCTGAGTAGCT
GGGACTACAGGTGCATGCCACCACTCCCGGCTAACTGTTGTATTTTTTTGTAGAGATGGG
GTTTTGTTATGATGCCCGGATTGGTCTTGAACTTCTGAGCCCAAGCAATCTGCCTGCCTC
CCCCTCCCAAAGTGCCAGAGTACAGGCCACTGCACCCAGCTACCTTTTTTTTTTTTTTTT
[T,-,A]
AACTAATTAGTGTTATTTTCCTAAAAAGTTAAATTCTAATTTCTAGGAAGAGTGAAGAAT
AGTATCGATTTAAAAATTTTCAGTAGCCCTCTTGCTATTTTATGTTCTTACTGGAAAGTA
ATAGTTCCATGTAATTTTGGTTTTTAGAAGTTCAGGCATTCATTTGATTAACTTAAAAAC
CCTGGACTTTTCTGTCAGCCATTTTGTATTTTGTTTTATAAAGTATTATACACACTTACC
CCTAGATCTTTCTTTATAGTAATTGTTCTTTAATGAAATATTGGTATATGAACTGTAAAC

38190 TGTAGTCACTCACTAATTTACCATAATTATTATACTGTACAAATATTTATTGTACTGTAT
ATTTGTGTGTTCATTACAGTCTTATGTAGGTATATTTAGACTAAATTTAAGGCACTTAAA
GATACCCACTGTGTAGGGACAGTAGCTTATTTGGATATAGGCTTGTGTGTTTCTCTTTGT
TTTTAGCTTCATAATGATCATTGGCCCCAGACTTCACTGTAAATGAGAAGCAGATACCTG
GAACAGCTTAAATCCAGTACCACTATTAGGAAAAAGTAAACCAGTGCCCTACTGACAGCA
[-,G]
ATTGATAGTGTTAACTACGTCCTTAGTTTGAACATGCAAAACCTTTTCTAATGGTTTTTA
TTTCTAGTAGACTTTGTGCTTTAAAAAGATAGTTATTTTGCACTTTAAAATCTTCAGTGT
GAAAATCAAACATGATTTTACCCACTTAAAATCTGATGACCTAAGAGCCCTTTTTTCTTT
AATATGTTGTGGCCAGCTTATCCAGATCTAGACATGCAAATGCTTGCTGGTAAGGTGATT
GATGATATTCCCTATCTTAGGTATTATAATAAGATTGTTGTGTACATTTTAACCTAATTT

38708 AAATGCTTGCTGGTAAGGTGATTGATGATATTCCCTATCTTAGGTATTATAATAAGATTG
TTGTGTACATTTTAACCTAATTTCTATCTGTCAACATTGGAATGGCCCTAGCTACCTAGA
CAAAAGCTTTTTGTGCTTTTTAGAGATAACTGTCACAGTTTATCATCACAGTTTAAGGCT
TATACTACCATTGTGAGATTATTGGGAAAAGAATTAATATGAACATAATTTTTTATTCCA
GAAATTCCATTACAGAAACCTTCTTCTTGGTGAACACGATGTCCCTTTAACATGTATTGA
[A,G]
CAAATTGTCACAGGTACGTAGTATTCCGTACATACTCTAAAAGTCAATTCCACTCTGGAA
GTATTATTTGAAAAGTCATACCTCTCAAAATACTTGGATTGGCGTTTTATTTCTGTAAGT
TTACTTTTGCCGTTTTTTTGAGTCCCGGGAACATAAAGAGGGATATGTTAATAAATTATT
TTAAAAGGAAGATATAAAATGTATAACTTTTCATAGTTTCTAGGTTTTTTGTCCTCTTTT
TAATTAAAATTAATCATTAAATGTGTCTAGATGGTGGTTTTATGCAAATAATCATTTAAA

38735 ATATTCCCTATCTTAGGTATTATAATAAGATTGTTGTGTACATTTTAACCTAATTTCTAT
CTGTCAACATTGGAATGGCCCTAGCTACCTAGACAAAAGCTTTTTGTGCTTTTTAGAGAT
AACTGTCACAGTTTATCATCACAGTTTAAGGCTTATACTACCATTGTGAGATTATTGGGA
AAAGAATTAATATGAACATAATTTTTTATTCCAGAAATTCCATTACAGAAACCTTCTTCT
TGGTGAACACGATGTCCCTTTAACATGTATTGAGCAAATTGTCACAGGTACGTAGTATTC
[-,A,C]
GTACATACTCTAAAAGTCAATTCCACTCTGGAAGTATTATTTGAAAAGTCATACCTCTCA
AAATACTTGGATTGGCGTTTTATTTCTGTAAGTTTACTTTTGCCGTTTTTTTGAGTCCCG
GGAACATAAAGAGGGATATGTTAATAAATTATTTTAAAAGGAAGATATAAAATGTATAAC
TTTTCATAGTTTCTAGGTTTTTTGTCCTCTTTTTAATTAAAATTAATCATTAAATGTGTC
TAGATGGTGGTTTTATGCAAATAATCATTTAAAATATCTTCCAAAGCAAAGTTAAAACCA

41983 CCTTCTGGTTGTCTTGTTGGTGTTGTTTCAATTGTATTATGACAAAATTAGATTGCTTTG
GGCACTTGTACTCATTAATATTCATCCTCATTATCCTCGAGCTGTCACAGGAAAATAGTG
ATATTTGGGAAAGGTCTGTATAAAGAAAGAAGGAATTTGATGGTGCAGAATTGGACATCT
AACCTCATAGCAACTTAGAACCACCATTTTCTTTTGCAGAACCTTTGCTCAAAACTGAAG
GGCAAAATAATAAAGGTTGTTTTTAATGATTTATCTATATATCTGTCTGTGTAGATAAAG
[A,G]
TAAATATATAGATACACATGAGTGACAAGTGAAATACATGCCTTTTGTCTCCACTTTGTT
CTCTGATTAGTGGGTTGTGAATCACTTCTTCAGGAATACTTTATAGAAGTGAATTCCATT
CATCTGATTAAGGAACAAGTTGGCCTTTTCATGAACTGTCATTTTTGACTTGAATCTGGT

FIGURE 3HH

ACTGTTTTTTGGTGGCTTTCAGGCCACAGAAATAAACCACTTTTGTTTGCAAATGAGATA
GAACTTAATGAGGTTTGAGTGTTTCCTGGATTTGAGTTTCTTCAGTACTGCACCCCAGGT

42127 GAAAGAAGGAATTTGATGGTGCAGAATTGGACATCTAACCTCATAGCAACTTAGAACCAC
CATTTTCTTTTGCAGAACCTTTGCTCAAAACTGAAGGGCAAAATAATAAAGGTTGTTTTT
AATGATTTATCTATATATCTGTCTGTGTAGATAAAGATAAATATATAGATACACATGAGT
GACAAGTGAAATACATGCCTTTTGTCTCCACTTTGTTCTCTGATTAGTGGGTTGTGAATC
ACTTCTTCAGGAATACTTTATAGAAGTGAATTCCATTCATCTGATTAAGGAACAAGTTGG
[C,T]
CTTTTCATGAACTGTCATTTTTGACTTGAATCTGGTACTGTTTTTTGGTGGCTTTCAGGC
CACAGAAATAAACCACTTTTGTTTGCAAATGAGATAGAACTTAATGAGGTTTGAGTGTTT
CCTGGATTTGAGTTTCTTCAGTACTGCACCCCAGGTGATCTTAGGAAAGAAACCATCCAC
TGTGGGTACTTCTGGCTTCTGTCCAGAGAAGATTATCAGCTTTGGTCCAAAAATTGATTT
AAAAGTAGTTTACTTCTTTTTCTCCAATAAAATATTTGCCATAATTTAATGTCTTTAATA

42449 TGACTTGAATCTGGTACTGTTTTTTGGTGGCTTTCAGGCCACAGAAATAAACCACTTTTG
TTTGCAAATGAGATAGAACTTAATGAGGTTTGAGTGTTTCCTGGATTTGAGTTTCTTCAG
TACTGCACCCCAGGTGATCTTAGGAAAGAAACCATCCACTGTGGGTACTTCTGGCTTCTG
TCCAGAGAAGATTATCAGCTTTGGTCCAAAAATTGATTTAAAAGTAGTTTACTTCTTTTT
CTCCAATAAAATATTTGCCATAATTTAATGTCTTTAATACCAACATTTTCTTCATTTCCT
[A,G]
TGGTAGCCAGGACAAATGAAGTATTTCAGATCTTTCAAAAACTCTTAGGATGAAAGGTAG
GAATTTGGACTTAGGTTTTTAAAATAGTGTGTATGTAAAAGTGCAAAGAATGGGGCCCTG
GCTTTCTCTTCTCGGAGTGTTCCACAGTAACAACATGAAGACAATCCAGGTACACAAGTT
TGTATGTGCCTTAGTCTGTGTGTCCAAAGAGGCCTCTTACTTAGGTCATATGAACATAAG
TTATACACTTGAAATTCACTACTGAAAAACAATGTATTTAGTTCGAGTTCTGCCACCCCA

42798 GATGAAAGGTAGGAATTTGGACTTAGGTTTTTAAAATAGTGTGTATGTAAAAGTGCAAAG
AATGGGGCCCTGGCTTTCTCTTCTCGGAGTGTTCCACAGTAACAACATGAAGACAATCCA
GGTACACAAGTTTGTATGTGCCTTAGTCTGTGTGTCCAAAGAGGCCTCTTACTTAGGTCA
TATGAACATAAGTTATACACTTGAAATTCACTACTGAAAAACAATGTATTTAGTTCGAGT
TCTGCCACCCCAAAAAAAATCAACGAGTAATTCAACTGACTTGCAGTTTTACAATATTTTT
[A,G]
TAGACTTCTTTCAGCGTAGATGCTTTTGGACATACTCATTTGTTTCCTAACCTGATGTGA
TATTGTGCTATTTTTAAGGGGCTTTTAAAAAATACGCTGTGTTGGGTTTTGCCTTGAAAA
TAGGCTTTATTTCTTTTTTGCCTCATGGCCACAAAAAAAGGATGTCCATGATCAATGATC
TGTGAATTTCTTTTCTGTAAACAGAAAGAGCATGTAACTGCTTTCTAATTGTTTTGGAGA
ATGTGATAGACATTAGTATTATTATTATTGGCTTGGAGCATTTTCCTTAATATGTTGGTA

43273 ATGATCTGTGAATTTCTTTTCTGTAAACAGAAAGAGCATGTAACTGCTTTCTAATTGTTT
TGGAGAATGTGATAGACATTAGTATTATTATTATTGGCTTGGAGCATTTTCCTTAATATG
TTGGTAACTACTTTTGTCAGTGAATATTAGTGTAGCCACTGTTGGACACAGAGCACCGTC
AGAAAGCTACTGAAGTGGTGCTGCAAAGTGCAGACATCTTCAGATCTTTACTCAAGTCTG
TGCAGAGAGGTCTTTCTTGGTCTCCTTCTCTACTTTTTAGCCTGTCTCCCTCTTCTCACT
[G,A]
TAACACTTCATATTCCCCTTCCCTGCTCTATTATTTTTCTCTTTTAGCATTCATAGTTAT
CTAACTTTCTGTATTTTTTCTCTTTATCTTGTTTAGTGTCTGTCTTCCCACTAGAATGTA
AGCTTCATGAGGACAGGGATTAGTGTCTGTTTTGTTCACTGCATCTCTAGGGCTTACAAC
ATTGTAGGTACTCAGTAAATATTTGTTAAATCAATGTGAAATGTGTCATTTATCCTTAAG
GAATTGACCTTCATGGTAGAAGTGTAACAGAACCACCTATATCCTACTTTTCATCCACAT

43743 GGGCTTACAACATTGTAGGTACTCAGTAAATATTTGTTAAATCAATGTGAAATGTGTCAT
TTATCCTTAAGGAATTGACCTTCATGGTAGAAGTGTAACAGAACCACCTATATCCTACTT
TTCATCCACATCATAACTATTATGTGAATACCTTGGAAGTAAAGCAAAATAAGCACTTAA
CTAAAGAGACGCTTTATATTGAAACTGTTGTTCTGGGTTTCTGGAATTAGTACTCTGAAA
TTGGCTCCCTCTAGGAAGGCTTGTGAAGAGAGTAGTGTTGAACAGACATGACAGTTTCCA
[G,A]
GAAAGCATAGTTGGCTAAGAGGAGTAGGATTTTCCAAGCAAAGAGTGTGACAGTGGAGAT
GGCTGGGGCTAAGTCAGGCAGAATGTGTTCAAACCTGTTTTTCTCTGACCTGAGATTGCG
GAGGGAATATTGGGAAGGTATAGTTACCTGGTGAGGAGAGCCAGTTTTGTGAAGAATCAA
GAATGAGGAGATTTAATTTGTTATGCAGATGTCTGGGAACCACAGCAGATTATCAGGAGA
GCAAAATTGTTAGTCAGAATTACATCGTTAGAAGGTAATCCTTAAGTTTTGTAGATTTCT

45407 TGTGTGTGTGTTGTTTTTTTTGATGTACCTCTTTGAGCCACCCATGCATTTTTGGAGTTTC
TTGCTAATTTTAATTTTTTTGTAATTATGTTTCTCTATTTAGATGTTTAAATCCATGAGGC
GTAAACTTTAAAGTTTCATGCCTTATATTAATCCTTTATAGTCCACCAAAAATGAAACTT
TTTTCTTCCTTTTTTGGAGTGGACATGTAGTCACTGCCTTTTTGGAGAATGCTTCTTTAG
TTTGAAGCTTTCTTTATTGGACTAAAATTACTTTCCAATTAAAATTTAACTCAGCAAATA

FIGURE 3II

[C,T]
TTACTGAATACTTGCCATGTGCTAGCTAAAGATAAACAATGTCTTGAGGGCATGAAAGTG
AATGAGATACCTGGCCTTAAGGAGCTCTTTTATATTCTAGGTCAACAGAAAAACATGTAA
ATAGTATCTATAATCACTGCCCCAAGATGATGCTCCCAGTGCCCAAGGCCTTATTGTACA
TTTCATTTAACTAAGTGTGTTAAAATCAAATTCTAAATGTAGAATTTTTCCTAGGTATGC
CTTGCAATAGCTCATTATTCCCAGCCAACAGACCTCCAGCTACTCTTTGCATTTGAATAT

45985 AGCTACTCTTTGCATTTGAATATGTTGGGAAAAAATACCACAATTCAGGTAAATATGAAA
ATATTAAATATTGTGACTAATTTTACATGTGTAAATTTTACTCTTATGTTTACCGGAAGC
CTCCAAGTACATGAGCTTTAATGATTGTAGAATTACTAGCTTCATACCTTAGAGAAGTAA
GCACTACATGCTAAAAGAGCCAATAGTTTGTCAGATTATTTCTTGACAAGTTACCAGGAA
GAACCTTTAATGCTATGAATATGGGCTTATAAGTTATGTCAGATATTTAATCTCCAGTCA
[T,C]
TGGCTTGTATTTTATGATGAAGAATATATAACCCACCCTTTTTAATTGATAGCTTGAGTT
AAAGTAATCTTATCTTTTAAGAAAACTGGCAGAAAACTAAAAGATATATTAAAAGCATAA
TCTTTTCTGGCAAGGTGTGATTTCATGCAAAAGCTAAAGTGATTAAAAACTTTTTGTGGA
CTTCATTAAGATTCTCAGAATACTGAGTTTCTATTTCTGAGTAATACTGATGAAAGGAAG
ATGAGCATTTTTCCAAGGACAAGTATATTCTAGACAGCTTTTGTGAAAGTAAATAGTTTT

46198 GATTATTTCTTGACAAGTTACCAGGAAGAACCTTTAATGCTATGAATATGGGCTTATAAG
TTATGTCAGATATTTAATCTCCAGTCACTGGCTTGTATTTTATGATGAAGAATATATAAC
CCACCCTTTTTAATTGATAGCTTGAGTTAAAGTAATCTTATCTTTTAAGAAAACTGGCAG
AAAACTAAAAGATATATTAAAAGCATAATCTTTTCTGGCAAGGTGTGATTTCATGCAAAA
GCTAAAGTGATTAAAAACTTTTTGTGGACTTCATTAAGATTCTCAGAATACTGAGTTTCT
[A,G]
TTTCTGAGTAATACTGATGAAAGGAAGATGAGCATTTTTCCAAGGACAAGTATATTCTAG
ACAGCTTTTGTGAAAGTAAATAGTTTTGTCTATATATCTGACAGTCATGACATGACCAGG
GAAGATTCCAGATGATCATGCAATTCTGTACATTCTGTTTCGTACAAATGTAATTTTAAT
AAACAATTTTTAAAAATATCTTGATAGAGAAAAACAAAGAGCCGTGTCTCCTGTTAGCCC
CATTGTCAGTTAGTGACTGCAAGTCAGTTAACTGAGCGAAGCCTGTGTTCTTTTATTTAA

46793 ATTTAAGCAAGAAAAATAAATCAGCTGTGTATTTATAATGAAAAATCCATTCACCCAGCA
TGCTCTGGGCCATACAAATTATTAATTGTACTGAAATTTTATATTTTGTTACCACGAAAC
ATGGTAGTAATTTAAATAACTGGCATAATAAAAGTATATTCCAGCAACACTATATTGTAA
ATACATTAAAATGTATCAGTGTACGGTATCTGAAGATGCATGTGTATAAGTAAATTTTCC
TTAGTTTAAAAGATAACTACCTTTCTGTTAAGCACTGAGAGGACCAAAAAAAAAAAAAAA
[-,A]
GAAAATACAGTAGAGATAATATATGAAAATAATGCTTTGCAGAGCAGCTTTTATCATACA
GTATTATATTTATAGAAATTGTATAACAAAAGTATTTGTAACTTAATTTTTCTTATCGAT
ATATACATAATTGTAACTGAGGCTTAAGCAATACAGTTATTTTTTTGAAGTTTATTAATAT
TAAGTAAATTCACTTACTGTCTAAAAATAAAGTATACAGATCCTGCACTATTAGGTAAAC
ACTCCTTGGGATCATCGTCAAGCTACAGAACAGTGATCAAGGTTATCTTCAATAAGATCC

46923 TTTAAATAACTGGCATAATAAAAGTATATTCCAGCAACACTATATTGTAAATACATTAAA
ATGTATCAGTGTACGGTATCTGAAGATGCATGTGTATAAGTAAATTTTCCTTAGTTTAAA
AGATAACTACCTTTCTGTTAAGCACTGAGAGGACCAAAAAAAAAAAAAAAAGAAAATACA
GTAGAGATAATATATGAAAATAATGCTTTGCAGAGCAGCTTTTATCATACAGTATTATAT
TTATAGAAATTGTATAACAAAAGTATTTGTAACTTAATTTTTCTTATCGATATATACATA
[-,A]
TTGTAACTGAGGCTTAAGCAATACAGTTATTTTTTTGAAGTTTATTAATATTAAGTAAATT
CACTTACTGTCTAAAAATAAAGTATACAGATCCTGCACTATTAGGTAAACACTCCTTGGG
ATCATCGTCAAGCTACAGAACAGTGATCAAGGTTATCTTCAATAAGATCCTCACCCAGAG
TTGCAAGGGTTGTAGGAGTGAGTCTTTGATTCCTGCTCAACTGTTTATGATACAGACCAG
TTCTTCATGCTGCTGTTTTTCCAATAGAAATGATTCATTTCAGTTTACAGATCCATAACT

47851 ATAGTTTTGTTAAGATTCCTCGTAGGGTAACATCCTTTAATATCCTTCCATGCTGTTACA
GAAGCATAAATACTGCATCTTTAAGATCAAAAGGAGCCTGAAATTTCCACACACTGCAGT
CAGAATTCATTAATTTGTGAGTGAAAGATGCCCACTCATCCACTCTTGAACTTCTGGATG
ACACCTTGATTCATTGGCTGGATTAAAGAAGTCCTTTTTGCAGGCAGGTAGGTGACAAAG
CTGTTTCCACAAATAAGATCCAAAGTTGGAGGAGCTCCCCTGCAGTTATCTGAGAAAATG
[A,G]
TATTTTAGCTGGCCTTAGTCACTCAGGTTTTCATTCATATTCAGTATCACATGAGGAAAA
GCCATCTCTGAAAGGTCCTGCAGTCATCCCAACACTTCTGTGAATATCCTGGAGTAAAGT
AAGATGTGTAGCACCCAGGCTTTGGAACATCGCTTTGCACAAACACCCCAGGAGATATTA
CTAGCACAAACAAGAACAATGATTCTGTTTTTTCTCTTTTAACTTTAAAGAAACCATGAG
GACTCTGTTTTCATCAGTCAGATTATTATTGGGCAAATAACGTCAAAAAAGTACAGATTC

48875 ACAGGTCAGAATCTCCCAGTTAAGAACCACTTTGTTGACTCATGCTTTTGAACTGATTAA

FIGURE 3JJ

TACTCACAGTCCTCTTTTTACCTTATTCCTTTGTGACTTCTAATTTCTGCAGTATCATCA
GAGTGGTGGGCTTTCTTTTCATATATTGATGACTTGTATTTTCTGTTGCTTGAAGCCATT
CTAGATATCAATTGGCCAATTCAGTGGAAATTATCTAAAATAACCCCAACAGTATAGGAT
TAGACTTTTGTACTGTCACAGAAGATAGCCAAGGTCAGGAGCATATAATATCTATTTCAC
[G,T]
CTTAGTCTGCTGTGGAGGCATGTCATAAAACCTCAGTCAGGTAGCGGTCAGCGGAGCCAG
GTCTCCCTGAGATGACCCACCTTTCACTGTGTTGGTCCAGCCCCTCATAGCGATCCACTC
ATAGAGCAGGCCACTGGTATCAGGTCTTTTGAACTTTGGAAAGCATTCAAATTTCTGGAC
TATAAAACCAGATTGAGTATACATTACACATTCTGTAATGAGCTCTAACTGAAGATGATA
TAGAACATATAAAAGACCTAGTCCCAGTTGTTTAGAAAAGTACAGGATTTGAACGAGAGA

50844 ATTTAAATGGGCTTGTGTGGCTAGAAGTTACGTTTTTGGGAAACATACTAGAGTCTAGGC
CCTATTTGATTTCCCGCCTCTCTTCCACCACCTGTTGAATCCCTATGCTCTAGCTGTATT
TAGTTACTTGATATTATACAGTTATACCATCTTTTTAAAGTTCTTCTCTGTCTAGCATGC
CTACCTCCTCCTCACCAGCTACCTGGCAACTTTTGACTTGTTCCTTAGAACTCTCTTTAG
TTGTGGTCAAGTCATGAAGCTTTTCCTGCCCCGGCCTCTCTCTGCAGCGAGAGTTAGGGG
[A,C]
CTTCTCTTTTGCATCTTCATTGCACTCAGACATCTGGTACTCTGTGATTATCACACTTAT
TAATGCTCTCAAGATAGAGATAAAATCTTATTCATCTTTTTGCTCTCAGGCATTAGCACA
TGGGGAGTTCTCAGAAAATACCTGTCTTATACCAGGAATTAATGAATAATCAGTAGGAAT
GAGCATGACATGTTCATGGGACGTTGGAGGGTAGTGCATGGCTGCAGAGGAGAATGGGAA
ATGAAGGTCAGATAAGTTACGTGAGGGATCTCTAAGGCCAAGAGAAGCCATTTAGGTTTG

51267 GGGAGTTCTCAGAAAATACCTGTCTTATACCAGGAATTAATGAATAATCAGTAGGAATGA
GCATGACATGTTCATGGGACGTTGGAGGGTAGTGCATGGCTGCAGAGGAGAATGGGAAAT
GAAGGTCAGATAAGTTACGTGAGGGATCTCTAAGGCCAAGAGAAGCCATTTAGGTTTGAT
TTGGTTGGAAAATGAGCTTATTGAAAGTTTAAGGCAAGGGACTAGCATCATGAACACATC
TTTTTAGGGAAGTGTGTCTTGTGGTAAGCTGCTGGCTGGTTTAAATGCAGCAGAATATTC
[C,T]
ATTGGGGATGCCAGCTGGGAGACTTGCCACAGTTGCAGCCTGCAGCAGAAAGACCCTGGG
CCAGAATGGGTTGTGCCATCTGTCACCAGATATTGCCAAGGTAGATCTGGCTGACTTTGT
GGGACAGCTTGTTTCTCAATAATCACTTTGCAGGCACTCTTGAGGCTGTGAGCATGCTCC
CAGAAGATAGCATTACTTCTCTCTCAGAGCAGGCTCCTTTCTAAGGAAATGCAAGTCTAG
GCCTGCCCTGCTGTAATCTTCATGTGGAAACAGCACTCTAGCAAAGAACAAGGAACCTGA

54073 TGCCTTATTTTAAGGTCATTGAAGTCCTCATTAGTTCACGCACATAAGCAGCTTTTTAGA
AAAAGGAAGAAAAGCACTACTGTGTTATTACTGGTTAATCCAGTACCAGGAACTTCTAGT
ACAGTTCTAGAAAGGTGCTTTGCAGCATGTAGCTTGTATCTTTTGCTTCCCCTGGAATTT
AAGCTTCAAGGCCAGCACACTCTGGTATATGTGCTGAGAAACATGTGATGGGGCTGCCCA
GCCACGTCGGGGAAAGAAGGAAGATGTCTTGAGGTGCAGTGAGCTTGCCCACTAGTAATT
[A,G]
TTGTCTGATCAGTGTCCTAGAGTCTGACTGTGCCTTTTAGGCATGGGGAAAGGTAGAAGA
GGGACTTAAGAAGAGAGCTAAAGCTCCTGGTAGATTTGTGGGGTTTTCTTTTGTTTGCCT
GGTGTCCTTAACCATAGCCTGTCAAGAGAACAAAGGTGGATATATTTTTCAGTGAACACA
TACATGTTTAATAGTCATTCTGGAAAATATTTCTAATACCTTCTTTGGAATTTTCTCATG
CTATAAATTTAGATTTTTAAGAATTGGTCATATCGCACCAATTTTAGACTAAGAGGTGTA

54206 GGTGCTTTGCAGCATGTAGCTTGTATCTTTTGCTTCCCCTGGAATTTAAGCTTCAAGGCC
AGCACACTCTGGTATATGTGCTGAGAAACATGTGATGGGGCTGCCCAGCCACGTCGGGGA
AAGAAGGAAGATGTCTTGAGGTGCAGTGAGCTTGCCCACTAGTAATTATTGTCTGATCAG
TGTCCTAGAGTCTGACTGTGCCTTTTAGGCATGGGGAAAGGTAGAAGAGGGACTTAAGAA
GAGAGCTAAAGCTCCTGGTAGATTTGTGGGGTTTTCTTTTGTTTGCCTGGTGTCCTTAAC
[C,G]
ATAGCCTGTCAAGAGAACAAAGGTGGATATATTTTTCAGTGAACACATACATGTTTAATA
GTCATTCTGGAAAATATTTCTAATACCTTCTTTGGAATTTTCTCATGCTATAAATTTAGA
TTTTTAAGAATTGGTCATATCGCACCAATTTTAGACTAAGAGGTGTAGGATCGTCACTGC
CCCCCCATGGTGCCCACCATGTGGCTACTAAGTGGGGTGCACATTAAATGCGGACAACTT
GCTTAATTATTTATAGGGTCTGCAGGAGCACACTATTCCTGCTTTTAGCACAGCACTCAT

54488 TTGCCTGGTGTCCTTAACCATAGCCTGTCAAGAGAACAAAGGTGGATATATTTTTCAGTG
AACACATACATGTTTAATAGTCATTCTGGAAAATATTTCTAATACCTTCTTTGGAATTTT
CTCATGCTATAAATTTAGATTTTTAAGAATTGGTCATATCGCACCAATTTTAGACTAAGA
GGTGTAGGATCGTCACTGCCCCCCCATGGTGCCCACCATGTGGCTACTAAGTGGGGTGCA
CATTAAATGCGGACAACTTGCTTAATTATTTATAGGGTCTGCAGGAGCACACTATTCCTG
[C,T]
TTTTAGCACAGCACTCATATAATTTTTTTTTTCCCCTCCAGCCTTCCAGAATACATTGTA
GTGCCAAGTTCTTTAGCAGACCAAGATCTAAAGATCTTTTCCCATTCTTTTGTTGGGAGA
AGGATGCCAGTAAGTGATTTCTGTTGGATTTTATGAATGCTGACGTCCATTGTTTCTACA

FIGURE 3KK

CAGTGAAGTAAGGATTCTACCTCTCCCCTAGCTCTGGTGCTGGAGCCACTCTAACGGCAG
TGCTCTTGTGCGAATGGCCCTCATCAAAGACGTGCTGCAGCAGAGGAAGATTGACCAGAG

54511 CCTGTCAAGAGAACAAAGGTGGATATATTTTTCAGTGAACACATACATGTTTAATAGTCA
TTCTGGAAAATATTTCTAATACCTTCTTTGGAATTTTCTCATGCTATAAATTTAGATTTT
TAAGAATTGGTCATATCGCACCAATTTTAGACTAAGAGGTGTAGGATCGTCACTGCCCCC
CCATGGTGCCCACCATGTGGCTACTAAGTGGGGTGCACATTAAATGCGGACAACTTGCTT
AATTATTTATAGGGTCTGCAGGAGCACACTATTCCTGCTTTTAGCACAGCACTCATATAA
[T,-]
TTTTTTTTTCCCCTCCAGCCTTCCAGAATACATTGTAGTGCCAAGTTCTTTAGCAGACCA
AGATCTAAAGATCTTTTCCCATTCTTTTGTTGGGAGAAGGATGCCAGTAAGTGATTTCTG
TTGGATTTTATGAATGCTGACGTCCATTGTTTCTACACAGTGAAGTAAGGATTCTACCTC
TCCCCTAGCTCTGGTGCTGGAGCCACTCTAACGGCAGTGCTCTTGTGCGAATGGCCCTCA
TCAAAGACGTGCTGCAGCAGAGGAAGATTGACCAGAGGTAATTGAGAAATGGTCATTGTC

56070 ATCATTTCCTCCTTCCATGTCTCCTCCACCCCTGGGCTCCAGCCCCCTGGACTTTCCCTG
GTGTTTTCAACCTCCTGACATTGTCCAGCGCTCTTCCCTTCTGGACTGCCTTCTTTGCAC
TCATCTGGGAACACTCTCCACGCTTACCCACTTGGCACTCCTTGTTTCTTTTTTTTTGAG
ACAGAGTCTCACTCTGTCACCCATGCTGGAGTGCAGTGGTACGATCTCGGCTCCCGGGTT
CAAGTGATTATCATGCCTCAGCCTCCTGAGTAGCTGGGATTACAGGCACCCACCACCACA
[T,A]
CCAGCTGATTTTTGTATTTTTAATAGAGACAAGATTTCACCATGTCGGCCAGGCTGGTCT
CGAACTCCTGACCTCAGGTGATCCACCCGCCTCGGCCTACCGAAGTGCTGGGATTACAGG
CGTGAGCCACTGCACCCGGCTCACTCATTCTTTATATCTCAATTCAAACATCATTTCCTC
AAGATAAGCCTTCTCTCCCCTCTAAAGTTTGATCAGACCTCAAAAGTCTATGTTCTTAGA
GCTCCTGAGTTTTTAACATTTATTTCAGTTTTTAATTATATATGTGTGTGTTACAGTTTG

57119 TGTTAAAGGGACAATTGTAGCATTGTTGGGTGAGAGTTAGTTATAAAACCTTATAATCAG
TGGCAGTTTCAGTGATTTATTAAGCTGAAAATTACTTTAATGCCTTTTGTGTTTTCAGCT
ATCCTATTCTTCATAAGTAGAACAGATCCTCTTTTTTGTCCAACCTCGTCTCCTAACCTT
TTTCCCTCAGGTGTGTCATCTAGCCCCACTGGCCTTCTTTAGGTTTCTCAGCAGCCATGC
TTGTTACCTGCCACAGGGCCCTTGCACTAGCTGCCCTCTGCCTAGAACATTTTCACCCCA
[G,C]
ATCTTTACATTGCTTCTCTATTCATTTAGGTTTCGGCTTCAGTACCATCTTCACAGAGCA
GCTGTTTTTCACCATGTGACCTAAAGTAGCCTGTAATCTCATGATTACATCATCCATGGC
ATTCACCACAGCCCATTTATCTTATCATCTACCCCACCCCACGAAGAATGTCAACCCCCC
ACTTGCTTGGGCAACACCAGTAGTAAAATTGGAATGATACAGGGAAGGTTAGCATAGCCC
TTGCACAAAGATGACATGCAGGTTCATGACACATTACATATTTTAATGAAATGGGAGCAT

58184 TTTGCATTCTCTAGAGCTGGAGAATGTGCATCTGGTTTGCCATCCTTCTGTCTACATCAT
GTGGAAAGATGTGGGAGTGTAGGGTCTCCTTAATCTAAATGCAGTGCTGCCCCGCCCCCC
CCTTGGCAGTGTTTCTGTTTCCCAGGCAAGTGTTCCAATGGATGTGCTTTATTTTCTCCC
ATCAGAAATAAGGGAATGAGCCCGGGCGCGGTGGCTCACGCCTGTAATCCCAGCACTTTG
GGAGGCCAAGGGGGGTGAATCACAAGGTCAGGAGTTTGAGACCAGCCTGGCCAACATGGT
[G,A]
AAACCCCGCCTCTACTAAAAATACAGAAATTTAGCCAGGTGTGGTGGCGGGTGCCTGTAA
TCCCAACTACTCGGGAGGGTGAGGCAGGAGAATCGCTTGAACCCGGGAGGGGGAGGTTGC
AGTGAGCCGAGATGGTGCCACTGCACTCCAGCCTGGGCGACAGTATGAGACTCCGTCTCA
AAAAGAAAAAGAAGGAAATGATCTAATTTGTTCTGTGCACTGCACGTGGGGGTGGCAGTG
AGGTGAATGGCAGCATTCTGCAGTAGTCAAAGCCAGATGGGTGGGAGAAGTTGGGTGCTA

58210 TGCATCTGGTTTGCCATCCTTCTGTCTACATCATGTGGAAAGATGTGGGAGTGTAGGGTC
TCCTTAATCTAAATGCAGTGCTGCCCCGCCCCCCCCTTGGCAGTGTTTCTGTTTCCCAGG
CAAGTGTTCCAATGGATGTGCTTTATTTTCTCCCATCAGAAATAAGGGAATGAGCCCGGG
CGCGGTGGCTCACGCCTGTAATCCCAGCACTTTGGGAGGCCAAGGGGGGTGAATCACAAG
GTCAGGAGTTTGAGACCAGCCTGGCCAACATGGTGAAACCCCGCCTCTACTAAAAATACA
[A,G]
AAATTTAGCCAGGTGTGGTGGCGGGTGCCTGTAATCCCAACTACTCGGGAGGGTGAGGCA
GGAGAATCGCTTGAACCCGGGAGGGGGAGGTTGCAGTGAGCCGAGATGGTGCCACTGCAC
TCCAGCCTGGGCGACAGTATGAGACTCCGTCTCAAAAAGAAAAAGAAGGAAATGATCTAA
TTTGTTCTGTGCACTGCACGTGGGGGTGGCAGTGAGGTGAATGGCAGCATTCTGCAGTAG
TCAAAGCCAGATGGGTGGGAGAAGTTGGGTGCTAAGAGGGAAACAAAGTTTACCTGTCTT

59015 CTGAAATGAATGAGTAATGACTAAAGTATTTTTGTCTTTATTAGGATTTGTAATGCAATA
ACTAAAAGTCACCCACAGAGAAGTGATGTTTACAAATCAGATTTGGATAAGACCTTGCCT
AATATTCAAGAAGTACAGGCAGCATTTGTAAAACTGAAGCAGCTATGCGTTAATGGTAAT
TTCATTCTTATTTCATATATATAATGAACACAGGATACAGAGTTGCATGAGATGTCAGGA
AAAGTGATGTTCTTAAAAATGTAGAAATAGATATATTTAAGGAGTCTATGGAACTATTTG

FIGURE 3LL

[T,C]
ACAAATTATATATTATTGTATGAGAACTTCAGAACCTCCTAAGGAATTAAGTTTAAACTA
CTTTTTGTTTTAGAGGGGGAAAAATGAGTGTATTAAATTTCCTTCAGATGATGAAAGGTA
TAGGAGAATACTTTTATAAAAGCATTTGCTGAGTAGAACACTGTATTACCTTACAGACAA
ACTTATTAAGATTGTAATACATACAGTTATACTTTGAGATAGGTGACTTGACATGGGTAT
CAAACAGCTGTGTTATATCTGTAGCATCAGAATTCTGATATATCTGAGCAAACGTACCAG

59201 CTTATTTCATATATATAATGAACACAGGATACAGAGTTGCATGAGATGTCAGGAAAAGTG
ATGTTCTTAAAAATGTAGAAATAGATATATTTAAGGAGTCTATGGAACTATTTGTACAAA
TTATATATTATTGTATGAGAACTTCAGAACCTCCTAAGGAATTAAGTTTAAACTACTTTT
TGTTTTAGAGGGGGAAAAATGAGTGTATTAAATTTCCTTCAGATGATGAAAGGTATAGGA
GAATACTTTTATAAAAGCATTTGCTGAGTAGAACACTGTATTACCTTACAGACAAACTTA
[T,C]
TAAGATTGTAATACATACAGTTATACTTTGAGATAGGTGACTTGACATGGGTATCAAACA
GCTGTGTTATATCTGTAGCATCAGAATTCTGATATATCTGAGCAAACGTACCAGGTGGCT
TTCATGTGTCCTGCGGGATGAGTCACATGAAAGCATCTTTGGTGTAATGTGGGTCCTCCT
CAAGAGATCCTCTAAGTCACCAGGGAGTCAGCAAAGGCAGCCTTGCAGCAGATCTTGAGC
AATGAGTAAGCACTTCCCTGGGGGAGGGCCTTGCAGGGGCGGGGCAGGGGCAAGTTGTTG

60695 CCACTAATCTCTTCTCAATCTCTATAGTTTTGTCATAAGTCAACCCCTTCCTTTTCATAA
AGGGTTTATGAATTTCCCTGATGAAAAAGTACAAAATGAGGCCAGGCGTGGTGGCTCATG
CCTGTAATCCCAGCACTTTGGGAGGCCAAGGCGGGTGGCTCACCTGAGGTCAGGAGTTCA
AGACCAGCCTGGCCAACATGGTGAAACCTTGTCTCTGCTAAAAATACAAAA
[G,A]
TTAGCCAAGCATGGTGGCACGCACCTGTAGTCCCAGCTACTCAGGAGGCTGAGGCAGGAG
AATCACTTGAACCTGGGAGGCAGAGGTTGCATTGAGTCAAGATCACGCCACTGCACTGCA
GCCTGGGTGATAGAGCAAGTCTCCATCTCAAAAAAAAAAATTTACAAAGTGGGGCCGGTT
GTGGTAGCTCATGCCAGTAATTCCAAAGCTCTGGGGAGGAAGATCACTTGA

61592 AAATATACTCCTTTGAGAAATCGTATAAGTAACTAAAGAAACTTTACGGTAATGCGAAAG
CTATGTGCATTCAGTAGAAAGCAGTCAATCCTCTCTTGTGATGCTGAGTAGCAGCAGGGA
GCCACAGCTGCCAGTCAGCCACACAGTCTCAGTTTAGGGTATTTTCAGCTTACAGTGGGT
TATCATGGGTCATGAGTTATGGGAATATCATGATCAGAGAGCATCTGTAAAGTGAGAAAT
TAGATTTGCTTGATTTCAAGTACTTTATGTATTTGTAGTGGAAATTTGATTTTTAACACT
[A,G]
CTTTTCCTTTTCTCTCTTCAGGGCATTCCTTAAGCATTCAGCAGAACTTGTATACATGCT
AGAAAGCAAACATCTCTCTGTAGTCCTACAAGGTAACTAAAGTAACTCCTGAAAGCACCA
TGACCACCATACCAGCCAGCCTTGGTTTACTGCTTGTCCCCATTCAAGTAAATCACATCA
GTTTTAGCTATTTCTTATTTACTACAGTACCATCAAATACATTACAGATTTTGCACATCA
TTTGAGTAAAACAGTGGCACAGGCTGGGCGCAGTGGCTGAAGCCTGTAATCCCAGACTTT

62577 TTTGACAGGGCATTCTCTCTCTGTAATTTTGCTGTCTAATTTGTACAAATTTGTTTTAGT
TTAAATACCTTCTGGCTCATGCTAGATTATGACTCTAAGGAAGCAGTTTGAGATGAAGAA
ATTTAGACTGAACTGCTGAATAGCTAGTAATGTAATATTTGGTAGGAATAAACGGTGATG
TAAAAATCTTTCAGTTAAGCAAAGGATAATTACATATTAAATAACTTACAGCTAATAGAA
TTTGTAAGTTTGCAGATAAAGTTCAATAGACTAAAAACTACCTTCGTATAATACAGTAGT
[G,A]
GGTCCTTTGTACCCATGGCTTCCCCATCTGTGGTCAACCAACCCAGGACTGAAAATATTG
GCGGGGGAAAGCTTTGGCCGTAATGAACATGAACAGACTTTTTTTTTGTTGTCATTATTC
TCTAAACAGTATAGTATAACAACTGTTTACATAGCATTTACATTGTATTAGGTGTTATAA
GTAATCTAGAGGTAACTTAAAGTGTACAGGAGGATGTGCATAGGTTATATGCAAATATTA
ACATCATTTTATATCCAGGACTTAAGCATTTGTGGATCTTGGTATCCAAAGGAGGCCCTG

62580 GACAGGGCATTCTCTCTCTGTAATTTTGCTGTCTAATTTGTACAAATTTGTTTTAGTTTA
AATACCTTCTGGCTCATGCTAGATTATGACTCTAAGGAAGCAGTTTGAGATGAAGAAATT
TAGACTGAACTGCTGAATAGCTAGTAATGTAATATTTGGTAGGAATAAACGGTGATGTAA
AAATCTTTCAGTTAAGCAAAGGATAATTACATATTAAATAACTTACAGCTAATAGAATTT
GTAAGTTTGCAGATAAAGTTCAATAGACTAAAAACTACCTTCGTATAATACAGTAGTAGG
[C,T]
CCTTTGTACCCATGGCTTCCCCATCTGTGGTCAACCAACCCAGGACTGAAAATATTGGCG
GGGGAAAGCTTTGGCCGTAATGAACATGAACAGACTTTTTTTTTGTTGTCATTATTCTCT
AAACAGTATAGTATAACAACTGTTTACATAGCATTTACATTGTATTAGGTGTTATAAGTA
ATCTAGAGGTAACTTAAAGTGTACAGGAGGATGTGCATAGGTTATATGCAAATATTAACA
TCATTTTATATCCAGGACTTAAGCATTTGTGGATCTTGGTATCCAAAGGAGGCCCTGGAA

62596 TCTGTAATTTTGCTGTCTAATTTGTACAAATTTGTTTTAGTTTAAATACCTTCTGGCTCA
TGCTAGATTATGACTCTAAGGAAGCAGTTTGAGATGAAGAAATTTAGACTGAACTGCTGA
ATAGCTAGTAATGTAATATTTGGTAGGAATAAACGGTGATGTAAAAATCTTTCAGTTAAG

FIGURE 3MM

CAAAGGATAATTACATATTAAATAACTTACAGCTAATAGAATTTGTAAGTTTGCAGATAA
AGTTCAATAGACTAAAAACTACCTTCGTATAATACAGTAGTAGGTCCTTTGTACCCATGG
[C,G]
TTCCCCATCTGTGGTCAACCAACCCAGGACTGAAAATATTGGCGGGGGAAAGCTTTGGCC
GTAATGAACATGAACAGACTTTTTTTTTGTTGTCATTATTCTCTAAACAGTATAGTATAA
CAACTGTTTACATAGCATTTACATTGTATTAGGTGTTATAAGTAATCTAGAGGTAACTTA
AAGTGTACAGGAGGATGTGCATAGGTTATATGCAAATATTAACATCATTTTATATCCAGG
ACTTAAGCATTTGTGGATCTTGGTATCCAAAGGAGGCCCTGGAATGAGTTCCCCATGGAT

62682 GTTTGAGATGAAGAAATTTAGACTGAACTGCTGAATAGCTAGTAATGTAATATTTGGTAG
GAATAAACGGTGATGTAAAAATCTTTCAGTTAAGCAAAGGATAATTACATATTAAATAAC
TTACAGCTAATAGAATTTGTAAGTTTGCAGATAAAGTTCAATAGACTAAAAACTACCTTC
GTATAATACAGTAGTAGGTCCTTTGTACCCATGGCTTCCCCATCTGTGGTCAACCAACCC
AGGACTGAAAATATTGGCGGGGGAAAGCTTTGGCCGTAATGAACATGAACAGACTTTTTT
[G,T]
TTGTTGTCATTATTCTCTAAACAGTATAGTATAACAACTGTTTACATAGCATTTACATTG
TATTAGGTGTTATAAGTAATCTAGAGGTAACTTAAAGTGTACAGGAGGATGTGCATAGGT
TATATGCAAATATTAACATCATTTTATATCCAGGACTTAAGCATTTGTGGATCTTGGTAT
CCAAAGGAGGCCCTGGAATGAGTTCCCCATGGATACTGAGGGAAGACTATATACTCATGT
TGCATAGTATATGAATACAAAATGTTGCTTAAGCTTGCAGAAGTACTTTTTTTTTTTTTG

64509 CAGGATCATATTGTCTTCAAAGACAGTTTTTACCTTTTTCTTTCTGATCTGAATGCCTTT
TATTTTCTTTTTCTTGCCTAATTGCTCTGGCTAGATTCTCCAGTTCAATGAGATGGAGAA
GTGTAGAGAACAGACATCCTTATCATCTTCCTGATCTTAGGGAGAGAGTATCCAGTCTTT
CACCAGTGAAATGGGAATAACATTAATTGTAGGTTTTTGTGGATGTCTCTGATCAGTTTA
AATATGTTTACTTTTATTCCTAATCAGGAATGAAGGTAGAATTGTATCAGATGCTTTTTC
[C,T]
GCATCTAATGAGATAATCGTGTTGGTTTTGTCCTTTATTACTGTGGTACGTTACTACAAT
TGACAGATGTTAAACCAACTTTGCATTCCTGGATAATTTGGTTTACTCATATTTTTATTG
ATTTTTACATCTGTAATCATAAGGGATATTGGTCAATAGTTGTCTTCTGATTTCCCTGGC
TGACTTTGATAGCGTGGCAATTCTGGCCTTATTGGAAAGGACAACAACTATAAAAGACAG
GAGGGAATCGTTTGCCACAGCTTCAGTTGGTAGTGAACAGTCCCACTCTCCCCATTCACT

64898 CTGGATAATTTGGTTTACTCATATTTTTATTGATTTTTACATCTGTAATCATAAGGGATA
TTGGTCAATAGTTGTCTTCTGATTTCCCTGGCTGACTTTGATAGCGTGGCAATTCTGGCC
TTATTGGAAAGGACAACAACTATAAAAGACAGGAGGGAATCGTTTGCCACAGCTTCAGTT
GGTAGTGAACAGTCCCACTCTCCCCATTCACTTCTCAGTATTGCCATGTGGCCTGTCAGT
AGAAAGATTACCTTATACTTAATACCTTGACAAAAGAGCAGTAGAATGGAGTCTAGACGG
[A,G]
TTTTCTACCACAAACCATTCGAATGTAAAAAGTATGAGTGATGAGCTTCTATTATCTGGC
AAATATCCATGTATAAAAGACCATCTCCTATTAAATGCTAATTTAGTTTATCTACAAGTC
TGTAATATTTTAGAGTTGCTGGAATCCAGTAAAATTTCCTTATACAGATTTGGAAGGCAG
CCTAGGTGTGCAGAATACTAAATTATCTAGTTTACCTTTCCTTCCCTTTCTCTCTCAGCA
TTTTTCTATGTTGTAATCATTTTCTTTCCATTTTATTAACAGAGGAGGAAGGAAGAGACT

67072 CTTTAACCACCTTAAATGTCATGCTTTTGTATTTATATTTCACATTTGGGCTATTGGGTA
GTAAAAAACAAAAGCCCTGTTACACGACATTTATTTCCTAGGTCAGTAGGATAAAAAGTT
GTACAAAACAAGATTATTTTCCTTCACGAGTTTGAAGTTTCTGGTCACAATTCATTGATG
TAGAGGATTTATGACTAAGCAGGGTCTCAAGCCAAACTTGAAACCATTCTGAACCAAAGT
GCCATTTCACCCACCTCGAACCAACAACAGAAGCTGACAAATGCCGTGGAGACCATTGAG
[A,G]
GAAACAGAAAGGGGCAGCTCTTGTGGACCTTCAGGAAGCCTTTCTAGGAAGAGGATTGCC
CTCATAGTGAGCTCCGGGGTCTTCAGCCTCAGCCGTAAGGCCCTGGGCTAGGCAGTGTGA
CCTAGGGAGCGGGAAACCTGAGTTCTGGCCCTGGTCTGGGAAAAGTGCTAGGCCCATGTT
CCACTCAGGCTTCAGCCTGAGAGTCCAGGTTGCTAACCTGTAAAATGGATCTGTCAAACT
AACACTTATGCCTTTAGTCTCATTGTATGAGGTGAAACATTTTGTAAACTGTGAATCATT

67283 CCAAACTTGAAACCATTCTGAACCAAAGTGCCATTTCACCCACCTCGAACCAACAACAGA
AGCTGACAAATGCCGTGGAGACCATTGAGAGAAACAGAAAGGGGCAGCTCTTGTGGACCT
TCAGGAAGCCTTTCTAGGAAGAGGATTGCCCTCATAGTGAGCTCCGGGGTCTTCAGCCTC
AGCCGTAAGGCCCTGGGCTAGGCAGTGTGACCTAGGGAGCGGGAAACCTGAGTTCTGGCC
CTGGTCTGGGAAAAGTGCTAGGCCCATGTTCCACTCAGGCTTCAGCCTGAGAGTCCAGGT
[T,C]
GCTAACCTGTAAAATGGATCTGTCAAACTAACACTTATGCCTTTAGTCTCATTGTATGAG
GTGAAACATTTTGTAAACTGTGAATCATTATGCAAATTTTCCTAAAGACATATGAATTAT
TCTGGATTTGTTGGTATAAAAGACAAAACACACTGGTCAGTTAAGGAGCTGATTTTATTT
AGGCTATTGCAGGAGGGAGAACTTAATTAATGGGCATCCCAAAGAAAAGGACAAGGCCTG
GGATTTTATAGTCAGAAGACAGGGGAATCAGGAGGGAGGGCAGTCTCAGTCCACAGGAGC

FIGURE 3NN

67432
CCTCATAGTGAGCTCCGGGGTCTTCAGCCTCAGCCGTAAGGCCCTGGGCTAGGCAGTGTG
ACCTAGGGAGCGGGAAACCTGAGTTCTGGCCCTGGTCTGGGAAAAGTGCTAGGCCCATGT
TCCACTCAGGCTTCAGCCTGAGAGTCCAGGTTGCTAACCTGTAAAATGGATCTGTCAAAC
TAACACTTATGCCTTTAGTCTCATTGTATGAGGTGAAACATTTTGTAAACTGTGAATCAT
TATGCAAATTTTCCTAAAGACATATGAATTATTCTGGATTTGTTGGTATAAAAGACAAAA
[C,T]
ACACTGGTCAGTTAAGGAGCTGATTTTATTTAGGCTATTGCAGGAGGGAGAACTTAATTA
ATGGGCATCCCAAAGAAAAGGACAAGGCCTGGGATTTTATAGTCAGAAGACAGGGGAATC
AGGAGGGAGGGCAGTCTCAGTCCACAGGAGCCAGTTCTCAGGACACAAAAGGCAGGAGAG
ATTGTCCAGCATTGCCACTTTTGGGGAACCCA

68079
GAGATTGCAGTGAGCTGAGACTGTGCCACTGCACTCCAGCCTGGGTGATAGAGCCAGAGT
CTGTCCCCTGCCCACCCCACCAGGAAAGTTTGACCTTTCCAGATACTGTGCTGAGAACCA
GTGATACAGGCTTAGAGGCTCCTGAGGCATGGAACGCTCATTTGTTCCTAAAATACATGC
TCTCCCAGTTGCTTGTTTTTATTTTTCGTCACCATAATCATTCTTGGGGCCCCTCTCTGC
CTCGAGCTAGGCTTTCCCCCTGGCCTTGTTTGCCTCCTTCAGCTCTTCCCCATTGTCTCC
[C,T]
GTCACTACCCCGTGCGCACACAGTGTGAGCCTGCAAAAGGTGCGTGAGGCGAGGACAAAG
ACTTTGGGGTCTGGGGACTGGGCAGTGCATGGGTGGGTATCTGCGTGGAGGACTCCCAGC
CCCCAGACACCACTGCCTCTGCTGCTTGGCTGATGCTGTGTGTGCGGACAGACTTCTCAC
CAGGAATGAACATTACTGAATTGTATTGAGGGAGCTGTAAAAAAATACTTTCTACAAGTAT
TTCCTCTGCTTTCCCTGTTCATGTTCTAGTGCTCTTTTTAATTTGGCTCTTTCAAAAGCC

69067
CGCATGCCACCACGCCTAGCTAATTTTTGTATTTTTTTGTAGAGTCAGGGTTTCGCCATG
TTGCCCAGTCTGGTCTTGAACTCCTGGACTCAAGCAATCCGCCCACCTCAGCTTCCCAAA
GTACTGGGATTACAGGCGTGAGCCACCGTGCTTGGCCAAGAGGACATTTTCTATATACTT
ACTGAAGGGCCATTAAAACACGTTTGGGTTCATGTTTTACTAGATTTCAGCTCTTAACAG
TGTTTGAAGCAAATGGATTGTTTTTAATCCATGTACATGATGAAATGTCAAGTAACTAAA
[T,A]
TTTTTTTTTTTTTTTTTTTGAGACAGAGTCTTGCTCTATCACCCAGGCTGGAGCACAGTG
GCATGATCTCGGCTCACTGCAACCTCTGCCTTCCAGGTTCAGGTGATTCTCCTGCCACAG
CCTCCCGAGTAGCTGGGACTACAGGTGCACACCACCATGCCTGGCTAATTTTTGTATTTT
TAGTAGAGACGGGGTTTCACCATATTGGCCAGGCTGGTCTTGAACTCCTGACCTCGTGAT
CCGCCTGCCTTCGGCCTCCCAAAGTGCTGGGATTACAGGCATGAGTCACCACTGCGCCTG

69122
CCATGTTGCCCAGTCTGGTCTTGAACTCCTGGACTCAAGCAATCCGCCCACCTCAGCTTC
CCAAAGTACTGGGATTACAGGCGTGAGCCACCGTGCTTGGCCAAGAGGACATTTTCTATA
TACTTACTGAAGGGCCATTAAAACACGTTTGGGTTCATGTTTTACTAGATTTCAGCTCTT
AACAGTGTTTGAAGCAAATGGATTGTTTTTAATCCATGTACATGATGAAATGTCAAGTAA
CTAAAATTTTTTTTTTTTTTTTTTTGAGACAGAGTCTTGCTCTATCACCCAGGCTGGAGC
[G,A]
CAGTGGCATGATCTCGGCTCACTGCAACCTCTGCCTTCCAGGTTCAGGTGATTCTCCTGC
CACAGCCTCCCGAGTAGCTGGGACTACAGGTGCACACCACCATGCCTGGCTAATTTTTGT
ATTTTTAGTAGAGACGGGGTTTCACCATATTGGCCAGGCTGGTCTTGAACTCCTGACCTC
GTGATCCGCCTGCCTTCGGCCTCCCAAAGTGCTGGGATTACAGGCATGAGTCACCACTGC
GCCTGGCCAAAACTGTTAAGAGTATGTGTATTTGGTGCTTAATGAATTTTTACTTATTTG

69951
CTGAAAGGTACAGAACAAAGAATCAGACATTTCCCATCATCCAGCGACTTTGTGTCTGGA
GTTATTTCCTCCAGCGAACTGTTGTGTATACACTGCTGTGGTAGCCTGCTGCCATCAATC
AGCTGAGATGAGAGTCCTTTCTCCACATTGCTAAATGTGACTGTGCTTCATAGAAATGGT
CTGGGCTGCCTTCCAGAGGAGCTCCATGTCTTCCTCACAATGCGGTGGTTGGCTGTCACC
CTGTAGCCTTGTGTTGCCTCAGTTTACTGTGGTGGGAAGCCAGATAACTAGGCTGCACCC
[A,G]
CCCAGAGTCCGGGCTAGAGGTGGACTCCTGTGAAGGAGGGGTCTCCTGTGTACATGGTCT
CCATGGTTTTAGCCACATGCTAGGACCACAGGGAGTTGATCCCTTCCTTCCTACCCTGAG
TCTGTGGTCTGTGATTTGAGATCACTGGCTCAGTGAAGTGTAGCTCCCCACTTACGAAGT
AAGTTATAAAATTGGTGGCAGTGATTTCCATCCAAAGATTTTGTTAATCCACTTACCAAC
AGGTAACTACTTAAATGTACTGACCGTGTGCTCATAAAAGTAAAATACTGTAATTATAGA

70498
CTACTTAAATGTACTGACCGTGTGCTCATAAAAGTAAAATACTGTAATTATAGAAATAAA
TTCAACATGTTTAAGACTTTCTAGTATCATGTTAGTGAAACTTCTCTTAATAACATTCTT
ATTGCCCAAAGGGCACGGCTTCCTTGGGGTCCTAAGGCAGAGGGCACCTGAAAAGCACAC
TCCTTGTTCATGGGGACTGTGGGGCCCTCTGAGCTCAAAGGCCAGGAGCGTCTCCTCTCT
TGAAGTGAAAGTGCCACTCTGGTGGGTTTTGAGGGCTGCAGTACAGAACATTTAACCTGT
[G,A]
TAATGATGAGTGGCTCATCTGAAAAAAGGCATTCATGAGAGAATCTTTAGTTTTGCAAAT
ATTTATTTATTTATTTTGCAGGAATTTGCTATAAGCAAAAACATCCAATTGGGTGATGAG

FIGURE 3OO

AAGGGCTTAAAATTCCCCTCTGTTTGGGACTGGTCTCTCCAGTTTACAGCAAAGGATCGC
ACCCTTTTCCATAACCCCTTCTACATTGGAAAGAGCACACCTTGTATACAGAATGGCTCC
GTGAAGTCTTTTAAACGGACAAAGGTAAATCACAGCTAACAAAACGTGATGTTGGCTCAC

70850 TTTGCAAATATTTATTTATTTATTTTGCAGGAATTTGCTATAAGCAAAAACATCCAATTG
GGTGATGAGAAGGGCTTAAAATTCCCCTCTGTTTGGGACTGGTCTCTCCAGTTTACAGCA
AAGGATCGCACCCTTTTCCATAACCCCTTCTACATTGGAAAGAGCACACCTTGTATACAG
AATGGCTCCGTGAAGTCTTTTAAACGGACAAAGGTAAATCACAGCTAACAAAACGTGATG
TTGGCTCACACGTAACCAAACACCTCTTTTTCAGAACAGAGAGCGTTAAAAGTAAAGGCA
[C,G]
TTCCAAGAGTAACACTGCTAATGCGGGTTTCTGAGGGGTCATTCCCTTTTTAACTCAAAT
GACTGTATCCCAGCTTTCTTCCTGGTGTCTGAGGCCCACAAAGTCTCAGTACCTGAGAGT
GGGCAGATTGCAGCTTTGAGCCTGCAAGCCTGATTTACTAAAGCCCCATTTATCCATTTC
TTGATGATTCAAGCCGCCACTGTGGCAGGGAATGCCGCCTGGCTGTGATGTAGTCATGGC
CTCCTGACTGCTATATTCTTGTCCTAATAACATTCATTGTTTGCCTTTTTAATAATTCCC

70874 TTGCAGGAATTTGCTATAAGCAAAAACATCCAATTGGGTGATGAGAAGGGCTTAAAATTC
CCCTCTGTTTGGGACTGGTCTCTCCAGTTTACAGCAAAGGATCGCACCCTTTTCCATAAC
CCCTTCTACATTGGAAAGAGCACACCTTGTATACAGAATGGCTCCGTGAAGTCTTTTAAA
CGGACAAAGGTAAATCACAGCTAACAAAACGTGATGTTGGCTCACACGTAACCAAACACC
TCTTTTTCAGAACAGAGAGCGTTAAAAGTAAAGGCACTTCCAAGAGTAACACTGCTAATG
[C,T]
GGGTTTCTGAGGGGTCATTCCCTTTTTAACTCAAATGACTGTATCCCAGCTTTCTTCCTG
GTGTCTGAGGCCCACAAAGTCTCAGTACCTGAGAGTGGGCAGATTGCAGCTTTGAGCCTG
CAAGCCTGATTTACTAAAGCCCCATTTATCCATTTCTTGATGATTCAAGCCGCCACTGTG
GCAGGGAATGCCGCCTGGCTGTGATGTAGTCATGGCCTCCTGACTGCTATATTCTTGTCC
TAATAACATTCATTGTTTGCCTTTTTAATAATTCCCAAATAAATTCTTGGGATTTTTTTT

70923 GCTTAAAATTCCCCTCTGTTTGGGACTGGTCTCTCCAGTTTACAGCAAAGGATCGCACCC
TTTTCCATAACCCCTTCTACATTGGAAAGAGCACACCTTGTATACAGAATGGCTCCGTGA
AGTCTTTTAAACGGACAAAGGTAAATCACAGCTAACAAAACGTGATGTTGGCTCACACGT
AACCAAACACCTCTTTTTCAGAACAGAGAGCGTTAAAAGTAAAGGCACTTCCAAGAGTAA
CACTGCTAATGCGGGTTTCTGAGGGGTCATTCCCTTTTTAACTCAAATGACTGTATCCCA
[A,G]
CTTTCTTCCTGGTGTCTGAGGCCCACAAAGTCTCAGTACCTGAGAGTGGGCAGATTGCAG
CTTTGAGCCTGCAAGCCTGATTTACTAAAGCCCCATTTATCCATTTCTTGATGATTCAAG
CCGCCACTGTGGCAGGGAATGCCGCCTGGCTGTGATGTAGTCATGGCCTCCTGACTGCTA
TATTCTTGTCCTAATAACATTCATTGTTTGCCTTTTTAATAATTCCCAAATAAATTCTTG
GGATTTTTTTTGGTAGAAAATTTGCAGACTACTGAAAGGTACAGAACAAAGAATCAGACA

71276 GATTGCAGCTTTGAGCCTGCAAGCCTGATTTACTAAAGCCCCATTTATCCATTTCTTGAT
GATTCAAGCCGCCACTGTGGCAGGGAATGCCGCCTGGCTGTGATGTAGTCATGGCCTCCT
GACTGCTATATTCTTGTCCTAATAACATTCATTGTTTGCCTTTTTAATAATTCCCAAATA
AATTCTTGGGATTTTTTTTGGTAGAAAATTTGCAGACTACTGAAAGGTACAGAACAAAGA
ATCAGACATTTGGCCTCCTGACTGCCTCTGTTCAGTTTGCCATTGTTCTTGATAGAATCG
[G,A]
CCAGGTCTAGTGTTTTTTTCTAGCCCGTCTTAGAACTTATCCTTAAGCAAATTAGTGGATA
GGAGGTACTCTCATCCCGCCCCCATTCAGGCTGATAGTAACAGCCTAGGTAGAGTCAACA
CATAAAAAAGTGTAATTCCAGGGGAGGAGGATTAGAATAAGGACACAAAGGAAGGGAGGA
AAATGTTCTTTGAGGCTGAAATTCCATTAATTTTTCATAGTATTGAGTTTATATTTGCCA
TTGCATCCTTCAATCTTTCTAAAAAGGGAATCCCCGGAACATAATAAAATCTCTTCTGTA

74663 AAAACCTTTGTGCCTAAAATTGATGACTTGAGTTCAAGTGGGATGAGCAAGAAGATGTGT
TATCTTGTTGTTCAACAGTATTGA
[G,A]
TGTGAAGGAAATTTTGATGGCTTAATAAAATTCCACAGCGACTGTTTGTTGTTGTCAGTA
TGAAATCATCTACTGGAACACAGT

74598 AAAACCTTTGTGCCTAAAA
[T,C]
TGATGACTTGAGTTCAAGT

81794 CTCCACCTCCTGGGTTCAAGCGATTCTCCTGCCTCAGCCTCCCAAGTAGCTGGGACTACA
GGCGCCCGCCACCACACCCGGCTAATTTTTTGTATTTTTAGTAGAGACGGGGTTTCACCA
TGTTAGCCAGGATGGTCTCAATCTCCTGACCTCGTGATCCGCCCACCTCTGTCTCCCAAA
GTGCTGGGATTACAGGTGTGAGCCACCGTACCCGGCCTCAGCTGGCTTTTTTTTTTTCTTG
GAAACTTAAAATTTGATGTTATAATTCAAATAAAAATGCAAAAGAGCCAGAACAACTTTG
[A,G]

FIGURE 3PP

AAAACAAGTCATTATAGGACTTACACTACCTGACTCCAAGATGTATCTAAAGCTACAATA
ATCAAGAAATACAGACAAACAGATCAATGGAACCGAAGAGTATATAGAAACAGACCCACA
TATATATGGGTTACTGATTTTTGACAAAGATACAGAGGGAATTCAGTGGAGGAAGCATGG
TCTTCTTGACACATGGAGCTGGAACAAGTGGATATCCACACACCACAAATGAATTCCAGT
GCATGCCCCACACTGTATACAAATGGCGTCTCAAATGATCATAAAACTGAATGTAAAACC

81752 CTCCACCTCCTGGGTTCAAGCGATTCTCCTGCCTCAGCCTCCCAAGTAGCTGGGACTACA
GGCGCCCGCCACCACACCCGGCTAATTTTTTGTATTTTTAGTAGAGACGGGGTTTCACCA
TGTTAGCCAGGATGGTCTCAATCTCCTGACCTCGTGATCCGCCCACCTCTGTCTCCCAAA
GTGCTGGGATTACAGGTGTGAGCCACCGTACCCGGCCTCAGCTGGCTTTTTTTTTTCTTG
GAAACTTAAAATTTGATG
[-,T]
TATAATTCAAATAAAAATGCAAAAGAGCCAGAACAACTTTGAAAAACAAGTCATTATAGG
ACTTACACTACCTGACTCCAAGATGTATCTAAAGCTACAATAATCAAGAAATACAGACAA
ACAGATCAATGGAACCGAAGAGTATATAGAAACAGACCCACATATATATGGGTTACTGAT
TTTTGACAAAGATACAGAGGGAATTCAGTGGAGGAAGCATGGTCTTCTTGACACATGGAG
CTGGAACAAGTGGATATC

81652 CTCCACCTCCTGGGTTCAAGCGATTCTCCTGCCTCAGCCTCCCAAGTAGCTGGGACTACA
GGCGCCCGCCACCACACCCGGCTAATTTTTTGTATTTTTAGTAGAGACGGGGTTTCACCA
TGTTAGCCAGGATGGTCTCAATCTCCTGACCTCGTGAT
[G,T,C]
CGCCCACCTCTGTCTCCCAAAGTGCTGGGATTACAGGTGTGAGCCACCGTACCCGGCCTC
AGCTGGCTTTTTTTTTTCTTGGAAACTTAAAATTTGATGTTATAATTCAAATAAAAATGC
AAAAGAGCCAGAACAACTTTGAAAAACAAGTCATTATA

81899 GACGGGGTTTCACCATGTTAGCCAGGATGGTCTCAATCTCCTGACCTCGTGATCCGCCCA
CCTCTGTCTCCCAAAGTGCTGGGATTACAGGTGTGAGCCACCGTACCCGGCCTCAGCTGG
CTTTTTTTTTTCTTGGAAACTTAAAATTTGATGTTATAATTCAAATAAAAATGCAAAAGA
GCCAGAACAACTTTGAAAAACAAGTCATTATAGGACTTACACTACCTGACTCCAAGATGT
ATCTAAAGCTACAATAATCAAGAAATACAGACAAACAGATCAATGGAACCGAAGAGTATA
[T,C]
AGAAACAGACCCACATATATATGGGTTACTGATTTTTGACAAAGATACAGAGGGAATTCA
GTGGAGGAAGCATGGTCTTCTTGACACATGGAGCTGGAACAAGTGGATATCCACACACCA
CAAATGAATTCCAGTGCATGCCCCACACTGTATACAAATGGCGTCTCAAATGATCATAAA
ACTGAATGTAAAACCTAAAACTATAACACTTCTAGAAGAAAACAAAGGAGAAACTCTTTG
TGACCTTGGATTAGGCAAGTATTTCTGACATGTGACACCAAAAGCATGATCCACTAGAGA

82828 CAAGGGGAATGGGGTATCTGTCCCCTCAAGCATTTATCCTTTGAGTTACAAACCATTATA
CTCTTTAAGTCATTTTAAAATGTACAATTATCGGTAAGCTTCTAAAATAGCTCCTGGTGT
CCACACCCGTTGTGACCCCCTCCCTTTGAGTGTCAGCTGGACTAGAGACTCGTTCCTAAC
CACAGAATACAGCAGGAGTGATGGAACATCATGTCCACATCAAGTCATAAGAGATGGAGC
TCTGTCTTGCTCACACTCTGGGGCTCCTCTCACCCGCCTGCTCTGATGAAGCCAGTCGCA
[G,C]
GGGACAGGCCCACAGGAACCCAGGCCCTCGGCCCAAAAGCTCTCAAGGAATTCAATCTTG
CCAACAGCCACTCAAGAAATGCCTACTTGTGGCCTCTGATTCAGTTGCTAATAAGGTTAC
CAACAGGACTTTCCATTCTGCCTCAACTGACCTTAAAGTGACGGCTCTGGGAGTTCCACA
CCACCAGGTCGGGGAGGCCCCCTCGACAGTGTCGAAAGTCAGCAGCCAGGTGCCTGCACA
CACCACTGAGCACAGGGCCCCCCAGGCAGGAGACAAGATCCTGAACACAAAACACAGGAC

FIGURE 3QQ

ISOLATED HUMAN PHOSPHATASE PROTEINS, NUCLEIC ACID MOLECULES ENCODING HUMAN PHOSPHATASE PROTEINS, AND USES THEREOF

RELATED APPLICATIONS

The present application is a divisional of U.S. application Ser. No. 09/811,469 filed on Mar. 20, 2001 and issued on Apr. 22, 2003 as U.S. Pat. No. 6,551,809.

FIELD OF THE INVENTION

The present invention is in the field of phosphatase proteins that are related to the dual specificity phosphatase subfamily, recombinant DNA molecules and protein production. The present invention specifically provides a novel phosphatase splice form and nucleic acid molecules encoding the novel splice form, all of which are useful in the development of human therapeutics and diagnostic compositions and methods.

BACKGROUND OF THE INVENTION

Phosphatase proteins, particularly members of the dual specificity phosphatase subfamily, are a major target for drug action and development. Accordingly, it is valuable to the field of pharmaceutical development to identify and characterize previously unknown members of this subfamily of phosphatase proteins. The present invention advances the state of the art by providing a previously unidentified human phosphatase proteins that have homology to members of the dual specificity phosphatase subfamily.

Protein Phosphatase

Cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation of certain residues on proteins. The phosphorylation state of a protein may affect its conformation and/or enzymic activity as well as its cellular location. The phosphorylation state of a protein is modified through the reciprocal actions of protein phosphatases (PKs) and protein phosphatases (PPs) at various specific amino acid residues.

Protein phosphorylation is the ubiquitous strategy used to control the activities of eukaryotic cells. It is estimated that 10% of the proteins active in a typical mammalian cell are phosphorylated. The high-energy phosphate that confers activation and is transferred from adenosine triphosphate molecules to protein-by-protein phosphatases is subsequently removed from the protein-by-protein phosphatases. In this way, the phosphatases control most cellular signaling events that regulate cell growth and differentiation, cell-to-cell contacts, the cell cycle, and oncogenesis.

The protein phosphorylation/dephosphorylation cycle is one of the major regulatory mechanisms employed by eukaryotic cells to control cellular activities. It is estimated that more than 10% of the active proteins in a typical mammalian cell are phosphorylated. During protein phosphorylation/dephosphorylation, phosphate groups are transferred from adenosine triphosphate molecules to protein-by-protein phosphatases and are removed from the protein-by-protein phosphatases.

Protein phosphatases function in cellular signaling events that regulate cell growth and differentiation, cell-to-cell contacts, the cell cycle, and oncogenesis. Three protein phosphatase families have been identified as evolutionarily distinct. These include the serine/threonine phosphatases, the protein tyrosine phosphatases, and the acid/alkaline phosphatases (Carbonneau H. and Tonks N. K. (1992) Annu. Rev. Cell Biol. 8:463–93).

The serine/threonine phosphatases are either cytosolic or associated with a receptor. On the basis of their sensitivity to two thermostable proteins, inhibitors 1 and 2, and their divalent cation requirements, the serine/threonine phosphatases can be separated into four distinct groups, PP-I, PP-IIA, PP-IIB, and PP-IIC.

PP-I dephosphorylates many of the proteins phosphorylated by cylic AMP-dependent protein phosphatase and is therefore an important regulator of many cyclic AMP mediated, hormone responses in cells. PP-IIA has broad specificity for control of cell cycle, growth and proliferation, and DNA replication and is the main phosphatase responsible for reversing the phosphorylations of serine/threonine phosphatases. PP-IIB, or calcineurin (Cn), is a Ca.sup.+2-activated phosphatase; it is involved in the regulation of such diverse cellular functions as ion channel regulation, neuronal transmission, gene transcription, muscle glycogen metabolism, and lymphocyte activation.

PP-IIC is a Mg.sup.++-dependent phosphatase which participates in a wide variety of functions including regulating cyclic AMP-activated protein-phosphatase activity, Ca.sup.++-dependent signal transduction, tRNA splicing, and signal transmission related to heat shock responses. PP-IIC is a monomeric protein with a molecular mass of about 40–45 kDa. One .alpha. and several .beta. isoforms of PP-IIC have been identified (Wenk, J. et al. (1992) FEBS Lett. 297: 135–138; Terasawa, T. et al. (1993) Arch. Biochem. Biophys. 307: 342–349; and Kato, S. et al. (1995) Arch. Biochem. Biophys. 318: 387–393).

The levels of protein phosphorylation required for normal cell growth and differentiation at any time are achieved through the coordinated action of PKs and PPS. Depending on the cellular context, these two types of enzymes may either antagonize or cooperate with each other during signal transduction. An imbalance between these enzymes may impair normal cell functions leading to metabolic disorders and cellular transformation.

For example, insulin binding to the insulin receptor, which is a PTK, triggers a variety of metabolic and growth promoting effects such as glucose transport, biosynthesis of glycogen and fats, DNA synthesis, cell division and differentiation. Diabetes mellitus, which is characterized by insufficient or a lack of insulin signal transduction, can be caused by any abnormality at any step along the insulin signaling pathway. (Olefsky, 1988, in "Cecil Textbook of Medicine," 18th Ed., 2:1360–81).

It is also well known, for example, that the overexpression of PTKs, such as HER2, can play a decisive role in the development of cancer (Slamon et al., 1987, Science 235:77–82) and that antibodies capable of blocking the activity of this enzyme can abrogate tumor growth (Drebin et al., 1988, Oncogene 2:387–394). Blocking the signal transduction capability of tyrosine phosphatases such as Flk-1 and the PDGF receptor have been shown to block tumor growth in animal models (Millauer et al., 1994, Nature 367:577; Ueno et al., Science, 252:844–848).

Relatively less is known with respect to the direct role of phosphatases in signal transduction; PPs may play a role in human diseases. For example, ectopic expression of RPT-P.alpha. produces a transformed phenotype in embryonic fibroblasts (Zheng et al., Nature 359:336–339), and overexpression of RPTP.alpha. in embryonal carcinoma cells causes the cells to differentiate into a cell type with neuronal phenotype (den Hertog et al., EMBO J 12:3789–3798). The gene for human RPTP.gamma. has been localized to chromosome 3p21 which is a segment frequently altered in renal and small lung carcinoma. Mutations may occur in the extracellular segment of RPTP.gamma. which renders a RPTP that no longer respond to external signals (LaForgia et al., Wary et al., 1993, Cancer Res 52:478–482). Mutations in the gene encoding PTP1C (also known as HCP, SHP) are the cause of the moth-eaten phenotype in mice that suffer severe immunodeficiency, and systemic autoimmune disease accompanied by hyperproliferation of macrophages (Schultz et al., 1993, Cell 73:1445–1454). PTP1D (also known as Syp or PTP2C) has been shown to bind through SH2 domains to sites of phosphorylation in PDGFR, EGFR and insulin receptor substrate 1 (IRS-1). Reducing the activity of PTP1D by microinjection of anti-PTP1D antibody has been shown to block insulin or EGF-induced mitogenesis (Xiao et al., 1994, J Biol Chem 269:21244–21248).

Myotubularin Dual Specificity Phosphatases

The novel human protein provided by the present invention is an alternative splice form of a known gene (referred to in Genbank as "hypothetical protein FLJ20313"; mRNA: gi8923296, protein sequences: gi11433679 and gi8923297). The alternative splice form of the present invention differs from the art-known protein at both the 5' and 3' ends.

The human protein, and encoding gene, of the present invention is related to dual specificity phosphatases (DSPs) in general, and myotubularin DSPs specifically. Mutations in myotubularin DSP genes are known to cause X-linked myotubular myopathy, which is a severe congenital muscle disorder (Laporte et al., *Hum Mol Genet* October 1998;7 (11):1703–12). Furthermore, is has been suggested that myotubularin DSP genes are good candidates for other genetic diseases (Laporte et al., *Hum Mol Genet* October 1998;7(11):1703–12).

Other than containing an active tyrosine phosphatase consensus site, myotubularin shares limited homology with other phosphatases. Myotubularin acts on both phosphotyrosine and phosphoserine, and has been shown to hydrolyze a synthetic analog of tyrosine phosphatase in a reaction that can be inhibited by orthovanadate. The myotubularin DSP family is strongly conserved throughout evolution and is the largest known DSP family (Laporte et al., *Hum Mol Genet* October 1998;7(11):1703–12).

The discovery of a new human protein phosphatase and the polynucleotides encoding it satisfies a need in the art by providing new compositions that are useful in the diagnosis, prevention and treatment of biological processes associated with abnormal or unwanted protein phosphorylation.

SUMMARY OF THE INVENTION

The present invention is based in part on the identification of amino acid sequences of a novel human phosphatase splice form that is related to the dual specificity phosphatase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate phosphatase activity in cells and tissues that express the phosphatase. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver.

DESCRIPTION OF THE FIGURE SHEETS

FIGS. 1(A–C) provides the nucleotide sequence of a cDNA molecule that encodes the phosphatase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver.

FIGS. 2(A–H) provides the predicted amino acid sequence of the phosphatase of the present invention. (SEQ ID NO:2) In addition, structure and functional information such as protein family, function, and modification sites is provided where available, allowing one to readily determine specific uses of inventions based on this molecular sequence.

FIGS. 3(A–QQ) provides genomic sequences that span the gene encoding the phosphatase protein of the present invention. (SEQ ID NO:3) As illustrated in FIG. 3, the chromosome map position has been determined to be on chromosome 15 and SNPs were identified at 96 different nucleotide positions. Specific uses of the inventions can readily be determined based on the molecular sequence and accompanying chromosome map and SNP information provided in FIGS. 3(A–QQ).

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phosphatase protein or part of a phosphatase protein and are related to the dual specificity phosphatase subfamily. Utilizing these sequences, additional genomic sequences were assembled and transcript and/or cDNA sequences were isolated and characterized. Based on this analysis, the present invention provides amino acid sequences of a novel human phosphatase splice form that is related to the dual specificity phosphatase subfamily, nucleic acid sequences in the form of transcript sequences, cDNA sequences and/or genomic sequences that encode this phosphatase splice form, nucleic acid variation (allelic information), tissue distribution of expression, and information about the closest art known protein/peptide/domain that has structural or sequence homology to the phosphatase of the present invention.

In addition to being previously unknown, the peptides that are provided in the present invention are selected based on their ability to be used for the development of commercially important products and services. Specifically, the present peptides are selected based on homology and/or structural relatedness to known phosphatase proteins of the dual specificity phosphatase subfamily and the expression pattern observed. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known dual specificity phosphatase family or subfamily of phosphatase proteins.

Specific Embodiments

Peptide Molecules

The present invention provides nucleic acid sequences that encode protein molecules that have been identified as being members of the phosphatase family of proteins and are related to the dual specificity phosphatase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the phosphatase peptides of the present invention, phosphatase peptides, or peptides/proteins of the present invention.

The present invention provides isolated peptide and protein molecules that consist of, consist essentially of, or comprise the amino acid sequences of the phosphatase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phosphatase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phosphatase peptide can be purified from cells that naturally express it, purified from cells that have been altered to express it (recombinant), or synthesized using known protein synthesis methods. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. For example, a nucleic acid molecule encoding the phosphatase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the phosphatase peptides of the present invention are the naturally occurring mature proteins. A brief description of how various types of these proteins can be made/isolated is provided below.

The phosphatase peptides of the present invention can be attached to heterologous sequences to form chimeric or fusion proteins. Such chimeric and fusion proteins comprise a phosphatase peptide operatively linked to a heterologous protein having an amino acid sequence not substantially homologous to the phosphatase peptide. "Operatively linked" indicates that the phosphatase peptide and the heterologous protein are fused in-frame. The heterologous protein can be fused to the N-terminus or C-terminus of the phosphatase peptide.

In some uses, the fusion protein does not affect the activity of the phosphatase peptide per se. For example, the fusion protein can include, but is not limited to, enzymatic fusion proteins, for example beta-galactosidase fusions, yeast two-hybrid GAL fusions, poly-His fusions, MYCtagged, HI-tagged and Ig fusions. Such fusion proteins, particularly poly-His fusions, can facilitate the purification of recombinant phosphatase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A phosphatase peptide-encoding nucleic acid can be cloned into such an expression vector such that the fusion moiety is linked in-frame to the phosphatase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phosphatase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phosphatase peptides of the present invention as well as being encoded by the same genetic locus as the phosphatase peptide provided herein. The gene encoding the novel phosphatase protein of the present invention is located on a genome component that has been mapped to human chromosome 15 (as indicated in FIG. 3), which is supported by multiple lines of evidence, such as STS and BAC map data.

Allelic variants of a phosphatase peptide can readily be identified as being a human protein having a high degree (significant) of sequence homology/identity to at least a portion of the phosphatase peptide as well as being encoded by the same genetic locus as the phosphatase peptide provided herein. Genetic locus can readily be determined based on the genomic information provided in FIG. 3, such as the genomic sequence mapped to the reference human. The gene encoding the novel phosphatase protein of the present invention is located on a genome component that has been mapped to human chromosome 15 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phosphatase peptide encoding nucleic acid molecule under stringent conditions as more fully described below.

FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements.

Paralogs of a phosphatase peptide can readily be identified as having some degree of significant sequence homology/identity to at least a portion of the phosphatase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phosphatase peptide encoding nucleic acid molecule under moderate to stringent conditions as more fully described below.

Orthologs of a phosphatase peptide can readily be identified as having some degree of significant sequence homology/identity to at least a portion of the phosphatase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phosphatase peptide encoding nucleic acid molecule under moderate to stringent conditions, as more fully described below, depending on the degree of relatedness of the two organisms yielding the proteins.

Non-naturally occurring variants of the phosphatase peptides of the present invention can readily be generated using recombinant techniques. Such variants include, but are not limited to deletions, additions and substitutions in the amino acid sequence of the phosphatase peptide. For example, one class of substitutions are conserved amino acid substitution. Such substitutions are those that substitute a given amino acid in a phosphatase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phosphatase peptides can be fully functional or can lack function in one or more activities, e.g. ability to bind substrate, ability to dephosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as phosphatase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the phosphatase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid-residues from a phosphatase peptide. Such fragments can be chosen based on the ability to retain one or more of the biological activities of the phosphatase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phosphatase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phosphatase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the phosphatase peptides of the present invention also encompass derivatives or analogs in which a substituted amino acid residue is not one encoded by the genetic code, in which a substituent group is included, in which the mature phosphatase peptide is fused with another compound, such as a compound to increase the half-life of the phosphatase peptide, or in which the additional amino acids are fused to the mature phosphatase peptide, such as a leader or secretory sequence or a sequence for purification of the mature phosphatase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a phosphatase-effector protein interaction or phosphatase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phosphatases isolated from humans and their human/mammalian orthologs serve as targets for identifying agents for use in mammalian therapeutic applications, e.g. a human drug, particularly in modulating a biological or pathological response in a cell or tissue that expresses the phosphatase. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. A large percentage of pharmaceutical agents are being developed that modulate the activity of phosphatase proteins, particularly members of the dual specificity phosphatase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. Such uses can readily be determined using the information provided herein, that which is known in the art, and routine experimentation.

The proteins of the present invention (including variants and fragments that may have been disclosed prior to the present invention) are useful for biological assays related to phosphatases that are related to members of the dual specificity phosphatase subfamily. Such assays involve any of the known phosphatase functions or activities or properties useful for diagnosis and treatment of phosphatase-related conditions that are specific for the subfamily of phosphatases that the one of the present invention belongs to, particularly in cells and tissues that express the phosphatase. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver.

The proteins of the present invention are also useful in drug screening assays, in cell-based or cell-free systems. Cell-based systems can be native, i.e., cells that normally express the phosphatase, as a biopsy or expanded in cell culture. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. In an alternate embodiment, cell-based assays involve recombinant host cells expressing the phosphatase protein.

The polypeptides can be used to identify compounds that modulate phosphatase activity of the protein in its natural state or an altered form that causes a specific disease or pathology associated with the phosphatase. Both the phosphatases of the present invention and appropriate variants and fragments can be used in high-throughput screens to assay candidate compounds for the ability to bind to the phosphatase. These compounds can be further screened against a functional phosphatase to determine the effect of the compound on the phosphatase activity. Further, these compounds can be tested in animal or invertebrate systems to determine activity/effectiveness. Compounds can be identified that activate (agonist) or inactivate (antagonist) the phosphatase to a desired degree.

Further, the proteins of the present invention can be used to screen a compound for the ability to stimulate or inhibit interaction between the phosphatase protein and a molecule that normally interacts with the phosphatase protein, e.g. a substrate or a component of the signal pathway that the phosphatase protein normally interacts (for example, another phosphatase). Such assays typically include the steps of combining the phosphatase protein with a candidate compound under conditions that allow the phosphatase protein, or fragment, to interact with the target molecule, and to detect the formation of a complex between the protein and the target or to detect the biochemical consequence of the interaction with the phosphatase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phosphatases or appropriate fragments containing mutations that affect phosphatase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phosphatase activity. The assays typically involve an assay of events in the signal transduction pathway that indicate phosphatase activity. Thus, the dephosphorylation of a substrate, activation of a protein, a change in the expression of genes that are up- or down-regulated in response to the phosphatase protein dependent signal cascade can be assayed.

Any of the biological or biochemical functions mediated by the phosphatase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the phosphatase can be assayed. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver.

Binding and/or activating compounds can also be screened by using chimeric phosphatase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phosphatase. Accordingly, a different set of signal transduction components is available as an end-point assay for activation. This allows for assays to be performed in other than the specific host cell from which the phosphatase is derived.

The proteins of the present invention are also useful in competition binding assays in methods designed to discover compounds that interact with the phosphatase (e.g. binding partners and/or ligands). Thus, a compound is exposed to a phosphatase polypeptide under conditions that allow the compound to bind or to otherwise interact with the polypeptide. Soluble phosphatase polypeptide is also added to the mixture. If the test compound interacts with the soluble phosphatase polypeptide, it decreases the amount of complex formed or activity from the phosphatase target. This type of assay is particularly useful in cases in which compounds are sought that interact with specific regions of the phosphatase. Thus, the soluble polypeptide that competes with the target phosphatase region is designed to contain peptide sequences corresponding to the region of interest.

To perform cell free drug screening assays, it is sometimes desirable to immobilize either the phosphatase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phosphatase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphatase-binding protein and a candidate compound are incubated in the phosphatase proteinpresenting wells and the amount of complex trapped in the well can be quantitated. Methods for detecting such complexes, in addition to those described above for the GST-immobilized complexes, include immunodetection of complexes using antibodies reactive with the phosphatase protein target molecule, or which are reactive with phosphatase protein and compete with the target molecule, as well as enzyme-linked assays which rely on detecting an enzymatic activity associated with the target molecule.

Agents that modulate one of the phosphatases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phosphatase protein activity identified according to these drug screening assays can be used to treat a subject with a disorder mediated by the kinase pathway, by treating cells or tissues that express the phosphatase. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. These methods of treatment include the steps of administering a modulator of phosphatase activity in a pharmaceutical composition to a subject in need of such treatment, the modulator being identified as described herein.

In yet another aspect of the invention, the phosphatase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the phosphatase and are involved in phosphatase activity. Such phosphatase-binding proteins are also likely to be involved in the propagation of signals by the phosphatase proteins or phosphatase targets as, for example, downstream elements of a kinase-mediated signaling pathway. Alternatively, such phosphatase-binding proteins are likely to be phosphatase inhibitors.

The two-hybrid system is based on the modular nature of most transcription factors, which consist of separable DNA-binding and activation domains. Briefly, the assay utilizes two different DNA constructs. In one construct, the gene that codes for a phosphatase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phosphatase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phosphatase protein.

This invention further pertains to novel agents identified by the above-described screening assays. Accordingly, it is within the scope of this invention to further use an agent identified as described herein in an appropriate animal model. For example, an agent identified as described herein (e.g., a phosphatase-modulating agent, an antisense phosphatase nucleic acid molecule, a phosphatase-specific antibody, or a phosphatase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phosphatase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. The method involves contacting a biological sample with a compound capable of interacting with the phosphatase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phosphatase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphatase protein in which one or more of the phosphatase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and phosphatase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. Accordingly, methods for treatment include the use of the phosphatase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In-general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phosphatase proteins. Antibodies can be prepared from any region of the peptide as described herein. However, preferred regions will include those involved in function/activity and/or phosphatase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. Thus, where a specific protein has been correlated with expression in a specific tissue, antibodies that are specific for this protein can be used to identify a tissue type.

The antibodies are also useful for inhibiting protein function, for example, blocking the binding of the phosphatase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a phosphatase peptide or protein of the present invention (cDNA, transcript and genomic sequence). Such nucleic acid molecules will consist of, consist essentially of, or comprise a nucleotide sequence that encodes one of the phosphatase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phosphatase peptide alone, the sequence encoding the mature peptide and additional coding sequences, such as a leader or secretory sequence (e.g., a pre- pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the phosphatase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel phosphatase protein of the present invention is located on a genome component that has been mapped to human chromosome 15 (as indicated in FIG. 3), which is supported by multiple lines of evidence, such as STS and BAC map data.

FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology,* John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 96 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel phosphatase protein of the present invention is located on a genome component that has been mapped to human chromosome 15 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid, molecules are also useful as hybridization probes for determining the presence, level, form and distribution of nucleic acid expression. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phosphatase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a phosphatase protein, such as by measuring a level of a phosphatase-encoding nucleic acid in a sample of cells from a subject e.g., mRNA or genomic DNA, or determining if a phosphatase gene has been mutated. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver.

Nucleic acid expression assays are useful for drug screening to identify compounds that modulate phosphatase nucleic acid expression.

The invention thus provides a method for identifying a compound that can be used to treat a disorder associated with nucleic acid expression of the phosphatase gene, particularly biological and pathological processes that are mediated by the phosphatase in cells and tissues that express it. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver. The method typically includes assaying the ability of the compound to modulate the expression of the phosphatase nucleic acid and thus identifying a compound that can be used to treat a disorder characterized by undesired phosphatase nucleic acid expression. The assays can be performed in cell-based and cell-free systems. Cell-based assays include cells naturally expressing the phosphatase nucleic acid or recombinant cells genetically engineered to express specific nucleic acid sequences.

The assay for phosphatase nucleic acid expression can involve direct assay of nucleic acid levels, such as mRNA levels, or on collateral compounds involved in the signal pathway. Further, the expression of genes that are up- or down-regulated in response to the phosphatase protein signal pathway can also be assayed. In this embodiment the regulatory regions of these genes can be operably linked to a reporter gene such as luciferase.

Thus, modulators of phosphatase gene expression can be identified in a method wherein a cell is contacted with a candidate compound and the expression of mRNA determined. The level of expression of phosphatase mRNA in the presence of the candidate compound is compared to the level of expression of phosphatase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phosphatase nucleic acid expression in cells and tissues that express the phosphatase. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. Modulation includes both up-regulation (i.e. activation or agonization) or down-regulation (suppression or antagonization) or nucleic acid expression.

Alternatively, a modulator for phosphatase nucleic acid expression can be a small molecule or drug identified using the screening assays described herein as long as the drug or small molecule inhibits the phosphatase nucleic acid expression in the cells and tissues that express the protein. Experimental data as provided in FIG. 1 indicates expression in humans in B-cell Burkitt's lymphoma, lymph germinal center B-cells, fetal lung, neural tissue, breast invasive ductal carcinoma, parathyroid tumor, carcinoid lung tissue, fetal liver/spleen, and liver.

The nucleic acid molecules are also useful for monitoring the effectiveness of modulating compounds on the expression or activity of the phosphatase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phosphatase nucleic acid expression, and particularly in qualitative changes that lead to pathology. The nucleic acid molecules can be used to detect mutations in phosphatase genes and gene expression products such as mRNA. The nucleic acid molecules can be used as hybridization probes to detect naturally occurring genetic mutations in the phosphatase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphatase gene associated with a dysfunction provides a diagnostic tool for an active disease or susceptibility to disease when the disease results from overexpression, underexpression, or altered expression of a phosphatase protein.

Individuals carrying mutations in the phosphatase gene can be detected at the nucleic acid level by a variety of techniques. FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements. The gene encoding the novel phosphatase protein of the present invention is located on a genome component that has been mapped to human chromosome 15 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phosphatase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phosphatase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phosphatase gene in an individual in order to select an appropriate compound or dosage regimen for treatment. FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phosphatase gene expression in cells, tissues, and organisms. A DNA antisense nucleic acid molecule is designed to be complementary to a region of the gene involved in transcription, preventing transcription and hence production of phosphatase protein. An antisense RNA or DNA nucleic acid molecule would hybridize to the mRNA and thus block translation of mRNA into phosphatase protein.

Alternatively, a class of antisense molecules can be used to inactivate mRNA in order to decrease expression of phosphatase nucleic acid. Accordingly, these molecules can treat a disorder characterized by abnormal or undesired phosphatase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphatase protein, such as substrate binding.

The nucleic acid molecules also provide vectors for gene therapy in patients containing cells that are aberrant in phosphatase gene expression. Thus, recombinant cells, which include the patient's cells that have been engineered ex vivo and returned to the patient, are introduced into an individual where the cells produce the desired phosphatase protein to treat the individual.

The invention also encompasses kits for detecting the presence of a phosphatase nucleic acid in a biological sample. Experimental data as provided in FIG. 1 indicates that the phosphatase proteins of the present invention are expressed in humans in B-cell Burkitt's lymphoma, lymph germinal center B-cells, fetal lung, neural tissue, breast invasive ductal carcinoma, parathyroid tumor, carcinoid lung tissue, and fetal liver/spleen, as indicated by virtual northern blot analysis. In addition, PCR-based tissue screening panels indicate expression in the liver. For example, the kit can comprise reagents such as a labeled or labelable nucleic acid or agent capable of detecting phosphatase nucleic acid in a biological sample; means for determining the amount of phosphatase nucleic acid in the sample; and means for comparing the amount of phosphatase nucleic acid in the sample with a standard. The compound or agent can be packaged in a suitable container. The kit can further comprise instructions for using the kit to detect phosphatase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phosphatase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phosphatase gene of the present invention. FIG. 3 provides information on SNPs that have been found in the gene encoding the phosphatase protein of the present invention. SNPs were identified at 96 different nucleotide positions. Changes in the amino acid sequence caused by these SNPs can readily be determined using the universal genetic code and the protein sequence provided in FIG. 2 as a reference. Some of these SNPs may also affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phosphatase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal; episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or-exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterophosphatase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kuijan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as phosphatases, appropriate secretion signals are incorporated into the vector. The signal sequence can be endogenous to the peptides or heterologous to these peptides.

Where the peptide is not secreted into the medium, which is typically the case with phosphatases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a phosphatase protein or peptide that can be further purified to produce desired amounts of phosphatase protein or fragments. Thus, host cells containing expression vectors are useful for peptide production.

Host cells are also useful for conducting cell-based assays involving the phosphatase protein or phosphatase protein fragments, such as those described above as well as other formats known in the art. Thus, a recombinant host cell expressing a native phosphatase protein is useful for assaying compounds that stimulate or inhibit phosphatase protein function.

Host cells are also useful for identifying phosphatase protein mutants in which these functions are affected. If the mutants naturally occur and give rise to a pathology, host cells containing the mutations are useful to assay compounds that have a desired effect on the mutant phosphatase protein (for example, stimulating or inhibiting function) which may not be indicated by their effect on the native phosphatase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphatase protein and identifying and evaluating modulators of phosphatase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphatase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the phosphatase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992).

Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo, and that could effect substrate binding, kinase protein activation, and signal transduction, may not be evident from in vitro cell-free or cell-based assays. Accordingly, it is useful to provide non-human transgenic animals to assay in vivo phosphatase protein function, including substrate interaction, the effect of specific mutant phosphatase proteins on phosphatase protein function and substrate interaction, and the effect of chimeric phosphatase proteins. It is also possible to assess the effect of null mutations, that is mutations that substantially or completely eliminate one or more phosphatase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

38

That which is claimed is:

1. An isolated polypeptide having an amino acid sequence consisting SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

* * * * *

SEQUENCE LISTING

<160> NUMBER OF SEQ ID NOS: 11

<210> SEQ ID NO 1
<211> LENGTH: 4458
<212> TYPE: DNA
<213> ORGANISM: Homo sapiens

<400> SEQUENCE: 1

```
gagagcttta cgcccggagg cgtcggcgct gccactggcc cgcgacggga acggggcgaa      60

aaggcggcgg caccatgttc tccctcaagc cgcccaaacc caccttcagg tcctacctcc     120
```

-continued

```
tgccaccgcc ccagactgac gataagatca attcggaacc gaagattaaa aaactggagc    180
cagtcctttt gccaggagaa attgtcgtaa atgaagtcaa ttttgtgaga aaatgcattg    240
caacagacac aagccagtac gatttgtggg gaaagctgat atgcagtaac ttcaaaatct    300
cctttattac agatgaccca atgccattac agaaattcca ttacagaaac cttcttcttg    360
gtgaacacga tgtcccttta acatgtattg aacaaattgt cacagtaaac gaccacaaga    420
ggaagcagaa agtcctaggc cccaaccaga aactgaaatt taatccaaca gagttaatta    480
tttattgtaa agatttcaga attgtcagat ttcgctttga tgaatcaggt cccgaaagtg    540
ctaaaaaggt atgccttgca atagctcatt attcccagcc aacagacctc cagctactct    600
ttgcatttga atatgttggg aaaaaatacc acaattcagc aaacaaaatt aatggaattc    660
cctcaggaga tggaggagga ggaggaggag gaggtaatgg agctggtggt ggcagcagcc    720
agaaaactcc actctttgaa acttactcgg attgggacag agaaatcaag aggacaggtg    780
cttccgggtg gagagtttgt tctattaacg agggttacat gatatccact tgccttccag    840
aatacattgt agtgccaagt tctttagcag accaagatct aaagatcttt tcccattctt    900
ttgttgggag aaggatgcca ctctggtgct ggagccactc taacggcagt gctcttgtgc    960
gaatggccct catcaaagac gtgctgcagc agaggaagat tgaccagagg atttgtaatg   1020
caataactaa aagtcaccca cagagaagtg atgtttacaa atcagatttg gataagacct   1080
tgcctaatat tcaagaagta caggcagcat ttgtaaaact gaagcagcta tgcgttaatg   1140
agccttttga agaaactgaa gagaaatggt tatcttcact ggaaaatact cgatggttag   1200
aatatgtaag ggcattcctt aagcattcag cagaacttgt atacatgcta gaaagcaaac   1260
atctctctgt agtcctacaa gaggaggaag gaagagactt gagctgttgt gtagcttctc   1320
ttgttcaagt gatgctggat ccctatttta ggacaattac tggatttcag agtctgatac   1380
agaaggagtg ggtcatggca ggatatcagt ttctagacag atgcaaccat ctaaagagat   1440
cagagaaaga gtctccttta tttttgctat tcttggatgc cacctggcag ctgttagaac   1500
aatatcctgc agcttttgag ttctccgaaa cctacctggc agtgttgtat gacagcaccc   1560
ggatctcact gtttggcacc ttcctgttca actcccctca ccagcgagtg aagcaaagca   1620
cggaatttgc tataagcaaa aacatccaat tgggtgatga gaagggctta aaattcccct   1680
ctgtttggga ctggtctctc cagtttacag caaaggatcg caccctttc cataacccct    1740
tctacattgg aaagagcaca ccttgtatac agaatggctc cgtgaagtct tttaaacgga   1800
caaagaaaag ctacagctcc acactaagag gaatgccgtc tgccttaaag aatggaatca   1860
tcagtgacca agaattactt ccaaggagaa attcattgat attaaaacca aagccagatc   1920
cagctcagca aaccgacagc cagaacagtg atacggagca gtattttaga gaatggtttt   1980
ccaaacccgc caacctgcac ggtgttattc tgccacgtgt ctctggaaca cacataaaac   2040
tgtggaaact gtgctacttc cgctgggttc ccgaggccca gatcagcctg ggtggctcca   2100
tcacagcctt tcacaagctc tccctcctgg ctgatgaagt cgacgtactg agcaggatgc   2160
tgcggcaaca gcgcagtggc cccctggagg cctgctatgg ggagctgggc cagagcagga   2220
tgtacttcaa cgccagcggc cctcaccaca ccgacacctc ggggacaccg gagtttctct   2280
cctcctcatt tccattttct cctgtaggga atctgtgcag acgaagcatt ttaggaacac   2340
cattaagcaa atttttaagt ggggccaaaa tatggttgtc tactgagaca ttagcaaatg   2400
aagactaaaa tagggtgttt tctgaacatt ttgagggaag ctgtcaactt ttttcctctg   2460
```

-continued

```
aattaacatt gctaacctag gcgtttgaat ctctaataac tttatatgta agaataatag   2520
ttggaatttg cactaatatt taaaaacatg ttgaatcatg cttctttcac acttatttta   2580
agagagatgt aaattttgtt cctgtcctct ttctgtcatt acaggtctgg ctcttgtaac   2640
cgtgatcaaa ctgttcatgt tgtctgctac atttttgtct ccatccattt ttcctaccac   2700
ctcctgaagg ctatctgata gtcagtcaca ttagcagccc caggcagcag acaacaggaa   2760
agttaggaaa tttgtgtttc gtgtcatttt taggagcatc tgataaaacc tccagcaggt   2820
tttaggaagt attcatgtat ttttctggtt actttctgtc atctctaatt gaactcacct   2880
gatgaaggtt cagtgttctg gggccagaat ttatgatttt agatcacctt ctttggaacc   2940
ttagatcact gtgttttgaa atcatgagtt tgcttttaac ttcatagggt caactttaaa   3000
atgatatgca ctgttaattt taaagcattt gctgcagata attaaactta gaagtgcctt   3060
tgactttagg atacaaatat tacagaagaa aatataattt cactttttaa aattggggtg   3120
ggaaaatccc attgcatatt tgaaataggc ttttcatact aagcttcata gccaggagtc   3180
cccagagtct tgttcctctg aaagccactg gggagtggcc tctggggtgc tgattccaca   3240
gaggtgtatg ctgtagacag gagagtgcca tctatgccaa aactcgccct caaaaacaaa   3300
caaggcttgc tgggaggcgt gctgggcttg gccatcagta tttccagtgt ggtaaactat   3360
tgctggcact tccccctgga aataactaat gaggttacga gttgggcacc tgcacagatg   3420
tccttctctc atagttccta atgcttagga atagaggaga aataaaaaaa tggattctct   3480
caaaacactg ccatttgaat agcgacagaa gtgctccccc agcccccaac tttggacagc   3540
aaagttgagg agaatgagca gacacagttg tttgcttgat ctgaatctct ctaaagtaaa   3600
gtatttccaa actgtgtgac aagagcctac ctaccactgt agcggtcaaa gctgaagctt   3660
cttacagcag tgaaacgggg caccacctcc cccacactcc tcattccccg cttaaaacat   3720
ggatactttc aaatttgact gtttcttaaa ctgccatcct aagatatgga aaatttttat   3780
agtaaagtgt ctagttagct tatttccttt tctaaaacaa gtgttttcaa gataactgta   3840
ttttaccttt atatgtactg aatagctgtt tctttttgaa ttatttgcct tttaaaattt   3900
gataatgtct ctggatataa caggacagga gttcttaaaa aatatcttaa gaaattcact   3960
ttatgggtaa acccaaggtt tttgccaact tgttgcctag aaaataaggg ctagtttcag   4020
tttatacaaa tagaattatt aaacatttta cagtccttga ttagaaacca gacccaatct   4080
ccttataaca ccacagcgta tcctgccatt gacagtgtaa tcacaattct cccttttttca  4140
tttagctgct tttttattat tactaaatgt tttggattga gcatttttcc ctctgtaatt   4200
ttcttccttc acgtttattt tattttaact cttgtagtat tttattgttg ttaatttaca   4260
agtttaaaaa tattaggtac tattaataat ggttaaaaat agaaaaatgc atatttttgt   4320
atgataatca aatgtaaaat acttttattt ttgctggaca gttgttatat catgattatt   4380
gtgctacagt ttattgtgca taatatgaaa aacaactatg acagccttca gtcgggccag   4440
ggtgaagctg cttatacc                                                 4458
```

```
<210> SEQ ID NO 2
<211> LENGTH: 777
<212> TYPE: PRT
<213> ORGANISM: Homo sapiens

<400> SEQUENCE: 2

Met Phe Ser Leu Lys Pro Pro Lys Pro Thr Phe Arg Ser Tyr Leu Leu
 1               5                  10                  15
```

-continued

```
Pro Pro Pro Gln Thr Asp Asp Lys Ile Asn Ser Glu Pro Lys Ile Lys
        20                  25                  30

Lys Leu Glu Pro Val Leu Leu Pro Gly Glu Ile Val Val Asn Glu Val
        35                  40                  45

Asn Phe Val Arg Lys Cys Ile Ala Thr Asp Thr Ser Gln Tyr Asp Leu
    50                  55                  60

Trp Gly Lys Leu Ile Cys Ser Asn Phe Lys Ile Ser Phe Ile Thr Asp
65                  70                  75                  80

Asp Pro Met Pro Leu Gln Lys Phe His Tyr Arg Asn Leu Leu Leu Gly
                85                  90                  95

Glu His Asp Val Pro Leu Thr Cys Ile Glu Gln Ile Val Thr Val Asn
            100                 105                 110

Asp His Lys Arg Lys Gln Lys Val Leu Gly Pro Asn Gln Lys Leu Lys
        115                 120                 125

Phe Asn Pro Thr Glu Leu Ile Ile Tyr Cys Lys Asp Phe Arg Ile Val
    130                 135                 140

Arg Phe Arg Phe Asp Glu Ser Gly Pro Glu Ser Ala Lys Lys Val Cys
145                 150                 155                 160

Leu Ala Ile Ala His Tyr Ser Gln Pro Thr Asp Leu Gln Leu Leu Phe
                165                 170                 175

Ala Phe Glu Tyr Val Gly Lys Lys Tyr His Asn Ser Ala Asn Lys Ile
            180                 185                 190

Asn Gly Ile Pro Ser Gly Asp Gly Gly Gly Gly Gly Gly Gly Gly Asn
        195                 200                 205

Gly Ala Gly Gly Gly Ser Ser Gln Lys Thr Pro Leu Phe Glu Thr Tyr
    210                 215                 220

Ser Asp Trp Asp Arg Glu Ile Lys Arg Thr Gly Ala Ser Gly Trp Arg
225                 230                 235                 240

Val Cys Ser Ile Asn Glu Gly Tyr Met Ile Ser Thr Cys Leu Pro Glu
                245                 250                 255

Tyr Ile Val Val Pro Ser Ser Leu Ala Asp Gln Asp Leu Lys Ile Phe
            260                 265                 270

Ser His Ser Phe Val Gly Arg Arg Met Pro Leu Trp Cys Trp Ser His
        275                 280                 285

Ser Asn Gly Ser Ala Leu Val Arg Met Ala Leu Ile Lys Asp Val Leu
    290                 295                 300

Gln Gln Arg Lys Ile Asp Gln Arg Ile Cys Asn Ala Ile Thr Lys Ser
305                 310                 315                 320

His Pro Gln Arg Ser Asp Val Tyr Lys Ser Asp Leu Asp Lys Thr Leu
                325                 330                 335

Pro Asn Ile Gln Glu Val Gln Ala Ala Phe Val Lys Leu Lys Gln Leu
            340                 345                 350

Cys Val Asn Glu Pro Phe Glu Glu Thr Glu Glu Lys Trp Leu Ser Ser
        355                 360                 365

Leu Glu Asn Thr Arg Trp Leu Glu Tyr Val Arg Ala Phe Leu Lys His
    370                 375                 380

Ser Ala Glu Leu Val Tyr Met Leu Glu Ser Lys His Leu Ser Val Val
385                 390                 395                 400

Leu Gln Glu Glu Glu Gly Arg Asp Leu Ser Cys Cys Val Ala Ser Leu
                405                 410                 415

Val Gln Val Met Leu Asp Pro Tyr Phe Arg Thr Ile Thr Gly Phe Gln
            420                 425                 430

Ser Leu Ile Gln Lys Glu Trp Val Met Ala Gly Tyr Gln Phe Leu Asp
```

-continued

```
        435                 440                 445

Arg Cys Asn His Leu Lys Arg Ser Glu Lys Glu Ser Pro Leu Phe Leu
    450                 455                 460

Leu Phe Leu Asp Ala Thr Trp Gln Leu Leu Glu Gln Tyr Pro Ala Ala
465                 470                 475                 480

Phe Glu Phe Ser Glu Thr Tyr Leu Ala Val Leu Tyr Asp Ser Thr Arg
                485                 490                 495

Ile Ser Leu Phe Gly Thr Phe Leu Phe Asn Ser Pro His Gln Arg Val
            500                 505                 510

Lys Gln Ser Thr Glu Phe Ala Ile Ser Lys Asn Ile Gln Leu Gly Asp
        515                 520                 525

Glu Lys Gly Leu Lys Phe Pro Ser Val Trp Asp Trp Ser Leu Gln Phe
    530                 535                 540

Thr Ala Lys Asp Arg Thr Leu Phe His Asn Pro Phe Tyr Ile Gly Lys
545                 550                 555                 560

Ser Thr Pro Cys Ile Gln Asn Gly Ser Val Lys Ser Phe Lys Arg Thr
                565                 570                 575

Lys Lys Ser Tyr Ser Ser Thr Leu Arg Gly Met Pro Ser Ala Leu Lys
            580                 585                 590

Asn Gly Ile Ile Ser Asp Gln Glu Leu Leu Pro Arg Arg Asn Ser Leu
        595                 600                 605

Ile Leu Lys Pro Lys Pro Asp Pro Ala Gln Gln Thr Asp Ser Gln Asn
    610                 615                 620

Ser Asp Thr Glu Gln Tyr Phe Arg Glu Trp Phe Ser Lys Pro Ala Asn
625                 630                 635                 640

Leu His Gly Val Ile Leu Pro Arg Val Ser Gly Thr His Ile Lys Leu
                645                 650                 655

Trp Lys Leu Cys Tyr Phe Arg Trp Val Pro Glu Ala Gln Ile Ser Leu
            660                 665                 670

Gly Gly Ser Ile Thr Ala Phe His Lys Leu Ser Leu Leu Ala Asp Glu
        675                 680                 685

Val Asp Val Leu Ser Arg Met Leu Arg Gln Gln Arg Ser Gly Pro Leu
    690                 695                 700

Glu Ala Cys Tyr Gly Glu Leu Gly Gln Ser Arg Met Tyr Phe Asn Ala
705                 710                 715                 720

Ser Gly Pro His His Thr Asp Thr Ser Gly Thr Pro Glu Phe Leu Ser
                725                 730                 735

Ser Ser Phe Pro Phe Ser Pro Val Gly Asn Leu Cys Arg Arg Ser Ile
            740                 745                 750

Leu Gly Thr Pro Leu Ser Lys Phe Leu Ser Gly Ala Lys Ile Trp Leu
        755                 760                 765

Ser Thr Glu Thr Leu Ala Asn Glu Asp
    770                 775
```

```
<210> SEQ ID NO 3
<211> LENGTH: 83450
<212> TYPE: DNA
<213> ORGANISM: Homo sapiens
<220> FEATURE:
<221> NAME/KEY: misc_feature
<222> LOCATION: (1)...(83450)
<223> OTHER INFORMATION: n = A,T,C or G

<400> SEQUENCE: 3

aaaaacagaa aaatgggtga agcaggacaa aacagtgaca ttagagccaa aagcaggggg     60
```

-continued

```
taggcaataa caccaaacat acagcgtagt caagggcatc agggtctgag aagaggttat     120
aaaactagtt ctacggactg aattgtgttc ctccaaaatg ctaatgttga aaccctaacc     180
cctggtatgg ctacatttgg agattttagg aggtaattaa agttaaataa ggtagtaaga     240
gtggggctct aatctgatag gattagcgtc cttacaagaa gagacatcaa gagatcccag     300
agagcatgtt atataccctc cccgcactgt gtgaggacat ggtgagatgg cagccatctg     360
caaatccggc agagagccct cacctgtctg cctgccacaa gttaggcaga tccctacctt     420
gccaacacct ggatcttgga cttcctatac tccagaattg tgagaaatta atgtctgctc     480
tttaagccat caacctgtgg tattttgtta tggcagcctg agcagactaa tacaaccaga     540
tatttgggaa atgccataaa atttagtgtt aagacaataa taaatgctgg aaatagagtt     600
tttccacttt tcagttgtat ggtcacatat tagaattgca gatcctaaga aaacctgtac     660
agaaaaaccc aaatcacaga gtcatttaag tgtaaagaaa aagccaatta ttgcttaaag     720
agtatttgta gaaaatatcc gttgaatata gaggaataac agcatattca taaaaatttt     780
ttaaaaagtg tgcacgacag tgattttaac acttctaatc caatggaact aacattttaa     840
agtacaatta tggccaggca cggtgcctca tgcccatagt cccggctact tgagaggcta     900
aggcacgtgg atcacttgag cccaggaggt ggaggcagca gtgagccctg atcatgccac     960
tgcacttcag cccaggtgat ggtgtgagac cctgactcta aaaaatacaa ttatggttac    1020
ggttcttggg cagagtggaa ttcaaacagg ttaacctgaa agatcagtag ggttctaaat    1080
ccaggataaa ttattttcag aaaaagaata actttttgaa tctttattta aattgttaaa    1140
tgttcctgtg agtaacactc atcagcgtga ttgtgactgg tatggctgca tggaagcttc    1200
cctgtggcat taatcataaa atgctggatt ggggtttgat tcttcaaggt ataagaagga    1260
cctagtctca agtaatagat tcaccaaaat gtaacaccac tagccccctc ccaccaaaat    1320
ctgctccagt cagaattacc gtaagagctc agaagtgacc tgtgcttggc ggcaccggcc    1380
cactttccca gtgccggttc ctcgcatcct gggcgcagac ggggtgaccg cctgacccct    1440
ggacccgagt cacctttccc tgccctgagc tcctccttga gagcttcaaa acaatgctcg    1500
cccaggccgg agggcgaagt cggcccatgt gtaagtcaag ggaactgtcc caggactgca    1560
gcccggccag aagacgcccc gcgccgccgt cccaggcagc caccgctgcc gccatggccc    1620
ccgcaggccg ccgtaggccc ccgcgggccg cctgacccct gcgggccgcc gtagaaggac    1680
cctccagagg ccgcgctctt gagatggccg tcgggctccg ctccccgcgg ggccccggct    1740
gagggcccgc cagcgggcac ctggcgccac cgctgcgttc cggcactagc acgggacacg    1800
gtcagggagc ggcgggccgc ggccttgcgc gcgccgtctc tcggggcggg gcaccgggcc    1860
ccttccgggg atgggccccg gcgcccgcgt cggcctggct gtgcccggcc cctccccgct    1920
cgggcgggcg ctgcgccgta tccccgcccg tcagtccgcc cggctcggct ggccgcagaa    1980
agggcctggg cggccgcact gagagcttta cgcccggagg cgtcggcgct gccactggcc    2040
cgcgacggga acggggcgaa aaggcggcgg caccatgttc tccctcaagc cgcccaaacc    2100
caccttcagg tcctacctcc tgccaccgcc ccaggtaaac aacccctccc cgcgagcgcc    2160
cgactctcct ctgcgcttcc gtggagcctc caggccgacc cccgggaact ggaggacccc    2220
aggaggctgc gcgcgtctcc ctgcccacag cagcgcggct gcctgattcc cggcgccgcg    2280
aaatgcgcct tctcgggagc ccccactggc tcggcgaaaa cttgtaaaac tcttctgcag    2340
ccattctctg cccgaagttc tgtcgtccgt agttttgcgg agtgttgagg cccaggggag    2400
ccttgggagc tggggttttc tttagtttcc aacccatcga ccctccctcc tatgaccgcc    2460
```

-continued

```
agcatgattg cagcgcttgg ggtcactggt cgaggcggtt acccgtctgt cataaatgtg    2520

aacacctgga agcgacactg gcagtttaaa cattttttat tattaggctt ccaagtcgat    2580

aatgagcaga tcttaaaaac agctcagtta atatgcgaaa gaatttaaat gggggggctgt   2640

gtgtctttcg catgtgtcat cacttagaaa acaacatttg ctgtagcatt ttacggaggg    2700

tgggggatt gagattttga tttattttgc taatgtattt cagactgacg ataagatcaa    2760

ttcgaaccg aagattaaaa aactggagcc agtccttttg ccaggtaaac attagttagg    2820

attctaacag atactttagc aacgtatttt ggtttaagat tattctgccg actagtatca    2880

tgtggttaac ttcccttctc tcattaaact ttctccagtt aaaagtctag tgactgagag    2940

gagaaaaagg aactgtcaag aatgtcatta cctcatttcc ttttttgtct cccgaatttc    3000

tttttgaaaa gatgtatatg tttaattgct tgggtagtaa aagtactctt tgctgacgtg    3060

tttgccactt attgcattaa tgattaatca ttttaatgca ttttgatagt ataaaaagac    3120

gcctttatta tgtgtgtgtc tctataccaa taacagagct tagtgaactt tgaattactt    3180

gcttggcaat tgttttttga agttgtcagc tgtatttgca aatttgcttg tttcagttta    3240

gaaccaggct tttcccagca gagacactta attgacattt ggggccagat aattcatagt    3300

tggacgggca ggctgtcctg tgtatagcaa caaagatggc ctccacccac tagatgccag    3360

tagtagtacc cttatccccc accacctagt tgcgacctag ttgccacacc aaaatgccac    3420

cagtcattgc caattttttt ttgtccccta cctctggggg acaaaaatct cacagttgag    3480

aatcactgct ttagaacaaa atttgctata ggtgacctta gagatggaag tagggattgg    3540

tggtagaaag gggtttgttt tagagcatac agaatattgg tatggtattt tgaattgtat    3600

aacaattgta taataattag gaaaagtcag ttgtttaatg cgattattag gggaagtagc    3660

cagatactta ggaaagcctg ttttaaacct gaaatcggcc gggcacggtg gctcatgcct    3720

gtaatcccag cactttggga ggccgaggcg ggtggatcac gtggtcaaga gaccgagacc    3780

atcctggcta acacggtgaa accccgtctc tactaaaaat acaaaaaaaa ttagccaggc    3840

atggtggcgg gcgcctgtag tcccagctac tcgggaggct gaggcaggag aatggcatga    3900

actcgggagg cggagcttgc agtgagccga gatcctgcca ctgcagtcca gcctgggcgg    3960

cagagtgaga caccgtctca aaaaaaaaaa aaaacctgaa atcaaatact agtttgtgtg    4020

gctactatca gcattgtaaa atctgactca ttacttaaag ccaaatcggt aaaataatta    4080

gaattttgta ggtaaaaatt gaacaaatgt ggaaacttta aaattttaaa tattatatag    4140

ggacaaaata ttaaaaacac caaactttgg ttccatatga aagtttaaaa agtgtttttt    4200

aaactttact atgggagtca taaatatttt cccttgattt tgttagtgct tttcactcaa    4260

cagtgtgtac taattaatca tttgtacttt tcctcagagt gaacagtaga attactaagt    4320

aacccttgct ccctgtgtgc tctgttttag tcttagtcac tctgagcatt taaaatgcag    4380

ggacgaggaa acagtactca tcttgaatga gtgcctatga gctattgaac tttgacttcg    4440

tttactctga acaggcctgg ttcttaggct ttgattcctc cactctgcat actatgattt    4500

cacactcaga acaacatgg tcttagctgt aaatgtcagt gcttgctttt taatttttta    4560

aaattttttt taaattttt tttttttttt tttgagacag agtctcactc ttacttgggc    4620

tggagtgcag tggcgtgatc tcggctcact gcaacctctg cctcccaggt tcaagcgatt    4680

ctcctgcctc tgtctcccaa gtagctggga ttacaggagc ccaccaccac acctggctaa    4740

tttttcgtat ttttagtaga aatggggttt ctccatgttg gccaggctgg tcttgaactc    4800
```

-continued

```
ctgccctcag gtgatccgcc cgccttggcc tcccaaagtg ctgggattac aggcgtgagc   4860
cactggcgcc tggccacttt tttaaaatta gcttttaaat ttaagatatg tgctaagaaa   4920
aggtgttact aagtatgcat aaacttgaag aactttctca ctgagggtta tcaattctat   4980
aaaatggcta aaagtcagag ttttctgggg aagttgtaaa ccaagtttct gactgtgctt   5040
ttcttgtccc agaaatggca gctaaattcc gtattatttt tagagaaatt ctaaaagagc   5100
tgtaacacta agtctgaacc ttttagttgc ccattaagga attctctgac ctgtgttaat   5160
ttttattgca ttggcggcca aatcatagct gaaatctgta catgcataca tgacggctct   5220
atcacccagc attctgtttg tacctgactt atccttaccc aacatttagc cggtcctgaa   5280
ttaggatgtc ttttgccccc ttcctctccc cttctgttct taccctctca ttctggcctt   5340
cctgcaccca tcctggctgt gttctgtctg gctgccctgt tgtggtctct gtttcctgct   5400
ttacctcgcc tgtcacatct ctcactgcta ccatttgctc tttgttggcc tgtagcctac   5460
tgctctaccc atgaaatctg gaagacaagt ggaaagttac cgaactattg gtgatctaaa   5520
gacctagact aggctagagc ttttactaag agggagtgaa taatatagtt cttgcctttg   5580
tgactatcag aatcaataga aaacctggcc acatcacnnn nnnnnnnnnn nnnnnnnnnn   5640
nnnnnnnnnn nnnnnnnnnn nnnnnnnnnn nnnnnnnnnn nnnnnnnnnn nnnnnnnnnn   5700
nnnnnnnnnn nnnnnnnnnn nnnnnnnnnn nnnnnnnnnn nnnnnnnnnn nnnnnnnnnn   5760
nnnnnnnnnn nnnnnnnnnn nnnnnnnnnn nnnnnnnnnn nnnnnnnnnn nnnnnnnnnn   5820
nnnnnnnnnn nnnnnnnnnn nnnnnnnnnn nnntgttggg ggtgggggat gagggaaggg   5880
agagcattag gacaaatacc taatgcgtgc ggggcttgaa attcccggcg tcatccctaa   5940
agacggggtt gatgggtgca gcaaaccagc atggcacgta tatacctatg taacaaacct   6000
gcacattctg cacatgtatc ccagaactta aaaaaaaaaa taaaaaaaga attaattgtt   6060
agagatatgg tattgcatgc tttgctttgg cataatgcct tgggtccaag ggtatcctac   6120
ttcagttgcc caaagtttga acttctaatt caataagcag atgaaaatta gaacacaaaa   6180
tgagttgttt atttgtgtgc tgtcaccatg tgcactgttg gaacttaagc ctaatttcaa   6240
aatgatcctc atcttttatt aagtaaagaa aacagaagaa aatgactagt aatttaattt   6300
agattgtggt ttatgttagt aattttcagc tttcctgata catgaaactc tgagatgggt   6360
attgtgccta cttcaacttt gtggtcttga tgtctcacaa agtgccagga atgtggtaga   6420
cactgagatg tttactgagg gactgaacga aaggacctct cagaccacct ggcttaaact   6480
gttaccttac ccaggcacac acacagacta actttcagat ttaggagtaa agggaagact   6540
gtgttatttt atgccagaca tttcaagaga tttatgtcgg agcctggaat tgaaatagag   6600
tactctgtca aagtagtcag cttttgtgta ggctttctct ttatcttcct ctcattatgt   6660
gaatttcatt ctttcagtga ttatattgta tatgtgtaaa atcactccaa tacttgaaaa   6720
ctgagtttga cttttaaagt gtgtgtgtgt atatatgttt gtgttccagt atatatttgt   6780
taagagcatg taatgccaga ctctgtcctg tttagctgct ggactggtgg atcggttcgg   6840
tgaggatgtg agtatctcct gggtgccagg tctgtcctgg atagcgagaa tgctggaggt   6900
gtcatgtgcc tgtatcgcag aaaggcgtgg ggtgagccct aagctgcctg ttgacaaggt   6960
agaagactgt gacctggatc actggtaccc agattccagc cagggcctgg tatcagattt   7020
ggatgaagtt tttaccagcc cttggtcaaa gtgagaaaat taagaaaagt gcagttttct   7080
ttaataaaga taaatttatt tgatttaaaa gattgtcttt tattctgaga ttatgttctt   7140
ctaacttact tggaatagat acttttttttg ttaaatgttg gtgataatag ctgtagcttt   7200
```

-continued

```
aaaaaagttt ttaagttaac aaaattaaaa agttaaaaac tctttattgg tcctttaaat   7260
tagttttgca ctatacctgg tttggaatct aaactagaac ctactagatg agattattat   7320
aatactatag atacaatttt gtgagcactc acacagagaa cattaattat tttgtctgcc   7380
taggagtact gccatttttt tgtttgtgtt ttgagacagg gtctcgctct gtcacccagt   7440
ttggactgta gtggtgtgat cacggcttac tgcagcttca acctcctggg ctcgagtgat   7500
cctcacagct cagcctccca agtagctagg actacagacg tgcgccacca cacctggcta   7560
atttttgtat tttttgtgga gatggggtcc aactatattg cccaggctgg tttcgaactc   7620
ctgggctcaa gcaattggct caccttggcc tcccaaagtg ttgggattat agccgtgagc   7680
caccacaccc agcccccttc caccatcctc tgaaaaatgc atcctccctc ttttgacaaa   7740
ttatcctttc ctgactaact ccacccaacc ttgggttcca gtgtggccag caaggttaat   7800
aacccaccct ggactgcaag catgaacaca ggtctgcctc tggatgttgt taggttggta   7860
ctaagggaag aggtcctctt tggtaatgct gcaagtggcc acagttccag aagaatctgt   7920
tgaaaagagt gaagaacccc aaggaagtgc actaatgtgt gttgaagtcc ctgggtttca   7980
ttgtccttgc aggccaggtg acacaaaagc cttgtattct tctttttgct aagctattac   8040
caggcatgtt tctgaacata ctttgaacga ggatccttaa ctaatatagc ttgcagatta   8100
atcatcataa cagtcttgtc agctaggata ccagtttatc tccatttgac agatgtgaaa   8160
actatagttt gctgaggtta agtaacttgc ccagtgtcac acagctagca aggcagagcc   8220
agagttctct gtccagctcc caggctgtgc cactaactgc taagtagcac ggcccacctg   8280
gctgcactgg tgacactagg gtacagattt atgctttgga actgttgggg agtagattgg   8340
atgtcagcct agagggagtt ctctagtgaa gtaaaaagag ctctgtcctt gtctttgccc   8400
ttttcacaac agtgacagat tttgacccag cgtgcagaag aactttcaga gaatttcagc   8460
tgccagaaaa tggaatgtct tagggaggta gtggacttcc tgttgctggc tgtgccgaag   8520
cacagtctgg tgaaatgcca gcagctttgt attgaggatg taagatttgc agtgagtggg   8580
gcttgatggc ctttgctctc ttctcacccc agggcatgct ctttttttaag ggagaagagt   8640
tgaaatgcca agactaacga taatgaattt gttctgcagg tattgagtgt gtgcttgatg   8700
cagtttggca gaagggtaaa atgctgagga gatgggatcc tgttcttaga cagtttcagt   8760
tcactggaga gatgcttcag tagaggagag aaaaagtagt aagagctcag aggaaggtca   8820
cctaagccag atttggagta gggcaggggt gtcaagaaag atctctggaa acaaatgctt   8880
gtgctctgaa tcttgagtgc ccgttgagcc tgggcccctg tgctgaggct gtgcgtcagc   8940
tcagttcttt cccctgttcg catctacagt gctcacagca ctttcattct tgagattaac   9000
tattagataa tgaatgcagt gattgtcaga gtcttttgta atcggatcag aaaagcatac   9060
aaccatgggc catctgggaa atgaaaatag ccattgttgt atagatgtct tgtttatttt   9120
ttacaagctc actggcccgt actgttcttg ttttctgtct caccatacgt cttatttcct   9180
cagttgggtt gttaattcct taaaggcaaa gactttatct ttcaagtgtt ttatgtaatt   9240
ccttttgta ggtaggcttc ataaatgatt gtagactgat ttttgtagta ttttaatttg   9300
tgaatgcatt gtttttgaaa gaccaaagga cttgtaacac accctcagaa cagtgaacag   9360
tgtaactgta ctatcttagc attagcttta taccttaccc gtagagcctt aggaatgttt   9420
ggagctgtcc attccttagg cttttgctgc agtaccttag gccagcattt tcttacccct   9480
ccaaactact cactatcgtt gtcaacaccg ttcatgaacc tccataaata aaatcctact   9540
```

-continued

```
taagcaggat aaaatccaaa ttctttaacc ttgtaatttg ctaacactgt acctcactga   9600
cttcatttct cagtatttcc caatattgat atttgcttca atcatgccgc ttccttggtc   9660
tcttccagat gccttattcc ttatttagga ccttgttact gttattatca cacattctct   9720
actatctcaa tgctcttctt ccttcaagat ttcattctac aatttttcct gagatcggca   9780
ctataccctt cctcctgccc catcctatcc tgagtgctac tcactggact tggtacttgc   9840
ttttttacat tgtgtgttag taccagcatt aaagatttgt gtttatcttc cacatagttt   9900
caatttcctg tgataacttt tgagccactt taattcctga atttacctaa agctagggtg   9960
accagcttgt cccagtttgc ttgagactgt cctggtttta gtgctaaaaa taccacatcc  10020
cagggaaacc cctctgtccc agacaaactg gggcagtcac cctactgtta aaagcccaag  10080
ttaagttatg cttttggcct ctacacatcc cacaggttaa ttagccacgt gtgccgtgag  10140
actttgcctt aaactgtgtt ccaacctaaa atgtatggga aacattattt ctgtccatca  10200
aacgtgatga atttctaaat gtataaggtg ttaggaaaga taatacaaca tggttttgag  10260
gtcctcaggg agttaaaaac tttcctagcc atatcatttg gaggtttatt aactgtaatt  10320
gcatttccct tcttatttat atttacagat gaaagggtct tgagaaaata aacttggatt  10380
tcttgatttc ttcccaggtg ttagtagaaa cctttggctc atcatcctct aatttagaag  10440
gtttttgctt accgcacact gaagctaatt tcctgctttt tctggcttca tgaggcttcc  10500
ttgtggcatc ctgggaagtg cttggtgctg taaatggtcc caccgtggct gatggcatag  10560
cacagagctg ggagagagga gtctggtggg ttctcacaag caggccagcc agccgtctct  10620
agcacaccac ccttttactg cataaaaagc acaggcgtat agtctccctg aaaacttcag  10680
atcctctaga gctttgaagc ttttattcgg agtttctct tcaaggtcac ttaatttaac  10740
atgtgaacaa gagcagtctc agtaccttct ttttatatat cctatctggg aagaggccac  10800
tttgtgtctt ctttttcttc cctgtgtata agctagtttt ctggcccaca gtgtttcagt  10860
gcatggcagg agcttatgac agctcctctt cagcattcct ttttttttaaa attatgaaca  10920
aatgacttac gtgagcagac agctgtgcta catgatccaa atattttaaa gactggttct  10980
gcatgaacaa aatttagcat tatcaaataa aactcatgtc actaactcga cacttaatta  11040
ttgtaatagg aagacccaat tgtagcatat cctcagaagt gcccttcttt tctttcttct  11100
tcccctgtat ccctctgtac ttctgttctt tgctctcttc caagggctca tttccattct  11160
gtaagaaaag gctgtgtggc gcttaaaaga ccctggccca gagagtcctt ctttcacttt  11220
ttttttcttt tttcttttttt ttggctgttg ttaatgttgt gtctcttgtt tattttcttc  11280
tttagtagtt ttattttgga atgaatttga atttgtaaga gttgtacaaa agaggataga  11340
gttaatgtga actcttcagc cagcttccgc taatgttaat agcttatgta accttggtga  11400
atttagctca actgagaaac caacaatact attagctaaa ctgcaggttt tattcgtatt  11460
tccctagttt ttccacaaat gttctttacc tgtttcaggt tcacatccag gatactacat  11520
agcatttagt tgtcgtgtct ccttattctc aatgtctcag tctgtgacag ctttttcatc  11580
tcatctttca agaccttgac gtgttttttt ctattgaatt tgattttctt ttttttcttt  11640
ttcttttctt ttttttttg agatggagtc ttgttctgtc acccaggctg gagtgcagtg  11700
gcgtgatctc cgctcaccgc aacctccagc tcccgagttt gagcgattct cctgcctcag  11760
cctgttgagt agctgggagt acaggtgcgc accaccaggc ccagctaatt ttttgtgttt  11820
ttagtagaga cggggtttta ccatgttggc caggctggtt tcgaactcct gacctcaagt  11880
gatctgcctg cctcagcctc ccaaagtgct aagattacag gcatgagaat gagattttta  11940
```

-continued

```
ttttgcctca aataatacat attaaagctc tttaaacata gaaatatact actacaaaag  12000
gaaaaatttt ataattacta gatttctgtt ctaacaaacc accccctaga aacgtcatca  12060
aattgactta aaaatgtaga cgtaatttca gacttagaga aaagttgcaa ataacagaag  12120
aatctgtgga taccctttcc ttagattccc caataaaacc ttgacgcttt ggaagattat  12180
tattcaggta gtgtcttgta gtatgcctct tggtttggat ttgtccgatg ttttcttttg  12240
attaagcaga ggttatggat tttgggaaag acccacagag gtggtatcct ttgcccttgt  12300
gtcatgtgag caggcacaag acatcaacat gattggttat tggtgaggtt aacctcgatc  12360
acttcaggtt aaagtgatat ctgtcaggtt tctcctctag aaagtgactg tttttccttt  12420
tctgtactgt ttgttagaaa caaatcacta agtgcagccc acattcaagg gattgggaat  12480
taagctccac ttcctggaga gaggagaatc acgaatttat gggcatacct taaaactacc  12540
acagtaatta gtcaatactt ttgggaagat agctttgtgc ttatacaaat aacctgtttc  12600
tccttaaagt ttggctctct gaatttagca ttcatcaatg catgttgcac acagcagtca  12660
ttcagtctat gacattgagt ccatgatagt ttcttgatct ttactgtaat gttctaatca  12720
tgattttgtt tccttattcc tcctacattt attaattgga attcttctgt gaggaagatt  12780
tgtctcttct ccgccattta tttatttatt attcagtcat ctgttgacaa cagtatggat  12840
tcacagatac tttttaattt actttctaat ccggcatttt tgttatttct tttgttgctc  12900
agattgttcc agctttggcc attgagagtt atttcatctt ggctcttgta tcctttggaa  12960
atgccgtccc cccgcttttc ttcacccccca cttccatatt ttctggtatt ctggcattac  13020
cagaggctac agactcatct tctgtttccc ctgccccagc cttggaatca gccatttctc  13080
taaagagccc tagttctttt tattggaaaa tggtatttta aaagcaagag ctgggtactg  13140
agtgtgtatg ttgttgctgg agcgtcactg cttttagcac tttcagaggg cagagctaga  13200
aaacatacac acatgtacca acccaggtgt acacacatct gttactgcat gtctatttgt  13260
atatttatta aggcaagcat aagttcattc tgctatctca aactcttaat ctagcccctc  13320
ggggttcatt tccaaattct tgcttttgct ttttgttgat ggagtatggg cagtacagca  13380
gttaaacctg gtttccatat ttactttctg ctgagtgctg tagctcattg gtgagaaagg  13440
gatcttttga cttgacttgc atggacacat tctagtagga aggttgtctg tcctcatcac  13500
tcctgtgagt ggtcctctag agctctttga aatggctaca acattgcaga tcaaaaacac  13560
ctgcttttca ggtgcttcac ttctcacctt tcagatggga catgcccagt tgtgtcttct  13620
aaaccttgtt tcagataatt ttaagagttg tcgcttcagt aactatctct aacacaggga  13680
tcagcaaacc ttttctgtga agtgcagtaa atattttagg ctttgcggac cataaggtat  13740
ttgtttcaag tactcagctc tgtctttgtc ctgtgaaagc agccatagat ggcacatgaa  13800
caaatgagta tggctatgtc ttactaaaat ttcatttaca aaaacaaggt tttgtatttg  13860
gcccgtgggc catggtttac catccgttgg acccattaag tatattctcc tcctcttctt  13920
tgtctcattc tcactgcgtt cataggcttg atacgttaac attcgtgcat cagtaaaaga  13980
atctggcttc tagagaagaa gggctgtcca tgggcgtttg actcctaaat acagtttgtt  14040
tatggtacta gtgtggccac aaggctctgc cacacaagct ctgtctcttc cttcctgtta  14100
ttacttctgc ttcccttctc aggaacctga aatcatatgg tagtttgttt gtttaagtga  14160
tttttttttt tgagatggag tctagctctg ttgcccagtc tggagtgcac tgcaacctcc  14220
acctcctggg ttcaagcagt tctcctgcct cagcctccca agtagctggg gctacaggtg  14280
```

-continued

```
cgcaccacca cgcctggcgc accaccacgc ctggctaaat tttttttttt tttaatagag  14340
atgggtttca ccatgttggc tcaggtggtc tcaaactgac ttcaggtgat ccacccgcct  14400
cagccaaagt gttgggatta tagatgtgag ccaccacgcc cagcctttaa gtgaattttt  14460
atttgagtat aacatgcata acaagtttgt gtggatcata agtcttagaa gtggatgaat  14520
ttttgtagca aggtttgaag agtctgtttt tagatgagtt tgctaaggtg gcacagtatg  14580
tgatgattcc gtgtaaagaa gtcattgtta cagggctgtg tcctctatct gaactggcat  14640
ggttagttta gttgtttaaa ttgagggcct gcttacaatt catatctaag atttactgga  14700
gaggagaaag ggttgagtat tcagtggccc agaatctgat atgggaattg gtaaggttta  14760
tgttcaagga gccaaagaag atttaaattt tatgtatttg aattactcag tgcgtctata  14820
tatatatata tttggtcatc ttaaattttt tttctcgtta gaattcagtt aaggccaata  14880
tttgaacttt aataagtttt ggtacttgct acactgcagt acatttaatt gtatgtaatt  14940
atagggaaag actatgggaa ttgaagtcag aacacttggt tataagtgcg aagtccacta  15000
cttcttttta agatcttagg aaagtgattt aacctctttg ggtgcaaatc ctttatctgt  15060
gtattaagga aaccatctgc cttcctcacc ttacaggttg ttgaaagaat cagacaggac  15120
agatgtccta tttatagctc tttaatgcat atgtaggcaa gcagtggcag ttctgtgact  15180
cttctctaac ttacatatca tttacccaaa cagcccttat cttccagcca gcttggctgc  15240
ttagccatat tgaattacta gtttctctta tctagaacaa cttctgccca actcatggtg  15300
gacagaacca agtgtcatga agtgatttta ttcattcttg cattcagcac tcttttcaca  15360
ggcacctacc ctgtgccaga cactgttcta ggcactaaca tttcagcagt gaataaagtc  15420
agtccatctt ctaccctcat ggagcatata atcctgaggg taatgcaggc attaatttaa  15480
aaatatataa atataattgt agctatcatg agtgctggaa atacaatgct tcgatatgtg  15540
aatgtaaact agataggaag atttttttaa agaggcattc cctagacagt ggttggacta  15600
aggtagaaga aaagaatatt ccatgaaatg ggaagaagca tggtcccatg agggattaat  15660
aggccaccac tgtgggcaga gcagtgaggg tgaggaaggc tggtagctgg ctgggtatgc  15720
agggctccca gccatgagag ggaggcttgt cttcaaagtg gaagttaact caagctgttg  15780
gcactgtgaa tttgacatga gcagatttta ggtaaatgtt aaggggcagt tactaaaact  15840
agccttgtac atttttaaga acttcgaata aaagttattg cagctcaaat ttgttataac  15900
ctatttgtta aagagaggat tgttttgaga ctatagttcc attcttcatg aattggtagg  15960
agtttggagt ttgtcagcaa acattctatc gggctaaagg tttttataat gaaagaaata  16020
ggcaaagtgg atcagtacac tcacttttct accattgacc ctggagacag atggcttaaa  16080
atgttctgcg tctagttgac ttttagatct tgaaattaag gtttaatgat gaccaagctt  16140
taaataaatt gtagaaaagt attctttcaa aagtacatta taacttttat attggtttct  16200
tatatttatt tcttttaatc ttttctttta actcaaacta cgttttaagg ttttgttgcc  16260
tactaagtta taatctgagt gcagaaggaa acttgatttg gctttatgga atacatttta  16320
cattcagtga agctgagctc tgtttctcat tccttacaaa aggaatcaaa ggcattggtt  16380
tgagagatca agtcatgtgt taataaaaca caaatattcc atcaagtaat actctgaagg  16440
agcaggtgta gtttatttct tctccagaaa gtcttccagc agataaataa tgagaggtag  16500
tatggcatag gaaaaaagta cactgaagtc agcctttctg gttcaaccag ctcagacccc  16560
tgagctattt ttgcctcagt tttacgcctt ggagaacaat gccttgtcat tactattcac  16620
tttatgacca tacagtgcct ggcacctggt gggcaattgg tgaatgtttt cactatcctc  16680
```

-continued atccttgccc tcatgaaaca ctccttctag gtcccacaaa gaccgttggt attttatgac 16740
aaagtacctt acaaatattt ttcttttttt aaaggagaaa ttgtcgtaaa tgaagtcaat 16800
tttgtgagaa aatgcattgc aacagacaca agccagtacg atttgtgggg aaagctgata 16860
tgcagtaact tcaaaatctc ctttattaca gatgacccaa tgccattaca ggtgtgtttt 16920
attagtacac tgtttcattc tatcaggctt tcaactctaa gtggtacata ttattatata 16980
aaacataggt atggaaaagt tatagtagaa gtattaggta atgcaatgtt tgggataaat 17040
tatattaaga tttaaagtaa agtttaagaa gaatgttgga acttgctaga ggagtattag 17100
tgagaggatt gtaagtcacc ttgctttatt tatcctctgt gatcgttcat tatatgtcct 17160
tttcattaag gaagttattc cctctgttgc agatctttta acctgcttat aaaaatgaca 17220
taaagagaaa aggttgtttg ctaaatgatt ttataaatgc cacacatttt agtgatttca 17280
taggtttttt tgttgttggg tttttgattt ttttgttttg agcctggatc tcgctctgtc 17340
ttgtctccca ggctggagtg cagtggcatg atgtcggctc actgcaacct ctgtctgctt 17400
cctgggctca agctatcctg ccacctcagc ctcctgagta gctgggacta caggtgcatg 17460
ccaccactcc cggctaactg ttgtattttt ttgtagagat ggggttttgt tatgatgccc 17520
ggattggtct tgaacttctg agcccaagca atctgcctgc ctccccctcc caaagtgcca 17580
gagtacaggc cactgcaccc agctaccttt tttttttttt tttaaactaa ttagagttat 17640
tttcctaaaa agttaaattc taatttctag gaagagtgaa gaatagtatc gatttaaaaa 17700
ttttcagtag ccctcttgct attttatgtt cttactggaa agtaatagtt ccatgtaatt 17760
ttggttttta gaagttcagg cattcatttg attaacttaa aaaccctgga cttttctgtc 17820
agccattttg tattttgttt tataaagtat tatacacact taccccctaga tctttcttta 17880 tagtaattgt tctttaatga aatattggta tatgaactgt aaacttttaa atttaaggat 17940
ctaatagttt agtgtaagta tatttcatgt agtcactcac taatttacca taattattat 18000
actgtacaaa tatttattgt actgtatatt tgtgtgttca ttacagtctt atgtaggtat 18060
atttagacta aatttaaggc acttaaagat acccactgtg tagggacagt agcttatttg 18120
gatataggct tgtgtgtttc tctttgtttt tagcttcata atgatcattg gccccagact 18180
tcactgtaaa tgagaagcag atacctggaa cagcttaaat ccagtaccac tattaggaaa 18240
aagtaaacca gtgccctact gacagcagat tgatagtgtt aactacgtcc ttagtttgaa 18300
catgcaaaac cttttctaat ggtttttatt tctagtagac tttgtgcttt aaaaagatag 18360
ttattttgca ctttaaaatc ttcagtgtga aaatcaaaca tgattttacc cacttaaaat 18420
ctgatgacct aagagccctt ttttctttaa tatgttgtgg ccagcttatc cagatctaga 18480
catgcaaatg cttgctggta aggtgattga tgatattccc tatcttaggt attataataa 18540
gattgttgtg tacattttaa cctaatttct atctgtcaac attggaatgg ccctagctac 18600
ctagacaaaa gctttttgtg ctttttagag ataactgtca cagtttatca tcacagttta 18660
aggcttatac taccattgtg agattattgg gaaaagaatt aatatgaaca taatttttta 18720
ttccagaaat tccattacag aaaccttctt cttggtgaac acgatgtccc tttaacatgt 18780
attgaacaaa ttgtcacagg tacgtagtat tccgtacata ctctaaaagt caattccact 18840
ctggaagtat tatttgaaaa gtcatacctc tcaaaatact tggattggcg ttttatttct 18900
gtaagtttac ttttgccgtt tttttgagtc ccgggaacat aaagagggat atgttaataa 18960
attattttaa aaggaagata taaaatgtat aacttttcat agtttctagg ttttttgtcc 19020

-continued

```
tctttttaat taaaattaat cattaaatgt atctagatgg tggttttatg caaataatca  19080
tttaaaatat cttccaaagc aaagttaaaa ccaaccccca agttctagga attacaagta  19140
tgaaacattc tagacaagca gagctcaaat gttgggtgac cttccaatta ttttcactaa  19200
gaatttgtat taaagggtga gtaacaaata actgttacgc attttatttt ctctattttt  19260
ttttcttttt tagtaaacga ccacaagagg aagcagaaag tcctaggccc caaccagaaa  19320
ctgaaattta atccaacaga gttaattatt tattgtaaag atttcagaat tgtcagattt  19380
cgctttgatg aatcaggtcc cgaaagtgct aaaaaggtaa tactgttaag gtttatcaag  19440
ttctgggttc tgtactgtgt ttactgattt caattccgta tggcagtttt catttctcaa  19500
ttgctcagat gtttttagg ggaagttatc agacatcttc ttaagtaaag tcaaagccaa  19560
gaatattaat agaactattt tcttggattg gtttatggct gttttaaagt gttctatata  19620
actttttatc agcttctcaa atattaaaga ctcttacgtg gaaattagca tttttttaca  19680
taaagatcat tacttgtcag tttcttggtt aaaaggttga aaagttggtg atatactgta  19740
attaaggttt ggttaggctt ttaattcagt actgcagaac tttaccaaca aactgtaagc  19800
tagacttatg ttacataaga tttaggtaaa tatataatta cgggaaaggc ctagtaatta  19860
ttagtggttt aaagaaatat tatgaattga gtgacactca acaggggcaa cacaaagcta  19920
gtaacttttt aactgcctta tttttccacg gccttccaga taatgactta ttaccctact  19980
tgtaagagtc aagggcatgt tttccatgtt ttgctttgcc agaggagtga agctggtaga  20040
cctaatatgg cccccgttcc agtctgtgct gcagcaaatg cagagtcaca gactttccag  20100
taggaagctt gcgcgtgtgt atgggaatag ggcaacagta tcttagtata ataggacgtg  20160
gctttctctc agaatggagg cagtctttgc accaccaagc aatgagtgcc tttgttttcc  20220
atggttagtc aactgactgc agtaaatctt ctgttgatac caaaacaagg ctggcaaaaa  20280
tactgtaagg cagctgtctt catatacttt ggtgaagagg tggtagattt gtttttagat  20340
tgagaaccaa cagtttcttc acaggaaggc aagcaggaga tgaatatatg aaaatacatc  20400
tgaaaatatg tgactgtcta gcagagtaga gtggttgtag gctcctctat gggtaaaagt  20460
tttcaaatgg tctgtataac catctctcag caagctgcat tattgaaaat tcaactagat  20520
aactcttaaa gcctctttca cctgttcgat tgtgctgttt gtgattttgg cattttacta  20580
atttaaagtg cctattatat agaaggactt tagaattcat gatgtattag actgtacata  20640
aaatatttca gacaggttaa ttcctcaagc ttatttatat ttgtaattta attgatcaaa  20700
gcatcaaaga cctgcttatg aaaaccttaa gatgtgtagc atctcaagat tagggacatc  20760
acagaacttg ctagattgag ttaggacagc atattcctaa ggaagaaatt gatgcaattg  20820
accggatctc tttcggaaag ttcaattctc cctcttttac tgtatttttc agtttacact  20880
attttaatga gtggaaataa taattatttg gcctagttct tgaaccatct gtagtacttg  20940
ttggtcattt ttcatgttga ggcagtgtgc taaattttgc aagtagaaag aagggtaaga  21000
tgcagtttct tgccctagag aacttaaatc tagtgaagaa gataaagcat gaacaaatga  21060
aaagtaatgg tacaaagtgg cagcataaaa tcaactacac aaatagttga tttccagatg  21120
aacagagcat aataagtgct gtggaaattc agaatatccc ctatgtgttg tgctgctggt  21180
tcatgaagag ggccttacta aaccgtctgc acaaaacaag ccagtccctc atatgccctt  21240
tcctaagacc aagtttcaga caaaaatctt ttccccagta tcctaaaata taaaaagcat  21300
gtgagtctct gtcttttgta tagccacggg ggttgcaggg caggggaggg tgcaggaaaa  21360
aaaaatagat gcaatgagaa tataaatagt ttttttggga tttacgcatt tcaaacaggg  21420
```

-continued

```
ttaagttgta tatggctacc aaagcttgac ggctttgtga gttaaaaaca aaaattatgg  21480
catattcttt tatttcaagt gaaaagtttt catctaaaat tcggtagcag ttaggaaatt  21540
atggctcatt tttacctcct ggaagcttgg aatactgttt tctctggaaa atgctttgct  21600
attttatcag ttgctttaaa atgatgaaat gcatgtttgg agttctctgg tgggtaaacc  21660
gttgattcat tttgaaatac ctaagccatt tatgtttttg ttttgaaaaa tgaaattcaa  21720
gaatactaaa ttggttcaca ttttgttaaa tgttctgaac ccttctggtt gtcttgttgg  21780
tgttgtttca attgtattat gacaaaatta gattgctttg ggcacttgta ctcattaata  21840
ttcatcctca ttatcctcga gctgtcacag gaaaatagtg atatttggga aaggtctgta  21900
taaagaaaga aggaatttga tggtgcagaa ttggacatct aacctcatag caacttagaa  21960
ccaccatttt cttttgcaga acctttgctc aaaactgaag ggcaaaataa taaaggttgt  22020
ttttaatgat ttatctatat atctgtctgt gtagataaag ataaatatat agatacacat  22080
gagtgacaag tgaaatacat gccttttgtc tccactttgt tctctgatta gtgggttgtg  22140
aatcacttct tcaggaatac tttatagaag tgaattccat tcatctgatt aaggaacaag  22200
ttggcctttt catgaactgt catttttgac ttgaatctgg tactgttttt tggtggcttt  22260
caggccacag aaataaacca cttttgtttg caaatgagat agaacttaat gaggtttgag  22320
tgtttcctgg atttgagttt cttcagtact gcaccccagg tgatcttagg aaagaaacca  22380
tccactgtgg gtacttctgg cttctgtcca gagaagatta tcagctttgg tccaaaaatt  22440
gatttaaaag tagtttactt ctttttctcc aataaaatat ttgccataat ttaatgtctt  22500
taataccaac attttcttca tttcctgtgg tagccaggac aaatgaagta tttcagatct  22560
ttcaaaaact cttaggatga aaggtaggaa tttggactta ggtttttaaa atagtgtgta  22620
tgtaaaagtg caaagaatgg ggccctggct ttctcttctc ggagtgttcc acagtaacaa  22680
catgaagaca atccaggtac acaagtttgt atgtgcctta gtctgtgtgt ccaaagaggc  22740
ctcttactta ggtcatatga acataagtta tacacttgaa attcactact gaaaaacaat  22800
gtatttagtt cgagttctgc caccccaaaa aaatcaacga gtaattcaac tgacttgcag  22860
ttttacaata tttttataga cttctttcag cgtagatgct tttggacata ctcatttgtt  22920
tcctaacctg atgtgatatt gtgctatttt taaggggctt ttaaaaaata cgctgtgttg  22980
ggttttgcct tgaaaatagg ctttatttct tttttgcctc atggccacaa aaaaaggatg  23040
tccatgatca atgatctgtg aatttctttt ctgtaaacag aaagagcatg taactgcttt  23100
ctaattgttt tggagaatgt gatagacatt agtattatta ttattggctt ggagcatttt  23160
ccttaatatg ttggtaacta cttttgtcag tgaatattag tgtagccact gttggacaca  23220
gagcaccgtc agaaagctac tgaagtggtg ctgcaaagtg cagacatctt cagatcttta  23280
ctcaagtctg tgcagagagg tctttcttgg tctccttctc tactttttag cctgtctccc  23340
tcttctcact gtaacacttc atattcccct tccctgctct attatttttc tcttttagca  23400
ttcatagtta tctaactttc tgtatttttt ctctttatct tgtttagtgt ctgtcttccc  23460
actagaatgt aagcttcatg aggacaggga ttagtgtctg ttttgttcac tgcatctcta  23520
gggcttacaa cattgtaggt actcagtaaa tatttgttaa atcaatgtga aatgtgtcat  23580
ttatccttaa ggaattgacc ttcatggtag aagtgtaaca gaaccaccta tatcctactt  23640
ttcatccaca tcataactat tatgtgaata ccttggaagt aaagcaaaat aagcacttaa  23700
ctaaagagac gctttatatt gaaactgttg ttctgggttt ctggaattag tactctgaaa  23760
```

-continued

```
ttggctccct ctaggaaggc ttgtgaagag agtagtgttg aacagacatg acagtttcca  23820
agaaagcata gttggctaag aggagtagga ttttccaagc aaagagtgtg acagtggaga  23880
tggctggggc taagtcaggc agaatgtgtt caaacctgtt tttctctgac ctgagattgc  23940
ggagggaata ttgggaaggt atagttacct ggtgaggaga gccagttttg tgaagaatca  24000
agaatgagga gatttaattt gttatgcaga tgtctgggaa ccacagcaga ttatcaggag  24060
agcaaaattg ttagtcagaa ttacatcgtt agaaggtaat ccttaagttt tgtagatttc  24120
tagaatgtaa ggaagctctc agaggtgcca taaggtgagt atggcctaag gatgtggcta  24180
tggcagtgta gcaaaatgga caactatgaa aaatgtctag agaaaagtgc aacatagctt  24240
atcaacggtg cccaaacaaa taggaaggat gagaactttt tcaagctaca gatttcagta  24300
gttttgctgc tagaaatgct ttaaggaaaa ctgttaaaaa gattaggaat gggaatatag  24360
ataaccggct cctaaatttt gcaagtggga ccgtcataga aagctctcct ataggtattg  24420
agaaatcgag ataccacgta agtttcaaga agcagttttt tttttctttt tggtcaaaac  24480
taatgacaaa ttctgtcccc ttgtttgtat attttaactt agtgagacag gaaacattta  24540
ttctatagaa gacttttaaa atgtagttta aacaagttga cacatgctta ctggttaatg  24600
aaatgtgcat caacccactc caaacaccac taatttgaca tgaactaaca attaactttt  24660
cttactcact gtcaaaagta tatcattctg ccttaactta acgctttacc ttctaaataa  24720
aatttaatct tttaaataag tttttctgct atgttttcct tgcatatgtc ttaaatttct  24780
tctttcgtct ttgctcactg aagagcattt tctcccacat tctagtgact accagggttt  24840
gtaagcctag agcaccatcc ttcattctat ctagcagcag ttgagaataa taacagccat  24900
atttctatat atggagctcc tccaaaggcc tagcctgcat taagcttgtt aattcttacc  24960
acagcctagg tattactttt gttttacaag tgagcaaact gaggctagaa aagaggaaat  25020
gacttcacac atgttatgta gcaagtactt gacagagcta ggattcaagc cccctgatct  25080
gtttgattct aaagcccgca cgttttccac cacagggcac acagtcccaa accattttac  25140
ttaaacacag tttgtgtgtg tgtgtgtgtg tgtgtgtgtg tgtgtgtgtg tgtgtgttgt  25200
ttttttgatg tacctctttg agccacccat gcatttttgg agtttcttgc taattttaat  25260
tttttgtaat tatgtttctc tatttagatg tttaaatcca tgaggcgtaa actttaaagt  25320
ttcatgcctt atattaatcc tttatagtcc accaaaaatg aaactttttt cttccttttt  25380
tggagtggac atgtagtcac tgccttttttg gagaatgctt ctttagtttg aagctttctt  25440
tattggacta aaattacttt ccaattaaaa tttaactcag caaatactta ctgaatactt  25500
gccatgtgct agctaaagat aaacaatgtc ttgagggcat gaaagtgaat gagatacctg  25560
gccttaagga gctcttttat attctaggtc aacagaaaaa catgtaaata gtatctataa  25620
tcactgcccc aagatgatgc tcccagtgcc caaggcctta ttgtacattt catttaacta  25680
agtgtgttaa aatcaaattc taaatgtaga atttttccta ggtatgcctt gcaatagctc  25740
attattccca gccaacagac ctccagctac tctttgcatt tgaatatgtt gggaaaaaat  25800
accacaattc aggtaaatat gaaaatatta aatattgtga ctaattttac atgtgtaaat  25860
tttactctta tgtttaccgg aagcctccaa gtacatgagc tttaatgatt gtagaattac  25920
tagcttcata ccttagagaa gtaagcacta catgctaaaa gagccaatag tttgtcagat  25980
tatttcttga caagttacca ggaagaacct ttaatgctat gaatatgggc ttataagtta  26040
tgtcagatat ttaatctcca gtcactggct tgtattttat gatgaagaat atataaccca  26100
cccttttttaa ttgatagctt gagttaaagt aatcttatct tttaagaaaa ctggcagaaa  26160
```

-continued

```
actaaaagat atattaaaag cataatcttt tctggcaagg tgtgatttca tgcaaaagct  26220
aaagtgatta aaaacttttt gtggacttca ttaagattct cagaatactg agtttctatt  26280
tctgagtaat actgatgaaa ggaagatgag catttttcca aggacaagta tattactaga  26340
cagcttttgt gaaagtaaat agttttgtct atatatctga cagtcatgac atgaccaggg  26400
aagattccag atgatcatgc aannnnnnnn nnnnnnnnnn nnnnnnnnnn nnnnnnnnnn  26460
nnnnnnnnnn nnnnnnnnnn nnnnnnnnnn nnnnnnnnnn nnnnnnnnnn nnnnnnnnnn  26520
nnnnnnnnnn nnnnnnnnnn nnnnnnnnnn nnnnnnnnnn nnnnnnnnnn nnnnnnnnnn  26580
nnnnnnnnnn nnnnnnnnnn nnnnnnnnnn nnnnnnnnnn nnnnnnnnnn nnnnnnnnnn  26640
nnnnnnnnnn nnnnnnnnnn nnnnnnnnnn nnnnnnnnnn nnnnnnnnnn nnnnnnnnnn  26700
nnnnnnnnnn nnnnnnnnnn nnnnnnnnnn nnnnnnnnnn nnnnnnnnnn nnnnnnnnnn  26760
nnnnnnnnnn nnnnnnnnnn nnnnnnnnnn nnnnnnnnnn nnnnnnnnnn nnnnnnnnnn  26820
nnnnnnnnnn nnnnnnnnnn nnnnnnnnnn nnnnnnnnnn nnnnnnnnnn nnnnnnnnnn  26880
nnnnnnnnnn nnnnnnnnnn nnnnnnnnnn nnnnnnnnnn nnnnnnnnnn nnnnnnnnnn  26940
nnnnnnnnnn nnnnnnnnnn nnnnnnnnnn nnnnnnnnnn nnnnnnnnnn nnnnnnnnnn  27000
nnnnnnnnnn nnnnnnnnnn nnnnnnnnnn nnnnnnnnnn nnnnnnnnnn nnnnnnnnnn  27060
nnnnnnnnnn nnnnnnnnnn nnnnnnnnnn nnnnnnnnnn nnnnnnnnnn nnnnnnnnnn  27120
nnnnnnnnnn nnnnnnnnnn nnnnnnnnnn nnnnnnnnnn nnnnnnnnnn nnnnnnnnnn  27180
nnnnnnnnnn nnnnnnnnnn nnnnnnnnnn nnnnnnnnnn nnnnnnnnnn nnnnnnnnnn  27240
nnnnnnnnnn nnnnnnnnnn nnnnnnnnnn nnnnnnnnnn nnnnnnnnnn nnnnnnnnnn  27300
nnnnnnnnnn nnnnnnnnnn nnnnnnnnnn nnnnnnnnnn nnnnnnnnnn nnnnnnnnnn  27360
nnnnnnnnnn nnnnnnnnnn nnnnnnnnnn nnnnnnnnnn nnnnnnnnnn nnnnnnnnnn  27420
nnnnnnnnnn nnnnnnnnnn nnnnnnnnnn nnnnnnnnnn nnnnnnnnnn nnnnnnnnnn  27480
nnnnnnnnnn nnnnnnnnnn nnnnnnnnnn nnnnnnnnnn nnnnnnnnnn nnnnnnnnnn  27540
nnnnnnnnnn nnnnnnnnnn nnnnnnnnnn nnnnnnnnnn nnnnnnnnnn nnnnnnnnnn  27600
nnnnnnnnnn nnnnnnnnnn nnnnnnnnnn nnnnnnnnnn nnnnnnnnnn nnnnnnnnnn  27660
nnnnnnnnnn nnnnnnnnnn nnnnnnnnnn nnnnnnnnnn nnnnnnnnnn nnnnnnnnnn  27720
nnnnnnnnnn nnnnnnnnnn nnnnnnnnnn nnnnnnnnnn nnnnnnnnnn nnnnnnnnnn  27780
nnnnnnnnnn nnnnnnnnnn nnnnnnnnnn nnnnnnnnnn nnnnnnnnnn nnnnnnnnnn  27840
nnnnnnnnnn nnnnnnnnnn nnnnnnnnnn nnnnnnnnnn nnnnnnnnnn nnnnnnnnnn  27900
nnnnnnnnnn nnnnnnnnnn nnnnnnnnnn nnnnnnnnnn nnnnnnnnnn nnnnnnnnnn  27960
nnnnnnnnnn nnnnnnnnnn nnnnnnnnnn nnnnnnnnnn nnnnnnnnnn nnnnnnnnnn  28020
nnnnnnnnnn nnnnnnnnnn nnnnnnnnnn nnnnnnnnnn nnnnnnnnnn nnnnnnnnnn  28080
nnnnnnnnnn nnnnnnnnnn nnnnnnnnnn nnnnnnnnnn nnnnnnnnnn nnnnnnnnnn  28140
nnnnnnnnnn nnnnnnnnnn nnnnnnnnnn nnnnnnnnnn nnnnnnnnnn nnnnnnnnnn  28200
nnnnnnnnnn nnnnnnnnnn nnnnnnnnnn nnnnnnnnnn nnnnnnnnnn nnnnnnnnnn  28260
nnnnnnnnnn nnnnnnnnnn nnnnnnnnnn nnnnnnnnnn nnnnnnnnnn nnnnnnnnnn  28320
nnnnnnnnnn nnnnnnnnnn nnnnnnnnnn nnnnnnnnnn nnnnnnnnnn nnnnnnnnnn  28380
nnnnnnnnnn nnnnnnnnnn nnnnnnnnnn nnnnnnnnnn nnnnnnnnnn nnnnnnnnnn  28440
nnnnnnnnnn nnnnnnnnnn nnnnnnnnnn nnnnnnnnnn nnnnnnnnnn nnnnnnnnnn  28500
```

-continued nnnnnnnnnn nnnnnnnnnn nnnnnnnnnn nnnnnnnnnn nnnnnnnnnn nnnnnnnnnn 28560
nnnnnnnnnn nnnnnnnnnn nnnnnnnnnn nnnnnnnnnn nnnnnnnnnn nnnnnnnnnn 28620
nnnnnnnnnn nnnnnnnnnn nnnnnnnnnn nnnnnnnnnn nnnnnnnnnn nnnnnnnnnn 28680
nnnnnnnnnn nnnnnnnnnn nnnnnnnnnn nnnnnnnnnn nnnnnnnnnn nnnnnnnnnn 28740
nnnnnnnnnn nnnnnnnnnn nnnnnnnnnn nnnnnnnnnn nnnnnnnnnn nnnnnnnnnn 28800
nnnnnnnnnn nnnnnnnnnn nnnnnnnnnn nnnnnnnnnn nnnnnnnnnn nnnnnnnnnn 28860
nnnnnnnnnn nnnnnnnnnn nnnnnnnnnn nnnnnnnnnn nnnnnnnnnn nnnnnnnnnn 28920
nnnnnnnnnn nnnnnnnnnn nnnnnnnnnn nnnnnnnnnn nnnnnnnnnn nnnnnnnnnn 28980
nnnnnnnnnn nnnnnnnnnn nnnnnnnnnn nnnnnnnnnn nnnnnnnnnn nnnnnnnnnn 29040
nnnnnnnnnn nnnnnnnnnn nnnnnnnnnn nnnnnnnnnn nnnnnnnnnn nnnnnnnnnn 29100
nnnnnnnnnn nnnnnnnnnn nnnnnnnnnn nnnnnnnnnn nnnnnnnnnn nnnnnnnnnn 29160
nnnnnnnnnn nnnnnnnnnn nnnnnnnnnn nnnnnnnnnn nnnnnnnnnn nnnnnnnnnn 29220
nnnnnnnnnn nnnnnnnnnn nnnnnnnnnn nnnnnnnnnn nnnnnnnnnn nnnnnnnnnn 29280
nnnnnnnnnn nnnnnnnnnn nnnnnnnnnn nnnnnnnnnn nnnnnnnnnn nnnnnnnnnn 29340
nnnnnnnnnn nnnnnnnnnn nnnnnnnnnn nnnnnnnnnn nnnnnnnnnn nnnnnnnnnn 29400
nnnnnnnnnn nnnnnnnnnn nnnnnnnnnn nnnnnnnnnn nnnnnnnnnn nnnnnnnnnn 29460
nnnnnnnnnn nnnnnnnnnn nnnnnnnnnn nnnnnnnnnn nnnnnnnnnn nnnnnnnnnn 29520
nnnnnnnnnn nnnnnnnnnn nnnnnnnnnn nnnnnnnnnn nnnnnnnnnn nnnnnnnnnn 29580
nnnnnnnnnn nnnnnnnnnn nnnnnnnnnn nnnnnnnnnn nnnnnnnnnn nnnnnnnnnn 29640
nnnnnnnnnn nnnnnnnnnn nnnnnnnnnn nnnnnnnnnn nnnnnnnnnn nnnnnnnnnn 29700
nnnnnnnnnn nnnnnnnnnn nnnnnnnnnn nnnnnnnnnn nnnnnnnnnn nnnnnnnnnn 29760
nnnnnnnnnn nnnnnnnnnn nnnnnnnnnn nnnnnnnnnn nnnnnnnnnn nnnnnnnnnn 29820
nnnnnnnnnn nnnnnnnnnn nnnnnnnnnn nnnnnnnnnn nnnnnnnnnn nnnnnnnnnn 29880
nnnnnnnnnn nnnnnnnnnn nnnnnnnnnn nnnnnnnnnn nnnnnnnnnn nnnnnnnnnn 29940
nnnnnnnnnn nnnnnnnnnn nnnnnnnnnn nnnnnnnnnn nnnnnnnnnn nnnnnnnnnn 30000
nnnnnnnnnn nnnnnnnnnn nnnnnnnnnn nnnnnnnnnn nnnnnnnnnn nnnnnnnnnn 30060
nnnnnnnnnn nnnnnnnnnn nnnnnnnnnn nnnnnnnnnn nnnnnnnnnn nnnnnnnnnn 30120
nnnnnnnnnn nnnnnnnnnn nnnnnnnnnn nnnnnnnnnn nnnnnnnnnn nnnnnnnnnn 30180
nnnnnnnnnn nnnnnnnnnn nnnnnnnnnn nnnnnnnnnn nnnnnnnnnn nnnnnnnnnn 30240
nnnnnnnnnn nnnnnnnnnn nnnnnnnnnn nnnnnnnnnn nnnnnnnnnn nnnnnnnnnn 30300
nnnnnnnnnn nnnnnnnnnn nnnnnnnnnn nnnnnnnnnn nnnnnnnnnn nnnnnnnnnn 30360
nnnnnnnnnn nnnnnnnnnn nnnnnnnnnn nnnnnnnnnn nnnnnnnnnn nnnnnnnnnn 30420
nnnnnnnnnn nnnnnnnnnn nnnnnnnnnn nnnnnnnnnn nnnnnnnnnn nnnnnnnnnn 30480
nnnnnnnnnn nnnnnnnnnn nnnnnnnnnn nnnnnnnnnn nnnnnnnnnn nnnnnnnnnn 30540
nnnnnnnnnn nnnnnnnnnn nnnnnnnnnn nnnnnnnnnn nnnnncagtg atggaaagta 30600
gggcagccca ctagaagcca ctagccacat gtggctgtta agtacttgaa atgtggctag 30660
tgcaaactga tggactgaat ttttaatttt atttaatttt catttcagtt taaatttaaa 30720
tgggcttgtg tggctagaag ttacgttttt gggaaacata ctagagtcta ggccctattt 30780
gatttcccgc ctctcttcca ccacctgttg aatccctatg ctctagctgt atttagttac 30840
ttgatattat acagttatac catcttttta aagttcttct ctgtctagca tgcctacctc 30900

-continued

```
ctcctcacca gctacctggc aacttttgac ttgttcctta gaactctctt tagttgtggt  30960
caagtcatga agcttttcct gccccggcct ctctctgcag cgagagttag ggacttctc  31020
ttttgcatct tcattgcact cagacatctg gtactctgtg attatcacac ttattaatgc  31080
tctcaagata gagataaaat cttattcatc tttttgctct caggcattag cacatgggga  31140
gttctcagaa aatacctgtc ttataccagg aattaatgaa taatcagtag gaatgagcat  31200
gacatgttca tgggacgttg gagggtagtg catggctgca gaggagaatg ggaaatgaag  31260
gtcagataag ttacgtgagg gatctctaag gccaagagaa gccatttagg tttgatttgg  31320
ttggaaaatg agcttattga aagtttaagg caagggacta gcatcatgaa cacatctttt  31380
tagggaagtg tgtcttgtgg taagctgctg gctggtttaa atgcagcaga atattccatt  31440
ggggatgcca gctgggagac ttgccacagt tgcagcctgc agcagaaaga ccctgggcca  31500
gaatgggttg tgccatctgt caccagatat tgccaaggta gatctggctg actttgtggg  31560
acagcttgtt tctcaataat cactttgcag gcactcttga ggctgtgagc atgctcccag  31620
aagatagcat tacttctctc tcagagcagg ctcctttcta aggaaatgca agtctaggcc  31680
tgccctgctg taatcttcat gtggaaacag cactctagca aagaacaagg aacctgatga  31740
gcttttcaaa ggaaaatcga gtagatacag gaaaccaaga attttctaat gagcagatag  31800
aaaagagcag gtaggtgaga agttggtatt agaaaaatta aagatttgaa gggcttgagg  31860
acagagatga ttgttggatg tttcattttt ccaggcaaaa tatgtggagc aaataatcaa  31920
atgacatgga cttaccccac aattagggac ggagatgagg aagggttagg aatagtttct  31980
gttagaatgg tagggatgga agacaattga aaattaaaga gaaaataaat ggagaggaaa  32040
tctaggcagc agccattctt cattctgggg gaaggtggtc aggaaaagga aggaagaaaa  32100
atgtatagca tagtagctag agtggtccgg cgtgatcaaa gtgttttcaa tatcatgttg  32160
actgacctgt ttacgtttga aggcagagaa gatagagcca gtagaaggag agaaaaatca  32220
aagctgtttt acggagttgt gaaagagctg gataaggaca agactaaatg agttattttt  32280
aggccaggca tggtggctca tgcctgtaat cccagcactt tgggaggcca aggcaggtgg  32340
ggcacctgag gtcaggagtt caagagcagc ctggccaaca tggtgaaacc ctgtctctat  32400
taaaaataca aaaattagct ggacatggtg catggtggca ggtgcctgta atcccagcta  32460
ctcaagaggc tgaggcagga gaatagcttg aacccggggg gcggaggttg cagtcagccg  32520
agatcatgcc agtgcattcc agcctgggcg acagaacgag actccgtcaa aaaaaaaaaa  32580
aggagttatt tttaaatgga aagggcaaga cagttactcg gagagacttg gaaggtgaag  32640
caggttagag acagcacatc agagtatgca tgtgacagga ggctcagaga agagggaatg  32700
ctggggaaaa tgtgactgtt aaaattcata atgttgcttt ttcctacagc aaacaaaatt  32760
aatggaattc cctcaggaga tggaggagga ggaggaggag gaggtaatgg agctggtggt  32820
ggcagcagcc agaaaactcc actctttgaa acttactcgg attgggacag agaaatcaag  32880
aggacaggtg cttccgggtg gagagtttgt tctattaacg agggttacat gatatccact  32940
tggtaagtac aattttagca atgttatata tggctggaag tcacttccct atgaataatc  33000
atcaaactct gttgtcattg atgactttca agttgtggtt aatggaatat ttgtttttaa  33060
taatgtttta ataaatattt tattttaaag atcaaggctt attaatataa attacggtat  33120
cccttaaaag aagttgatag taattcctta ctgtcatcag tagtcagtgt ttattgcatt  33180
atatcttgta actggtgttt tacagttggt ttgttcatat caggatctaa agtcttcaca  33240
```

-continued

```
ttgaatttgc ttaatatgtc tcttaggcct tttaatctac aacagtctcc tcccacctct  33300
tttttaccta ctatttgttg acaaaccagg tcatttgttc cctagaattt tccacattgt  33360
agatattgct tgttttatcc ccagggtgtc ccgtaatgtg ttcctctgtc tctaatattt  33420
cctttaaaat gttagcaaca gaggcttaat cggattcagg ttcagtactt ttggcaagaa  33480
tgtttcatta ggtggttctg tgttctcctg tggagtcaca tcccatctca ggctggctgg  33540
ctgtgtctct ctcattgtaa tcctgacgac cagtgggctt agagggtgtc aacctgatcc  33600
acccagtaaa agttcccctc ttatatcatg gtttgagctc ccaaaaatag ttttgcactg  33660
ggagggagga tcattgctca gatcgttatt tcactaagga ttgctattgt tcaccttcta  33720
attctatcat ctttctgctt ttatcgaact tttctctcac cagctcttta gtgccctgta  33780
acacagttcg tacaagaaaa gcaatataaa tatctacatt ttctccttta cttaacattt  33840
ttccaaatag tgagctggtt ccctagggga tctttctaga agtgactagg aatttgtttt  33900
tttaatttgt ttaatgtcat ttagttatta tgaatttttt ggaatgcctt attttaaggt  33960
cattgaagtc ctcattagtt cacgcacata agcagctttt tagaaaaagg aagaaaagca  34020
ctactgtgtt attactggtt aatccagtac caggaacttc tagtacagtt ctagaaaggt  34080
gctttgcagc atgtagcttg tatgcttttg cttcccctgg aatttaagct tcaaggccag  34140
cacactctgg tatatgtgct gagaaacatg tgatggggct gccnnnnnnn nnnnnnnnnn  34200
nnnnnnnnnn nnnnnnnnnn nnnnnnnnnn nnnnnnnnnn nnnnnnnnnn nnnnnnnnnn  34260
nnnnnnnnnn nnnnnnnnnn nnnnnnnnnn nnnnnnnnnn nnnnnnnnnn nnnnnnnnnn  34320
nnnnnnnnnn nnnnnnnnnn nnnnnnnnnn nnnnnnnnnn nnnnnnnnnn nnnnnnnnnn  34380
nnnnnnnnnn nnnnnnnnnn nnnnnnnnnn nnnnnnnnnn nnnnnnnnnn nnnnnnnnnn  34440
nnnnnnnnnn nnnnnnnnnn nnnnnnnnnn nnnnnnnnnn nnnnnnnnnn nnnnnnnnnn  34500
nnnnnnnnnn nnnnnnnnnn nnnnnnnnnn nnnnnnnnnn nnnnnnnnnn nnnnnnnnnn  34560
nnnnnnnnnn nnnnnnnnnn nnnnnnnnnn nnnnnnnnnn nnnnnnnnnn nnnnnnnnnn  34620
nnnnnnnnnn nnnnnnnnnn nnnnnnnnnn nnnnnnnnnn nnnnnnnnnn nnnnnnnnnn  34680
nnnnnnnnnn nnnnnnnnnn nnnnnnnnnn nnnnnnnnnn nnnnnnnnnn nnnnnnnnnn  34740
nnnnnnnnnn nnnnnnnnnn nnnnnnnnnn nnnnnnnnnn nnnnnnnnnn nnnnnnnnnn  34800
nnnnnnnnnn nnnnnnnnnn nnnnnnnnnn nnnnnnnnnn nnnnnnnnnn nnnnnnnnnn  34860
nnnnnnnnnn nnnnnnnnnn nnnnnnnnnn nnnnnnnnnn nnnnnnnnnn nnnnnnnnnn  34920
nnnnnnnnnn nnnnnnnnnn nnnnnnnnnn nnnnnnnnnn nnnnnnnnnn nnnnnnnnnn  34980
nnnnnnnnnn nnnnnnnnnn nnnnnnnnnn nnnnnnnnnn nnnnnnnnnn nnnnnnnnnn  35040
tggtaaaacc ccgcctctac taaaaataca aaaatttagc caggtgtggt ggcgggtgcc  35100
tgtaatccca actactcggg agggtgaggc aggagaatcg cttgaacccg ggaggggggag  35160
gttgcagtga gccgagatgg tgccactgca ctccagcctg ggcgacagta tgagactccg  35220
tctcaaaaag aaaaagaagg aaatgatcta atttgttctg tgcactgcac gtgggggtgg  35280
cagtgaggtg aatggcagca ttctgcagta gtcaaagcca gatgggtggg agaagttggg  35340
tgctaagagg gaaacaaagt ttacctgtct tctccttgat ttcactctca gttttatgag  35400
aatacagaaa aatcatgcag agaaacctga tggaatagtc tctaaaacta aaaaataaga  35460
taagcaatgg ttctgtctta aaaaaaaaaa agtaaactcc atgaaggcag agaccttacc  35520
tgtctcattc ctctctctat cccctggtct atagtaaggg ttaaataaat atatgctgaa  35580
atgaatgagt aatgactaaa gtatttttgt ctttattagg atttgtaatg caataactaa  35640
```

-continued

```
aagtcaccca cagagaagtg atgtttacaa atcagatttg gataagccct tgcctaatat  35700
tcannnnnnn nnnnnnnnnn nnnnnnnnnn nnnnnnnnnn nnnnnnnnnn nnnnnnnnnn  35760
nnnnnnnnnn nnnnnnnnnn nnnnnnnnnn nnnnnnnnnn nncagctcaa atttgttata  35820
acctatttgt taaagagagg attgttttga gactatagtt ccattcttca tgaattggta  35880
ggagtttgga gtttgtcagc aaacattcta tcgggctaaa ggtttttata atgaaagaaa  35940
taggcaaagt ggatcagtac actcactttt ctaccattga ccctggagac agatggctta  36000
aaatgttctg cgtctagttg acttttagat cttgaaatta aggtttaatg atgaccaagc  36060
tttaaataaa ttgtagaaaa gtattctttc aaaagtacat tataactttt atattggttt  36120
cttatattta tttcttttaa tcttttcttt taacacaaac tacgttttaa ggttttgttg  36180
cctactaagt tataatctga gtgcagaagg aaacttgatt tggctttatg gaatacattt  36240
tacattcagt gaagctgagc tctgtttctc attccttaca aaaggaatca aaggcattgg  36300
tttgagagat caagtcatgt gttaataaaa cacaaatatt ccatcaagta atactctgaa  36360
ggagcaggtg tagtttattt cttctccaga aagtcttcca gcagataaat aatgagaggt  36420
agtatggcat aggaaaaaag tacactgaag tcagcctttc tggttcaacc agctcagacc  36480
cctgagctat ttttgcctca gttttacgcc ttggagaaca atgccttgtc attactattc  36540
actttatgac catacagtgc ctggcacctg gtgggcaatt ggtgaatgtt ttcactatcc  36600
tcatccttgc cctcatgaaa cactccttct aggtcccaca aagaccgttg gtattttatg  36660
acaaagtacc ttacaaatat ttttcttttt ttaaaggaga aattgtcgta aatgaagtca  36720
attttgtgag aaaatgcatt gcaacagaca caagccagta cgatttgtgg ggaaagctga  36780
tatgcagtaa cttcaaaatc tcctttatta cagatgaccc aatgccatta caggtgtgtt  36840
ttattagtac actgtttcat tctatcaggc tttcaactct aagtggtaca tattattata  36900
taaaacatag gtatggaaaa gttatagtag aagtattagg taatgcaatg tttgggataa  36960
attatattaa gatttaaagt aaagtttaag aagaatgttg gaacttgcta gaggagtatt  37020
agtgagagga ttgtaagtca ccttgcttta tttatcctct gtgatcgttc attatatgtc  37080
cttttcatta aggaagttat tccctctgtt gcagatcttt taacctgctt ataaaaatga  37140
cataaagaga aaaggttgtt tgctaaatga ttttataaat gccacacatt ttagtgattt  37200
cataggtttt tttgttgttg ggtttttgat ttttttgttt tgagcctgga tctcgctctg  37260
tcttgtctcc caggctggag tgcagtggca tgatgtcggc tcactgcaac ctctgtctgc  37320
ttcctgggct caagctatcc tgccacctca gcctcctgag tagctgggac tacaggtgca  37380
tgccaccact cccggctaac tgttgtattt ttttgtagag atggggtttt gttatgatgc  37440
ccggattggt cttgaacttc tgagcccaag caatctgcct gcctccccct cccaaagtgc  37500
cagagtacag gccactgcac ccagctacct tttttttttt tttttaaact aattagtgtt  37560
attttcctaa aaagttaaat tctaatttct aggaagagtg aagaatagta tcgatttaaa  37620
aattttcagt agccctcttg ctattttatg ttcttactgg aaagtaatag ttccatgtaa  37680
ttttggtttt tagaagttca ggcattcatt tgattaactt aaaaaccctg gacttttctg  37740
tcagccattt tgtattttgt tttataaagt attatacaca cttaccccta gatctttctt  37800
tatagtaatt gttctttaat gaaatattgg tatatgaact gtaaactttt aaatttaagg  37860
atctaatagt ttagtgtaag tatatttcat gtagtcactc actaatttac cataattatt  37920
atactgtaca aatatttatt gtactgtata tttgtgtgtt cattacagtc ttatgtaggt  37980
```

-continued

```
atatttagac taaatttaag gcacttaaag atacccactg tgtagggaca gtagcttatt  38040
tggatatagg cttgtgtgtt tctctttgtt tttagcttca taatgatcat tggccccaga  38100
cttcactgta aatgagaagc agatacctgg aacagcttaa atccagtacc actattagga  38160
aaaagtaaac cagtgcccta ctgacagcag attgatagtg ttaactacgt ccttagtttg  38220
aacatgcaaa accttttcta atggttttta tttctagtag actttgtgct ttaaaaagat  38280
agttattttg cactttaaaa tcttcagtgt gaaaatcaaa catgatttta cccacttaaa  38340
atctgatgac ctaagagccc tttttctttt aatatgttgt ggccagctta tccagatcta  38400
gacatgcaaa tgcttgctgg taaggtgatt gatgatattc cctatcttag gtattataat  38460
aagattgttg tgtacatttt aacctaattt ctatctgtca acattggaat ggccctagct  38520
acctagacaa aagcttttttg tgctttttag agataactgt cacagtttat catcacagtt  38580
taaggcttat actaccattg tgagattatt gggaaaagaa ttaatatgaa cataattttt  38640
tattccagaa attccattac agaaaccttc ttcttggtga acacgatgtc cctttaacat  38700
gtattgagca aattgtcaca ggtacgtagt attccgtaca tactctaaaa gtcaattcca  38760
ctctggaagt attatttgaa aagtcatacc tctcaaaata cttggattgg cgttttattt  38820
ctgtaagttt acttttgccg tttttttgag tcccgggaac ataaagaggg atatgttaat  38880
aaattatttt aaaaggaaga tataaaatgt ataacttttc atagtttcta ggttttttgt  38940
cctcttttta attaaaatta atcattaaat gtgtctagat ggtggtttta tgcaaataat  39000
catttaaaat atcttccaaa gcaaagttaa aaccaacccc caagttctag gaattacaag  39060
tatgaaacat tctagacaag cagagctcaa atgttgggtg accttccaat tattttcact  39120
aagaatttgt attaaagggt gagtaacaaa taactgttac gcattttatt ttctctattt  39180
ttttttcttt tttagtaaac gaccacaaga ggaagcagaa agtcctaggc cccaaccaga  39240
aactgaaatt taatccaaca gagttaatta tttattgtaa agatttcaga attgtcagat  39300
ttcgctttga tgaatcaggt cccgaaagtg ctaaaaaggt aatactgtta aggtttatca  39360
agttctgggt tctgtactgt gtttactgat ttcaattccg tatggcagtt ttcatttctc  39420
aattgctcag atgtttttta ggggaagtta tcagacatct tcttaagtaa agtcaaagcc  39480
aagaatatta atagaactat tttcttggat tggtttatgg ctgttttaaa gtgttctata  39540
taacttttta tcagcttctc aaatattaaa gactcttacg tggaaattag cattttttta  39600
cataaagatc attacttgtc agtttcttgg ttaaaaggtt gaaaagttgg tgatatactg  39660
taattaaggt ttggttaggc ttttaattca gtactgcaga actttaccaa caaactgtaa  39720
gctagactta tgttacataa gatttaggta aatatataat tacgggaaag gcctagtaat  39780
tattagtggt ttaaagaaat attatgaatt gagtgacact caacaggggc aacacaaagc  39840
tagtaacttt ttaactgcct tatttttcca cggccttcca gataatgact tattacccta  39900
cttgtaagag tcaagggcat gttttccatg ttttgctttg ccagaggagt gaagctggta  39960
gacctaatat ggcccccgtt ccagtctgtg ctgcagcaaa tgcagagtca cagactttcc  40020
agtaggaagc ttgcgcgtgt gtatgggaat agggcaacag tatcttagta taataggacg  40080
tggctttctc tcagaatgga ggcagtcttt gcaccaccaa gcaatgagtg cctttgtttt  40140
ccatggttag tcaactgact gcagtaaatc ttctgttgat accaaaacaa ggctggcaaa  40200
aatactgtaa ggcagctgtc ttcatatact ttggtgaaga ggtggtagat ttgtttttag  40260
attgagaacc aacagtttct tcacaggaag gcaagcagga gatgaatata tgaaaataca  40320
tctgaaaata tgtgactgtc tagcagagta gagtggttgt aggctcctct atgggtaaaa  40380
```

-continued

```
gttttcaaat ggtctgtata accatctctc agcaagctgc attattgaaa attcaactag  40440
ataactctta aagcctcttt cacctgttcg attgtgctgt ttgtgatttt ggcattttac  40500
taatttaaag tgcctattat atagaaggac tttagaattc atgatgtatt agactgtaca  40560
taaaatattt cagacaggtt aattcctcaa gcttatttat atttgtaatt taattgatca  40620
aagcatcaaa gacctgctta tgaaaacctt aagatgtgta gcatctcaag attagggaca  40680
tcacagaact tgctagattg agttaggaca gcatattcct aaggaagaaa ttgatgcaat  40740
tgaccggatc tctttcggaa agttcaattc tccctctttt actgtatttt tcagtttaca  40800
ctattttaat gagtggaaat aataattatt tggcctagtt cttgaaccat ctgtagtact  40860
tgttggtcat ttttcatgtt gaggcagtgt gctaaatttt gcaagtagaa agaagggtaa  40920
gatgcagttt cttgccctag agaacttaaa tctagtgaag aagataaagc atgaacaaat  40980
gaaaagtaat ggtacaaagt ggcagcataa aatcaactac acaaatagtt gatttccaga  41040
tgaacagagc ataataagtg ctgtggaaat tcagaatatc ccctatgtgt tgtgctgctg  41100
gttcatgaag agggccttac taaaccgtct gcacaaaaca agccagtccc tcatatgccc  41160
tttcctaaga ccaagtttca gacaaaaatc ttttccccag tatcctaaaa tataaaaagc  41220
atgtgagtct ctgtcttttg tatagccacg ggggttgcag ggcaggggag ggtgcaggaa  41280
aaaaaaatag atgcaatgag aatataaata gttttttttgg gatttacgca tttcaaacag  41340
ggttaagttg tatatggcta ccaaagcttg acggctttgt gagttaaaaa caaaaattat  41400
ggcatattct tttatttcaa gtgaaaagtt ttcatctaaa attcggtagc agttaggaaa  41460
ttatggctca tttttacctc ctggaagctt ggaatactgt tttctctgga aaatgctttg  41520
ctattttatc agttgcttta aaatgatgaa atgcatgttt ggagttctct ggtgggtaaa  41580
ccgttgattc attttgaaat acctaagcca tttatgtttt tgttttgaaa aatgaaattc  41640
aagaatacta aattggttca cattttgtta aatgttctga acccttctgg ttgtcttgtt  41700
ggtgttgttt caattgtatt atgacaaaat tagattgctt tgggcacttg tactcattaa  41760
tattcatcct cattatcctc gagctgtcac aggaaaatag tgatatttgg gaaaggtctg  41820
tataaagaaa gaaggaattt gatggtgcag aattggacat ctaacctcat agcaacttag  41880
aaccaccatt ttcttttgca gaacctttgc tcaaaactga agggcaaaat aataaaggtt  41940
gtttttaatg atttatctat atatctgtct gtgtagataa agataaatat atagatacac  42000
atgagtgaca agtgaaatac atgccttttg tctccacttt gttctctgat tagtgggttg  42060
tgaatcactt cttcaggaat actttataga agtgaattcc attcatctga ttaaggaaca  42120
agttggcctt ttcatgaact gtcatttttg acttgaatct ggtactgttt tttggtggct  42180
ttcaggccac agaaataaac cacttttgtt tgcaaatgag atagaactta atgaggtttg  42240
agtgtttcct ggatttgagt ttcttcagta ctgcacccca ggtgatctta ggaaagaaac  42300
catccactgt gggtacttct ggcttctgtc cagagaagat tatcagcttt ggtccaaaaa  42360
ttgatttaaa agtagtttac ttctttttct ccaataaaat atttgccata atttaatgtc  42420
tttaatacca acattttctt catttcctgt ggtagccagg acaaatgaag tatttcagat  42480
ctttcaaaaa ctcttaggat gaaaggtagg aatttggact taggttttta aaatagtgtg  42540
tatgtaaaag tgcaaagaat ggggccctgg ctttctcttc tcggagtgtt ccacagtaac  42600
aacatgaaga caatccaggt acacaagttt gtatgtgcct tagtctgtgt gtccaaagag  42660
gcctcttact taggtcatat gaacataagt tatacacttg aaattcacta ctgaaaaaca  42720
```

-continued

```
atgtatttag ttcgagttct gccaccccaa aaaaatcaac gagtaattca actgacttgc  42780
agttttacaa tatttttata gacttctttc agcgtagatg cttttggaca tactcatttg  42840
tttcctaacc tgatgtgata ttgtgctatt tttaaggggc ttttaaaaaa tacgctgtgt  42900
tgggttttgc cttgaaaata ggctttattt cttttttgcc tcatggccac aaaaaaagga  42960
tgtccatgat caatgatctg tgaatttctt ttctgtaaac agaaagagca tgtaactgct  43020
ttctaattgt tttggagaat gtgatagaca ttagtattat tattattggc ttggagcatt  43080
ttccttaata tgttggtaac tacttttgtc agtgaatatt agtgtagcca ctgttggaca  43140
cagagcaccg tcagaaagct actgaagtgg tgctgcaaag tgcagacatc ttcagatctt  43200
tactcaagtc tgtgcagaga ggtctttctt ggtctccttc tctacttttt agcctgtctc  43260
cctcttctca ctgtaacact tcatattccc cttccctgct ctattatttt tctcttttag  43320
cattcatagt tatctaactt tctgtatttt ttctctttat cttgtttagt gtctgtcttc  43380
ccactagaat gtaagcttca tgaggacagg gattagtgtc tgttttgttc actgcatctc  43440
tagggcttac aacattgtag gtactcagta aatatttgtt aaatcaatgt gaaatgtgtc  43500
atttatcctt aaggaattga ccttcatggt agaagtgtaa cagaaccacc tatatcctac  43560
ttttcatcca catcataact attatgtgaa taccttggaa gtaaagcaaa ataagcactt  43620
aactaaagag acgctttata ttgaaactgt tgttctgggt ttctggaatt agtactctga  43680
aattggctcc ctctaggaag gcttgtgaag agagtagtgt tgaacagaca tgacagtttc  43740
caagaaagca tagttggcta agaggagtag gattttccaa gcaaagagtg tgacagtgga  43800
gatggctggg gctaagtcag gcagaatgtg ttcaaacctg tttttctctg acctgagatt  43860
gcggagggaa tattgggaag gtatagttac ctggtgagga gagccagttt tgtgaagaat  43920
caagaatgag gagatttaat ttgttatgca gatgtctggg aaccacagca gattatcagg  43980
agagcaaaat tgttagtcag aattacatcg ttagaaggta atccttaagt tttgtagatt  44040
tctagaatgt aaggaagctc tcagaggtgc cataaggtga gtatggccta aggatgtggc  44100
tatggcagtg tagcaaaatg gacaactatg aaaaatgtct agagaaaagt gcaacatagc  44160
ttatcaacgg tgcccaaaca aataggaagg atgagaactt tttcaagcta cagatttcag  44220
tagttttgct gctagaaatg ctttaaggaa aactgttaaa aagattagga atgggaatat  44280
agataaccgg ctcctaaatt ttgcaagtgg gaccgtcata gaaagctctc ctataggtat  44340
tgagaaatcg agataccacg taagtttcaa gaagcagttt ttttttcttt tttggtcaaa  44400
actaatgaca aattctgtcc ccttgtttgt atattttaac ttagtgagac aggaaacatt  44460
tattctatag aagactttta aaatgtagtt taaacaagtt gacacatgct tactggttaa  44520
tgaaatgtgc atcaacccac tccaaacacc actaatttga catgaactaa caattaactt  44580
ttcttactca ctgtcaaaag tatatcattc tgccttaact taacgcttta ccttctaaat  44640
aaaatttaat cttttaaata agtttttctg ctatgttttc cttgcatatg tcttaaattt  44700
cttctttcgt ctttgctcac tgaagagcat tttctcccac attctagtga ctaccagggt  44760
ttgtaagcct agagcaccat ccttcattct atctagcagc agttgagaat aataacagcc  44820
atatttctat atatggagct cctccaaagg cctagcctgc attaagcttg ttaattctta  44880
ccacagccta ggtattactt ttgttttaca agtgagcaaa ctgaggctag aaaagaggaa  44940
atgacttcac acatgttatg tagcaagtac ttgacagagc taggattcaa gccccctgat  45000
ctgtttgatt ctaaagcccg cacgttttcc accacagggc acacagtccc aaaccatttt  45060
acttaaacac agtttgtgtg tgtgtgtgtg tgtgtgtgtg tgtgtgtgtg tgtgtgttgt  45120
```

-continued

```
tttttttgatg tacctctttg agccacccat gcatttttgg agtttcttgc taattttaat  45180
tttttgtaat tatgtttctc tatttagatg tttaaatcca tgaggcgtaa actttaaagt  45240
ttcatgcctt atattaatcc tttatagtcc accaaaaatg aaactttttt cttccttttt  45300
tggagtggac atgtagtcac tgccttttttg gagaatgctt ctttagtttg aagctttctt  45360
tattggacta aaattacttt ccaattaaaa tttaactcag caaatattta ctgaatactt  45420
gccatgtgct agctaaagat aaacaatgtc ttgagggcat gaaagtgaat gagatacctg  45480
gccttaagga gctcttttat attctaggtc aacagaaaaa catgtaaata gtatctataa  45540
tcactgcccc aagatgatgc tcccagtgcc caaggcctta ttgtacattt catttaacta  45600
agtgtgttaa aatcaaattc taaatgtaga atttttccta ggtatgcctt gcaatagctc  45660
attattccca gccaacagac ctccagctac tctttgcatt tgaatatgtt gggaaaaaat  45720
accacaattc aggtaaatat gaaaatatta aatattgtga ctaattttac atgtgtaaat  45780
tttactctta tgtttaccgg aagcctccaa gtacatgagc tttaatgatt gtagaattac  45840
tagcttcata ccttagagaa gtaagcacta catgctaaaa gagccaatag tttgtcagat  45900
tatttcttga caagttacca ggaagaacct ttaatgctat gaatatgggc ttataagtta  45960
tgtcagatat ttaatctcca gtcactggct tgtattttat gatgaagaat atataaccca  46020
cccttttttaa ttgatagctt gagttaaagt aatcttatct tttaagaaaa ctggcagaaa  46080
actaaaagat atattaaaag cataatcttt tctggcaagg tgtgatttca tgcaaaagct  46140
aaagtgatta aaaacttttt gtggacttca ttaagattct cagaatactg agtttctatt  46200
tctgagtaat actgatgaaa ggaagatgag catttttcca aggacaagta tattctagac  46260
agcttttgtg aaagtaaata gttttgtcta tatatctgac agtcatgaca tgaccaggga  46320
agattccaga tgatcatgca attctgtaca ttctgtttcg tacaaatgta attttaataa  46380
acaattttta aaaatatctt gatagagaaa aacaaagagc cgtgtctcct gttagcccca  46440
ttgtcagtta gtgactgcaa gtcagttaac tgagcgaagc ctgtgttctt ttatttaagc  46500
aagaaaaata aatcagctgt gtatttataa tgaaaaatcc attcacccag catgctctgg  46560
gccatacaaa ttattaattg tactgaaatt ttatattttg ttaccacgaa acatggtagt  46620
aatttaaata actggcataa taaaagtata ttccagcaac actatattgt aaatacatta  46680
aaatgtatca gtgtacggta tctgaagatg catgtgtata agtaaatttt ccttagttta  46740
aaagataact acctttctgt taagcactga gaggaccaaa aaaaaaaaaa aaagaaaata  46800
cagtagagat aatatatgaa aataatgctt tgcagagcag cttttatcat acagtattat  46860
atttatagaa attgtataac aaaagtattt gtaacttaat ttttcttatc gatatataca  46920
taattgtaac tgaggcttaa gcaatacagt tattttttga agtttattaa tattaagtaa  46980
attcacttac tgtctaaaaa taaagtatac agatcctgca ctattaggta aacactcctt  47040
gggatcatcg tcaagctaca gaacagtgat caaggttatc ttcaataaga tcctcaccca  47100
gagttgcaag ggttgtagga gtgagtcttt gattcctgct caactgttta tgatacagac  47160
cagttcttca tgctgctgtt tttccaatag aaatgattca tttcagttta cagatccata  47220
acttctacag taatgtagtg acttgggctc agcaaagaca gtaaacttca ttatacagtt  47280
ggtaacctga tgcctgcttc agttactttc cacatttttc ttcattcata ccttgtgggc  47340
atctctggtt tacagtactt tagtttatcc acccataggt cttctactac tggaatttta  47400
aaatctacat cattcagttc cactatttct tcttatatag cttattgata aaatttgatg  47460
```

-continued attaatactg aaaatattca gggatgcttt tttatattac atccttcaga ctcctccttt 47520
gacaagtacc tcataaacat aacactggcc atagttttgt taagattcct cgtagggtaa 47580
catcctttaa tatccttcca tgctgttaca gaagcataaa tactgcatct ttaagatcaa 47640
aaggagcctg aaatttccac acactgcagt cagaattcat taatttgtga gtgaaagatg 47700
cccactcatc cactcttgaa cttctggatg acaccttgat tcattggctg gattaaagaa 47760
gtcctttttg caggcaggta ggtgacaaag ctgtttccac aaataagatc caaagttgga 47820
ggagctcccc tgcagttatc tgagaaaatg atattttagc tggccttagt cactcaggtt 47880
ttcattcata ttcagtatca catgaggaaa agccatctct gaaaggtcct gcagtcatcc 47940
caacacttct gtgaatatcc tggagtaaag taagatgtgt agcacccagg ctttggaaca 48000
tcgctttgca caaacacccc aggagatatt actagcacaa acaagaacaa tgattctgtt 48060
ttttctcttt taactttaaa gaaaccatga ggactctgtt ttcatcagtc agattattat 48120
tgggcaaata acgtcaaaaa agtacagatt catctttctt atagaattga taagatgtca 48180
gattatgctt ctggaccaaa aatattgaaa gtttcatgaa gttatctgca gcctagtgtc 48240
agcaactgct tcatgacaga catcctgctt acagatgctg tgatgtaatc tgaagttgta 48300
atgaaatttc acatcagaag ttgtacattt tcagtgacat ttaattttat ccttttttatt 48360
aacatagatc ttgttattag attttcctta aaatgcctat ttgaaaaaca caaggtacac 48420
aatccatttg aaacagtata ggaattttta aactttgttg cttaagattc tcagaatagc 48480
tataaatgat tgttgaatat tggtggttcc agccagctgt atacatcagg attactggag 48540
gaacctttag aaatgcagcc atgttggctc cagcacaggt cagaatctcc cagttaagaa 48600
ccactttgtt gactcatgct tttgaactga ttaatactca cagtcctctt tttaccttat 48660
tcctttgtga cttctaattt ctgcagtatc atcagagtgg tgggctttct tttcatatat 48720
tgatgacttg tattttctgt tgcttgaagc cattctagat atcaattggc caattcagtg 48780
gaaattatct aaaataaccc caacagtata ggattagact tttgtactgt cacagaagat 48840
agccaaggtc aggagcatat aatatctatt tcacgcttag tctgctgtgg aggcatgtca 48900
taaaacctca gtcaggtagc ggtcagcgga gccaggtctc cctgagatga cccacctttc 48960
actgtgttgg tccagcccct catagcgatc cactcataga gcaggccact ggtatcaggt 49020
cttttgaact ttggaaagca ttcaaatttc tggactataa aaccagattg agtatacatt 49080
acacattctg taatgagctc taactgaaga tgatatagaa catataaaag acctagtccc 49140
agttgtttag aaaagtacag gatttgaacg agagaaatgg caaaaataac aaacgataga 49200
ggatctcact ttatgcttag aaaatataga tgttctcatt ttacgtttag aaaaatttgt 49260
gtaagttaga tcttgaaaca aaatttggcc agagaaacaa tctcataaac aatagcacat 49320
tcttagccta gcttattaaa gtctgcaacc caaaacacta aaaagtattc agtgctgctg 49380
gactcagtca ccaaactgtt ttacataact gttaaaattt tgagtgtgtt ttttataatt 49440
ctttttggt ggtggtggtt ttattgtttg gctaggactg ctggttcagt gttgaatagc 49500
agtaatatta gcaggcataa tttcacttcc cgcttttaat gaagatgctc ttagctatgt 49560
ctttttgata aacaccctct atccagttaa ggaaattccc ttttattcca aacttgctaa 49620
cgttgttggg tttttttttt taagtcataa acaggtatct atcatatgtt tttctgcact 49680
tacagagcta gtcattcata tagccttttt cgtgtttaat gtagtcatat gatgaattac 49740
ttagattttc taatattgaa tagctttctt tgttttggtg cactggaaca ctgtatagat 49800
tgggctttgc caaaaattcc atatgcaggt tttgtgttct ggagagatca taactcctaa 49860

-continued gtcttccttc tcacagacac gctttttagt tgtgttactc cagagaaggc cctgagatgg 49920
agtgggactc taggatgtgg gcttagaatg agcattttac tatctatcta tctatctatc 49980
tgtctgtcta tctatctatc tgtctattta tttttgagac agagtctcgc tgtgtcgctc 50040
aggctggagt gcactggtac gatctcggct cactgcaagc tctgcctgcc aggttcacac 50100
catctcctgc ctcaccctcc caagtagctg ggactacagg cacgtgccgc cacacccggc 50160
ttattttttt ttttttagta tttttaatag agacagggtt tcaccgtgtt agccaagatg 50220
gtctcgatct cctgaccttg tgatccgccc acctcggcct cccaaagtgt tgggattaca 50280
ggcatgagcc accgcgccca gcaacatttt actttttaat gagctttgtt aaaatcagaa 50340
tcactggata attctgatac cacttaagag gagtccaaat tcctaacata gcccctccgt 50400
aatctagagc agcaccgtcc agtgatggaa gtagggcagc cactagagcc actagccaca 50460
tgtggctgtt aagtacttga aatgtggcta gtgcaactga tggactgaat ttttaatttt 50520
atttaatttt catttcagtt taaatttaaa tgggcttgtg tggctagaag ttacgttttt 50580
gggaaacata ctagagtcta ggccctattt gatttcccgc ctctcttcca ccacctgttg 50640
aatccctatg ctctagctgt atttagttac ttgatattat acagttatac catcttttta 50700
aagttcttct ctgtctagca tgcctacctc ctcctcacca gctacctggc aacttttgac 50760
ttgttcctta gaactctctt tagttgtggt caagtcatga agcttttcct gccccggcct 50820
ctctctgcag cgagagttag gggacttctc ttttgcatct tcattgcact cagacatctg 50880
gtactctgtg attatcacac ttattaatgc tctcaagata gagataaaat cttattcatc 50940
tttttgctct caggcattag cacatgggga gttctcagaa aatacctgtc ttataccagg 51000
aattaatgaa taatcagtag gaatgagcat gacatgttca tgggacgttg gagggtagtg 51060
catggctgca gaggagaatg ggaaatgaag gtcagataag ttacgtgagg gatctctaag 51120
gccaagagaa gccatttagg tttgatttgg ttggaaaatg agcttattga aagtttaagg 51180
caagggacta gcatcatgaa cacatctttt tagggaagtg tgtcttgtgg taagctgctg 51240
gctggtttaa atgcagcaga atattccatt ggggatgcca gctgggagac ttgccacagt 51300
tgcagcctgc agcagaaaga ccctgggcca gaatgggttg tgccatctgt caccagatat 51360
tgccaaggta gatctggctg actttgtggg acagcttgtt tctcaataat cactttgcag 51420
gcactcttga ggctgtgagc atgctcccag aagatagcat tacttctctc tcagagcagg 51480
ctcctttcta aggaaatgca agtctaggcc tgccctgctg taatcttcat gtggaaacag 51540
cactctagca aagaacaagg aacctgatga gcttttcaaa ggaaaatcga gtagatacag 51600
gaaaccaaga attttctaat gagcagatag aaaagagcag gtaggtgaga agttggtatt 51660
agaaaaatta aagatttgaa gggcttgagg acagagatga ttgttggatg tttcattttt 51720
ccaggcaaaa tatgtggagc aaataatcaa atgacatgga cttaccccac aattagggac 51780
ggagatgagg aagggttagg aatagtttct gttagaatgg tagggatgga agacaattga 51840
aaattaaaga gaaaataaat ggagaggaaa tctaggcagc agccattctt cattctgggg 51900
gaaggtggtc aggaaaagga aggaagaaaa atgtatagca tagtagctag agtggtccgg 51960
cgtgatcaaa gtgttttcaa tatcatgttg actgacctgt ttacgtttga aggcagagaa 52020
gatagagcca gtagaaggag agaaaaatca aagctgtttt acggagttgt gaaagagctg 52080
gataaggaca agactaaatg agttattttt aggccaggcg tggtggctca tgcctgtaat 52140
cccagcactt tgggaggcca aggcaggtgg ggcacctgag gtcaggagtt caagagcagc 52200

-continued

```
ctagccaaca tggtgaaacc ctgtctctat taaaaataca aaaattagct ggacatggtg  52260
catggtggca ggtgcctgta atcccagcta ctcaagaggc tgaggcagga gaatagcttg  52320
aacccggggg gcggaggttg cagtcagccg agatcatgcc agtgcattcc agcctgggcg  52380
acagaacgag actccgtcaa aaaaaaaaaa aggagttatt tttaaatgga aagggcaaga  52440
cagttctcgg agagacttgg aaggtgaagc aggttagaga cagcacatca gagtatgcat  52500
gtgacaggag gctcagagaa gagggaatgc tggggaaaat gtgactgtta aaattcataa  52560
tgttgctttt tcctacagca aacaaaatta atggaattcc ctcaggagat ggaggaggag  52620
gaggaggagg aggtaatgga gctggtggtg gcagcagcca gaaaactcca ctctttgaaa  52680
cttactcgga ttgggacaga gaaatcaaga ggacaggtgc ttccgggtgg agagtttgtt  52740
ctattaacga gggttacatg atatccactt ggtaagtaca attttagcaa tgttatatat  52800
ggctggaagt cacttcccta tgaataatca tcaaactctg ttgtcattga tgactttcaa  52860
gttgtggtta atggaatatt tgtttttaat aatgttttaa taaatatttt attttaaaga  52920
tcaaggctta ttaatataaa ttacggtatc ccttaaaaga agttgatagt aattccttac  52980
tgtcatcagt agtcagtgtt tattgcatta tatcttgtaa ctggtgtttt acagttggtt  53040
tgttcatatc aggatctaaa gtcttcacat tgaatttgct taatatgtct cttaggcctt  53100
ttaatctaca acagtctcct cccacctctt ttttacctac tatttgttga caaaccaggt  53160
catttgttcc ctagaatttt ccacattgta gatattgctt gttttatccc cagggtgtcc  53220
cgtaatgtgt tcctctgtct ctaatatttc ctttaaaatg ttagcaacag aggcttaatc  53280
ggattcaggt tcagtacttt tggcaagaat gtttcattag gtggttctgt gttctcctgt  53340
ggagtcacat cccatctcag gctggctggc tgtgtctctc tcattgtaat cctgacgacc  53400
agtgggctta gagggtgtca acctgatcca cccagtaaaa gttcccctct tatatcatgg  53460
tttgagctcc caaaaatagt tttgcactgg gagggaggat cattgctcag atcgttattt  53520
cactaaggat tgctattgtt caccttctaa ttctatcatc tttctgcttt tatcgaactt  53580
ttctctcacc agctctttag tgccctgtaa cacagttcgt acaagaaaag caatataaat  53640
atctacattt tctcctttac ttaacatttt tccaaatagt gagctggttc cctaggggat  53700
cttctagaag tgactaggaa tttgtttttt taatttgttt aatgtcattt agttattatg  53760
aattttttgg aatgccttat tttaaggtca ttgaagtcct cattagttca cgcacataag  53820
cagcttttta gaaaaaggaa gaaaagcact actgtgttat tactggttaa tccagtacca  53880
ggaacttcta gtacagttct agaaaggtgc tttgcagcat gtagcttgta tcttttgctt  53940
cccctggaat ttaagcttca aggccagcac actctggtat atgtgctgag aaacatgtga  54000
tggggctgcc cagccacgtc ggggaaagaa ggaagatgtc ttgaggtgca gtgagcttgc  54060
ccactagtaa ttattgtctg atcagtgtcc tagagtctga ctgtgccttt taggcatggg  54120
gaaaggtaga agagggactt aagaagagag ctaaagctcc tggtagattt gtggggtttt  54180
cttttgtttg cctggtgtcc ttaaccatag cctgtcaaga gaacaaaggt ggatatattt  54240
ttcagtgaac acatacatgt ttaatagtca ttctggaaaa tatttctaat accttctttg  54300
gaattttctc atgctataaa tttagatttt taagaattgg tcatatcgca ccaattttag  54360
actaagaggt gtaggatcgt cactgccccc ccatggtgcc caccatgtgg ctactaagtg  54420
gggtgcacat taaatgcgga caacttgctt aattatttat agggtctgca ggagcacact  54480
attcctgctt ttagcacagc actcatataa tttttttttt cccctccagc cttccagaat  54540
acattgtagt gccaagttct ttagcagacc aagatctaaa gatcttttcc cattcttttg  54600
```

-continued

```
ttgggagaag gatgccagta agtgatttct gttggatttt atgaatgctg acgtccattg  54660
tttctacaca gtgaagtaag gattctacct ctcccctagc tctggtgctg gagccactct  54720
aacggcagtg ctcttgtgcg aatggccctc atcaaagacg tgctgcagca gaggaagatt  54780
gaccagaggt aattgagaaa tggtcattgt cactttagat agttttactt gttgtgtaac  54840
tacagtgagt tccctactaa ttgaaaataa caaaatgcat agtcttacta attagttagc  54900
accatgtttt atataagaat tgccattttg aaaagaatgt gataatatta aaattaactg  54960
acattggagt tacactaaat ataatttaat tatttggttt gtaagacact tgtggatctt  55020
acattgctga catcttgcta tagcatttcc tataacatac tttcaaagtg cagtgatatc  55080
cagttgagac acttcaggat aaatcaaact tttcttgtag atctgatgtg tcttatttag  55140
gtctacacat ttgcaaatag cctagacagt gcttttaatt agccaccaca gacgagtctg  55200
gcatcatctg ctgtgggtca tagtaactcc ccgtcattaa agtaggaggc ctttctcagt  55260
tgtgctcata gcagtgagca atactattga tcactctctc cttaaacccg cctgggccct  55320
cagcctctgc tcctctccac tctcctgaag ctcctcttcc tcactggcac tccgtgcctt  55380
ctgcagaccc atcctcttct ctccagacat tacacagatt ctaaggccgc ttcctcatgt  55440
tctgtattct tttcctaaag aagtttcccc aagaatgtgg ctttagtgac caacacattt  55500
atatcttcag tctaccttga cttctacatg gaggtctcaa agaccctta aactcattat  55560
gtccaaaacc aaactcaagg atatggcctc catgccctcc cccagcctgc tctcagaaac  55620
cggggggtca tcctggatgc cttcctcttt ctttcccttc cccatcacca atccctcctc  55680
aggttttctc acttcacttt tcagacacct tgcaaaccca tgtgcttcca caaacccagc  55740
tccacctctg cctgtgtgtt ataagtgcta tcatttcctc cttccatgtc tcctccaccc  55800
ctgggctcca gccccctgga ctttccctgg tgttttcaac ctcctgacat tgtccagcgc  55860
tcttcccttc tggactgcct tctttgcact catctgggaa cactctccac gcttacccac  55920
ttggcactcc ttgtttcttt ttttttgaga cagagtctca ctctgtcacc catgctggag  55980
tgcagtggta cgatctcggc tcccgggttc aagtgattat catgcctcag cctcctgagt  56040
agctgggatt acaggcaccc accaccacat ccagctgatt tttgtatttt taatagagac  56100
aagatttcac catgtcggcc aggctggtct cgaactcctg acctcaggtg atccacccgc  56160
ctcggcctac cgaagtgctg ggattacagg cgtgagccac tgcacccggc tcactcattc  56220
tttatatctc aattcaaaca tcatttcctc aagataagcc ttctctcccc tctaaagttt  56280
gatcagacct caaaagtcta tgttcttaga gctcctgagt ttttaacatt tatttcagtt  56340
tttaattata tatgtgtgtg ttacagtttg attaccgcct gtcgttttta ctccatgaga  56400
tgagggacta tgtctgtttt gcacaccgtt atatatttag cacccaggaa gcatatatga  56460
tatttattca atacttgttg aataaatgag gagtaaatga acagatctta taaaacaggc  56520
ttatggagcc tcagaaattg tgtatcacag tcctttttgg tacagccaga gtgtagggtt  56580
tttccactgt accgtaactg acagagccat attcactgaa gcaaataacc atcaagtgac  56640
cctcaaatga ccttcagttt tctggaaagg aaggtgacta tagttcacac gagtccgtat  56700
tctctgtgga ttttgattta cctgaactcc atttggaatt aactgtctgc tgtgtcatac  56760
tccaagcctt gttttcatta gcatacatgc tgatgaagtg cacagttagg aattttgctg  56820
ttaaagggac aattgtagca ttgttgggtg agagttagtt ataaaacctt ataatcagtg  56880
gcagtttcag tgatttatta agctgaaaat tactttaatg ccttttgtgt tttcagctat  56940
```

-continued

```
cctattcttc ataagtagaa cagatcctct tttttgtcca acctcgtctc ctaacctttt  57000
tccctcaggt gtgtcatcta gccccactgg ccttctttag gtttctcagc agccatgctt  57060
gttacctgcc acagggccct tgcactagct gccctctgcc tagaacattt tcaccccaga  57120
tctttacatt gcttctctat tcatttaggt ttcggcttca gtaccatctt cacagagcag  57180
ctgtttttca ccatgtgacc taaagtagcc tgtaatctca tgattacatc atccatggca  57240
ttcaccacag cccatttatc ttatcatcta ccccacccca cgaagaatgt caacccccca  57300
cttgcttggg caacaccagt agtaaaattg gaatgataca gggaaggtta gcatagccct  57360
tgcacaaaga tgacatgcag gttcatgaca cattacatat tttaatgaaa tgggagcata  57420
ttcttgttat ttaattttta aaaatcagtt tatcaagcaa atgtacagcg ccattttatt  57480
tttcatgcct acattaaatt ccatacacat aaaggtgcat agaggaaacc tagaaagatt  57540
gcaccaaaat tttagaattc tgagtgattt tgtttttctt atcttttcta ggtgttttta  57600
aacattccac actaatttat attacttttt ctattcagga aaaaaaaaaa caacagcagg  57660
gttttgtttt gtttttttaa agtggtgtgg aagttaccca ttgaatatag atgggaatcc  57720
cagtcctggc tgtttccttt gaaaagatct agagacccca tggcacatat ttatagtagc  57780
ccattctctc ctaagaatag aggaagggtg ggaggaattt tggtgaatgt ctgtacttgc  57840
agtttatcct acagcaaatc gttaagactg tgggaatagg tgctttgcat tctctagagc  57900
tggagaatgt gcatctggtt tgccatcctt ctgtctacat catgtggaaa gatgtgggag  57960
tgtagggtct ccttaatcta aatgcagtgc tgccccgccc ccccccttggc agtgtttctg  58020
tttcccaggc aagtgttcca atggatgtgc tttattttct cccatcagaa ataagggaat  58080
gagcccgggc gcggtggctc acgcctgtaa tcccagcact ttgggaggcc aagggggggtg  58140
aatcacaagg tcaggagttt gagaccagcc tggccaacat ggtgaaaccc cgcctctact  58200
aaaaatacag aaatttagcc aggtgtggtg gcgggtgcct gtaatcccaa ctactcggga  58260
gggtgaggca ggagaatcgc ttgaacccgg gagggggagg ttgcagtgag ccgagatggt  58320
gccactgcac tccagcctgg gcgacagtat gagactccgt ctcaaaaaga aaaagaagga  58380
aatgatctaa tttgttctgt gcactgcacg tgggggtggc agtgaggtga atggcagcat  58440
tctgcagtag tcaaagccag atgggtggga gaagttgggt gctaagaggg aaacaaagtt  58500
tacctgtctt ctccttgatt tcactctcag ttttatgaga atacagaaaa atcatgcaga  58560
gaaacctgat ggaatagtct ctaaaactaa aaaataagat aagcaatggt tctgtcttaa  58620
aaaaaaaaaa gtaaactcca tgaaggcaga gaccttacct gtctcattcc tctctctatc  58680
ccctggtcta tagtaagggt taaataaata tatgctgaaa tgaatgagta atgactaaag  58740
tatttttgtc tttattagga tttgtaatgc aataactaaa agtcacccac agagaagtga  58800
tgtttacaaa tcagatttgg ataagacctt gcctaatatt caagaagtac aggcagcatt  58860
tgtaaaactg aagcagctat gcgttaatgg taatttcatt cttatttcat atatataatg  58920
aacacaggat acagagttgc atgagatgtc aggaaaagtg atgttcttaa aaatgtagaa  58980
atagatatat ttaaggagtc tatggaacta tttgtacaaa ttatatatta ttgtatgaga  59040
acttcagaac ctcctaagga attaagttta aactactttt tgttttagag ggggaaaaat  59100
gagtgtatta aatttccttc agatgatgaa aggtatagga gaatactttt ataaaagcat  59160
ttgctgagta gaacactgta ttaccttaca gacaaactta ttaagattgt aatacataca  59220
gttatacttt gagataggtg acttgacatg ggtatcaaac agctgtgtta tatctgtagc  59280
atcagaattc tgatatatct gagcaaacgt accaggtggc tttcatgtgt cctgcgggat  59340
```

-continued gagtcacatg aaagcatctt tggtgtaatg tgggtcctcc tcaagagatc ctctaagtca 59400
ccagggagtc agcaaaggca gccttgcagc agatcttgag caatgagtaa gcacttccct 59460
gggggagggc cttgcagggg cggggcaggg gcaagttgtt gaaaaaacta gtgtcctgaa 59520
tgattatgtg cactctgggc agggcagtga ggatgcctgt cctcatgcag tggctagccc 59580
tcggccacgt gagccatgca cagaggcacc actggcagca ggggtggggc agggaagcag 59640
gagggcaagg cttgcagtga gaaagccaag ggctagggcc tgggcagctg acctcacagg 59700
tcaggagggc caggatcaag gcataggctg agcagggacg gctggaattc ttagctgttg 59760
ggagtcagag ttggttggac tccaagattt ccctgaaaga gcgagagaga agatgatgga 59820
gccccagggg aatgctttgt tttgctttgt tacagaattg taatgtcttc ttaaatgctt 59880
attccatgtt attaaagtga aaatgcatga tatttactta aagctaactt ttaaatatta 59940
gaaactgatg tatctcttta ctctgatagg gatcgtataa aataaaaagt aaaaatgtgt 60000
atgtatataa tttattacag agccttttga agaaactgaa gagaaatggt tatcttcact 60060
ggaaaatact cgatggttag aatatgtaag gtttgtactt ctttactttc ttttccttta 60120
actttttatt ttgagataac tacagactca ctggaggtac aaaaatagca cagagggcca 60180
tgtacttact cttcatccaa cttcccccaa tagtaacatc tcgtaactag agtacagcat 60240
ccaaaccagg aagctgacac tgggacactg gatagctctt actcaccagt tcatacatgc 60300
tgtcgtctgt gtgcatgccc ttaacacagc tgtgcgattt tatcacgtgt gtaggttcac 60360
gtaaccacca ccacagggag atacagacct gttccatgac aaggctcccc tgtgctagcc 60420
ttcttatagg tgcaccctca tcgccatctg tgtctgttga ctaccactaa tctcttctca 60480
atctctatag ttttgtcata agtcaacccc ttccttttca taaagggttt atgaatttcc 60540
ctgatgaaaa agtacaaaat gaggccaggc gtggtggctc atgcctgtaa tcccagcact 60600
ttgggaggcc aaggcgggtg gctcacctga ggtcaggagt tcaagaccag cctggccaac 60660
atggtgaaac cttgtctctg ctaaaaatac aaaaattagc caagcatggt ggcacgcacc 60720
tgtagtccca gctactcagg aggctgaggc aggagaatca cttgaacctg ggaggcagag 60780
gttgcattga gtcaagatca cgccactgca ctgcagcctg ggtgatagag caagtctcca 60840
tctcaaaaaa aaaaatttac aaagtggggc cggttgtggt agctcatgcc agtaattcca 60900
aagctctggg gaggaagatc acttgaggcc agtagttcac aaccagcctg agcaacacag 60960
tgagacccca tctccacaaa aaagttggaa actagccagg catggtggca tgtgcctgct 61020
gtcctaggga gcctgaggca ggaggatcac ttgaggccag gagttcacaa ccagccgagg 61080
aacatagtga gatgcccatc tccacaaaaa aattttaaaa ctaggcaggc atggtggctc 61140
gtgcctgtgg tcctagctgc tcaggaggtg gaggcaggag gatcacttga ggccaggagt 61200
tcagggttac aatgagctgt gatatgccac tgcactctag tgtgggtgac aaaatgagag 61260
cctgtctctt aaaaagaaaa caaaaattac aaaatatact cctttgagaa atcgtataag 61320
taactaaaga aactttacgg taatgcgaaa gctatgtgca ttcagtagaa agcagtcaat 61380
cctctcttgt gatgctgagt agcagcaggg agccacagct gccagtcagc cacacagtct 61440
cagtttaggg tattttcagc ttacagtggg ttatcatggg tcatgagtta tgggaatatc 61500
atgatcagag agcatctgta aagtgagaaa ttagatttgc ttgatttcaa gtactttatg 61560
tatttgtagt ggaaatttga tttttaacac tgcttttcct tttctctctt cagggcattc 61620
cttaagcatt cagcagaact tgtatacatg ctagaaagca aacatctctc tgtagtccta 61680

-continued

```
caaggtaact aaagtaactc ctgaaagcac catgaccacc ataccagcca gccttggttt  61740
actgcttgtc cccattcaag taaatcacat cagttttagc tatttcttat ttactacagt  61800
accatcaaat acattacaga ttttgcacat catttgagta aaacagtggc acaggctggg  61860
cgcagtggct gaagcctgta atcccagact ttgggaggtc gaggcgggcg gatcacttga  61920
ggtcagaagt ttgagatcag cctggccaac gtggtgaaac cttgtctcta ctaaaaatac  61980
aaaaattagt caggagtggt ggtgtgcgcc tgtagtctca gctactcggg aggccgaggc  62040
aggagtatca cttgaaccta ggaggcggag gttgcagtga gcagagatcg caccactgca  62100
ctccagcctg ggcaacacag caagactcaa aaaaaaaata aataaaaacc agtggcacaa  62160
ggactgcaaa tagaagaata gaaagtagtc cagtttttac cctttattaa attatccttc  62220
ctattttatg ggaagggtgg gtcccatccc ctaatggatt aatacttagt gttaattttg  62280
acagggcatt ctctctctgt aattttgctg tctaatttgt acaaatttgt tttagtttaa  62340
ataccttctg gctcatgcta gattatgact ctaaggaagc agtttgagat gaagaaattt  62400
agactgaact gctgaatagc tagtaatgta atatttggta ggaataaacg gtgatgtaaa  62460
aatctttcag ttaagcaaag gataattaca tattaaataa cttacagcta atagaatttg  62520
taagtttgca gataaagttc aatagactaa aaactacctt cgtataatac agtagtaggt  62580
cctttgtacc catggcttcc ccatctgtgg tcaaccaacc caggactgaa aatattggcg  62640
ggggaaagct ttggccgtaa tgaacatgaa cagacttttt ttttgttgtc attattctct  62700
aaacagtata gtataacaac tgtttacata gcatttacat tgtattaggt gttataagta  62760
atctagaggt aacttaaagt gtacaggagg atgtgcatag gttatatgca aatattaaca  62820
tcattttata tccaggactt aagcatttgt ggatcttggt atccaaagga ggccctggaa  62880
tgagttcccc atggatactg agggaagact atatactcat gttgcatagt atatgaatac  62940
aaaatgttgc ttaagcttgc agaagtactt tttttttttt tgagatggag tttcgctcct  63000
gtcacctagg ctggagtgca gtggaacgat ctcagctcac tgcaacctcc acctcctggg  63060
ttcaagcgat tctcctgctt cagcctccca agtagctggg attacaagca tgcaccacca  63120
cgcccggcta atttttgtat ttttactaga gatggggttt caccttgttg gccaggctgc  63180
tctcgaactc ctgccctcag gtggtctgcc cacctcagcc tcccaaagtg ctaggattat  63240
aggcgtgagc caccgtgcct ggccaggctt gcagaagtac atttaacaac tgccaaactt  63300
gattgacttt aacaaggcaa aaatctttaa gactcttaga aaaaaatcaa atagtaatgt  63360
gtcatataaa gtaatcctga actgatacag tcagagtgtg tgtttaactc acaaatgcat  63420
gcagagccta ataatcacaa tttctctcat ccagtgggtg ttctcatcgt attggagaac  63480
cctactcatc ctccatttct ccatgcattt gtaatagaaa aggcctcaga agtagcactg  63540
aaccttcatt ttactagcat ttttatatac gtttattttt aaacagtttg ttaaaaattt  63600
acatactatg gaattcaccc atttttaatt tgtaattcag taaattttag taaatataca  63660
gagtctagtt ttggaaattt ttcatcaccc caaaagtccc agctccaggc agccactaat  63720
ctttctgtct ctagattttc cctttctggg catttcatat aaatggaatc atacaatatg  63780
tggccttttg ccgctggctt ctttcattca acatacatgt ttttgaggtt cattcatgta  63840
gtgtgtatca gcaatctttt ccttttttatt tctgaattgt attccactgt ttgtaaatgc  63900
attttgctta cccatttacc tgttgatgga catttgggtt gtttccactt tgtggctgtt  63960
atgaattatg ctgcttcatt tatttagatc tttcatttta tcagcagtgt tttattatgt  64020
aagtcttata tttattttgt taaatctctt aagtatttta tttttatgtc actgtgaata  64080
```

-continued taattgttaa tttcattttc aggtttacta tgtactcaga ttgttgtgta cagaatttct 64140
gtaaccttac tgacctcatt tattaattct agtagttatt ttgtggattc cgtaggagtt 64200
tttacataca ggatcatatt gtcttcaaag acagttttta ccttttttctt tctgatctga 64260
atgcctttta ttttcttttt cttgcctaat tgctctggct agattctcca gttcaatgag 64320
atggagaagt gtagagaaca gacatcctta tcatcttcct gatcttaggg agagagtatc 64380
cagtctttca ccagtgaaat gggaataaca ttaattgtag gtttttgtgg atgtctctga 64440
tcagtttaaa tatgtttact tttattccta atcaggaatg aaggtagaat tgtatcagat 64500
gctttttccg catctaatga gataatcgtg ttggttttgt cctttattac tgtggtacgt 64560
tactacaatt gacagatgtt aaaccaactt tgcattcctg gataatttgg tttactcata 64620
tttttattga tttttacatc tgtaatcata agggatattg gtcaatagtt gtcttctgat 64680
ttccctggct gactttgata gcgtggcaat tctggcctta ttggaaagga caacaactat 64740
aaaagacagg agggaatcgt ttgccacagc ttcagttggt agtgaacagt cccactctcc 64800
ccattcactt ctcagtattg ccatgtggcc tgtcagtaga aagattacct tatacttaat 64860
accttgacaa aagagcagta gaatggagtc tagacggatt ttctaccaca aaccattcga 64920
atgtaaaaag tatgagtgat gagcttctat tatctggcaa atatccatgt ataaaagacc 64980
atctcctatt aaatgctaat ttagtttatc tacaagtctg taatatttta gagttgctgg 65040
aatccagtaa aatttcctta tacagatttg gaaggcagcc taggtgtgca gaatactaaa 65100
ttatctagtt tacctttcct tccctttctc tctcagcatt tttctatgtt gtaatcattt 65160
tctttccatt ttattaacag aggaggaagg aagagacttg agctgttgtg tagcttctct 65220
tgttcaagtg atgctggatc cctattttag gacaattact ggatttcaga gtctgataca 65280
gaaggagtgg gtcatggcag gatatcagtt tctagacaga tgcaaccatc taaagagatc 65340
agagaaagag gtaacaaaat cttgatgcct ttttatcagt ctttaaggat acacaaaata 65400
aaatttgtgt cattaaaaga tgaaggggct tttaaaaaat actgtattta gtacaactta 65460
atttccttag tccaaagcta actaatggat tagagttcaa attgatgtac ttattataaa 65520
gattatcgta actatgaagg tgaaattttt aaaagttgtc tattgaattt gtctaagtgg 65580
aaaactactg aaaaaattct gaataaaata ctgaaaaaca gataacaagc acattggcta 65640
ttttgaaaaa tcacttttgg aatatcatat tttcttaaaa tgggatacat aggttaagat 65700
gaaaagtttg agagggccac ctttgcaaca gctgtggagt tagtggctgc ctcggatctc 65760
tagttaggct gcggaaggcc ttacaaatat cttaccggcc aggcaggtca gtcagatcag 65820
tttttagaag gttgtttcag agagcgccat ttgacttgtg gtgtctcata aaaaatagtg 65880
gtcacccgct actgcacttg gggacacacc acgtgaccta ggctcatccc aaagtgtttt 65940
ctgaaatatg gggatgtttt ctggatgctg agcctacagg atcaaccaaa cattagagaa 66000
gtttggttga tggttttgtt ttgttatata atctaaagaa ttgtttctaa gacatgctta 66060
aacacatatt ttgctcttcc cccttcatat agtggcaacc cgctcaactg tgtgctttgc 66120
tgtttcaact tgttacatgt actgggcaaa taagggttgt gatgtttatc acggttgaat 66180
gttacttctt gggtttgata gatgtgtata gctcagctta gaaggcaagt gttttaggct 66240
tcgatgtttt ctcattcatc tcttctttaa catcagcagt acattttgaa gtaaatgtga 66300
acggctgaag gataacatta aatgatccca ttgtctcttt gtatttgcca gtctccttta 66360
tttttgctat tcttggatgc cacctggcag ctgttagaac aatatcctgc agcttttgag 66420

-continued

```
ttctccgaaa cctacctggc agtgttgtat gacagcaccc ggatctcact gtttggcacc  66480
ttcctgttca actcccctca ccagcgagtg aagcaaagca cggtaagcaa ccctgtggct  66540
gtggctacgt tttccctgtt tttacaactt tatcgaggca taattgaagt ataattcact  66600
gcctatttaa aatcttatga tttaaaattc ttactgccat tttcagctga aatttctgaa  66660
tggattattt tgaagacaca aaaatctagg aaattatttt tatgaatgaa catttttttgt  66720
tttactctaa tgtaaatgtt ttgtagtaaa ccccctttaaa gatgtaaatt actttaacca  66780
ccttaaatgt catgcttttg tatttatatt tcacatttgg gctattgggt agtaaaaaac  66840
aaaagccctg ttacacgaca tttatttcct aggtcagtag gataaaaagt tgtacaaaac  66900
aagattattt tccttcacga gtttgaagtt tctggtcaca attcattgat gtagaggatt  66960
tatgactaag cagggtctca agccaaactt gaaaccattc tgaaccaaag tgccatttca  67020
cccacctcga accaacaaca gaagctgaca aatgccgtgg agaccattga gagaaacaga  67080
aaggggcagc tcttgtggac cttcaggaag cctttctagg aagaggattg ccctcatagt  67140
gagctccggg gtcttcagcc tcagccgtaa ggccctgggc taggcagtgt gacctaggga  67200
gcgggaaacc tgagttctgg ccctggtctg ggaaaagtgc taggcccatg ttccactcag  67260
gcttcagcct gagagtccag gttgctaacc tgtaaaatgg atctgtcaaa ctaacactta  67320
tgcctttagt ctcattgtat gaggtgaaac attttgtaaa ctgtgaatca ttatgcaaat  67380
tttcctaaag acatatgaat tattctggat ttgttggtat aaaagacaaa acacactggt  67440
cagttaagga gctgatttta tttaggctat tgcaggaggg agaacttaat taatgggcat  67500
cccaaagaaa aggacaaggc ctgggatttt atagtcagaa gacaggggaa tcaggaggga  67560
gggcagtctc agtccacagg agccagttct caggacacaa aaggcaggag agattgtcca  67620
gcattgccac ttttggggaa cccagggctc aaagaaactc aacaccgtca gcctgtctct  67680
acaaaaaata caaaaattag ccagacatgg tggtgcgcac ctgtggtccc agctactggg  67740
gaggctgagg tgggaggatg gcttaagccc aggaggcaga gattgcagtg agctgagact  67800
gtgccactgc actccagcct gggtgataga gccagagtct gtcccctgcc caccccacca  67860
ggaaagtttg acctttccag atactgtgct gagaaccagt gatacaggct tagaggctcc  67920
tgaggcatgg aacgctcatt tgttcctaaa atacatgctc tcccagttgc ttgtttttat  67980
ttttcgtcac cataatcatt cttggggccc ctctctgcct cgagctaggc tttccccctg  68040
gccttgtttg cctccttcag ctcttcccca ttgtctcccg tcactacccc gtgcgcacac  68100
agtgtgagcc tgcaaaaggt gcgtgaggcg aggacaaaga ctttggggtc tggggactgg  68160
gcagtgcatg ggtgggtatc tgcgtggagg actcccagcc cccagacacc actgcctctg  68220
ctgcttggct gatgctgtgt gtgcggacag acttctcacc aggaatgaac attactgaat  68280
tgtattgagg gagctgtaaa aaatactttc tacaagtatt tcctctgctt tccctgttca  68340
tgttctagtg ctctttttaa tttggctctt tcaaaagcct tttctgacaa atactaacat  68400
gaatcccccct ctcccttcct ccctagcagg aactggtcat tgtctaaggg tcgtgattct  68460
taaccgttct cagcccccttc cacacaggca aaagcccaaa gcatttcttc cttttttttc  68520
cattctgagg ccaccttagg tgctagtggc caggtagtgt ttatagaaaa tctggtctct  68580
cttgggataa atatttttaa tttttacctt ttaaaaaaga gaacatcttt tttttttttt  68640
ttaagacagt ttggctctgt cacccaggct ggagtacagt ggtacaatat cagctcactg  68700
caacctctgc ctcctgggtc caagcactgc tctcgcctca accacctgag tagctaggac  68760
tgcaggcgca tgccaccacg cctagctaat ttttgtattt ttttgtagag tcagggtttc  68820
```

-continued gccatgttgc ccagtctggt cttgaactcc tggactcaag caatccgccc acctcagctt 68880
cccaaagtac tgggattaca ggcgtgagcc accgtgcttg gccaagagga cattttctat 68940
atacttactg aagggccatt aaaacacgtt tgggttcatg ttttactaga tttcagctct 69000
taacagtgtt tgaagcaaat ggattgtttt taatccatgt acatgatgaa atgtcaagta 69060
actaaaattt tttttttttt ttttttgaga cagagtcttg ctctatcacc caggctggag 69120
cacagtggca tgatctcggc tcactgcaac ctctgccttc caggttcagg tgattctcct 69180
gccacagcct cccgagtagc tgggactaca ggtgcacacc accatgcctg gctaattttt 69240
gtatttttag tagagacggg gtttcaccat attggccagg ctggtcttga actcctgacc 69300
tcgtgatccg cctgccttcg gcctcccaaa gtgctgggat tacaggcatg agtcaccact 69360
gcgcctggcc aaaactgtta agagtatgtg tatttggtgc ttaatgaatt tttacttatt 69420
tgaaatagaa aattttgtaa aactttacaa aatgccctgt gctgttacac agcttagcca 69480
tttcttgatg attcaagccg ccactgtgcc agggaatgcc acctggctgt gatgtagtca 69540
tggcctcctg actgctatat tcttgtccta ataacattca ttgtttgcct ttttaataat 69600
ttccaaataa attcttgggg gttttttttt ggtagaaaat ttggagagta ctgaaaggta 69660
cagaacaaag aatcagacat ttcccatcat ccagcgactt tgtgtctgga gttatttcct 69720
ccagcgaact gttgtgtata cactgctgtg gtagcctgct gccatcaatc agctgagatg 69780
agagtccttt ctccacattg ctaaatgtga ctgtgcttca tagaaatggt ctgggctgcc 69840
ttccagagga gctccatgtc ttcctcacaa tgcggtggtt ggctgtcacc ctgtagcctt 69900
gtgttgcctc agtttactgt ggtgggaagc cagataacta ggctgcaccc gcccagagtc 69960
cgggctagag gtggactcct gtgaaggagg ggtctcctgt gtacatggtc tccatggttt 70020
tagccacatg ctaggaccac agggagttga tcccttcctt cctaccctga gtctgtggtc 70080
tgtgatttga gatcactggc tcagtgaagt gtagctcccc acttacgaag taagttataa 70140
aattggtggc agtgatttcc atccaaagat tttgttaatc cacttaccaa caggtaacta 70200
cttaaatgta ctgaccgtgt gctcataaaa gtaaaatact gtaattatag aaataaattc 70260
aacatgttta agactttcta gtatcatgtt agtgaaactt ctcttaataa cattcttatt 70320
gcccaaaggg cacggcttcc ttggggtcct aaggcagagg gcacctgaaa agcacactcc 70380
ttgttcatgg ggactgtggg gccctctgag ctcaaaggcc aggagcgtct cctctcttga 70440
agtgaaagtg ccactctggt gggttttgag ggctgcagta cagaacattt aacctgtgta 70500
atgatgagtg gctcatctga aaaaaggcat tcatgagaga atctttagtt ttgcaaatat 70560
ttatttattt attttgcagg aatttgctat aagcaaaaac atccaattgg gtgatgagaa 70620
gggcttaaaa ttcccctctg tttgggactg gtctctccag tttacagcaa aggatcgcac 70680
ccttttccat aaccccttct acattggaaa gagcacacct tgtatacaga atggctccgt 70740
gaagtctttt aaacggacaa aggtaaatca cagctaacaa aacgtgatgt tggctcacac 70800
gtaaccaaac acctcttttt cagaacagag agcgttaaaa gtaaaggcac ttccaagagt 70860
aacactgcta atgcgggttt ctgaggggtc attccctttt taactcaaat gactgtatcc 70920
cagctttctt cctggtgtct gaggcccaca aagtctcagt acctgagagt gggcagattg 70980
cagctttgag cctgcaagcc tgatttacta aagccccatt tatccatttc ttgatgattc 71040
aagccgccac tgtggcaggg aatgccgcct ggctgtgatg tagtcatggc ctcctgactg 71100
ctatattctt gtcctaataa cattcattgt ttgccttttt aataattccc aaataaattc 71160

-continued

```
ttgggatttt ttttggtaga aaatttgcag actactgaaa ggtacagaac aaagaatcag  71220
acatttggcc tcctgactgc ctctgttcag tttgccattg ttcttgatag aatcggccag  71280
gtctagtgtt ttttctagcc cgtcttagaa cttatcctta agcaaattag tggataggag  71340
gtactctcat cccgccccca ttcaggctga tagtaacagc ctaggtagag tcaacacata  71400
aaaaagtgta attccagggg aggaggatta gaataaggac acaaaggaag ggaggaaaat  71460
gttctttgag gctgaaattc cattaatttt tcatagtatt gagtttatat ttgccattgc  71520
atccttcaat ctttctaaaa agggaatccc cggaacataa taaaatctct tctgtataga  71580
aaagctacag ctccacacta agaggaatgc cgtctgcctt aaagaatgga atcatcagtg  71640
accaagaatt acttccaagg agaaattcat tgatattaaa accaaagcca gatccagctc  71700
agcaaaccga cagccagaac agtgatacgg agcagtattt tagagaatgg ttttccaaac  71760
ccgccaacct gcacggtgtt attctgccac gtgtctctgg aacacacata aaactgtgga  71820
aactgtgcta cttccgctgg gttcccgagg cccagatcag cctgggtgct ccatcacagc  71880
ctttcacaag ctctccctcc tggctgatga agtcgacgta ctgagcagga tgctgcggca  71940
acagcgcagt ggccccctgg aggcctgcta tggggagctg ggccagagca ggatgtactt  72000
caacgccagc ggccctcacc acaccgacac ctcggggaca ccggagtttc tctcctcctc  72060
atttccattt tctcctgtag ggaatctgtg cagacgaagc attttaggaa caccattaag  72120
caaattttta agtggggcca aaatatggtt gtctactgag acattagcaa atgaagacta  72180
aaatagggtg ttttctgaac attttgaggg aagctgtcaa ctttttttcct ctgaattaac  72240
attgctaacc taggcgtttg aatctctaat aactttatat gtaagaataa tagttggaat  72300
ttgcactaat atttaaaaac atgttgaatc atgcttcttt cacacttatt ttaagagaga  72360
tgtaaatttt gttcctgtcc tctttctgtc attacaggtc tggctcttgt aaccgtgatc  72420
aaactgttca tgttgtctgc tacatttttg tctccatcca tttttcctac cacctcctga  72480
aggctatctg atagtcagtc acattagcac cccaggcagc agacaacagg aaagttagga  72540
aatttgtgtt tcgtgtcatt tttaggagca tctgataaaa cctccagcag gttttaggaa  72600
gtattcatgt atttttctgg ttactttctg tcgtctctaa ttgaactcac ctgatgaagg  72660
ttcagtgttc tggggccaga atttatgatt ttagatcacc ttctttggaa ccttagatca  72720
ctgtgttttg aaatcatgag tttgctttta acttcatagg gtcaacttta aaatgatatg  72780
cactgttaat tttaaagcat ttgctgcaga taattaaact tagaagtgcc tttgacttta  72840
ggatacaaat attacagaag aaaatataat ttcacttttt aaaattgggg tgggaaaatc  72900
ccattgcata tttgaaatag gcttttcata ctaagcttca tagccaggag tccccagagt  72960
cttgttcctc tgaaagccac tggggagtgg cctctggggt gctgattcca cagaggtgta  73020
tgctgtagac aggagagtgc catctatgcc aaaactcgcc ctcaaaaaca aacaaggctt  73080
gctgggaggc gtgctgggct tggccatcag tatttccagt gtggtaaact attgctggca  73140
cttccccctg gaaataacta atgaggttac gagttgggca cctgcacaga tgtccttctc  73200
tcatagttcc taatgcttag gaatagagga gaaataaaaa aatggattct ctcaaaacac  73260
tgccatttga atagcgacag aagtgctccc ccagccccca actttggaca gcaaagttga  73320
ggagaatgag cagacacagt tgtttgcttg atctgaatct ctctaaagta aagtatttcc  73380
aaactgtgtg acaagagcct acctaccact gtagcggtca aagctgaagc ttcttacagc  73440
agtgaaacgg ggcaccacct cccccacact cctcattccc cgcttaaaac atggatactt  73500
tcaaatttga ctgtttctta aactgccatc ctaagatatg gaaaattttt atagtaaagt  73560
```

-continued

```
gtctagttag cttatttcct tttctaaaac aagtgttttc aagataactg tattttacct  73620
ttatatgtac tgaatagctg tttctttttg aattatttgc cttttaaaat ttgataatgt  73680
ctctggatat aacaggacag gagttcttaa aaaatatctt aagaaattca ctttatgggt  73740
aaacccaagg tttttgccaa cttgttgcct agaaaataag ggctagtttc agtttataca  73800
aatagaatta ttaaacattt tacagtcctt gattagaaac cagacccaat ctccttataa  73860
caccacagcg tatcctgcca ttgacagtgt aatcacaatt ctcccttttt catttagctg  73920
ctttttttatt attactaaat gttttggatt gagcattttt ccctctgtaa ttttcttcct  73980
tcacgtttat tttaactctt gtagtatttt attgttgtta atttacaagt ttaaaaatat  74040
taggtactat taataatggt taaaaataga aaaatgcata tttttgtatg ataatcaaat  74100
gtaaaatact tttatttttg ctggacagtt gttatatcat gattattgtg ctacagttta  74160
ttgtgcataa tatgaaaaac aactatgaca gccttcagtc gggccagggt gaagctgctt  74220
ataccacctc tgccgtcaga gggacatgtg gtgacagcag tggtgtggct gcacagggcg  74280
cactagagag agctcagcac ccctgctgcc cgccagcaga gcccgtgctg agggaatgcc  74340
gcacagatgc tgatgcactg ggtgaaattt ctagtattga acgtaaaggt gtacagtgtc  74400
ttgctgttat tttatgatgg aaactgattt tgaaaccaaa aatagctaac taactttatt  74460
taaggaaagg atattaattt gtactaacag agggtgaaag ctgttcacat ttgtcaacaa  74520
aatctgcttg ctgcagtagt aacctcaagt ggttaaaact tgatttcccg agaaaactaa  74580
aacctttgtg cctaaaattg atgacttgag ttcaagtggg atgagcaaga agatgtgtta  74640
tcttgttgtt caacagtatt gaatgtgaag gaaattttga tggcttaata aaattccaca  74700
gcgactgttt gttgttgtca gtatgaaatc atctactgga acacagtgat tgatagaaga  74760
ggtgaaggca tcttctccta cccatacttc tgtgtcatcc atgggatgtt tctgcttgcc  74820
ctctaaagcc aggtagtgat cagtaacttt ttttaacagc aattcggaag tggctaaagt  74880
taaagccatg tggatattga tagatcatgc cctaactggt ccttccattc aataaataaa  74940
tataaaaact ggggagtaat attcccccaa gaaggcttca aagaagtcaa gagacagact  75000
ggggttccag tccctgactc ccgggcctgg cgcatggata aatcaccttt ctaccacacc  75060
cccttgccca gcctgagacc ctcccacaat ggtgatgagc agccgatttg actgtactgt  75120
caacagagaa aataccccta tctagttatt agggatggtc ccagggagat ggacaatgaa  75180
ggacaactgc ctctgataaa gacttcattc ctttcatgat ccgggcccaa tcagtagaac  75240
aagcatttac atgttataaa tcaacacaac ttcatgagaa tgttttgatt cctaaagaaa  75300
ttggaatttc aactgtttca gcccttctta gataatcata aaagtttaac agctaaatgt  75360
gtatagggca gtaaagaaaa acttaattca agaatctcgg tttcccatat aattaattac  75420
ttgaaggaaa cactggttat gctagttttt aaatttttttt ttttttgaga cagagtctcg  75480
ctctgtctcc caggctggag tgcagtggtg caatctcggc tcactgcaag ctccacctcc  75540
cgggttcacg ccatcctcct gcctcagcct cctgagtagc tgggaccaca ggcgtgtgcc  75600
accaagccca cccaattttt tgtattttta gtagagatgg gtttcaccat gttggccagg  75660
atggtctcga tctcttgacc tcatgatgcg cctgcctcgc tcagcctccc aaagtgctgg  75720
gattacaggc atgagccact gtgcccagcc actacttttt tataaaaaaa acctaaagat  75780
gaatcatcac ttgtttttga gttttccagc tttttgcaca tctaatcata tagatgcatc  75840
cagctccaat aatggtcaac aaaatttttc tcttttaaaa aagttcatta tgagctgggt  75900
```

-continued

```
acagtggctc aatgcctgta atccccagca ctttgggagg ccaaggtgag taggtcagtt  75960
gaggtcagaa gttccagacc aacctggcca accaacatgg tgaaaccccg tctctactaa  76020
aaatacaaaa tttagccagg cgtggtggcg cacacctgta gtcccagcta ctggggaccc  76080
tgaggcagga gaatcacttg aacctagcag gcggaggttg cagtgagccg agatcacacc  76140
actgcactcc agcctgggtg acagagcgag actctgtctc aaaaaaaaaa aaaaaaaaaa  76200
aagtttatta cccactgtgt ggaatcaatg agtgtattca agcaaacact gttttgtgat  76260
atgcagacac tgtaaaatga caagtcaaac tatcaggttt ataatgcacg ataacaaaat  76320
taaataaaac atgttttata ctcttgaaaa tcttacatta atgtatgacc aaatatcccc  76380
aattccatac cttttagcta aggctttggc tcttagctcc aactgcaacc acatggcaga  76440
cttctacttc agcccccagc ttctgcagtt cagccagcca gatcatctgc ttatgtgaaa  76500
gacgatcatt ggggccttta acttccacca gctggaaaag aaatttttaa aagttgttat  76560
tagtatctta ctgaatgaaa agccattcaa gtaagttgta gttgtcactg acaactattt  76620
aaatggctct tctgctctct cactgtattt gtaagtgtaa cacaaatata cggatggtcc  76680
ttcacttaca atggttcacc ttaggatttt ttgacttaaa aatggtgcaa aagtgatata  76740
cattcaacag aaaccatact ctgagtgttg atcttttccc agtatgatac tccatgctgg  76800
gcagcagcag tgagccacag ctcccagtca gccacatgat catgaggata accagtactc  76860
tacggtttgc agtgaactac atgatctgcc caactgtagg ctaatgcaca cattctgagc  76920
acatttaagg taggctaagc taagctatga ggtttggtgg gataaatatg ttaaatgcat  76980
tttcaactta acaatatttt cagttgatgt gtaggattta tcaggacata aggccatcat  77040
aagttgagaa gcgtctgtat gtagctaaga aatttattca gaaattcttc tattctgtag  77100
aaactagaca gttcttcaca gaggatgagt aaactgattc ttagtatagc aaatgaaaaa  77160
ttgttttaaa gcatgcactg gattttactt ccttgcttaa aaccctccga ttactctgtt  77220
acattttcaa ttaaatctaa ccttcttgcc atgaccagtc tcttccctac cccaaggccc  77280
tcacttccac ttgctacttg ctgttcccgc tgcctgggac atttctccct gttcttgaca  77340
tgcctgactt cttacctttc aatgctcagc ttaaactgat ctggagaggt cacagctcta  77400
agtatatcct ccctatgcac ttctttcatg gcattcataa gataaaaata tatactacat  77460
gtcatcttca tgaaggcaag aattgtgtgt tttgttcact acacatcact agacttgaag  77520
acacagcaat aaaaactata ggtaaaatat agaaaaaaat tgtttaaata cagcatttag  77580
cagcctaagg gacatttaat tagagtcccc aaaggaacga gaaaaaaaaa tacttaaaga  77640
aaaaatggcc aaaaattttc caaatttgat gaaaacagta aacccaaaga ttgaagaaaa  77700
tcaatgaatc ccaggcacac aaatgtaacg gcaccctagg aaatatcaca actgtataat  77760
caggggatat agtcaaagca gccagaattt ttaaagccag aggaaaaaaa aagattctct  77820
gattggaaac catgctagtt agaagacagt agactaatat ttttaaagta ttgaaaaata  77880
actgtcaaca taaaattcat tgcacggaga aaatatcttt caaaaacaaa ggtgaaataa  77940
aggctaagac atacaaaacc taaatacagc catccctcag tatccatggg ggactgattc  78000
aaggaccccc tctgttacca aaatccatgg atgctcaagt ccctgatata aaatggcatc  78060
gcatctgcat attctagcac atcttctcat atactttaaa tcatctctac ttataatacc  78120
taatataaat gctatgaaaa tagttgttat gctgtatttt tatttgattt gtttattgtt  78180
gtagttactt tttattgttt ttcttttttc caaatacttt cagtccatgg ttgcatctac  78240
agaagcagaa accatggata cagagggcta actactgtaa ttcattacta gcagaacttc  78300
```

-continued tagacatgga aatttttttct ttttcttttt ttctttttttt ttgagacaag gtctcactct 78360
gttgcccagg ctggtataca gtggtatgat ctcagcacac tgcagccttg acctcccagc 78420
ctcaagcagt tctctcacct cagcctccca agcagctggg actacaagtg cacaccacca 78480
cacccagcta atttgtttat cgttttgtag agatgaggtc tcactgtgtt tgcccaagct 78540
ggtctccaac tcctgagccc aagcaatccg cccacctcag cctcccaaag tgctggaatt 78600
acaggcgtga aaggaaattc ttcaagcagg agaatgagac tacacagaaa cctggatcta 78660
cacaaaagaa tagcaagcac tggaaatgct atgtacatga gtaaatacag actcattaat 78720
caactgtaga aagcaaaaat aatatgttat agaacatata acacgtagaa gtaaaatata 78780
tgaaaacacc acaaaggctg gaagggaaga tatatattat tgaaaggttc tttttactct 78840
aaagtgtgta tcacctgaag gtggataagt ttaagatata taatatacta acgcaaccac 78900
ttcaacacaa tgaacagtta cagctaacaa gccagcaaag ctatcaaatg caatctttaa 78960
aaataagaca gggccaggca ctgtggctca tgcctgcaat cccaacacta agagaccacg 79020
gcaggtgaac tgcttgagcc tggggatttg agatcagcct gggcaacatg gtggaacccc 79080
atctctaaaa aatacaaaaa ccacaaaaat tagccaggca tggtggcgtg cacctgtggt 79140
tccagctact caggaaaaag acaagggaca aaagagttct gagacaaaga gaaaataagt 79200
atcaggattt aaagctaagg atatcaataa tcaaattaaa tgtaaatgtt ccaaacaccc 79260
cattaaaaga cagaggttaa gttggattca aaagtaagac ccaactatat gatgcctaca 79320
ggaaatccac attaaaaata agataaaaca ggtcaaaagt aaaagaatgg aaaaatgtat 79380
catgttaaca ttaaaaaaaa gaaggctgaa gtggctacat gttgacaata tcggacaaag 79440
ttgatttcag agcaaagatt accaggtgta aagggggggt cactgcataa tgataaaagg 79500
gtagactcat gaagaggaca tgacagtcct aaaagtctat gcgtcttata acagaccttc 79560
aaaatacatg aagcaaatag tgatagaaac gcaagaagaa atacacaaat tggctgggca 79620
cggtatactc tcagcatttt gggaggccaa cgtggagccc aggagtttga gaccagcctg 79680
ggcaacatgg tggaacccca tctctacaaa aaataaaaaa aatcagctgg gcatgatggt 79740
gcatgcctat agttcgggct actcaacagg ctgaggcaga agaattgctt gagcctggga 79800
gatcaaggct gcagcgatcc aggatcgcac tgccactaca ctccagccta ggtgatagtg 79860
agagtctgtc tcaaaaaaca aaaacaaaaa aaaaaagaaa agaaatacca caattataat 79920
cagagatatc aatattctct caataattta tagaacaagt aaataagaaa tcagtaagga 79980
cacagacaac ttaaacaaca ctatcaacca acttgaccta attgacattt aaaaatactg 80040
cccacaacaa atgctaaaca cacattcttt tcaagtacaa acagaatatt caccagggaa 80100
taccatattc tggaccataa aacaagtctc aacaaattta gtgggattca aatcatacaa 80160
aatatgtcct ctgaatacaa tggagttaaa ttacaaatca atagcagaaa gatacctgaa 80220
aatctctcaa gtgtttggaa atgtaaatga ctcacttcta aataagccaa ggatcaaaga 80280
agagtcaaaa gggaaatcag aaagtattgt gaactgaatg aaaatgaaaa caactactaa 80340
atttgtgagg ttcagataaa gcagcactga gaaggaaatt tggagcacta cctaactcta 80400
ttagaaaaga agttctcaaa gcaatcacca tagcttccac cttgagaaac taggaaataa 80460
aaaaacaaat gaaaccaaaa gctgattctt cgagaaaatc agtaaattga taaacctcct 80520
gccagactca ttagggaaaa aagagaaaag acacaaatta ccaatatcaa gaataagagc 80580
atgacagaga taaagattct acagatatta aaatacagta agaaatacat ggccgtgtgc 80640

-continued

```
ggtggctcac accctgtaat cccagcactt tgggaggcca aggtgggcag atctgaagcc  80700
aggagttcaa gaccagcctg gccaacatgg caaaacctca tctctactaa aaatacaaaa  80760
aaaaaaaaaa attatccagg catggtggtg cacagctgta atcccagcta ctagggaggc  80820
tgaggcacga gaatcacttg aacccaggag gcggaagttg cagtgagcta actcacgcta  80880
ctacactcca gtctgggcga cagagcgaga ctccatctca aaaaaaaaaa aaaagaaaag  80940
aaacaaatat aaacaacttt aagacaatac ttaaatgaaa tggacaaatt ccttgaaaga  81000
cacaaactag caaagcgcaa tcaagaagaa acagataata tgaacagcct tatgttgttt  81060
aaaaataaat ttaatttata gctttaaatt ttcctccccc caaaatctcc aggcccatac  81120
tgcttcactg gggaattcta tcaaatgttt agggaataat actaattcta caccaactat  81180
tccatcccac tctgatgctg gtatgactct gaaaccaaaa cccaacaaag agataataag  81240
aaaagaaaag tacagctcaa tatccttcat gaacatatat gcaaaaattc ttaatatttt  81300
acaaaatcaa ctcccatttt tgctgatcaa aataatgctg ttaagatacc aattcctctc  81360
agattggtct acagattcaa aggaattcca attaaaatct cagctggctt tttttttttt  81420
tttttttttg agatggagtc ttgctctgtc gcccaggctg gagggcagtg gtgccatctc  81480
ggctcttgac aacctccacc tcctgggttc aagcgattct cctgcctcag cctcccaagt  81540
agctgggact acaggcgccc gccaccacac ccggctaatt ttttgtattt ttagtagaga  81600
cggggtttca ccatgttagc caggatggtc tcaatctcct gacctcgtga tccgcccacc  81660
tctgtctccc aaagtgctgg gattacaggt gtgagccacc gtacccggcc tcagctggct  81720
tttttttttc ttggaaactt aaaatttgat gttataattc aaataaaaat gcaaaagagc  81780
cagaacaact ttgaaaaaca agtcattata ggacttacac tacctgactc caagatgtat  81840
ctaaagctac aataatcaag aaatacagac aaacagatca atggaaccga agagtatata  81900
gaaacagacc cacatatata tgggttactg atttttgaca aagatacaga gggaattcag  81960
tggaggaagc atggtcttct tgacacatgg agctggaaca agtggatatc cacacaccac  82020
aaatgaattc cagtgcatgc cccacactgt atacaaatgg cgtctcaaat gatcataaaa  82080
ctgaatgtaa aacctaaaac tataacactt ctagaagaaa acaaaggaga aactctttgt  82140
gaccttggat taggcaagta tttctgacat gtgacaccaa aagcatgatc cactagagaa  82200
caaataagtt ggattttgtc aaactttgaa acctctgctc ttcaaaagac actattaaga  82260
aaatgaaaag acaagccata gactgggatg aaatgtcact gataaaggac ttgtatccag  82320
gatatataat tttttaatct caaaactcaa taatgagaaa acaaatcacc agtgatgggc  82380
agcagggctg ggctagtgga cagcgttcaa ggaagtgttc actctctgag ctttttaaaa  82440
aatttttttgt gggtacatag tagatgtata tatttatggg gtacatgaga tgttttgata  82500
caggcatgca atgtgaacta agcacatcaa ggggaatggg gtatctgtcc cctcaagcat  82560
ttatcctttg agttacaaac cattatactc tttaagtcat tttaaaatgt acaattatcg  82620
gtaagcttct aaaatagctc ctggtgtcca cacccgttgt gaccccctcc ctttgagtgt  82680
cagctggact agagactcgt tcctaaccac agaatacagc aggagtgatg gaacatcatg  82740
tccacatcaa gtcataagag atggagctct gtcttgctca cactctgggg ctcctctcac  82800
ccgcctgctc tgatgaagcc agtcgcaggg gacaggccca caggaaccca ggccctcggc  82860
ccaaaagctc tcaaggaatt caatcttgcc aacagccact caagaaatgc ctacttgtgg  82920
cctctgattc agttgctaat aaggttacca acaggacttt ccattctgcc tcaactgacc  82980
ttaaagtgac ggctctggga gttccacacc accaggtcgg ggaggccccc tcgacagtgt  83040
```

-continued cgaaagtcag cagccaggtg cctgcacaca ccactgagca cagggccccc caggcaggag 83100
acaagatcct gaacacaaaa cacaggacag ttagccactt ccctcgtgac agagaatgga 83160
aataggctcc agggatcacg agacggagaa aagctcagtg tatatgtaat tcagtgcaca 83220
tggaccccag gcccaccatg cgctgttctg ctgcttgtac cagagctgca gagccatggc 83280
tggaatccca ctggcaagtg gtgggagact ggtcctcctg tggtcagttt ccaggcttct 83340
gcagcgtggc catgctgggg agcgctgagg aagagggatg tggaggatgc actcaggaac 83400
gcgacagcat ggcctcatag agggcagcag ttgaaggaac acagaaggta 83450

<210> SEQ ID NO 4
<211> LENGTH: 476
<212> TYPE: PRT
<213> ORGANISM: Homo sapiens

<400> SEQUENCE: 4

Gly Glu Ile Val Val Asn Glu Val Asn Phe Val Arg Lys Cys Ile Ala
1 5 10 15

Thr Asp Thr Ser Gln Tyr Asp Leu Trp Gly Lys Leu Ile Cys Ser Asn
20 25 30

Phe Lys Ile Ser Phe Ile Thr Asp Asp Pro Met Pro Leu Gln Lys Phe
35 40 45

His Tyr Arg Asn Leu Leu Leu Gly Glu His Asp Val Pro Leu Thr Cys
50 55 60

Ile Glu Gln Ile Val Thr Val Asn Asp His Lys Arg Lys Gln Lys Val
65 70 75 80

Leu Gly Pro Asn Gln Lys Leu Lys Phe Asn Pro Thr Glu Leu Ile Ile
85 90 95

Tyr Cys Lys Asp Phe Arg Ile Val Arg Phe Arg Phe Asp Glu Ser Gly
100 105 110

Pro Glu Ser Ala Lys Lys Val Cys Leu Ala Ile Ala His Tyr Ser Gln
115 120 125

Pro Thr Asp Leu Gln Leu Leu Phe Ala Phe Glu Tyr Val Gly Lys Lys
130 135 140

Tyr His Asn Ser Ala Asn Lys Ile Asn Gly Ile Pro Ser Gly Asp Gly
145 150 155 160

Gly Gly Gly Gly Gly Gly Gly Asn Gly Ala Gly Gly Gly Ser Ser Gln
165 170 175

Lys Thr Pro Leu Phe Glu Thr Tyr Ser Asp Trp Asp Arg Glu Ile Lys
180 185 190

Arg Thr Gly Ala Ser Gly Trp Arg Val Cys Ser Ile Asn Glu Gly Tyr
195 200 205

Met Ile Ser Thr Cys Leu Pro Glu Tyr Ile Val Val Pro Ser Ser Leu
210 215 220

Ala Asp Gln Asp Leu Lys Ile Phe Ser His Ser Phe Val Gly Arg Arg
225 230 235 240

Met Pro Leu Trp Cys Trp Ser His Ser Asn Gly Ser Ala Leu Val Arg
245 250 255

Met Ala Leu Ile Lys Asp Val Leu Gln Gln Arg Lys Ile Asp Gln Arg
260 265 270

Ile Cys Asn Ala Ile Thr Lys Ser His Pro Gln Arg Ser Asp Val Tyr
275 280 285

Lys Ser Asp Leu Asp Lys Thr Leu Pro Asn Ile Gln Glu Val Gln Ala
290 295 300

-continued

```
Ala Phe Val Lys Leu Lys Gln Leu Cys Val Asn Glu Pro Phe Glu Glu
305                 310                 315                 320

Thr Glu Glu Lys Trp Leu Ser Ser Leu Glu Asn Thr Arg Trp Leu Glu
                325                 330                 335

Tyr Val Arg Ala Phe Leu Lys His Ser Ala Glu Leu Val Tyr Met Leu
            340                 345                 350

Glu Ser Lys His Leu Ser Val Val Leu Gln Glu Glu Glu Gly Arg Asp
        355                 360                 365

Leu Ser Cys Cys Val Ala Ser Leu Val Gln Val Met Leu Asp Pro Tyr
    370                 375                 380

Phe Arg Thr Ile Thr Gly Phe Gln Ser Leu Ile Gln Lys Glu Trp Val
385                 390                 395                 400

Met Ala Gly Tyr Gln Phe Leu Asp Arg Cys Asn His Leu Lys Arg Ser
                405                 410                 415

Glu Lys Glu Ser Pro Leu Phe Leu Leu Phe Leu Asp Ala Thr Trp Gln
            420                 425                 430

Leu Leu Glu Gln Tyr Pro Ala Ala Phe Glu Phe Ser Glu Thr Tyr Leu
        435                 440                 445

Ala Val Leu Tyr Asp Ser Thr Arg Ile Ser Leu Phe Gly Thr Phe Leu
    450                 455                 460

Phe Asn Ser Pro His Gln Arg Val Lys Gln Ser Thr
465                 470                 475


<210> SEQ ID NO 5
<211> LENGTH: 434
<212> TYPE: PRT
<213> ORGANISM: Homo sapiens

<400> SEQUENCE: 5

Met Pro Leu Gln Lys Phe His Tyr Arg Asn Leu Leu Leu Gly Glu His
 1               5                  10                  15

Asp Val Pro Leu Thr Cys Ile Glu Gln Ile Val Thr Val Asn Asp His
            20                  25                  30

Lys Arg Lys Gln Lys Val Leu Gly Pro Asn Gln Lys Leu Lys Phe Asn
        35                  40                  45

Pro Thr Glu Leu Ile Ile Tyr Cys Lys Asp Phe Arg Ile Val Arg Phe
    50                  55                  60

Arg Phe Asp Glu Ser Gly Pro Glu Ser Ala Lys Lys Val Cys Leu Ala
65                  70                  75                  80

Ile Ala His Tyr Ser Gln Pro Thr Asp Leu Gln Leu Leu Phe Ala Phe
                85                  90                  95

Glu Tyr Val Gly Lys Lys Tyr His Asn Ser Ala Asn Lys Ile Asn Gly
            100                 105                 110

Ile Pro Ser Gly Asp Gly Gly Gly Gly Gly Gly Gly Gly Asn Gly Ala
        115                 120                 125

Gly Gly Gly Ser Ser Gln Lys Thr Pro Leu Phe Glu Thr Tyr Ser Asp
    130                 135                 140

Trp Asp Arg Glu Ile Lys Arg Thr Gly Ala Ser Gly Trp Arg Val Cys
145                 150                 155                 160

Ser Ile Asn Glu Gly Tyr Met Ile Ser Thr Cys Leu Pro Glu Tyr Ile
                165                 170                 175

Val Val Pro Ser Ser Leu Ala Asp Gln Asp Leu Lys Ile Phe Ser His
            180                 185                 190

Ser Phe Val Gly Arg Arg Met Pro Leu Trp Cys Trp Ser His Ser Asn
```

-continued

```
        195                 200                 205

Gly Ser Ala Leu Val Arg Met Ala Leu Ile Lys Asp Val Leu Gln Gln
    210                 215                 220

Arg Lys Ile Asp Gln Arg Ile Cys Asn Ala Ile Thr Lys Ser His Pro
225                 230                 235                 240

Gln Arg Ser Asp Val Tyr Lys Ser Asp Leu Asp Lys Thr Leu Pro Asn
                245                 250                 255

Ile Gln Glu Val Gln Ala Ala Phe Val Lys Leu Lys Gln Leu Cys Val
            260                 265                 270

Asn Glu Pro Phe Glu Glu Thr Glu Glu Lys Trp Leu Ser Ser Leu Glu
        275                 280                 285

Asn Thr Arg Trp Leu Glu Tyr Val Arg Ala Phe Leu Lys His Ser Ala
    290                 295                 300

Glu Leu Val Tyr Met Leu Glu Ser Lys His Leu Ser Val Val Leu Gln
305                 310                 315                 320

Glu Glu Glu Gly Arg Asp Leu Ser Cys Cys Val Ala Ser Leu Val Gln
                325                 330                 335

Val Met Leu Asp Pro Tyr Phe Arg Thr Ile Thr Gly Phe Gln Ser Leu
            340                 345                 350

Ile Gln Lys Glu Trp Val Met Ala Gly Tyr Gln Phe Leu Asp Arg Cys
        355                 360                 365

Asn His Leu Lys Arg Ser Glu Lys Glu Ser Pro Leu Phe Leu Leu Phe
    370                 375                 380

Leu Asp Ala Thr Trp Gln Leu Leu Glu Gln Tyr Pro Ala Ala Phe Glu
385                 390                 395                 400

Phe Ser Glu Thr Tyr Leu Ala Val Leu Tyr Asp Ser Thr Arg Ile Ser
                405                 410                 415

Leu Phe Gly Thr Phe Leu Phe Asn Ser Pro His Gln Arg Val Lys Gln
            420                 425                 430

Ser Thr


<210> SEQ ID NO 6
<211> LENGTH: 668
<212> TYPE: PRT
<213> ORGANISM: Homo sapiens

<400> SEQUENCE: 6

Lys Ala Pro Lys Pro Ser Phe Val Ser Tyr Val Arg Pro Glu Glu Ile
 1               5                  10                  15

His Thr Asn Glu Lys Glu Val Thr Glu Lys Glu Val Thr Leu His Leu
            20                  25                  30

Leu Pro Gly Glu Gln Leu Leu Cys Glu Ala Ser Thr Val Leu Lys Tyr
        35                  40                  45

Val Gln Glu Asp Ser Cys Gln His Gly Val Tyr Gly Arg Leu Val Cys
    50                  55                  60

Thr Asp Phe Lys Ile Ala Phe Leu Gly Asp Asp Glu Ser Ala Leu Asp
65                  70                  75                  80

Asn Asp Glu Thr Gln Phe Lys Asn Lys Val Ile Gly Glu Asn Asp Ile
                85                  90                  95

Thr Leu His Cys Val Asp Gln Ile Tyr Gly Val Phe Asp Glu Lys Lys
            100                 105                 110

Lys Thr Leu Phe Gly Gln Leu Lys Lys Tyr Pro Glu Lys Leu Ile Ile
        115                 120                 125

His Cys Lys Asp Leu Arg Val Phe Gln Phe Cys Leu Arg Tyr Thr Lys
```

-continued

```
    130                 135                 140

Glu Glu Glu Val Lys Arg Ile Val Ser Gly Ile Ile His His Thr Gln
145                 150                 155                 160

Ala Pro Lys Leu Leu Lys Arg Leu Phe Leu Phe Ser Tyr Ala Thr Ala
                165                 170                 175

Ala Gln Asn Asn Thr Val Thr Asp Pro Lys Asn His Thr Val Met Phe
            180                 185                 190

Asp Thr Leu Lys Asp Trp Cys Trp Glu Leu Glu Arg Thr Lys Gly Asn
        195                 200                 205

Met Lys Tyr Lys Ala Val Ser Val Asn Glu Gly Tyr Lys Val Cys Glu
    210                 215                 220

Arg Leu Pro Ala Tyr Phe Val Val Pro Thr Pro Leu Pro Glu Glu Asn
225                 230                 235                 240

Val Gln Arg Phe Gln Gly His Gly Ile Pro Ile Trp Cys Trp Ser Cys
                245                 250                 255

His Asn Gly Ser Ala Leu Leu Lys Met Ser Ala Leu Pro Lys Glu Gln
            260                 265                 270

Asp Asp Gly Ile Leu Gln Ile Gln Lys Ser Phe Leu Asp Gly Ile Tyr
        275                 280                 285

Lys Thr Ile His Arg Pro Pro Tyr Glu Ile Val Lys Thr Glu Asp Leu
    290                 295                 300

Ser Ser Asn Phe Leu Ser Leu Gln Glu Ile Gln Thr Ala Tyr Ser Lys
305                 310                 315                 320

Phe Lys Gln Leu Phe Leu Ile Asp Asn Ser Thr Glu Phe Trp Asp Thr
                325                 330                 335

Asp Ile Lys Trp Phe Ser Leu Leu Glu Ser Ser Ser Trp Leu Asp Ile
            340                 345                 350

Ile Arg Arg Cys Leu Lys Lys Ala Ile Glu Ile Thr Glu Cys Met Glu
        355                 360                 365

Ala Gln Asn Met Asn Val Leu Leu Leu Glu Glu Asn Ala Ser Asp Leu
    370                 375                 380

Cys Cys Leu Ile Ser Ser Leu Val Gln Leu Met Met Asp Pro His Cys
385                 390                 395                 400

Arg Thr Arg Ile Gly Phe Gln Ser Leu Ile Gln Lys Glu Trp Val Met
                405                 410                 415

Gly Gly His Cys Phe Leu Asp Arg Cys Asn His Leu Arg Gln Asn Asp
            420                 425                 430

Lys Glu Glu Val Pro Val Phe Leu Leu Phe Leu Asp Cys Val Trp Gln
        435                 440                 445

Leu Val His Gln His Pro Pro Ala Phe Glu Phe Thr Glu Thr Tyr Leu
    450                 455                 460

Thr Val Leu Ser Asp Ser Leu Tyr Ile Pro Ile Phe Ser Thr Phe Phe
465                 470                 475                 480

Phe Asn Ser Pro His Gln Lys Asp Thr Asn Met Gly Arg Glu Gly Gln
                485                 490                 495

Asp Thr Gln Ser Lys Pro Leu Asn Leu Leu Thr Val Trp Asp Trp Ser
            500                 505                 510

Val Gln Phe Glu Pro Lys Ala Gln Thr Leu Leu Lys Asn Pro Leu Tyr
        515                 520                 525

Val Glu Lys Pro Lys Leu Asp Lys Gly Gln Arg Lys Gly Met Arg Phe
    530                 535                 540

Lys His Gln Arg Gln Leu Ser Leu Pro Leu Thr Gln Ser Lys Ser Ser
545                 550                 555                 560
```

-continued

```
Pro Lys Arg Gly Phe Phe Arg Glu Glu Thr Asp His Leu Ile Lys Asn
                565                 570                 575

Leu Leu Gly Lys Arg Ile Ser Lys Leu Ile Asn Ser Ser Asp Glu Leu
            580                 585                 590

Gln Asp Asn Phe Arg Glu Phe Tyr Asp Ser Trp His Ser Lys Ser Thr
        595                 600                 605

Asp Tyr His Gly Leu Leu Leu Pro His Ile Glu Gly Pro Glu Ile Lys
    610                 615                 620

Val Trp Ala Gln Arg Tyr Leu Arg Trp Ile Pro Glu Ala Gln Ile Leu
625                 630                 635                 640

Gly Gly Gly Gln Val Ala Thr Leu Ser Lys Leu Leu Glu Met Met Glu
                645                 650                 655

Glu Val Gln Ser Leu Gln Glu Lys Ile Asp Glu Arg
            660                 665


<210> SEQ ID NO 7
<211> LENGTH: 508
<212> TYPE: PRT
<213> ORGANISM: Homo sapiens

<400> SEQUENCE: 7

Lys Ala Pro Lys Pro Ser Phe Val Ser Tyr Val Arg Pro Glu Glu Ile
 1               5                  10                  15

His Thr Asn Glu Lys Glu Val Thr Glu Lys Glu Val Thr Leu His Leu
            20                  25                  30

Leu Pro Gly Glu Gln Leu Leu Cys Glu Ala Ser Thr Val Leu Lys Tyr
        35                  40                  45

Val Gln Glu Asp Ser Cys Gln His Gly Val Tyr Gly Arg Leu Val Cys
    50                  55                  60

Thr Asp Phe Lys Ile Ala Phe Leu Gly Asp Asp Glu Ser Ala Leu Asp
65                  70                  75                  80

Asn Asp Glu Thr Gln Phe Lys Asn Lys Val Ile Gly Glu Asn Asp Ile
                85                  90                  95

Thr Leu His Cys Val Asp Gln Ile Tyr Gly Val Phe Asp Glu Lys Lys
            100                 105                 110

Lys Thr Leu Phe Gly Gln Leu Lys Lys Tyr Pro Glu Lys Leu Ile Ile
        115                 120                 125

His Cys Lys Asp Leu Arg Val Phe Gln Phe Cys Leu Arg Tyr Thr Lys
    130                 135                 140

Glu Glu Glu Val Lys Arg Ile Val Ser Gly Ile Ile His His Thr Gln
145                 150                 155                 160

Ala Pro Lys Leu Leu Lys Arg Leu Phe Leu Phe Ser Tyr Ala Thr Ala
                165                 170                 175

Ala Gln Asn Asn Thr Val Thr Val Pro Lys Asn His Thr Val Met Phe
            180                 185                 190

Asp Thr Leu Lys Asp Trp Cys Trp Glu Leu Glu Arg Thr Lys Gly Asn
        195                 200                 205

Met Lys Tyr Lys Ala Val Ser Val Asn Glu Gly Tyr Lys Val Cys Glu
    210                 215                 220

Arg Leu Pro Ala Tyr Phe Val Val Pro Thr Pro Leu Pro Glu Glu Asn
225                 230                 235                 240

Val Gln Arg Phe Gln Gly His Gly Ile Pro Ile Trp Cys Trp Ser Cys
                245                 250                 255

His Asn Gly Ser Ala Leu Leu Lys Met Ser Ala Leu Pro Lys Glu Gln
```

-continued

```
            260                 265                 270

Asp Asp Gly Ile Leu Gln Ile Gln Lys Ser Phe Leu Asp Gly Ile Tyr
        275                 280                 285

Lys Thr Ile His Arg Pro Pro Tyr Glu Ile Val Lys Thr Glu Asp Leu
    290                 295                 300

Ser Ser Asn Phe Leu Ser Leu Gln Glu Ile Gln Thr Ala Tyr Ser Lys
305                 310                 315                 320

Phe Lys Gln Leu Phe Leu Ile Asp Asn Ser Thr Glu Phe Trp Asp Thr
                325                 330                 335

Asp Ile Lys Trp Phe Ser Leu Leu Glu Ser Ser Ser Trp Leu Asp Ile
            340                 345                 350

Ile Arg Arg Cys Leu Lys Lys Ala Ile Glu Ile Thr Glu Cys Met Glu
        355                 360                 365

Ala Gln Asn Met Asn Val Leu Leu Leu Glu Glu Asn Ala Ser Asp Leu
    370                 375                 380

Cys Cys Leu Ile Ser Ser Leu Val Gln Leu Met Met Asp Pro His Cys
385                 390                 395                 400

Arg Thr Arg Ile Gly Phe Gln Ser Leu Ile Gln Lys Glu Trp Val Met
                405                 410                 415

Gly Gly His Cys Phe Leu Asp Arg Cys Asn His Leu Arg Gln Asn Asp
            420                 425                 430

Lys Glu Glu His Gln Arg Gln Leu Ser Leu Pro Leu Thr Gln Ser Lys
        435                 440                 445

Ser Ser Pro Lys Arg Gly Phe Phe Arg Glu Glu Thr Asp His Leu Ile
    450                 455                 460

Lys Asn Leu Leu Gly Lys Arg Ile Ser Lys Leu Ile Asn Ser Ser Asp
465                 470                 475                 480

Glu Leu Gln Asp Asn Phe Arg Glu Phe Tyr Asp Ser Trp His Ser Lys
                485                 490                 495

Ser Thr Asp Tyr His Gly Leu Leu Leu Pro His Ile
            500                 505


<210> SEQ ID NO 8
<211> LENGTH: 80
<212> TYPE: PRT
<213> ORGANISM: Homo sapiens

<400> SEQUENCE: 8

Ser Asp Glu Leu Gln Asp Asn Phe Arg Glu Phe Tyr Asp Ser Trp His
 1               5                  10                  15

Ser Lys Ser Thr Asp Tyr His Gly Leu Leu Leu Pro His Ile Glu Gly
            20                  25                  30

Pro Glu Ile Lys Val Trp Ala Gln Arg Tyr Leu Arg Trp Ile Pro Glu
        35                  40                  45

Ala Gln Ile Leu Gly Gly Gly Gln Val Ala Thr Leu Ser Lys Leu Leu
    50                  55                  60

Glu Met Met Glu Glu Val Gln Ser Leu Gln Glu Lys Ile Asp Glu Arg
65                  70                  75                  80


<210> SEQ ID NO 9
<211> LENGTH: 638
<212> TYPE: PRT
<213> ORGANISM: Drosophila melanogaster

<400> SEQUENCE: 9

Phe Gly Leu Leu Ser Val Thr Asn Phe Lys Leu Ala Phe Val Pro Leu
```

-continued

```
1               5                   10                  15

His Glu Lys Arg Asn Gln Ala Ile Thr Ala Pro Leu Ile Asp Leu Tyr
            20                  25                  30

Gln Glu Asn Thr Tyr Leu Gly Arg Asn Glu Ile Thr Leu Asn Asn Ile
        35                  40                  45

Asp His Ile Tyr Thr Ile Thr Glu Leu Gly Arg Ala Ala Ser Ala Leu
    50                  55                  60

Gln Ala Ala Arg Gly Met Ala Ser His Ala Gly Met Ser Arg Arg Lys
65                  70                  75                  80

Lys Leu Glu Pro Phe Lys Gln Gln Asn Ile Ser Gly Arg Ile Ala Ala
                85                  90                  95

Leu His Ile Val Cys Lys Asn Phe Arg Leu Leu Lys Phe Ala Phe Gln
            100                 105                 110

Gln Gln Asp Ser Lys Met Phe Gly Ala Ser Asp Gln Gly Lys Leu Ile
        115                 120                 125

Ala Ser Ala Leu Val Arg Phe Ala Tyr Pro Met Arg His Asp Leu Ser
    130                 135                 140

Phe Ala Tyr Ala His Arg Glu Pro Tyr Tyr Ser Thr Leu Gly Ala Ser
145                 150                 155                 160

Gly Thr Ser Met Tyr Ala Thr Lys Asn Asp Trp Ala Arg Glu Leu Ile
                165                 170                 175

Arg Cys Gly Ala Thr Glu Trp Gln Val Val Ser Cys Ala Ser Val Gln
            180                 185                 190

Leu Leu Gln Asn Pro Leu Gln Ala Gly Lys Tyr Thr Val Pro Pro His
        195                 200                 205

Phe Val Ile Pro Lys Ser Cys Ser Val Asp Arg Phe Leu Asp Leu Ser
    210                 215                 220

Arg Ala Phe Cys Asp Ser Arg Ala Ala Phe Trp Val Tyr Ser Tyr Gly
225                 230                 235                 240

Ser Ser Ala Ala Leu Val Arg Leu Ala Glu Leu Gln Pro Ala Ala Gln
                245                 250                 255

Gln Asp Thr Lys Ser Glu Asn Val Met Leu Glu Leu Val Arg Lys Cys
            260                 265                 270

Asp Ala Gly Arg Gln Leu Lys Leu Leu Gln Leu Thr Asp Arg Leu Pro
        275                 280                 285

Ser Ile Gln Asp Val Leu Arg Ala Tyr Gln Lys Leu Arg Arg Leu Cys
    290                 295                 300

Thr Pro Glu Thr Pro Glu Lys Phe Met Leu Gln Asp Asp Lys Tyr Leu
305                 310                 315                 320

Gly Leu Leu Glu Lys Thr Asn Trp Leu Phe Tyr Val Ser Leu Cys Leu
                325                 330                 335

Arg Tyr Ala Ser Glu Ala Ser Ala Thr Leu Arg Ser Gly Val Thr Cys
            340                 345                 350

Val Leu Gln Glu Ser Asn Gly Arg Asp Leu Cys Cys Val Ile Ser Ser
        355                 360                 365

Leu Ala Gln Leu Leu Leu Asp Pro His Phe Arg Thr Ile Asp Gly Phe
    370                 375                 380

Gln Ser Leu Val Gln Lys Glu Trp Val Ala Leu Glu His Pro Phe Gln
385                 390                 395                 400

Arg Arg Leu Gly His Val Tyr Pro Ala Gln Pro Ala Gly Gly Asn Ala
                405                 410                 415

Glu Leu Phe Asp Ser Glu Gln Ser Pro Val Phe Leu Leu Phe Leu Asp
            420                 425                 430
```

-continued

Cys Val Trp Gln Leu Leu Gln Gln Phe Pro Asp Glu Phe Glu Phe Thr
        435                 440                 445

Gln Thr Tyr Leu Thr Thr Leu Trp Asp Ser Cys Phe Met Pro Ile Phe
    450                 455                 460

Asp Thr Phe Gln Phe Asp Thr Gln Ala Gln Arg Leu Lys Ala Val Thr
465                 470                 475                 480

Asp Ser Gln Leu Val Leu Arg Pro Val Trp Asp Trp Gly Glu Gln Phe
                485                 490                 495

Ser Asp Lys Asp Lys Met Phe Phe Ser Asn Pro Leu Tyr Gln Arg Gln
            500                 505                 510

Arg Gly Asp Leu Gly Ala Gln Ala Ala Ala Val Ala His Arg Arg Ser
        515                 520                 525

Leu Ala Val Gly Ser Lys Gly Ala His Gly Ala Ala Ser Gly Val Thr
    530                 535                 540

Pro Ser Arg Asn Thr Ile Asn Pro Gln Leu Phe Ala Thr Ala Ser Ser
545                 550                 555                 560

Val Pro Gln Asp Arg Tyr Leu Gln Pro Ala His Arg Ile Phe Asp Leu
                565                 570                 575

Gln Val Trp Asp Gln Cys Tyr Tyr Arg Trp Leu Pro Ile Leu Asp Ile
            580                 585                 590

Arg Gly Gly Gly Gln Pro Gln Val Asp Leu Tyr His Arg Leu Leu Leu
        595                 600                 605

Ser Asn Ile Ala Lys Val Gln Arg Cys Leu Asp Tyr Gln Asn Phe Asp
    610                 615                 620

Asp Leu Pro Asp Ala Tyr Tyr Glu Phe Ala Gly Glu Ser Arg
625                 630                 635

<210> SEQ ID NO 10
<211> LENGTH: 458
<212> TYPE: PRT
<213> ORGANISM: Homo sapiens

<400> SEQUENCE: 10

Glu Pro Pro Leu Leu Pro Gly Glu Asn Ile Lys Asp Met Ala Lys Asp
1               5                   10                  15

Val Thr Tyr Ile Cys Pro Phe Thr Gly Ala Val Arg Gly Thr Leu Thr
            20                  25                  30

Val Thr Asn Tyr Arg Leu Tyr Phe Lys Ser Met Glu Arg Asp Pro Pro
        35                  40                  45

Phe Val Leu Asp Ala Ser Leu Gly Val Ile Asn Arg Val Glu Lys Ile
    50                  55                  60

Gly Gly Ala Ser Ser Arg Gly Glu Asn Ser Tyr Gly Leu Glu Thr Val
65                  70                  75                  80

Cys Lys Asp Ile Arg Asn Leu Arg Phe Ala His Lys Pro Glu Gly Arg
                85                  90                  95

Thr Arg Arg Ser Ile Phe Glu Asn Leu Met Lys Tyr Ala Phe Pro Val
            100                 105                 110

Ser Asn Asn Leu Pro Leu Phe Ala Phe Glu Tyr Lys Glu Val Phe Pro
        115                 120                 125

Glu Asn Gly Trp Lys Leu Tyr Asp Pro Leu Leu Glu Tyr Arg Arg Gln
    130                 135                 140

Gly Ile Pro Asn Glu Ser Trp Arg Ile Thr Lys Ile Asn Glu Arg Tyr
145                 150                 155                 160

Glu Leu Cys Asp Thr Tyr Pro Ala Leu Leu Val Val Pro Ala Asn Ile

-continued

```
                165                 170                 175

Pro Asp Glu Glu Leu Lys Arg Val Ala Ser Phe Arg Ser Arg Gly Arg
            180                 185                 190

Ile Pro Val Leu Ser Trp Ile His Pro Glu Ser Gln Ala Thr Ile Thr
        195                 200                 205

Arg Cys Ser Gln Pro Met Val Gly Val Ser Gly Lys Arg Ser Lys Glu
    210                 215                 220

Asp Glu Lys Tyr Leu Gln Ala Ile Met Asp Ser Asn Ala Gln Ser His
225                 230                 235                 240

Lys Ile Phe Ile Phe Asp Ala Arg Pro Ser Val Asn Ala Val Ala Asn
                245                 250                 255

Lys Ala Lys Gly Gly Gly Tyr Glu Ser Glu Asp Ala Tyr Gln Asn Ala
            260                 265                 270

Glu Leu Val Phe Leu Asp Ile His Asn Ile His Val Met Arg Glu Ser
        275                 280                 285

Leu Arg Lys Leu Lys Glu Ile Val Tyr Pro Asn Ile Glu Glu Thr His
    290                 295                 300

Trp Leu Ser Asn Leu Glu Ser Thr His Trp Leu Glu His Ile Lys Leu
305                 310                 315                 320

Ile Leu Ala Gly Ala Leu Arg Ile Ala Asp Lys Val Glu Ser Gly Lys
                325                 330                 335

Thr Ser Val Val Val His Cys Ser Asp Gly Trp Asp Arg Thr Ala Gln
            340                 345                 350

Leu Thr Ser Leu Ala Met Leu Met Leu Asp Gly Tyr Tyr Arg Thr Ile
        355                 360                 365

Arg Gly Phe Glu Val Leu Val Glu Lys Glu Trp Leu Ser Phe Gly His
    370                 375                 380

Arg Phe Gln Leu Arg Val Gly His Gly Asp Lys Asn His Ala Asp Ala
385                 390                 395                 400

Asp Arg Ser Pro Val Phe Leu Gln Phe Ile Asp Cys Val Trp Gln Met
                405                 410                 415

Thr Arg Gln Phe Pro Thr Ala Phe Glu Phe Asn Glu Tyr Phe Leu Ile
            420                 425                 430

Thr Ile Leu Asp His Leu Tyr Ser Cys Leu Phe Gly Thr Phe Leu Cys
        435                 440                 445

Asn Ser Glu Gln Gln Arg Gly Lys Glu Asn
    450                 455


<210> SEQ ID NO 11
<211> LENGTH: 458
<212> TYPE: PRT
<213> ORGANISM: Homo sapiens

<400> SEQUENCE: 11

Glu Pro Pro Leu Leu Pro Gly Glu Asn Ile Lys Asp Met Ala Lys Asp
 1               5                  10                  15

Val Thr Tyr Ile Cys Pro Phe Thr Gly Ala Val Arg Gly Thr Leu Thr
            20                  25                  30

Val Thr Asn Tyr Arg Leu Tyr Phe Lys Ser Met Glu Arg Asp Pro Pro
        35                  40                  45

Phe Val Leu Asp Ala Ser Leu Gly Val Ile Asn Arg Val Glu Lys Ile
    50                  55                  60

Gly Gly Ala Ser Ser Arg Gly Glu Asn Ser Tyr Gly Leu Glu Thr Val
65                  70                  75                  80
```

-continued

```
Cys Lys Asp Ile Arg Asn Leu Arg Phe Ala His Lys Pro Glu Gly Arg
                85                  90                  95

Thr Arg Arg Ser Ile Phe Glu Asn Leu Met Lys Tyr Ala Phe Pro Val
            100                 105                 110

Ser Asn Asn Leu Pro Leu Phe Ala Phe Glu Tyr Lys Glu Val Phe Pro
        115                 120                 125

Glu Asn Gly Trp Lys Leu Tyr Asp Pro Leu Leu Glu Tyr Arg Arg Gln
    130                 135                 140

Gly Ile Pro Asn Glu Ser Trp Arg Ile Thr Lys Ile Asn Glu Arg Tyr
145                 150                 155                 160

Glu Leu Cys Asp Thr Tyr Pro Ala Leu Leu Val Val Pro Ala Asn Ile
                165                 170                 175

Pro Asp Glu Glu Leu Lys Arg Val Ala Ser Phe Arg Ser Arg Gly Arg
            180                 185                 190

Ile Pro Val Leu Ser Trp Ile His Pro Glu Ser Gln Ala Thr Ile Thr
        195                 200                 205

Arg Cys Ser Gln Pro Met Val Gly Val Ser Gly Lys Arg Ser Lys Glu
    210                 215                 220

Asp Glu Lys Tyr Leu Gln Ala Ile Met Asp Ser Asn Ala Gln Ser His
225                 230                 235                 240

Lys Ile Phe Ile Phe Asp Ala Arg Pro Ser Val Asn Ala Val Ala Asn
                245                 250                 255

Lys Ala Lys Gly Gly Gly Tyr Glu Ser Glu Asp Ala Tyr Gln Asn Ala
            260                 265                 270

Glu Leu Val Phe Leu Asp Ile His Asn Ile His Val Met Arg Glu Ser
        275                 280                 285

Leu Arg Lys Leu Lys Glu Ile Val Tyr Pro Asn Ile Glu Glu Thr His
    290                 295                 300

Trp Leu Ser Asn Leu Glu Ser Thr His Trp Leu Glu His Ile Lys Leu
305                 310                 315                 320

Ile Leu Ala Gly Ala Leu Arg Ile Ala Asp Lys Val Glu Ser Gly Lys
                325                 330                 335

Thr Ser Val Val Val His Cys Ser Asp Gly Trp Asp Arg Thr Ala Gln
            340                 345                 350

Leu Thr Ser Leu Ala Met Leu Met Leu Asp Gly Tyr Tyr Arg Thr Ile
        355                 360                 365

Arg Gly Phe Glu Val Leu Val Glu Lys Glu Trp Leu Ser Phe Gly His
    370                 375                 380

Arg Phe Gln Leu Arg Val Gly His Gly Asp Lys Asn His Ala Asp Ala
385                 390                 395                 400

Asp Arg Ser Pro Val Phe Leu Gln Phe Ile Asp Cys Val Trp Gln Met
                405                 410                 415

Thr Arg Gln Phe Pro Thr Ala Phe Glu Phe Asn Glu Tyr Phe Leu Ile
            420                 425                 430

Thr Ile Leu Asp His Leu Tyr Ser Cys Leu Phe Gly Thr Phe Leu Cys
        435                 440                 445

Asn Ser Glu Gln Gln Arg Gly Lys Glu Asn
    450                 455
```